US010266565B2

(12) United States Patent
Burke, Jr. et al.

(10) Patent No.: US 10,266,565 B2
(45) Date of Patent: *Apr. 23, 2019

(54) PEPTIDE MIMETIC LIGANDS OF POLO-LIKE KINASE 1 POLO BOX DOMAIN AND METHODS OF USE

(75) Inventors: Terrence R. Burke, Jr., Bethesda, MD (US); Fa Liu, Indianapolis, IN (US); Kyung S. Lee, Gaithersburg, MD (US); Jung-Eun Park, Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 396 days.

This patent is subject to a terminal disclaimer.

(21) Appl. No.: 14/111,540

(22) PCT Filed: Apr. 12, 2012

(86) PCT No.: PCT/US2012/033259
§ 371 (c)(1),
(2), (4) Date: Jan. 24, 2014

(87) PCT Pub. No.: WO2012/142245
PCT Pub. Date: Oct. 18, 2012

(65) Prior Publication Data
US 2014/0142044 A1    May 22, 2014

Related U.S. Application Data

(60) Provisional application No. 61/474,621, filed on Apr. 12, 2011, provisional application No. 61/588,470, filed on Jan. 19, 2012.

(51) Int. Cl.
| | |
|---|---|
| *C07K 7/06* | (2006.01) |
| *C07K 1/00* | (2006.01) |
| *C07K 5/08* | (2006.01) |
| *C12N 9/12* | (2006.01) |
| *A61K 47/60* | (2017.01) |
| *A61K 38/00* | (2006.01) |

(52) U.S. Cl.
CPC ............... *C07K 7/06* (2013.01); *A61K 47/60* (2017.08); *C07K 1/006* (2013.01); *C07K 5/0827* (2013.01); *C12N 9/12* (2013.01); *C12Y 207/11021* (2013.01); *A61K 38/00* (2013.01)

(58) Field of Classification Search
None
See application file for complete search history.

(56) References Cited

U.S. PATENT DOCUMENTS 9,175,038 B2 * 11/2015 Burke, Jr. et al. ......... C07K 7/06

FOREIGN PATENT DOCUMENTS

WO      2010/132869 A2    11/2010
WO      WO 2010/132869 *  11/2010

OTHER PUBLICATIONS

Roberts et al, Chemistry for peptide and protein PEGylation, Advanced Drug Delivery Reviews 54 (2002) 459-476.*
International Search Report and Written Opinion, PCT/US2012/033259, dated Oct. 29, 2012.
Liu F. et al: "Serendipitous alkylation of a Plk1 ligand uncovers a new binding channel", Nature Chemical Biology, vol. 7, No. 9, Jul. 17, 2011 (Jul. 17, 2011), pp. 595-601.
Yun Sang-Moon et al: "Structural and functional analysus of minimal phosphopeptides targeting the polo-box domain of polo-like kinase 1", Nature Structural & Molecular Biology, vol. 16, No. 8. Aug. 1, 2009 (Aug. 1, 2009), pp. 876-9985.
Bhadra D et al: "Pegnology: A Review of Peg-Ylated Systems", Die Pharmazie, Govi Verlag Pharmazeutischer Verlag GMBH, Eschborn, DE, vol. 57, No. 1, Jan. 1, 2002 (Jan. 1, 2002), pp. 5-29.
Khedkar A. et al: "A dose range finding study of novel oral insulin (IN-105) under fed conditions in type 2 *Diabetes mellitus* subjects", Diabetes, Obesity and Metabolism, vol. 12, No. 8, Aug. 1, 2010 (Aug. 1, 2010), pp. 659-664.
Miller M. et al: Amphiphilic Conjugates of Human Brain Natriuretic Peptide Designed for Oral Delivery: In Vitro Actitvity Screening:, Bioconjugate Chemistry, vol. 17, No. 2, Mar. 1, 2006 (Mar. 1, 2006), pp. 267-274.
Johnson Eric F et al: "Pharmacological and functional comparison of the polo-like kinase family: Insight into inhibitor and substrate specificity", Biomchemistry, Americal Chemical Society, US, vol. 46, No. 33, Jul. 27, 2007 (Jul. 27, 2007), pp. 9551-9563.
Liu F et al: "Preparation of orthogonally protected (2S, 3R)-2-amino-3-methyl-4-phosphonobutyric acid (Pmab) as a phosphatase-stable phosphothreonine mimetic and its use in the synthesis of polo-box domain-binding peptides", Tetrahedron, Elsevier Science Publishers, Amsterdam, NL., vol. 65, No. 47, Nov. 21, 2009 (Nov. 21, 2009), pp. 9673-9679.
Kui-Thong Tan et al: :"Design, Synthesis, and Characterization of Peptide-Based Rab Geranylgeranyl Transferase Inhibitors", Journal of Medicinal Chemistry, vol. 52, No. 24, Dec. 24, 2009 (Dec. 24, 2009), pp. 8025-8037.

(Continued)

*Primary Examiner* — Sergio Coffa
(74) *Attorney, Agent, or Firm* — Locke Lord LLP; Nicholas J. DiCeglie, Jr.

(57) ABSTRACT

Novel compounds are provided that bind to polo-like kinases through the polo-box domain. In certain embodiments, the novel compounds are PEGylated peptides. The PEGylated peptides in accordance with the invention demonstrate high PBD-binding affinity. In certain embodiments, the PEGylated peptides have also achieved activities in whole cell systems. The invention also provides compounds that bind polo-like kinases through the polo-box domain and possess reduced anionic charge. Further provided are methods of design and/or synthesis of the PEGylated peptides and methods of use thereof. The invention provides methods of use of the compounds and methods of synthesis of the compounds.

14 Claims, 31 Drawing Sheets

Specification includes a Sequence Listing.

(56) References Cited

OTHER PUBLICATIONS

Sharma R et al: "New Antimicrobial Hexapeptides: Synthesis, Antimicrobial Activities, Cytotoxicity, and Mechanistic Studies", Chemmedchem, vol. 5, No. 1, Jan. 4, 2010 (Jan. 4, 2010), pp. 86-95.
International Search Report for International Application No. PCT/US2012/033259, dated Oct. 29, 2012.
International Preliminary Report on Patentability for International Application No. PCT/US2012/033259, dated Oct. 15, 2013.
Felix, Arthur, M., et al., "Pegylated peptides IV Enhanced biological activity of site-direcged pegylated GRF analogs", Int J. Peptide Protein Res., 46., 1995, 253-264.
Felix, Arthur M., "Site-Specific Poly(ethylene glycol)ylation of Peptieds", Chapter 16, American Chemical Society, 1997, p. 218-238.
Swaminathan, Janani, J. Aerosol Med Pulm Drug Deliv. Feb. 2014, 27(1):1-11.
Chan, Linda J., Mol Pharm. Mar. 2, 2015;12(3): 794-809.
Pegylation of Peptides. © Bachem Group, Nov. 2015.
Bellouard, Frederic, "A Convenient Synthetic Route to Polyether-Tagged Cyclam Ligands and Their Nickel Devivatives", Eur J. Org Chem., 1999, 3257-3261.
Acta Crystallogr. D Biol. Crystallogr. D50, 760-3 (1994), "The CCP4 Suite: Programs for Protein Crystallography".
Adams, P.D. et al., "PHENIX: a comprehensive python-based system for macromolecular structure solution", Acta Crystallogr. D Biol. Crystallogr. 66, 213-221, 2010.
Adams, P.D. et al., "PHENIX: building new software for automated crystallographic structure determination", Acta Crystallogr. D. Biol. Crystallogr. 58, 1948-1954 (2002).
Berge et al. (1977), "Pharmaceutical Salts", J. Pharm. Sci. 66:1-19.
Brunger, A.T., "Version 1.2 of the crystallography and NMR system", Nat. Protoc. 2, 2728-2733 (2007).
Garrus, J.E., "Tsq101 and the vacuolar protein sorting pathway are essential for HIV-1 budding", et al., Cell, 107, 2001, 55-65.
Hanisch, A. et al., "Different Plk1 functions show distinct dependencies on polo-box domain-mediated targeting", Mol. Biol. Cell 17, 448-459 (2006).
Hermida-Matsumoto, L., et al., "Localization of human immunodeficiency virus type 1 gag and env at the plasma membrane by confocal imaging", J. Virol, 74, 2000, 8670-8679.
Humphrey, J. M.; Bridges, R. J.; Hart, J. A Chamberlin, "2,3-pyrrolidinedicarboxylates as neurotransmitter conformer mimics: enantioselective synthesis via chelation-controlled enolate alkylation", A. R. J. Org. Chem. 1994, 59, 2467.
Kraulis, P.J., "Molscript: a program to produce both detailed and schematic plots of protein structures", J. Appl. Crystallogr. 24, 946-950 (1991).
Liu, F. et al., "Preparation of orthogonally protected (2S,3R)-2-amino-3-methyl-4-phosphonobutryic acid (Pmab) as a phosphatase-stable phosphothreonine mimetic and its use in the syntheses of polo-box domain-binding peptides", Tetrahedron 65, 9673-9679 (2009).
Liu, Fa, et al., "Serendipitous alkylation of a Plk 1 ligand uncovers a new binding channel", Nat Chern Biol 7:595-601.
McRee, D.E., "Xtalview/xfit—a versatile program for manipulating atomic coordinates and electron density", J. Struct. Biol. 125, 156-65 (1999).
Minor, W. et al., "HKL-3000: the integration of data reduction and structure solution—from diffraction images to an initial model in minutes", Acta Crystallogr. D Biol. Crystallogr. 62, 859-66 (2006).
Navaza, J., "Implementation of molecular replacement in AMORE", Acta Crystallogr. D Biol. Crystallogr. 57, 1367-72 (2001).
Navaza, J., "AMORE: an automated package for molecular replacement", Acta Cryst. A50, 157-163 (1994).
Qian, Wenjian, et al., "Investigation of unanticipated alkylation at the N(II) position of a histidyl residue under mitsunobu conditions and synthesis of orthogonally protected histidine analogues", Journal Org Chem, 2011, 76, 8885.
Saulnier et al., "An efficient method for the synthesis of Guanidino prodrugs", (1994), Bioorganic and Medicinal Chemistry Letters, vol. 4, p. 1985.
Seong, Y.S. et al., "A spindle checkpoint arrest and a cytokinesis failure by the dominant-negative polo-box domain of plk1 in U-2 OS cells", J. Biol. Chem. 277, 32282-32293 (2002).
Strebhardt, K. et al., "Targeting polo-like kinase 1 for cancer therapy", Nat. Rev. Cancer 6, 321-330. (2006).
Swamy et al., "Mitsunobu and related reactions: advances and applications", Chem. Rev. 109, 2551-2651 (2009).
Tavassoli et al., "Inhibition of HIV budding by a genetically selected cyclic peptide targeting the gag-TSG101 Interaction", ACS Chem. Bio., 3, 12, 2008, 757-764.
Tavassoli et al., "Genetically selected cyclic-peptide inhibitors of AICAR transformylase Homodimerization", Angew. Chem. Int. Ed. Engl. 44, 2005, 2760-2763.
Yun et al., "Structural and functional analyses of minimal phosphopeptides targeting the polo-box domain of polo-like kinase 1", Nat. Struct. Mol. Biol. 16, 876-882 (2009).

* cited by examiner

| No | X | R¹ | R² |
|---|---|---|---|
| 1 | O | H | Ac |
| 1* | CH$_2$ | H | Ac |
| (PEG)-1* | CH$_2$ | H | H$_3$C[O⌒O]$_4$⌒C(O)- |
| 4j | O | Ph-(CH$_2$)$_8$- | Ac |
| (PEG)-4j* | CH$_2$ | Ph-(CH$_2$)$_8$- | H$_3$C[O⌒O]$_4$⌒C(O)- |

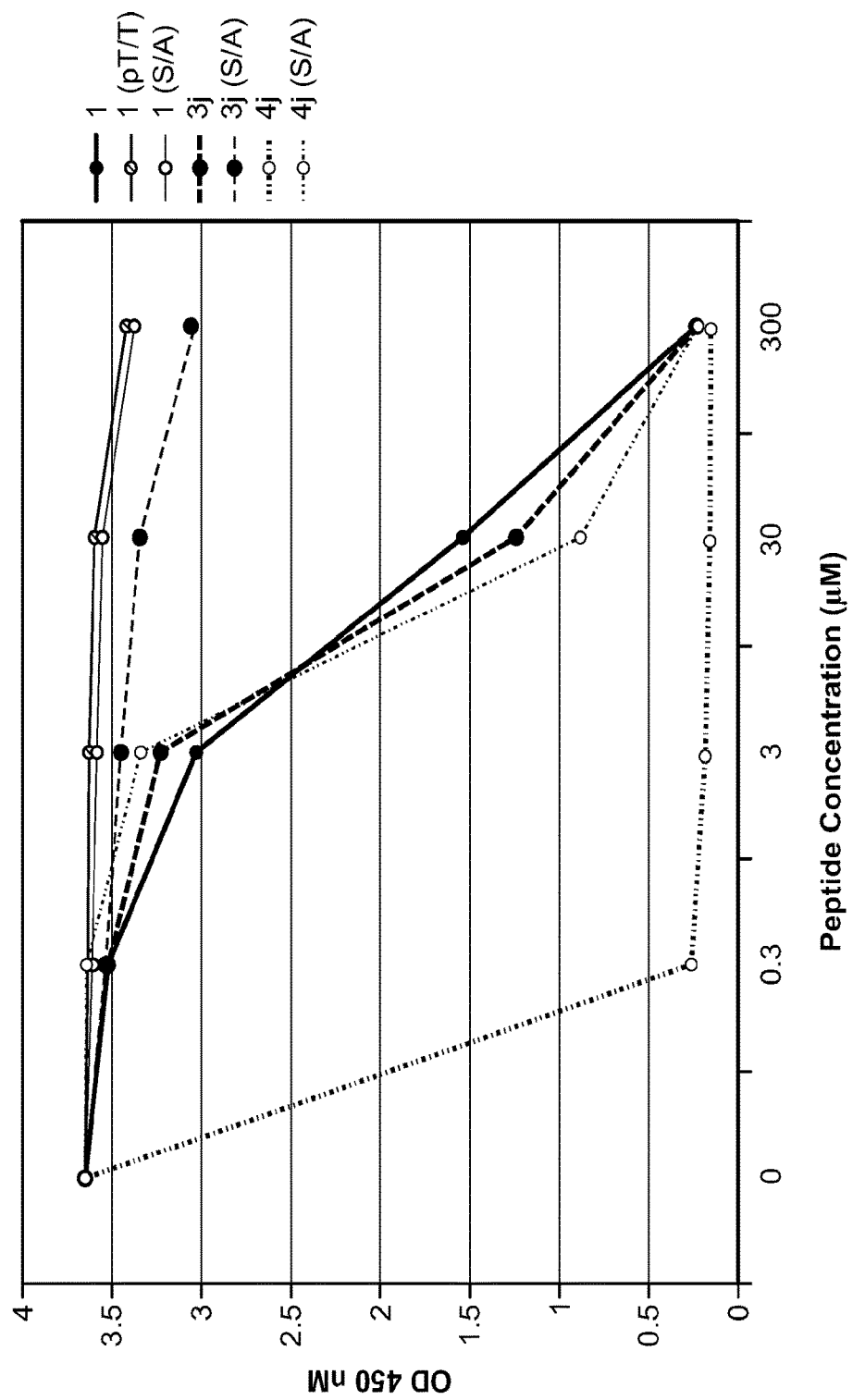

| NO | LOT | STRUCTURE |
|---|---|---|
| Qian048 | 184B-43-1 | 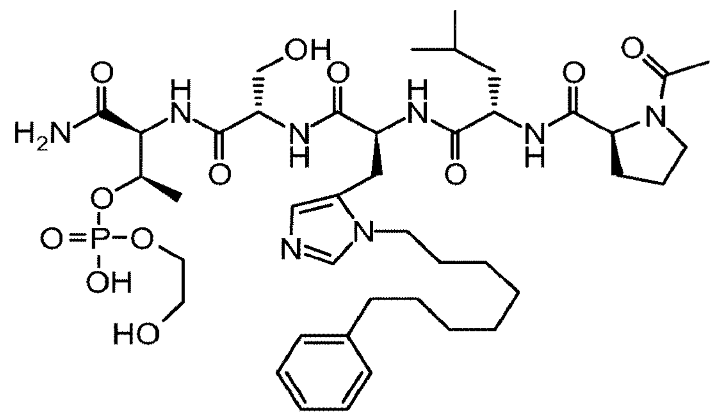 |
| Qian049 | 184D-63-1 | 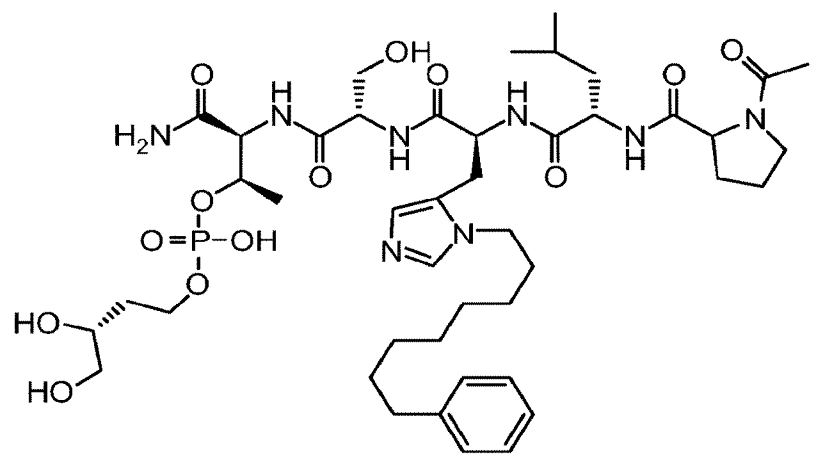 |

| | | |
|---|---|---|
| Qian056 | 184C-78-1 | |
| Qian030 | 184B-91-1 | |

FIG. 11A-1

| NO | LOT | STRUCTURE |
|---|---|---|
| Qian064 | 184E-40-1 | 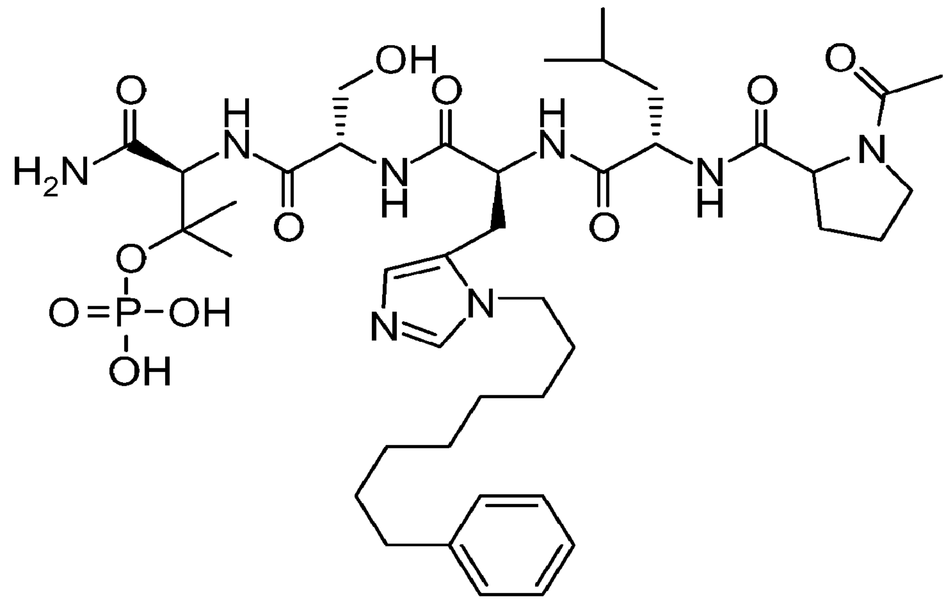 |

| 184E-59-1 |
| Qian065 |

184E-60-1

Qian066

184E-61-1

Qian068

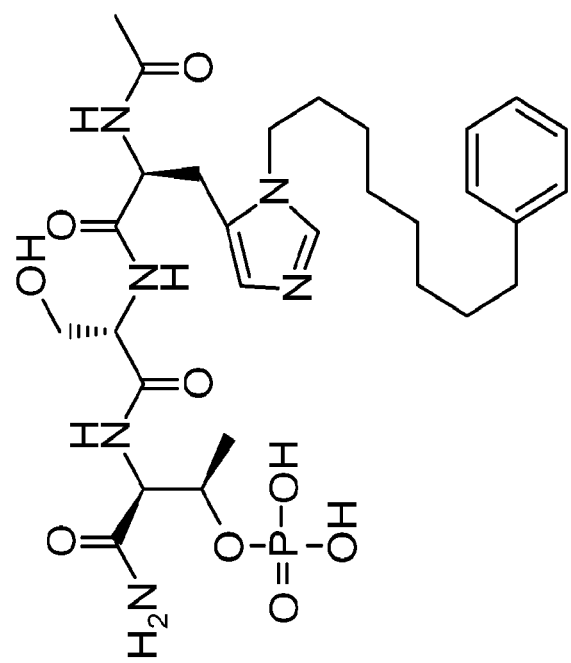
FIG. 11A-6 | 184E-36-1 | Qian069

| Qian070 | 184E-38-1 |

SEQUENCE LISTING

<160> NUMBER OF SEQ ID NOS: 23

<210> SEQ ID NO 1
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 1

Pro Leu His Ser Thr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 2

Pro Pro His Ser Thr
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: pThr

<400> SEQUENCE: 3

Leu His Ser Thr Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 4

Pro Met Gln Ser Thr Pro Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: pThr

<400> SEQUENCE: 5

Met Gln Ser Thr Pro Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Leu His Ser Thr Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: F2Pmab

<400> SEQUENCE: 7

Pro Leu His Ser Xaa Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: F2Pmab

<400> SEQUENCE: 8

Pro Leu His Ser Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 9

Pro Leu His Ser Thr Ala
1               5

<210> SEQ ID NO 10
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(CH2)6-(CH2)6
<220> FEATURE:
<221> NAME/KEY: MOD_RES
<222> LOCATION: (8)..(8)
<223> OTHER INFORMATION: pThr

<400> SEQUENCE: 10

Cys Asp Pro Pro Leu His Ser Thr Ala Ile
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Leu His Ser Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 13

Pro Leu His Ser Thr Ala Ile Tyr Ala Asp
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: pThr

<400> SEQUENCE: 14
```

```
Leu His Ser Thr
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: pThr

<400> SEQUENCE: 15

His Ser Thr Ala
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr

<400> SEQUENCE: 16

Ser Thr Ala Ile
1

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: pThr

<400> SEQUENCE: 17

Leu His Ser Thr Ala Ile
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 18

Met Leu His Ser Thr
1               5

<210> SEQ ID NO 19
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: P-mab

<400> SEQUENCE: 19

Pro Leu His Ser Xaa
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: P-mab

<400> SEQUENCE: 20

Pro Leu His Ala Xaa
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cys-(CH2)5-CO
<220> FEATURE:
<221> NAME/KEY: MOD_RES
<222> LOCATION: (8)..(8)
<223> OTHER INFORMATION: pThr

<400> SEQUENCE: 21

Cys Asp Pro Pro Leu His Ser Thr Ala Ile
1               5                   10

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Thr Ala Pro
1

<210> SEQ ID NO 23
<211> LENGTH: 4
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 23

Leu Ile Arg Leu
1

PEPTIDE MIMETIC LIGANDS OF POLO-LIKE KINASE 1 POLO BOX DOMAIN AND METHODS OF USE

RELATED APPLICATIONS

This application claims the benefit of U.S. Provisional application 61/474,621, filed on Apr. 12, 2011, and U.S. Provisional application 61/588,470, filed on Jan. 19, 2012. The entire contents of the above-referenced applications are incorporated herein by reference.

STATEMENT OF RIGHTS TO INVENTIONS MADE UNDER FEDERALLY SPONSORED RESEARCH

This work was supported by the Intramural Research Program of the National Institutes of Health and the National Cancer Institute under Grant No. ZIA BC 006198. This work was supported by the Intramural Research Program of the National Institutes of Health and under Grant No. R01 GM60594; and the National Cancer Institute under Grant No. N01-CO-12400. The government has certain rights in the invention.

SEQUENCE LISTING

The instant application contains a Sequence Listing which has been submitted electronically in ASCII format and is hereby incorporated by reference in its entirety. Said ASCII copy, created on Dec. 15, 2014, is named 88184(47992)_SL.txt and is 6,183 bytes in size.

BACKGROUND

Found in various eukaryotic organisms, polo-like kinases (collectively, Plks) are a conserved subfamily of Ser/Thr protein kinases that play critical roles in cell proliferation. Plks are characterized by the presence of a highly conserved C-terminal polo-box domain (PBD) composed of two structurally-related PB1 (residues 411-489 in Plk1) and PB2 (residues 511-592) motifs. Multiple forms of Plks, designated Plk1, Plk2/Snk, Plk3/Prk/Fnk, and Plk4/Sak, exist in mammals. Plk4 is the most distantly related member of the Plk subfamily and one of the two Plk4 variants, Sak-a, contains only the PB1 motif near the end of an unusually long C-terminal extension. Among the Plks, Plk1 has been studied most extensively because of its ability to override cellular checkpoints and induce genetic instability, leading to oncogenic transformation of human cells. Not surprisingly, Plk1 is over-expressed in a broad spectrum of human cancers and has been proposed as a new prognostic marker for many types of malignancies. Furthermore, interference with Plk1 function induces apoptotic cell death in most tumor cells, but not in normal cells, and reduces tumor growth in mouse xenograft models. In contrast to the role of Plk1 in cell proliferation and tumorigenesis, the two most closely related kinases, Plk2 and Plk3, appear to play a role in checkpoint-mediated cell cycle arrest to ensure genetic stability and prevent oncogenic transformation.

The PBD of Plk1 plays a critical role in proper subcellular localization and mitotic functions of Plk1 by interacting with phosphorylated Ser/Thr peptides with the invariable Ser residue at the −1 position (S-p-S/T motif). Crystal structures of the Plk1 PBD in complex with artificial phosphopeptides optimized for PBD binding have revealed that the PB1 and PB2 motifs have identical folds described as 36a (a six-stranded anti-parallel β-sheet and an α-helix) and form a hetero-dimeric phosphopeptide-binding module. The phosphopeptide binds to a cleft formed between PB1 and PB2 and interacts with key amino acid residues from both polo-boxes. His538 and Lys540 from PB2 are pivotal for electrostatic interactions with the negatively charged phosphate group of phospho-Ser/Thr (p-Ser/Thr) residue, whereas Trp414 from PB1 is critical for the selection of Ser at the −1 position by engaging in two hydrogen bonding interactions and van der Waals interactions with the Ser-1 residue. These residues are conserved in the PBDs of Plk1, Plk2, and Plk3 (in short, Plk1-3), attesting to their importance (Plk4 has a distinct binding module and forms a homodimer through a single PB1 motif. However, minimal elements required for stable PBD binding and the interactions critical for achieving the specificity between Plk1 and its binding targets are poorly understood.

SUMMARY

The invention comprises peptide-mimetic ligands of the polo-like kinase 1 (Plk1) which is a regulator of mitotic events and cellular proliferative potential. In particular, the invention provides novel compounds that bind to polo-like kinases through the polo-box domain.

By examining PBD-binding phosphopeptides, the 5-mer phosphopeptide "PLHSpT" (SEQ ID NO: 1) was identified that specifically interacts with the Plk1 PBD with a high affinity, but not with the two closely-related Plk2 and Plk3 PBDs. Based on this peptide sequence, peptides with high PBD-binding affinity may be designed and prepared. However, possibly due to poor bioavailability arising from poor solubility or limited membrane transport (or both), it is difficult for the peptides (even with high PBD-binding affinity) to achieve activity in whole-cell systems. There is a need in the art to design and prepare PBD-binding peptides with improved pharmaceutical properties, including increased bioavailability.

In certain embodiments, the novel compounds are peptide derivatives with polyethyleneglycol units (hereinafter, also referred to as "PEGylated peptides"). The PEGylated peptides in accordance with the invention demonstrate high PBD-binding affinity. Some PEGylated peptides have also achieved activities in whole cell systems. The invention also provides methods of design and/or synthesis of the PEGylated peptides and methods of use thereof.

We now have recognized that specific inhibition of Plk1, but not Plk2 or Plk3, can be important for anti-Plk1 cancer therapy. In accordance with preferred aspects of the invention, specifically inhibiting Plk1 function and reduced uptake of Plk1 antagonists into whole cells can be addressed by preferred compounds that can bind polo-like kinases through the polo-box domain, and that can exhibit reduced anionic charge to enhance uptake into whole cells.

In one aspect, the invention provides a compound of Formula (I):

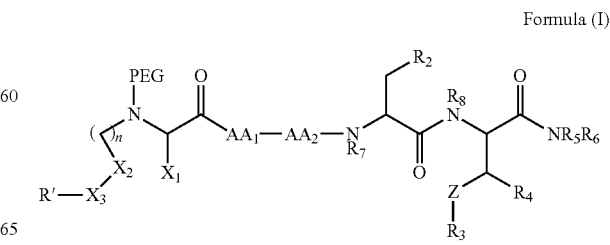

Formula (I)

wherein

PEG is a polyethylene glycol moiety or a derivative thereof;

Z is O, (C$_{1-6}$)alkylene, or CY$_2$; wherein Y, for each occurrence independently, is F, Cl, or Br;

n is 0, 1 or 2;

R$_7$, and R$_8$, each independently, is H or (C$_{1-6}$)alkyl-carbonyl;

R$_2$ is H or R$_9$O—;

R$_9$ is H, (C$_{1-6}$)alkyl-carbonyl, or (C$_{1-6}$)alkyl;

R$_5$ and R$_6$, each independently, is H, (C$_{1-6}$)alkyl-carbonyl, X$_5$—O—(C$_{1-6}$)alkyl, or a glycine moiety;

R$_3$ is H or (X$_4$O)$_2$P(O)—;

R$_4$ is H, acyl, (C$_{1-6}$)alkyl, (C$_{1-6}$)alkyl-carbonate, or (C$_{1-6}$)alkyl-O—C(S)—O—;

X$_1$ is H or (C$_{1-6}$)alkyl; or X$_1$ and X$_2$, taken together with the bonds they are connected to, form a 5 to 8-membered heterocyclic ring;

X$_2$ is a bond, or (C$_{1-6}$)alkylene; or X$_1$ and X$_2$, taken together with the bonds they are connected to, form a 5 to 8-membered heterocyclic ring;

R'—X$_3$ is R', R'—CH=N—O—, R'—(C$_{1-6}$)alkyl-O—, R'—C(O)—NH—O—, R'—(C$_{1-6}$)alkyl-S—, or R'—(C$_{1-6}$)alkyl;

R' is H, amino-O—, (C$_{1-6}$)alkyl-C(O)—, (C$_{2-6}$)alkenyl, cycloalkyl, heterocyclic, aryl-(C$_{0-6}$)alkyl, or heretoaryl-(C$_{0-6}$)alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups; or R' connected to one of the X$_4$ groups to form a macrocyclic ring;

X$_4$, for each occurrence independently, is H, (C$_{1-20}$)alkyl, (C$_{1-20}$)alkyl-Si—, aryl-(C$_{1-20}$)alkyl-, alkenyl-(C$_{1-20}$)alkyl, heteroaryl-(C$_{1-20}$)alkyl, (C$_{0-6}$)alkoxy-carbonyl-(C$_{1-6}$)alkyl, or amino(C$_{1-6}$)alkyl, wherein each alkyl moiety as appears at the X$_4$ position is further optionally substituted by one or more hydroxyl or alkoxy groups; or one of the X$_4$ groups is connected to R' to form a macrocyclic ring;

X$_5$ is (C$_{1-6}$)alkyl, —N=R$_{10}$, wherein R$_{10}$ is derived from a sugar moiety;

AA1 is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and AA2 is absent or an amino acid moiety selected from the group of His, Gln, Ala, Cys, Glu, Phe, Ile, Met, Asn, Ser, Thr, Val, and Tyr;

wherein each of the amino acid moieties for AA1 or AA2 is optionally substituted by aryl-(C$_{1-10}$)alkyl, heteroaryl-(C$_{1-10}$)alkyl, aryl-(C$_{1-10}$)alkyl-CH=N—O—, aryl-(C$_{1-10}$)alkoxy, aryl-(C$_{1-10}$)alkoxy, aryl-(C$_{1-10}$)alkyl-S—, aryl-(C$_{1-10}$)alkyl-C(O)—NH—O—, heteroaryl-(C$_{1-10}$)alkyl-C(O)—NH—O—, and wherein each aryl or heteroaryl moiety is further optionally substituted by one or more same or different substituents selected from the group of aryl, heteroaryl, alkenyl, alkyl, halogen, hydroxyl, amine, amide, carboxyl, ester groups;

or a pharmaceutically acceptable salt, solvate, hydrate, or stereoisomer thereof.

In another aspect, the invention provides a compound of formula III or IV:

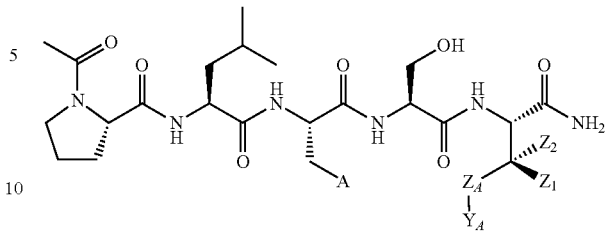

(III)

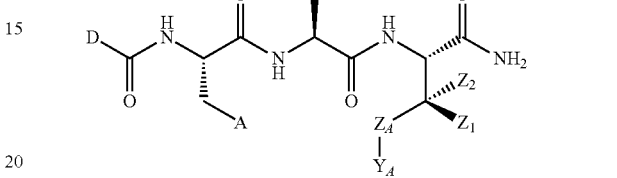

(IV)

wherein,

A is

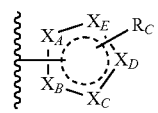

or —(CH$_2$)$_n$—X—R$_C$;

each of X$_A$, X$_B$, X$_C$, X$_D$, and X$_E$ are independently N or CR$_A$(R$_B$); wherein at least one of X$_A$, X$_B$, X$_C$, X$_D$, and X$_E$ is N;

X is O, S(O)$_m$, NR$_M$, NR$_M$C(O), C(O)NR$_M$, OC(O), or C(O)O;

R$_C$ is

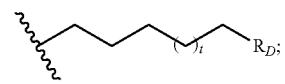

R$_D$ is optionally substituted aryl or optionally substituted heteroaryl;

t is 1, 2, 3, 4, or 5;

each R$_A$ is independently H, optionally substituted alkyl, optionally substituted carbocyclic, optionally substituted heterocyclic, optionally substituted aryl, or optionally substituted heteroaryl;

each R$_B$ is independently absent, H, optionally substituted alkyl, optionally substituted carbocyclic, optionally substituted heterocyclic, optionally substituted aryl, or optionally substituted heteroaryl;

or any two of R$_A$ groups, together with the atoms to which each is attached, may form a fused carbocyclic, heterocyclic, aryl, or heteroaryl ring, wherein each is optionally substituted;

wherein each A is optionally further substituted with one or more of R$_D$; wherein each R$_D$ is independently alkyl, alkenyl, or alkynyl, each containing 0, 1, 2, or 3 heteroatoms selected from O, S, or N; carbocyclic, heterocyclic, aryl, or heteroaryl; each of which is optionally substituted; or halogen, amino, hydroxy, oxo, or cyano;

D is optionally substituted alkyl or optionally substituted alkoxy;

$Z_A$ is absent, O or $CR_A(R_B)$;

$Y_A$ is

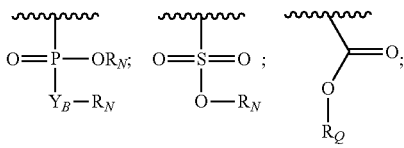

$Y_B$ is O or $CR_AR_A$;

each $Z_1$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

each $Z_2$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

or $Z_A$, $Y_A$, $Z_1$, and the atoms to which each is attached, form an optionally substituted heterocyclic or optionally substituted heteroaromatic ring;

each $R_N$ is independently H, optionally substituted alkyl, or optionally substituted alkoxy;

$R_Q$ is H, alkyl, benzyl, aryl, cycloalkyl, heterocycloalkyl, or heteroaryl, each of which is optionally substituted;

each $R_M$ is independently H or optionally substituted alkyl;

m is 0, 1, or 2; and n is 0, 1, 2, or 3;

wherein in formula I, if A is

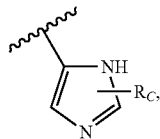

then $—Z_A—Y_A$ is not

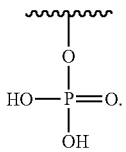

The invention also provides the compounds as pharmaceutically acceptable salts, solvates, hydrates, or stereoisomers. In other aspects, the invention provides compositions including any of the compounds of the invention described above, a pharmaceutically acceptable carrier, for use, for example, for the preparation of a medicament. The medicament can be, for example, a medicament for the prevention, amelioration, or treatment of a hyperproliferative disorder such as cancer.

In other aspects, the invention provides a kit comprising at least one compound of the invention and instructions for use. The invention further provides kits containing the compounds of the invention, and kits for synthesizing the compounds of the invention.

In another aspect, the invention provides a chemical library comprising two or more compounds of the invention.

In certain embodiments, the compounds of the invention can be used in methods for the prevention, amelioration, or treatment of a subject for a hyperproliferative disorder. The compounds of the invention can also be used in methods for the prevention, amelioration, or treatment of a subject for acquired immunodeficiency syndrome (AIDS).

The invention also includes methods of using the compounds of the invention, and methods of synthesizing the compounds of the invention.

Other aspects of the invention are discussed infra.

BRIEF DESCRIPTION OF THE FIGURES

FIG. 4b discloses "PLHSpT" and "PLHST" as SEQ ID NOS 1 and 11, respectively. (c) Asynchronously growing HeLa cells were treated with 200 μM of the indicated compounds for 24 h (all the compounds were dissolved in DMSO). The cells were additionally treated with Hoechst 33342 for 10 min, fixed with paraformaldehyde, and then quantified. (d-g), HeLa cells synchronously released from a single thymidine block were treated with 200 μM of the indicated compounds 4 h after release [All the PEGylated compounds were dissolved in phosphate-buffered saline (PBS)]. The cells were quantified at various time points to determine the fraction of mitotic cells with rounded-up morphology (d; dead cells were excluded from quantification). The same samples at the 13 h time point were photographed (e) and immunostained to examine Plk1 localization (f) and to quantify aberrant mitotic cells with abnormal spindle and DAPI morphologies among total mitotic population (g). Symbols in (f): Asterisks, centrosomally-localized Plk1 signals; arrowed brackets, kineotchore-associated Plk1 signals; arrowheads, misaligned chromosomes. Note that the PEG-4j*-treated cell in (f) shows greatly weakened centrosomal Plk1 at one pole (asterisk) and undetectable Plk1 at the other pole.

DETAILED DESCRIPTION

Definitions

Figure 1A:
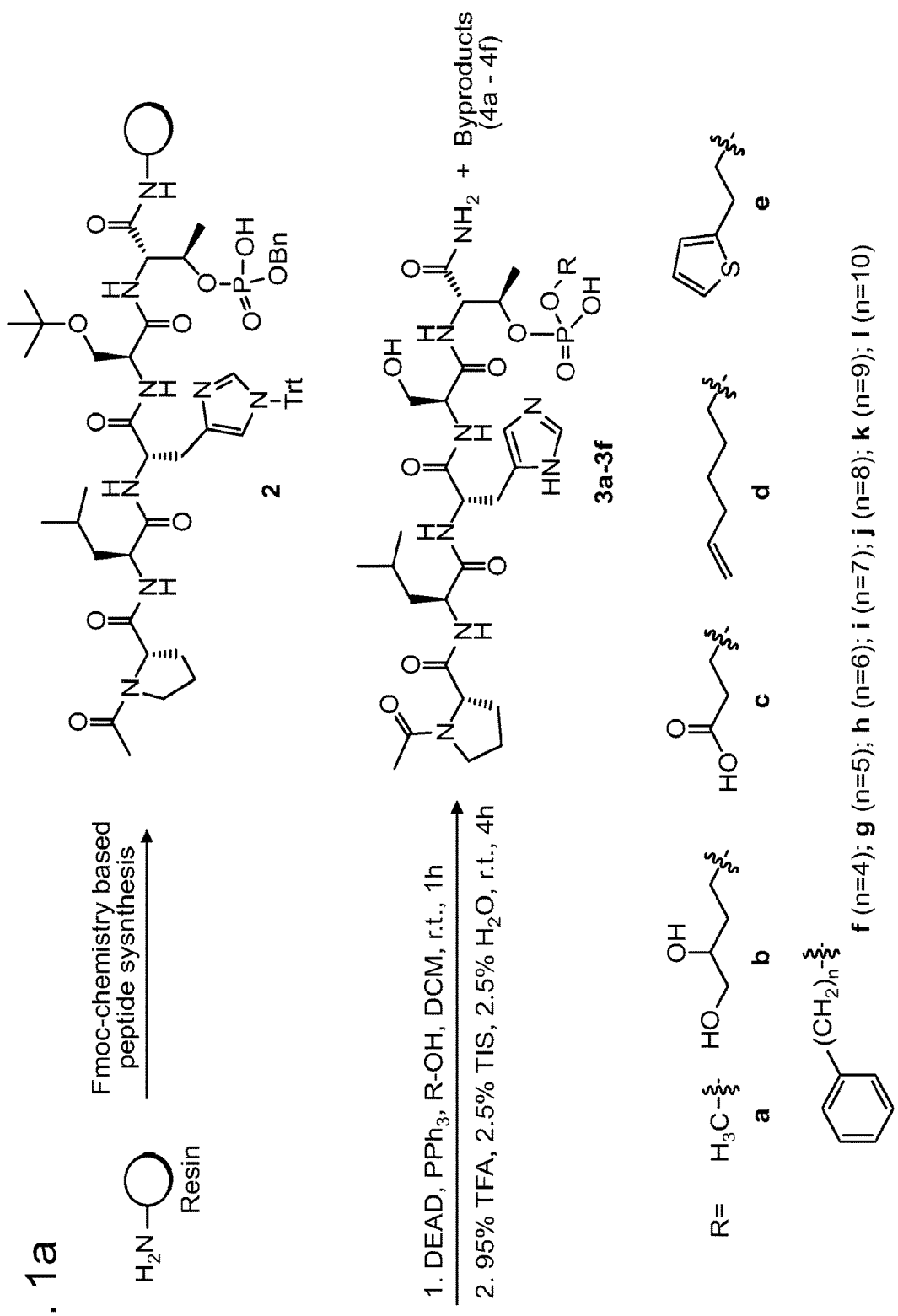
FIG. 1a-b. (a) Solid-phase synthesis of peptides; (b) Structures of peptides as synthesized.

An "agent" is understood herein to include a therapeutically active compound or a potentially therapeutic active compound. An agent can be a previously known or unknown compound. As used herein, an agent is typically a non-cell based compound, however, an agent can include a biological therapeutic agent, e.g., peptide or nucleic acid therapeutic, cytokine, antibody, etc.

An "agonist" is understood herein as a chemical substance capable of initiating the same reaction or activity typically produced by the binding of an endogenous substance or ligand to its target. An "antagonist" is understood herein as a chemical substance capable of inhibiting the reaction or activity typically produced by the binding of an endogenous substance (e.g., an endogenous agonist) to its target to prevent signaling through a receptor, to prevent downstream signaling, or to prevent cellular events (e.g., progression through cell cycle) that are the normal result of activation of the target. The antagonist can bind directly to the target or can act through other proteins or factors required for signaling. Agonists and antagonists can modulate some or all of the activities of the endogenous substance or ligand that binds to the target. Antagonists are typically characterized by determining the amount of the antagonist is required to inhibit the activity of the endogenous agonist. For example, an inhibitor at 0.01-, 0.1-, 1-, 5-, 10-, 50-, 100-, 200-, 500-, or 1000-fold molar concentration relative to the agonist can inhibit the activity of the agonist by at least 10%, 50%, 90%, or more.

As used herein "amelioration" or "treatment" is understood as meaning to lessen or decrease at least one sign, symptom, indication, or effect of a specific disease or condition. For example, amelioration or treatment of cancer can be determined using the standard RECIST (Response Evaluation Criteria in Solid Tumors) criteria including the assessment of tumor burden, by survival time, reduced presence of tumor markers (e.g., prostate specific antigen), or any other clinically acceptable indicators of disease state or progression. Amelioration and treatment can require the administration of more than one dose of an agent or therapeutic. As used herein, "prevention" is understood as to limit, reduce the rate or degree of onset, or inhibit the development of at least one sign or symptom of a disease or condition. For example, a subject having a genetic predisposition to develop a disease may develop disease later in life, e.g., delay of breast cancer development from third or fourth decade of life to fifth or beyond. Prevention can require the administration of more than one dose of an agent or therapeutic.

As used herein, an "aminooxy-containing amino acid" can be a modified proline, or an amino acid modified to provide a universal scaffold for modification with an aldehyde. Exemplary structures are provided:

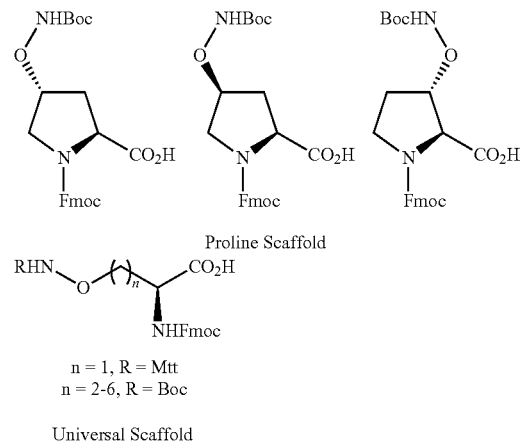

n = 1, R = Mtt
n = 2-6, R = Boc

Universal Scaffold

Chemical classes and groups are provided herein and referred to by chemical names, common names, and/or chemical structures. In the absence of an explicit definition herein, definitions of chemical structures can be found in chemical dictionaries, science textbooks, such as organic chemistry textbooks, or in databases such as the IUPAC Compendium of Chemical Terminology which can be accessed at Hypertext Transfer Protocol://old.iupac.org/publications/compendium/. Chemical classes and groups commonly referred to herein are provided as follows.

As used herein, "alkyl group" is understood as a univalent group derived from alkanes by removal of a hydrogen atom from any carbon atom —$C_nH_{2n+1}$. The groups derived by removal of a hydrogen atom from a terminal carbon atom of unbranched alkanes form a subclass of normal alkyl (n-alkyl) groups $H(CH_2)_n$. The groups $RCH_2$, $R_2CH$ (R≠H), and $R_3C$ (R≠H) are primary, secondary and tertiary alkyl groups, respectively. A "lower alkyl" is understood as an alkyl of the formula —$C_nH_{2n+1}$ wherein n is less than or equal to 6. A "higher alkyl" is understood as an alkyl of the formula —$C_nH_{2n+1}$ wherein n is greater than or equal to 6.

As used herein, an "alkene group" is understood as an acyclic branched or unbranched hydrocarbons having one carbon-carbon double bond and the general formula $C_nH_{2n-1}$. A "lower alkene" is understood as an alkyl of the formula —$C_nH_{2n-1}$ wherein n is less than or equal to 6. A "higher alkene" is understood as an alkyl of the formula —$C_nH_{2n-1}$ wherein n is greater than or equal to 6. Acyclic branched or unbranched hydrocarbons having more than one double bond are alkadienes, alkatrienes, etc. Heteroalkenes are analogues of alkenes in which a doubly bonded carbon atom is replaced by a heteroatom.

The term "alkoxy," as used herein, refers to an alkyl or a cycloalkyl group which is linked to another moiety though an oxygen atom. Alkoxy groups can be optionally substituted with one or more substituents.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

As used herein, an amide is understood as a derivative of an oxoacids in which an acidic hydroxy group has been replaced by an amino or substituted amino group. Compounds having one, two or three acyl groups on a given nitrogen are generically included and may be designated as primary, secondary and tertiary amides, respectively, e.g. $PhC(=O)NH_2$ benzamide, $CH_3S(=O)2NMe_2$ N,N-dimethylmethanesulfonamide, $[RC(=O)]_2NH$ secondary amides (see imides), $[RC(=O)]_3N$ tertiary amides, $PhP(=O)(OH)NH_2$ phenylphosphonamidic acid. An amide group as used herein is understood as a group with —$NH_2$, $NHR$ and $NR_2$. Amide groups should not be distinguished by means of the terms primary, secondary and tertiary.

As used herein, amine is understood as compounds formally derived from ammonia by replacing one, two or three hydrogen atoms by hydrocarbyl groups, and having the general structures $RNH_2$ (primary amines), $R_2NH$ (secondary amines), $R_3N$ (tertiary amines). An amino group is understood as having the structure —$NH_2$, —$NHR$, or —$NR_2$.

As used herein, "aryl group" is understood as refers to any functional group or substituent derived from a simple aromatic ring, may it be phenyl, thiophene, indolyl, etc (see IUPAC nomenclature, goldbook.iupac.org/A00464.html). Aryl groups derived from arenes by removal of a hydrogen atom from a ring carbon atom. Groups similarly derived from heteroarenes are sometimes subsumed in this definition. "Aryl" is used for the sake of abbreviation or generalization. For example, a simple aryl group is phenyl, $C_6H_5$; it is derived from benzene. The tolyl group, $CH_3C_6H_4$, is derived from toluene (methylbenzene). The xylyl group, $(CH_3)_2C_6H_3$, is derived from xylene (dimethylbenzene).

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 18 carbon ring atoms, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 π electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As used herein, "carboxylic acid" is understood as a group having the structure RC(=O)OH. A carboxylic acid group is understood to denote the —C(=O)OH group including its carbon atom.

As used herein, "carbonyl group" is understood as a group containing the carbonyl group, C=O. The term is commonly used in the restricted sense of aldehydes and ketones, however as used herein it includes carboxylic acids and derivatives.

As used herein, a "halogen," "halo," or "hal" is understood as an element located in Group VIIA of the periodic table. Halogens are reactive nonmetals having seven valence electrons. Halogen groups include —F, —Cl, —Br, and —I.

As used herein, modification of a class of chemical group with the term "hetero" is understood as the class of functional groups derived from the particular class of the functional group by removal of a hydrogen atom from any carbon atom.

As used herein, "olefin group" is understood as an acyclic and or cyclic hydrocarbon having one or more carbon-carbon double bonds, apart from the formal ones in aromatic compounds. The class olefins subsumes alkenes and cycloalkenes and the corresponding polyenes.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —C$_1$, —Br, —I,
—OH, protected hydroxy, alkoxy, oxo, thiooxo,
—NO$_2$, —CN, CF$_3$, N$_3$,
—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino,
—O-alkyl, —O-alkenyl, —O-alkynyl, —O-cycloalkyl, —O-aryl, —O-heteroaryl, —O-heterocyclic,
—C(O)-alkyl, —C(O)-alkenyl, —C(O)-alkynyl, —C(O)-carbocyclyl, —C(O)-aryl, —C(O)-heteroaryl, —C(O)-heterocyclyl,
—CONH$_2$, —CONH-alkyl, —CONH-alkenyl, —CONH-alkynyl, —CONH-carbocyclyl, —CONH-aryl, —CONH-heteroaryl, —CONH-heterocyclyl,
—OCO$_2$-alkyl, —OCO$_2$-alkenyl, —OCO$_2$-alkynyl, —OCO$_2$-carbocyclyl, —OCO$_2$-aryl, —OCO$_2$-heteroaryl, —OCO$_2$-heterocyclyl, —OCONH$_2$, —OCONH-alkyl, —OCONH-alkenyl, —OCONH-alkynyl, —OCONH-carbocyclyl, —OCONH-aryl, —OCONH-heteroaryl, —OCONH-heterocyclyl,
—NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —NHCO$_2$-alkyl, —NHCO$_2$-alkenyl, —NHCO$_2$-alkynyl, —NHCO$_2$-carbocyclyl, —NHCO$_2$-aryl, —NHCO$_2$-heteroaryl, —NHCO$_2$-heterocyclyl, —NHC(O)NH$_2$, —NHC(O)NH-alkyl, —NHC(O)NH-alkenyl, —NHC(O)NH— alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH— alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH— alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl,
—C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl,
—S(O)-alkyl, —S(O)-alkenyl, —S(O)-alkynyl, —S(O)-carbocyclyl, —S(O)-aryl, —S(O)-heteroaryl, —S(O)-heterocyclyl —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl,
—NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,
—CH$_2$NH$_2$, —CH$_2$SO$_2$CH$_3$,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

It is understood that the aryls, heteroaryls, carbocycles, heterocycles, alkyls, and the like can be further substituted.

Structures are provided in which a group is indicated as potentially being attached at any position of the ring as shown:

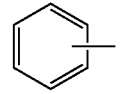

In compounds, amino acid positions are determined relative to the phosphothreonine which is arbitrarily defined as position zero (0). Amino acids to the C-terminus of the peptide (to the right) are indicated as positions +1 (adjacent to the phosphothreonine), +2 (adjacent to the +1 position, but not the phosphothrenine), etc. Similarly, amino acids towards the N– terminus are defined as positions –1 (adjacent to the phosphothreonine), –2 (adjacent to the –1 position, but not the phosphothrenine), etc.

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., PSA) or a substance produced by a reporter construct (e.g, β-galactosidase or luciferase). Depending on the method used for detection the amount and measurement of the change can vary. For example, a change in the amount of cleavage of analyte present will depend on the exact reaction conditions and the amount of time after exposure to the agent the sample is collected. Changed as compared to a control reference sample can also include decreased binding of a ligand to a receptor in the presence of an antagonist or other inhibitor. Determination of statistical significance is within the ability of those skilled in the art.

As used herein, "detecting", "detection" and the like are understood that an assay performed for identification of a specific analyte in a sample or a product from a reporter construct in a sample. Detection can also include identification of activation of a kinase or other enzyme. Detection can include the identification of a mutation in a gene sequence, such as a point mutation, a deletion of all or part of the coding sequence or transcriptional/translational regulatory sequences of the gene, a truncation of the gene sequence, or any other alteration that can alter the expression level or the sequence of the protein expressed by the gene, particularly when the alteration of the sequence results in a phenotypic change in the subject. Detection can include the determination of the size of a tumor, the presence or absence of metastases, the presence or absence of angiogenesis. The amount of analyte detected in the sample can be none or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition by physical examination, imaging, further laboratory tests, etc.

As used herein, a "diagnostic marker" is understood as one or more signs or symptoms of a disease or condition that can be assessed, preferably quantitatively to monitor the progress or efficacy of a disease treatment or prophylactic treatment or method. A diagnostic marker can be a substance that is released by a tumor (e.g., antigens such as PSA or enzymes). A diagnostic marker can be tumor size and/or grade of tumor and/or growth rate of tumor. A diagnostic marker can be the presence or absence of angiogenesis. A diagnostic marker can be a change in blood counts or cellular function measured in an in vitro assay, or the presence and characteristics of metastases (number and size).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

As used herein, "Fmoc" is understood as 9-Fluorenylmethyloxycarbonyl having the molecular formula $C_{15}H_{11}ClO_2$. The structure of this protective group is well known.

As used herein, "heterologous" as in "heterologous protein" is understood as a protein not natively expressed in the cell in which it is expressed. The heterologous protein may be, but need not be, from a different species.

The term "hyperproliferative disorder" or "neoplasia" includes malignancies characterized by excess cell proliferation or growth, or reduced cell death. In specific embodiments, the term "cancer" includes but is not limited to carcinomas, sarcomas, leukemias, and lymphomas. The term "cancer" also includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor. Tumors include solid tumors (i.e., non-blood tumors) and blood tumors. Cancers include, but are not limited to, Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

The term "stereoisomers" as used herein refers to isomeric molecules are that have the same molecular formula and sequence of bonded atoms (constitution), but that differ only in the three-dimensional orientations of their atoms in space. The structural isomers share the same molecular formula, but the bond connections and/or their order between different atoms/groups differs. In certain embodiments of the invention, stereoisomers refer to the compounds having the same order and bond connections of the constituent atoms, but different orientation in space (such as, enantiomers, and diastereomers).

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

As used herein, "kits" are understood to contain at least the non-standard laboratory reagents for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

The term "label" or "detectable label" as used herein refers to any atom or molecule which can be used to provide a detectable (preferably quantifiable) signal, and which can be attached to a chemical compound, a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP), Yellow Fluorescent Protein (YFP).

"Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

"Obtaining" is understood herein as manufacturing, purchasing, or otherwise coming into possession of.

As used herein, "oligonucleotide sequence" is understood as a non-coding nucleic acid sequence prepared by chemical synthesis methods or by transcription from a construct including an appropriate promoter sequence. A double stranded RNA oligonucleotide sequence as used herein includes a single strand forming a hairpin structure (e.g., shRNA) or joined by other non-nucleic acid linkages, or two separate strands annealed to form a double stranded structure.

An "oxime modified peptide" and the like are understood as a peptide in which at least one amino acid includes an aminooxy group, —O—NH$_2$, that will be reacted with an aldehyde to make a oxime modified peptide. In an embodiment, the aminooxy containing peptide is reacted with a library of aldehyde compounds to provide a library of oxmine modified peptides. An exemplary reaction scheme is shown:

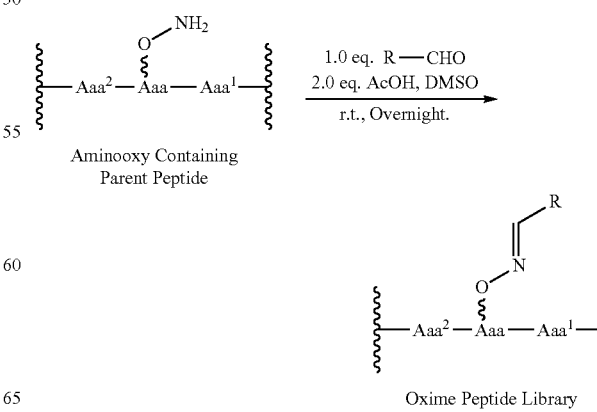

Aminooxy Containing
Parent Peptide

Oxime Peptide Library

A "peptide" as used herein is understood as two or more independently selected natural or non-natural amino acids joined by a peptide bond. A peptide can include 2, 3, 4, 5, 6, 7, 8, 9, 10, 11, 12 or more natural or non-natural amino acids joined by peptide bonds.

A "peptide-peptoid hybrid" as used herein is understood as a peptide in which at least one amino acid comprises the non-natural amino acid N-alkylglycine having the below structure.

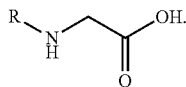

"Peptoids" are polymers of N-substituted glycine residues (NSG). These have emerged as an important class of peptide mimetic that can retain bioactivity while exhibiting resistance to proteolytic degradation. Peptide-peptoid hybrids containing both peptide and NSG residues have also shown significant utility. Examples are provided by the replacement of key Pro residues with NSG residues in WW and SH3 domain-binding peptides to achieve greater ligand selectivity and affinity.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, pharmaceutically acceptable salts include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of peptide mimentic is suitable for use in the methods of the present invention, e.g., a pharmaceutically acceptable salt of a peptide mimentic, a free base of a peptide mimentic, or a mixture thereof.

As used herein, "plurality" is understood to mean more than one. For example, a plurality refers to at least two, three, four, five, or more.

A "polo-like kinase" or "Plk" as used herein collectively refers to the proteins called Plk-1, (human sequence available as under Accession No. P53350.1 GI:1709658; mouse sequence available under Accession No. Q07832.2 GI:1709659; rat sequence available under Accession No. Q62673.1 GI: 12230396; Pan troglodytes sequence available under Accession No. XP_001163585.1 GI:114661620); Plk-2 (human sequence available under Accession No. Q9NYY3.3 GI:22096374); Plk-3 (human sequence available under Accession No. Q9H4B4.2 GI:51338822); and Plk-4 (human sequence available under Accession No. 000444.3 GI:160113150), from any organism, preferably a mammalian organism, preferably from a human organism. Such proteins can be encoded by any nucleic acid that provides the appropriate translation product; however, in certain embodiments, the polo-like kinases are encoded by the native genes which can easily be identified using GenBank or any of a number of publicly available databases. All GenBank Nos. incorporated herein by reference as of the filing date of the instant application.

"Reporter construct" as used herein is understood to be an exogenously inserted gene, often present on a plasmid, with a detectable gene product, under the control of a promoter sequence. The activity of the promoter is modulated upon signaling through one or more known cellular pathways. Preferably, the gene product is easily detectable using a quantitative method. Common reporter genes include luciferase and beta-galactosidase. The reporter construct can be transiently inserted into the cell by transfection or infection methods. Alternatively, stable cell lines can be made using methods well known to those skilled in the art, or cells can be obtained from transgenic animals expressing a reporter construct. The specific reporter gene or method of detection is not a limitation of the invention.

"RNA interference" refers to a target directed disruption of expression from a particular RNA transcript using a double stranded RNA molecule, either a siRNA or a shRNA. "siRNA" refers to a small interfering RNA, sometimes known as short interfering RNA or silencing RNA, is a class of 20-25 nucleotide-long double-stranded RNA molecules involved in the RNA interference (RNAi) pathway, where it interferes with the expression of a specific gene. SiRNAs have a well-defined structure: a short (usually 21-nt) double strand of RNA (dsRNA) with 2-nt 3' overhangs on either end. However, siRNAs can vary in length from about 19 to about 24 nucleotides in length. Each strand has a 5' phosphate group and a 3' hydroxyl (—OH) group. Structures of siRNAs and methods for design are provided, for example in WO02/44321, incorporated herein by reference. As used herein, "small hairpin RNA" or "short hairpin RNA" (shRNA) is a sequence of RNA that makes a tight hairpin turn that can be used to silence gene. A shRNA is composed of a single-stranded RNA with two self-complementary regions that allow the RNA to fold back upon itself and form a stem-loop structure with an intramolecular duplex region and an unpaired loop region.

A "sample" as used herein refers to a biological material that isolated from its environment (e.g., blood or tissue from an animal, cells, or conditioned media from tissue culture) and is suspected of containing, or known to contain an analyte, such as a tumor cell or a product from a reporter construct. A sample can also be a partially purified fraction of a tissue or bodily fluid. A reference sample can be a "normal" sample, from a donor not having the disease or condition fluid, or from a normal tissue in a subject having the disease or condition (e.g., normal tissue vs. tumor tissue). A reference sample can also be from an untreated donor or cell culture not treated with an active agent (e.g., no treatment or administration of vehicle only) and/or stimulus. A reference sample can also be taken at a "zero time point" prior to contacting the cell or subject with the agent or cell to be tested.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures, e.g., two kinases, particularly 2 polo-like kinases. For example, an agent, antibody, polypeptide, nucleic acid, or other compound can "specifically bind" one polo-like kinase (e.g., Plk1) with at least a 10-fold, 50-fold, 100-fold, 500-fold, 1000-fold, 5000-fold, 10,000-fold or more preference over another polo-like kinase, e.g., Plk2, Plk3, or Plk4. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as cancer is within the ability of those in the art.

Subjects suffering from, and suspected of suffering from, a specific disease, condition, or syndrome are not necessarily two distinct groups.

"Therapeutically effective amount," as used herein refers to an amount of an agent which is effective, upon single or multiple dose administration to the cell or subject, in prolonging the survivability of the patient with such a disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments such as radiation.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications (e.g. deletions, substitutions, etc.) in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. Chemical bonds not specifically defined as cis- or trans- can be either cis- or trans. The compounds of the invention can include mixtures of stereoisomers of the comounds or may include only specific stereoisomers, or may only include specific stereoisomers at specific positions.

All oligonucleotide sequences are written from the 5'-end to the 3'-end unless otherwise specifically noted.

Any compositions or methods provided herein can be combined with one or more of any of the other compositions and methods provided herein.

Compounds

Polo-like kinases (Plks) are a conserved subfamily of Ser/Thr protein kinases that play pivotal roles in cell proliferation. Since Plk1 overexpression is closely associated with oncogenesis, Plk1 is considered an attractive target for anti-cancer therapy. The polo-box domain (PBD) uniquely found in the C-terminal non-catalytic region of Plks forms a phosphoepitope-binding module for protein-protein interaction. Provided herein is the identification of minimal phosphopeptides that specifically interacted with the PBD of Plk1, but not the two closely-related Plk2 and Plk3, with a high affinity. Comparative binding studies and analyses of the crystal structures of the Plk1 PBD in complex with a minimal phosphopeptide (PLHSpT (SEQ ID NO: 1)) or its derivative PPHSpT (SEQ ID NO: 2), LHSpTA (SEQ ID NO: 3), or no peptide revealed that the C-terminal SpT dipeptide functions as a high affinity anchor, whereas the N-terminal PLH residues are critical for providing both specificity and affinity to the PBD. Testing of minimal phospho-Thr mimetic peptides demonstrated that inhibition of the PBD of Plk1 is sufficient to induce mitotic arrest and apoptotic cell death. Thus, the mode of PLHSpT (SEQ ID NO: 1) binding to the PBD may provide an important template for designing anti-Plk1 therapeutic agents.

The compounds, compositions and methods provided herein represent new approaches to the design and synthesis of the PEGylated peptides that can lead to the development of further therapeutically relevant PBD-directed agents. Besides, certain PEGylated peptides have also achieved activities in whole cell systems.

The invention provides high affinity compounds bearing non-natural amino acids as well as peptide-peptoid hybrids (containing N-alkylglycine residues). In certain embodiments, the compounds of the invention are PEGylated peptide. The PEGylated peptides demonstrate high PBD-binding affinity. In certain embodiments, the PEGylated peptides have also achieved activities in whole cell systems.

In one aspect, the invention provides a compound of Formula (I):

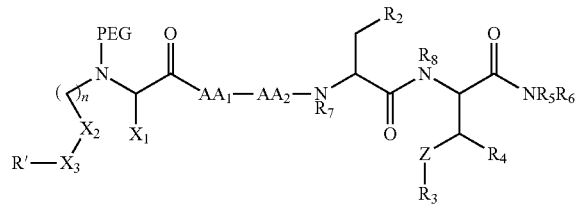

Formula (I)

wherein

PEG is a polyethylene glycol moiety or a derivative thereof;

Z is O, $(C_{1-6})$alkylene, or $CY_2$; wherein Y, for each occurrence independently, is F, Cl, or Br;

n is 0, 1 or 2;

$R_7$, and $R_8$, each independently, is H or $(C_{1-6})$alkyl-carbonyl;

$R_2$ is H or $R_9O$—;

$R_9$ is H, $(C_{1-6})$alkyl-carbonyl, or $(C_{1-6})$alkyl;

$R_5$ and $R_6$, each independently, is H, $(C_{1-6})$alkyl-carbonyl, $X_5$—O—$(C_{1-6})$alkyl, or a glycine moiety;

$R_3$ is H or $(X_4O)_2P(O)$—;

$R_4$ is H, acyl, $(C_{1-6})$alkyl, $(C_{1-6})$alkyl-carbonate, or $(C_{1-6})$alkyl-O—C(S)—O—;

$X_1$ is H or $(C_{1-6})$alkyl; or $X_1$ and $X_2$, taken together with the bonds they are connected to, form a 5 to 8-membered heterocyclic ring;

$X_2$ is a bond, or $(C_{1-6})$alkylene; or $X_1$ and $X_2$, taken together with the bonds they are connected to, form a 5 to 8-membered heterocyclic ring;

R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl;

R' is H, amino-O—, $(C_{1-6})$alkyl-C(O)—, $(C_{2-6})$alkenyl, cycloalkyl, heterocyclic, aryl-$(C_{0-6})$alkyl, or heteroaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups; or R' connected to one of the $X_4$ groups to form a macrocyclic ring;

$X_4$, for each occurrence independently, is H, $(C_{1-20})$alkyl, $(C_{1-20})$alkyl-Si—, aryl-$(C_{1-20})$alkyl-, alkenyl-$(C_{1-20})$alkyl, heteroaryl-$(C_{1-20})$alkyl, $(C_{0-6})$alkoxy-carbonyl-$(C_{1-6})$alkyl, or amino$(C_{1-6})$alkyl, wherein each alkyl moiety as appears at the $X_4$ position is further optionally substituted by one or more hydroxyl or alkoxy groups; or one of the $X_4$ groups is connected to R' to form a macrocyclic ring;

$X_5$ is $(C_{1-6})$alkyl, —N=$R_{10}$, wherein $R_{10}$ is derived from a sugar moiety;

AA1 is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and AA2 is absent or an amino acid moiety selected from the group of His, Gln, Ala, Cys, Glu, Phe, Ile, Met, Asn, Ser, Thr, Val, and Tyr;

wherein each of the amino acid moieties for AA1 or AA2 is optionally substituted by aryl-$(C_{1-10})$alkyl, heteroaryl-$(C_{1-10})$alkyl, aryl-$(C_{1-10})$alkyl-CH=N—O—, aryl-$(C_{1-10})$alkoxy, aryl-$(C_{1-10})$alkoxy, aryl-$(C_{1-10})$alkyl-S—, aryl-$(C_{1-10})$alkyl-C(O)—NH—O—, heteroaryl-$(C_{1-10})$alkyl-C(O)—NH—O—, and wherein each aryl or heteroaryl moiety is further optionally substituted by one or more same or different substituents selected from the group of aryl, heteroaryl, alkenyl, alkyl, halogen, hydroxyl, amine, amide, carboxyl, ester groups;

or a pharmaceutically acceptable salt, solvate, hydrate, or stereoisomer thereof.

In one embodiment, AA1 is Leu that is optionally substituted. In another embodiment, AA2 is His or Gln, wherein His and Gln are optionally substituted. In one particular embodiment, AA2 is His that is optionally substituted.

In certain embodiments, the compound of the invention is a compound of Formula (IA):

Formula (IA)

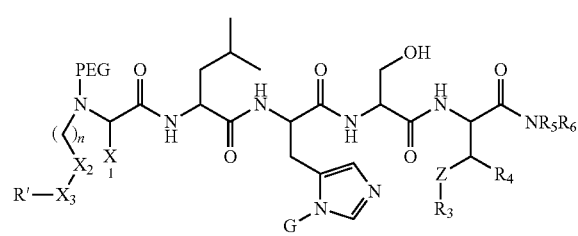

wherein
Z is O, $CH_2$, or $CF_2$;
n is 0, 1 or 2;
$X_1$ is H; and $X_2$ is a bond or $CH_2$; or $X_1$ and $X_2$, taken together with the bonds they are connected to, form a 5-membered heterocyclic ring;
$R_3$ is H or $(X_4O)_2P(O)$—;
$R_4$ is H, or $(C_{1-6})$alkyl;
$R_5$ and $R_6$ are both H; or one of $R_5$ and $R_6$ is H, the other is $X_5$—O—$(C_{1-6})$alkyl or a glycine moiety; wherein $X_5$ is —N=$R_9$, and $R_9$ is derived from a sugar moiety;
R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl-;
R' is H, amino-O—, $(C_{1-6})$alkyl-C(O)—, cycloalkyl, heterocyclic, aryl-$(C_{0-6})$alkyl, or heteroaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups; and G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino$(C_{1-20})$alkyl, aryl-$(C_{1-20})$alkyl, $(C_{1-20})$alkyl, or heretoaryl-$(C_{1-20})$alkyl, wherein each of alkyl, aryl and heretoaryl moieties is optionally substituted by one or more halogen, hydroxyl or alkoxy groups;

or a pharmaceutically acceptable salt, solvate, hydrate, or stereoisomer thereof.

In one embodiment of the compounds of Formula (IA), PEG is

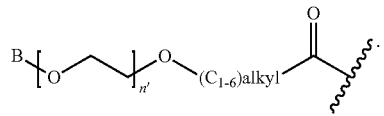

One embodiment provides that B is H, $(C_{1-6})$alkyl, or hydrosulfide-$(C_{1-6})$alkyl-C(O)—NH—$(C_{1-6})$alkyl, wherein each $(C_{1-6})$alkyl moiety as appears herein, independently, is further optionally substituted by an amino or N-Fmoc-amino group; and n' is an integer selected from 5-200.

In another embodiment, $X_1$ and $X_2$, taken together with the bonds they are connected to, form a 5-membered heterocyclic ring. In still another embodiment, $R_5$ and $R_6$ are both H.

In certain embodiments of Formula (IA), the compounds of the invention are compounds of Formula (a):

Formula (a)

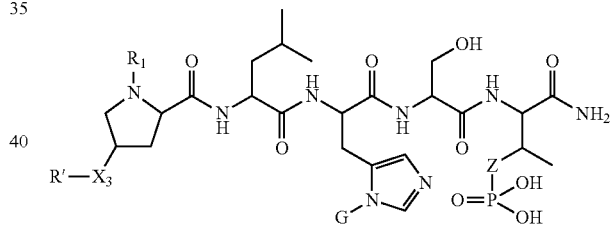

wherein
Z is O, $CH_2$, or $CF_2$;
$R_1$ is

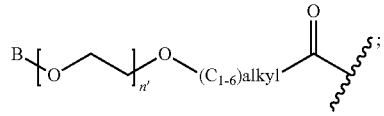

B is H, $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;
n' is an integer selected from 5-100;
R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl;
R' is H, $H_2NO$—, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$cycloalkyl, imidazolyl, quinolinyl, pyridinyl, pyrimidinyl, dioxo-pyrimidinyl, phenanthrenyl, or bicyclo[2.2.1]hept-2-enyl, wherein $R_3$ is further optionally substituted by one or more substituents selected from the group of halogen, $(C_{6-10})$aryl, heteroaryl, $(C_{1-6})$alkyl, $(C_{1-6})$alkoxy, hydroxyl, hydrosulfide, $(C_{1-6})$alkoxy-carbonyl, cyano, $(C_{6-10})$aryl-$(C_{1-6})$alkoxy, hydroxyl$(C_{1-6})$alkyl, trifluoromethyl, amino, and nitro; and G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino$(C_{1-20})$alkyl, aryl-$(C_{1-20})$alkyl, $(C_{1-20})$alkyl, or heretoaryl-$(C_{1-20})$alkyl, wherein each of alkyl, aryl and heretoaryl moieties is optionally substituted by one or more halogen, hydroxyl or alkoxy groups;

or a pharmaceutically acceptable salt, solvate, hydrate, or stereoisomer thereof.

In certain embodiments of Formula (a), Z is O or $CH_2$; and n' is an integer between 5 and 20.

In one embodiment, B is $(C_{1-6})$alkyl or hydrosulfide-$(C_{1-6})$alkyl-C(O)—NH—$(C_{1-6})$alkyl, wherein each $(C_{1-6})$alkyl moiety as appears herein, independently, is further optionally substituted by an amino or N-Fmoc-amino group. For example, B is methyl,

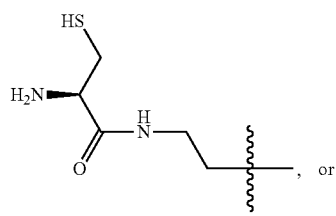

, or

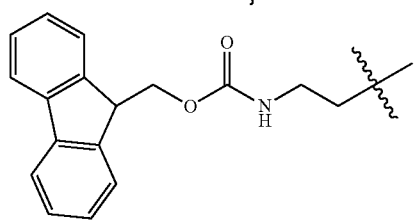

.

In one embodiment, $R'$—$X_3$ is $R'$, $R'$—CH=N—O—, $R'$—C(O)—NH—O—, or $R'$—$(CH_2)_2$—O—, wherein $R'$ is H, $H_2NO$—, or phenyl-$(C_{1-6})$alkyl.

For example, $R'$ is selected from the group of

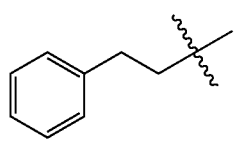
A-1

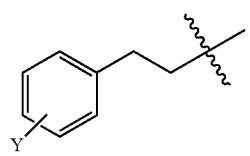
A-2

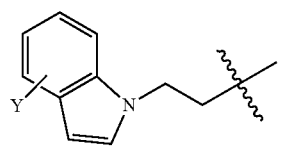
A-3

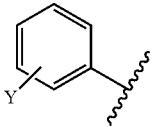
A-4

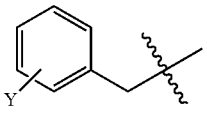
A-5

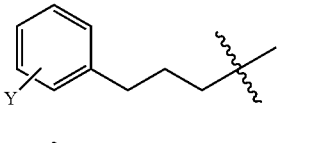
A-6

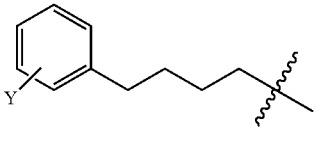
A-7

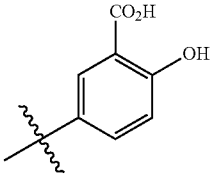
A-8

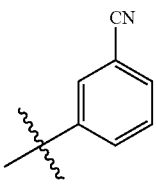
A-9

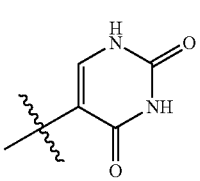
A-10

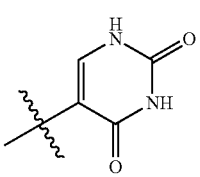
A-11

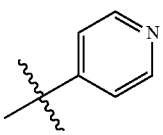
A-13

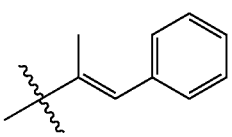
A-13

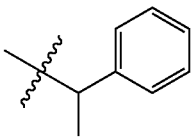
A-14

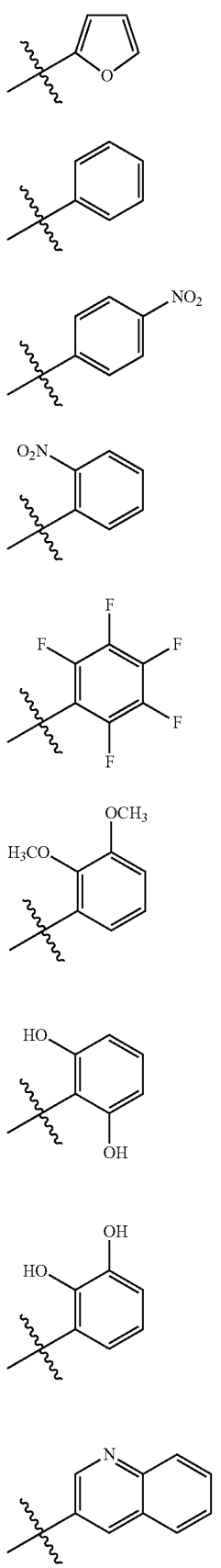
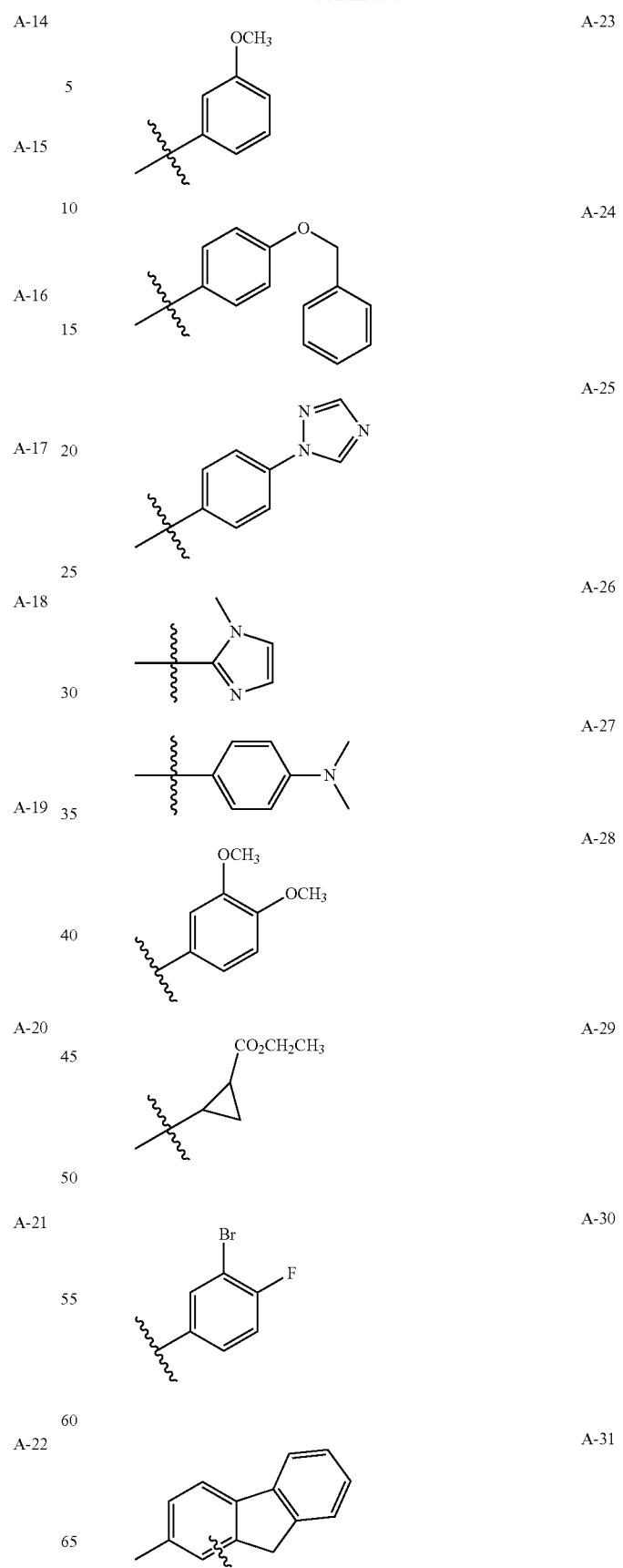

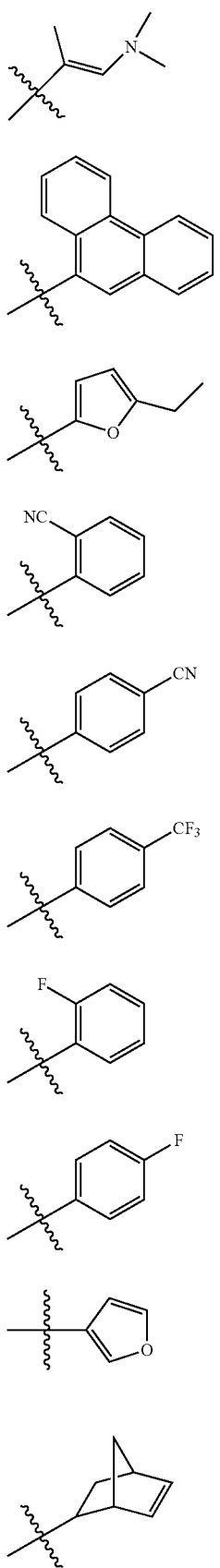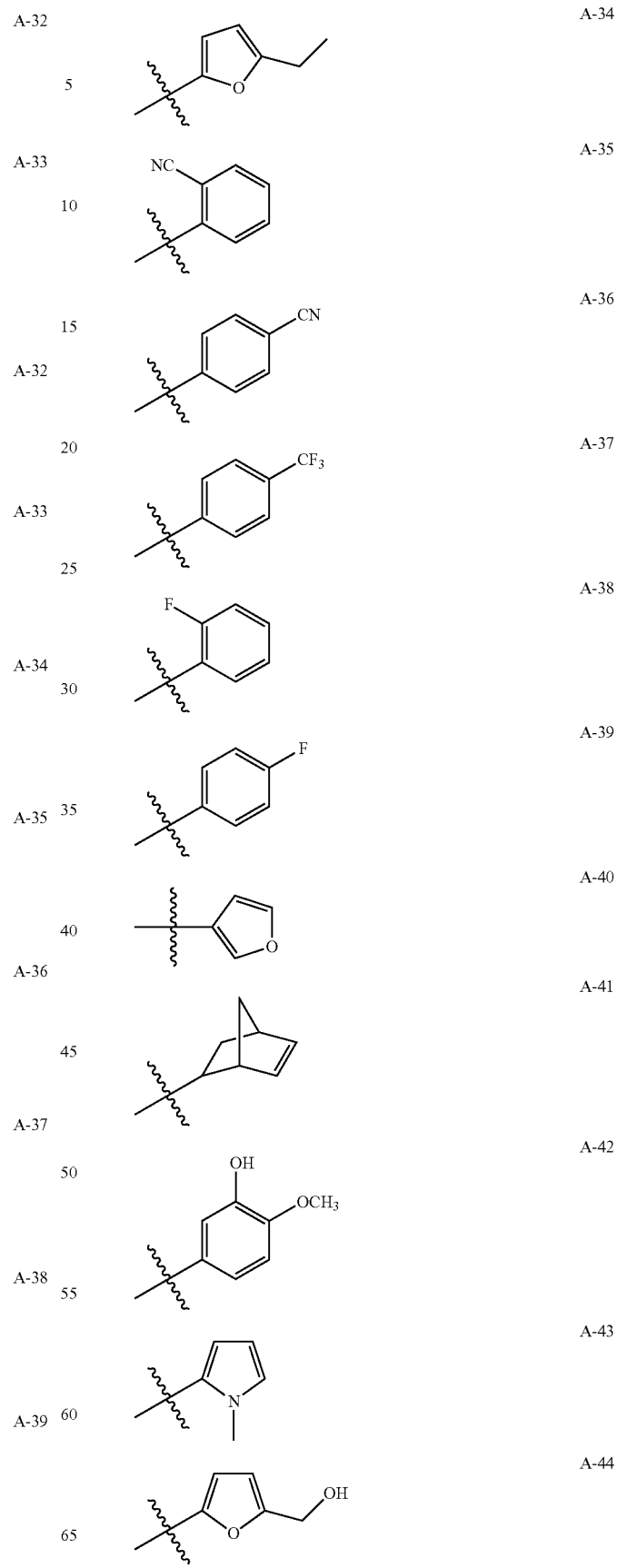

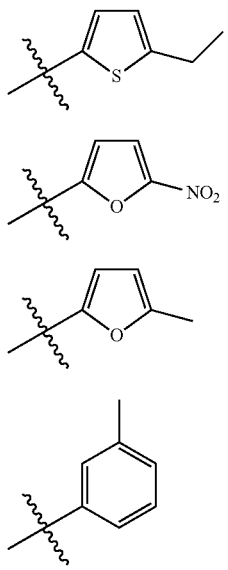

In one embodiment, G is H. In another embodiment, G is alkenyl-$(C_{1-10})$alkyl, hydroxyl-carbonyl-$(C_{1-6})$alkyl, amino $(C_{1-6})$alkyl, aryl-$(C_{1-10})$alkyl, $(C_{1-10})$alkyl, or heteroaryl-$(C_{1-10})$alkyl, wherein each alkyl moiety is further optionally substituted by one or more hydroxyl or amino groups. In a specific embodiment, Z is O; R'—$X_3$ is H; and B is methyl, Certain exemplified compounds of Formula (a) include, but are not limited to, the compounds of Table 1 as follows:

TABLE 1

|  |  | Expected ESI (M + H)+ | Observed ESI (M + H)+ |
|---|---|---|---|
| PEG-1* |  | 1025.5 | 1025.2 |
| PEG-4j* |  | 1213.7 | 1213.3 |
| Cys-PEG-4j* |  | 1345.7 | 1345.5 |

TABLE 1-continued

|   | Expected ESI (M + H)+ | Observed ESI (M + H)+ |
|---|---|---|
| a-1 | | |
| a-1A | | |
| a-2 | | |
| a-2A | | |

TABLE 1-continued
|  | Expected ESI (M + H)+ | Observed ESI (M + H)+ |
|---|---|---|
a-3
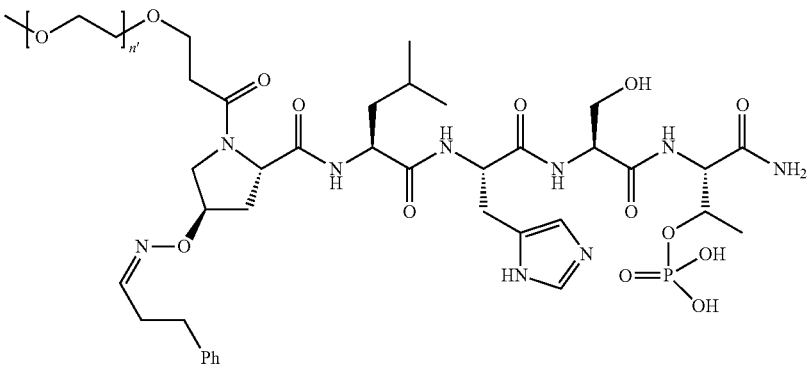
a-3
a-3A
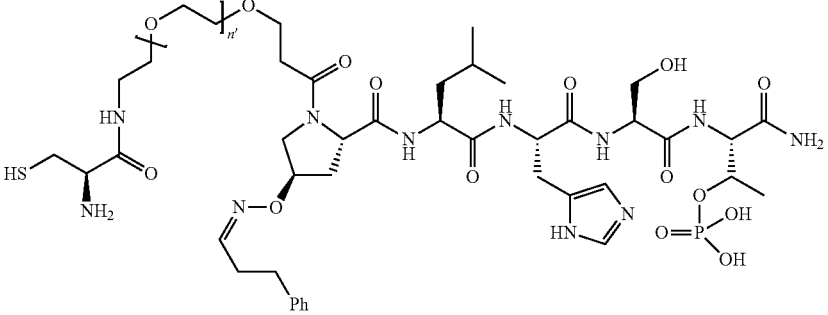
a-3A
a-4
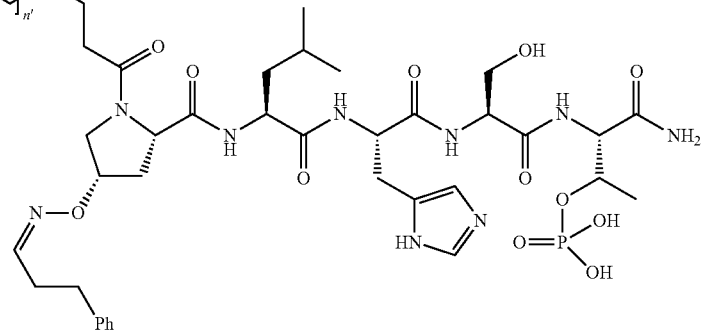
a-4
a-4A
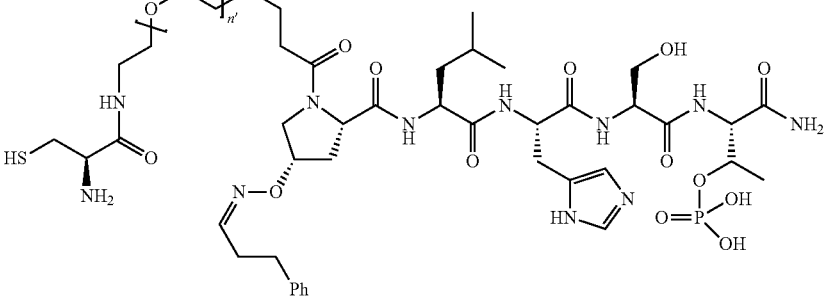
a-4A TABLE 1-continued

| | Expected ESI (M + H)+ | Observed ESI (M + H)+ |
|---|---|---| a-5 a-5A a-6 a-6A

TABLE 1-continued
| | | Expected ESI (M + H)+ | Observed ESI (M + H)+ |
|---|---|---|---|
a-7 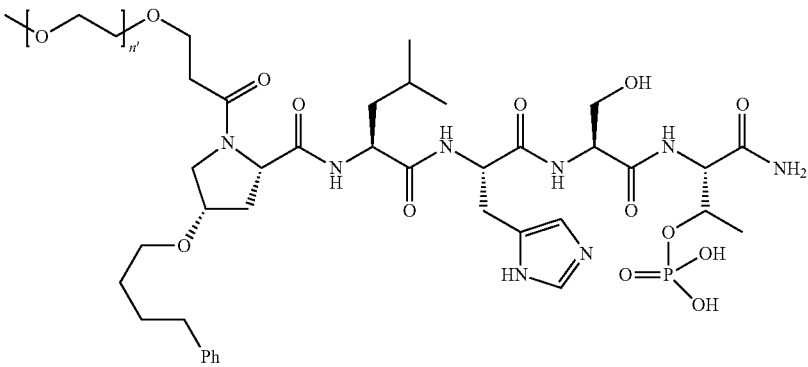
a-7A 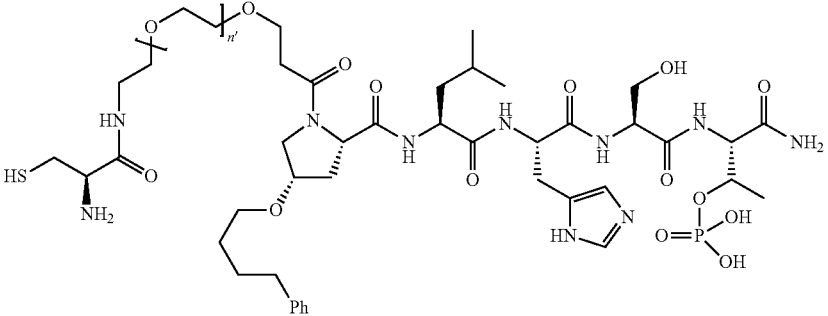
a-7A
a-8 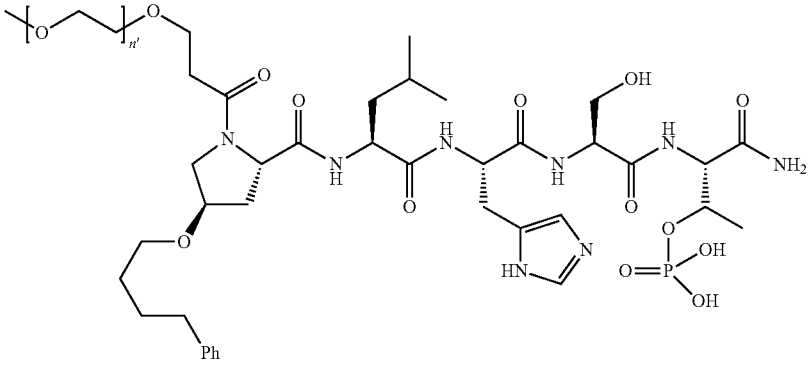
a-8A 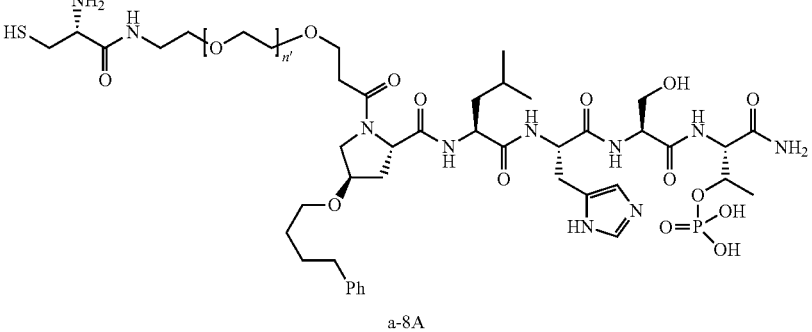
a-8A TABLE 1-continued
| | | Expected ESI (M + H)+ | Observed ESI (M + H)+ |
|---|---|---|---|
a-9
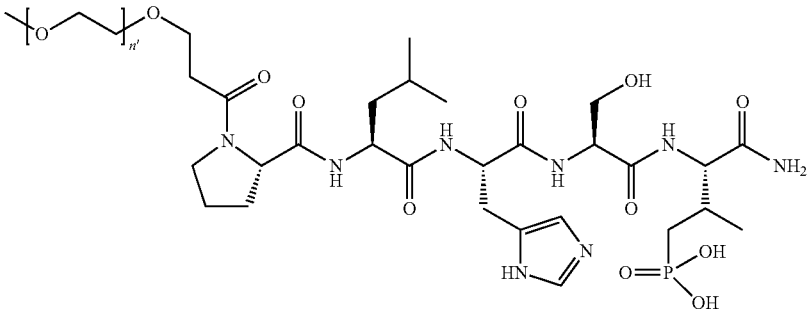
a-9A
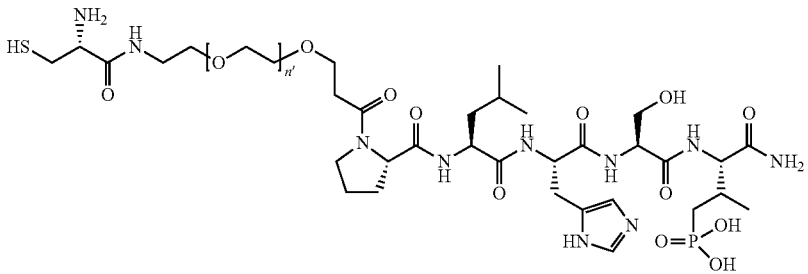
a-9A
a-10
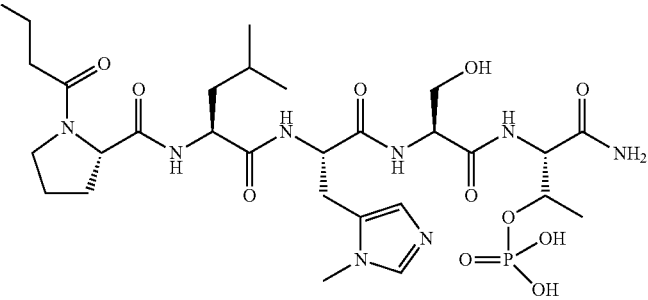
a-10A
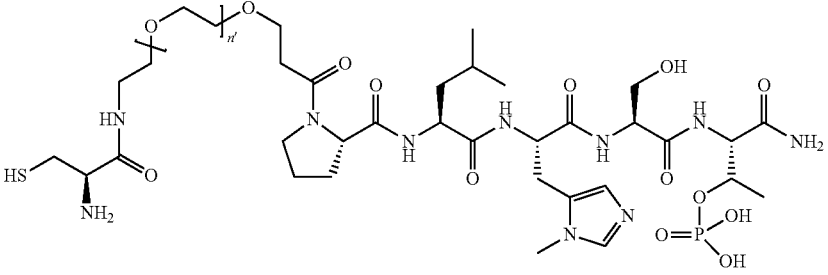
a-10A TABLE 1-continued

|  | Expected ESI (M + H)+ | Observed ESI (M + H)+ |
|---|---|---| a-11 a-11A a-12 a-12A

TABLE 1-continued
| | | Expected ESI (M + H)+ | Observed ESI (M + H)+ |
|---|---|---|---|
a-13
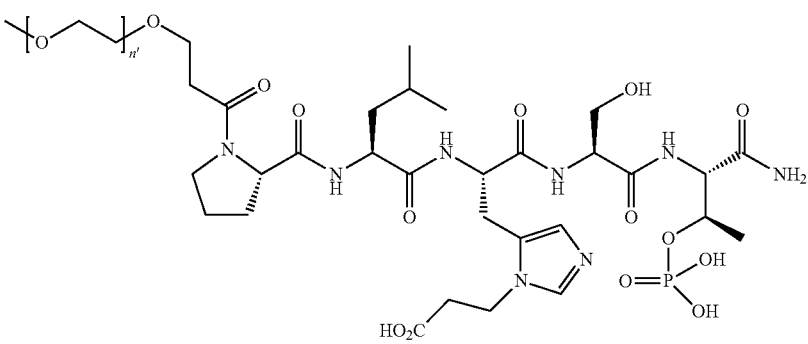
a-13A
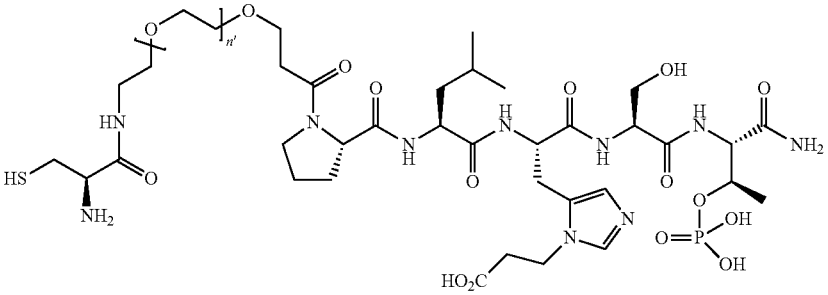
a-13A
a-14
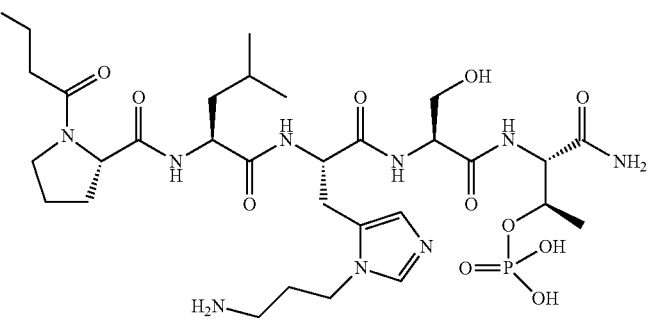
a-14A
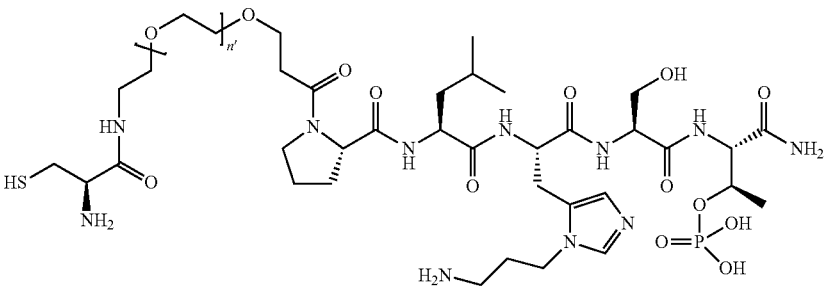
a-14A TABLE 1-continued

|  | Expected ESI (M + H)+ | Observed ESI (M + H)+ |
|---|---|---| a-15 a-15A a-16 a-16A

TABLE 1-continued
| | Expected ESI (M + H)$^+$ | Observed ESI (M + H)$^+$ |
|---|---|---|
a-17
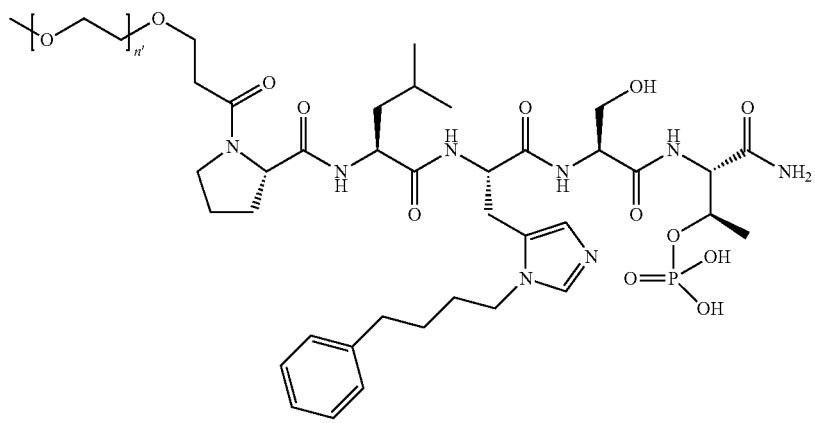
a-17A
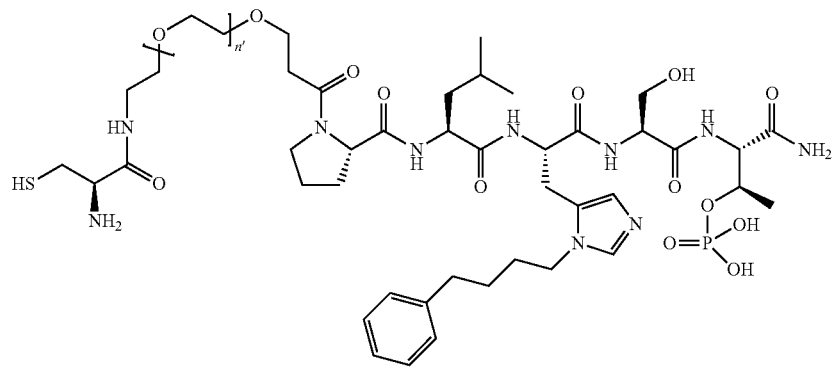
a-17A
a-18
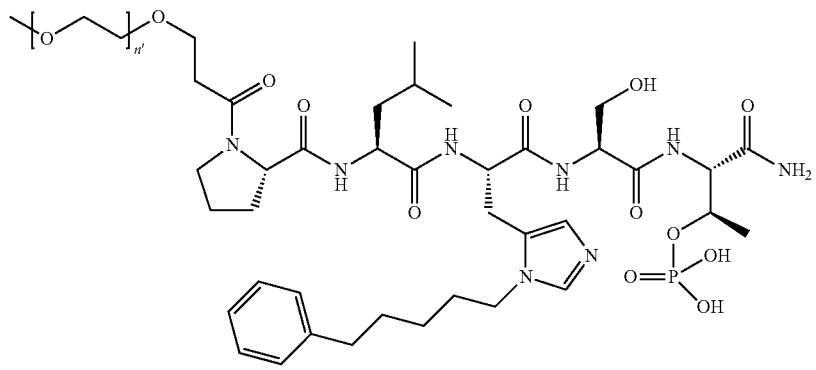

TABLE 1-continued
| | | Expected ESI (M + H)+ | Observed ESI (M + H)+ |
|---|---|---|---|
a-18A
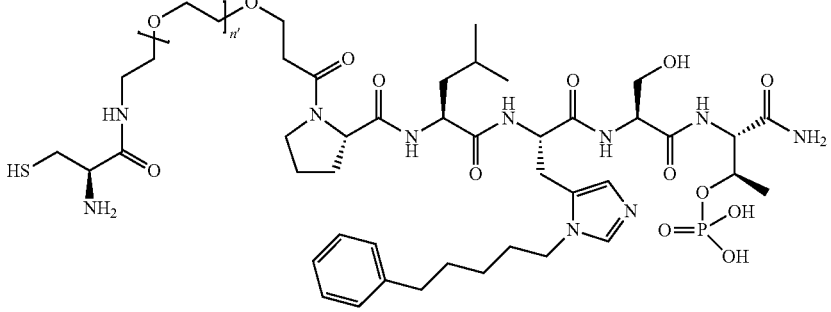
a-18A
a-19
a-19A
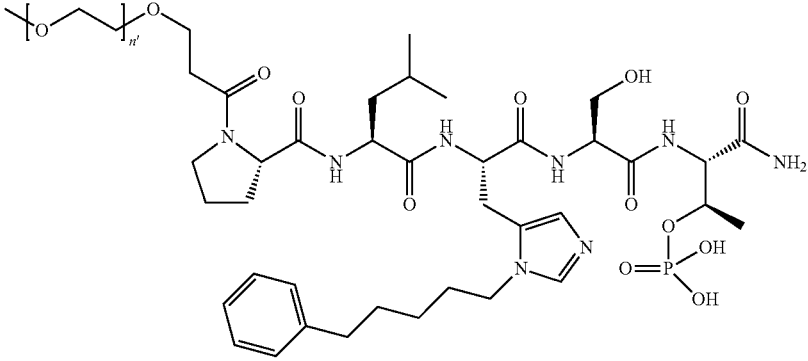
a-19A
a-20
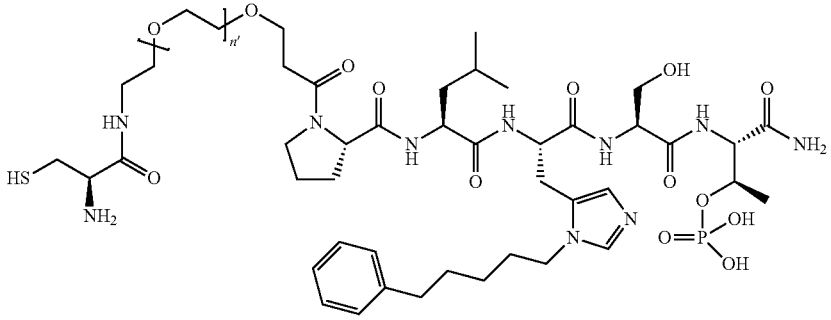

TABLE 1-continued
|  | Expected ESI (M + H)+ | Observed ESI (M + H)+ |
|---|---|---|
a-20A
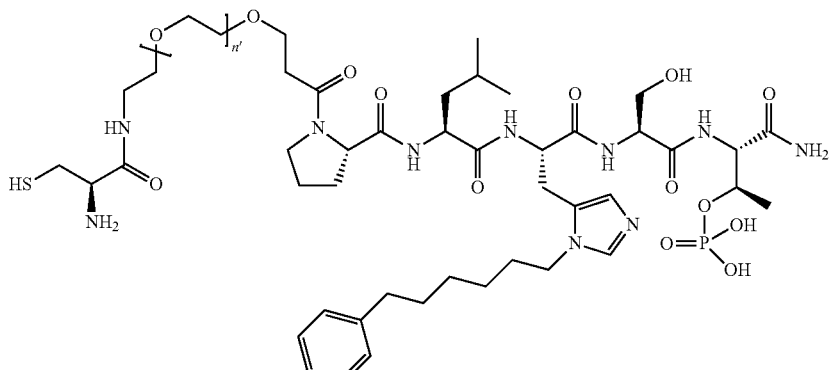
a-20A
a-21
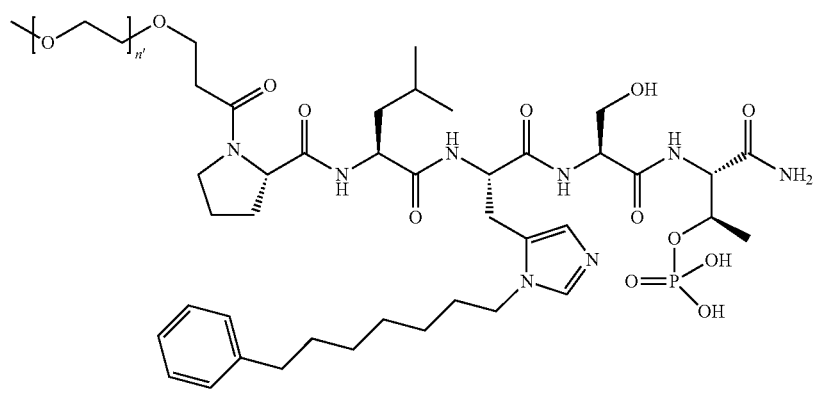
a-21A
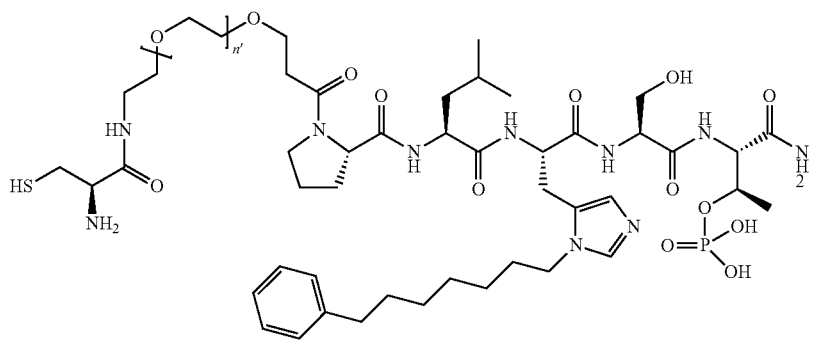
a-21A TABLE 1-continued

| | Expected ESI (M + H)+ | Observed ESI (M + H)+ |
|---|---|---| a-22 a-22A a-22A a-23

TABLE 1-continued
| | Expected ESI (M + H)+ | Observed ESI (M + H)+ |
|---|---|---|
a-23A
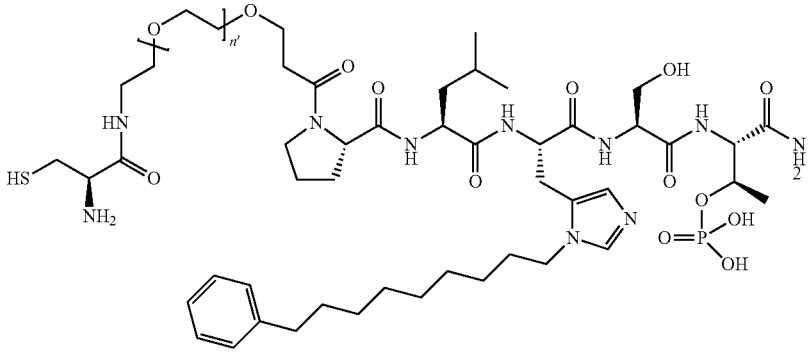
a-23A
a-24
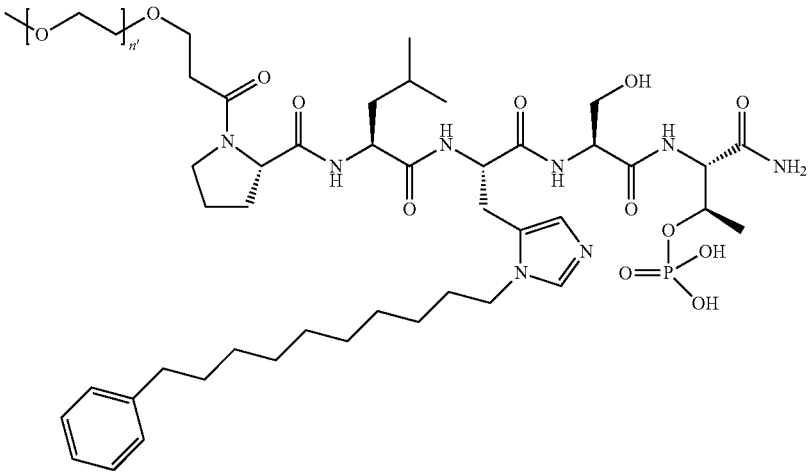
a-24A
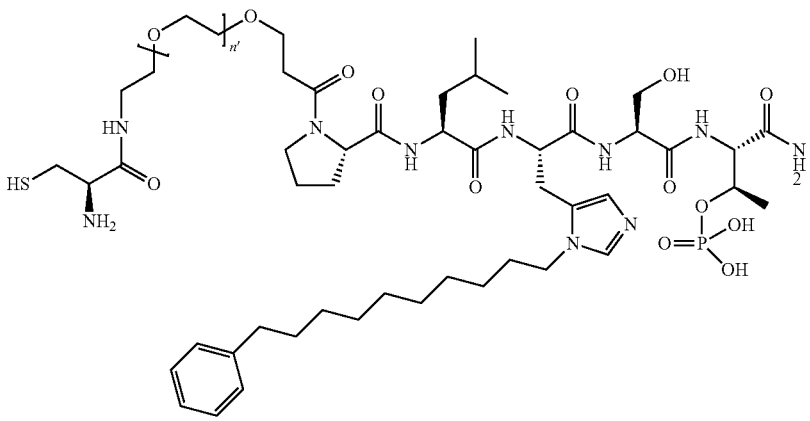
a-24A

TABLE 1-continued

|  | Expected ESI (M + H)+ | Observed ESI (M + H)+ |
|---|---|---| a-25

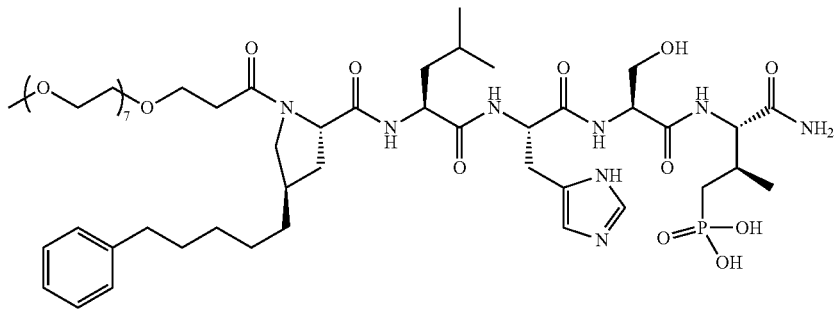

n' is an integer from 5-8

Exemplified compounds of the invention also include compounds with the moiety

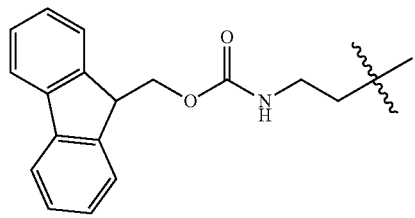 [SMILES: *CCNC(=O)OCC1c2ccccc2-c2ccccc21]

as the corresponding "B" group in the chemical structures as appears in the preceding table. As illustration, such compounds include the following structure:

In certain embodiments of Formula (IA), the compounds of the invention are compounds of Formula (b):

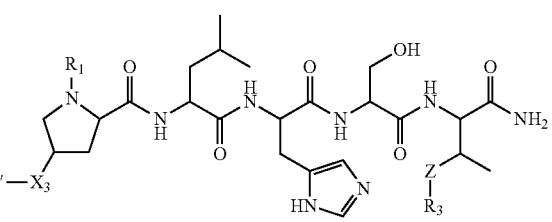

Formula (b)

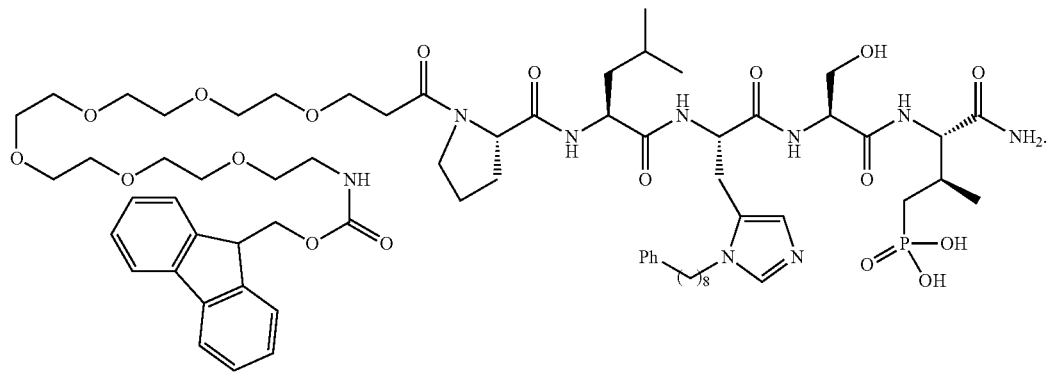

PEG-4j*-A' wherein
Z is O or CH$_2$;
R$_1$ is

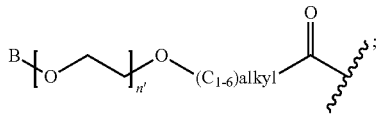

B is H, (C$_{1-6}$)alkyl, or hydrosulfide-(C$_{1-6}$)alkyl-C(O)—NH—(C$_{1-6}$)alkyl, wherein each (C$_{1-6}$)alkyl moiety, independently, is further optionally substituted by an amino or N-Fmoc-amino group;

n' is an integer selected from 5-100;

R$_3$ is H or (X$_4$O)$_2$P(O)—;

R'—X$_3$ is R', R'—CH=N—O—, R'—(C$_{1-6}$)alkyl-O—, R'—C(O)—NH—O—, R'—(C$_{1-6}$)alkyl-S—, or R'—(C$_{1-6}$)alkyl;

R' is H, H$_2$NO—, (C$_{2-6}$)alkenyl, phenyl-(C$_{0-6}$)alkyl, furanyl-(C$_{0-6}$)alkyl, thiophenyl-(C$_{0-6}$)alkyl, N-indolyl-(C$_{1-6}$)alkyl, fluorenyl, (C$_{3-8}$)cycloalkyl, imidazolyl, quinolinyl, pyridinyl, pyrimidinyl, dioxo-pyrimidinyl, phenanthrenyl, or bicyclo[2.2.1]hept-2-enyl, wherein R$_3$ is further optionally substituted by one or more substituents selected from the group of halogen, (C$_{6-10}$)aryl, heteroaryl, (C$_{1-6}$)alkyl, (C$_{1-6}$)alkoxy, hydroxyl, hydrosulfide, (C$_{1-6}$)alkoxy-carbonyl, cyano, (C$_{6-10}$)aryl-(C$_{1-6}$)alkoxy, hydroxyl(C$_{1-6}$)alkyl, trifluoromethyl, amino, and nitro; and One X$_4$ is H, and the other X$_4$ is (C$_{1-20}$)alkyl, (C$_{1-20}$)alkyl-Si—, aryl-(C$_{1-20}$)alkyl-, alkenyl-(C$_{1-20}$)alkyl, heteroaryl-(C$_{1-20}$)alkyl, (C$_{0-6}$)alkoxy-carbonyl-(C$_{1-6}$)alkyl, or amino(C$_{1-6}$)alkyl, wherein each alkyl moiety is further optionally substituted by one or more hydroxyl or alkoxy groups;

or a pharmaceutically acceptable salt, solvate, hydrate, or stereoisomer thereof.

In certain embodiments of compounds of Formula (b), Z is O; R$_3$ is (X$_4$O)$_2$P(O)—; n' is an integer between 5 and 20; B is (C$_{1-6}$)alkyl,

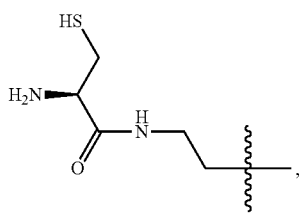 [SMILES: *CCNC(=O)[C@@H](N)CS]

or

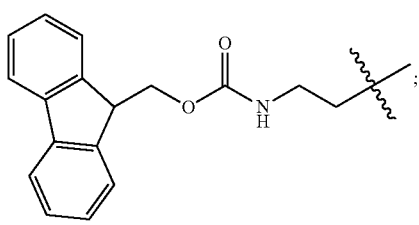 [SMILES: *CCNC(=O)OCC1c2ccccc2-c2ccccc21]

R'—X$_3$ is R', R'—CH=N—O—, R'—C(O)—NH—O—, or R'—(CH$_2$)$_2$—O—; and R' is H, H$_2$NO—, or phenyl-(C$_{1-6}$)alkyl.

In one embodiment, B is methyl. In another embodiment, B is

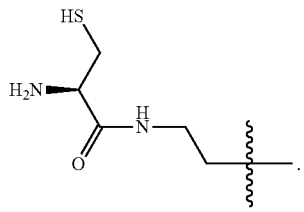 [SMILES: *CCNC(=O)[C@@H](N)CS]

In still another embodiment, B is

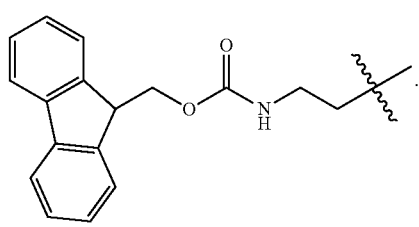 [SMILES: *CCNC(=O)OCC1c2ccccc2-c2ccccc21]

In an embodiment, R'—X$_3$ is R', and R' is H or (C$_{2-6}$)alkenyl.

In one embodiment, one of X$_4$ is H, and the other one is (C$_{1-10}$)alkyl, aryl-(C$_{1-10}$)alkyl, alkenyl-(C$_{1-10}$)alkyl, heteroaryl-(C$_{1-10}$)alkyl, (C$_{0-6}$)alkoxy-carbonyl-(C$_{1-6}$)alkyl, or amino(C$_{1-6}$)alkyl; and wherein each alkyl moiety is further optionally substituted by one or more hydroxyl, amino, or alkoxy groups.

In other embodiments of compounds of Formula (b), Z is O; R$_3$ is H; n' is an integer between 5 and 20; B is (C$_{1-6}$)alkyl,

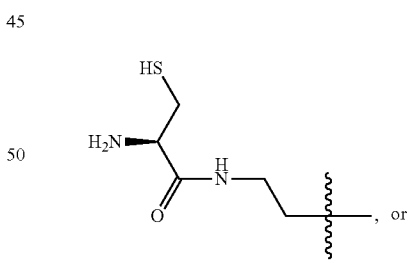

, or

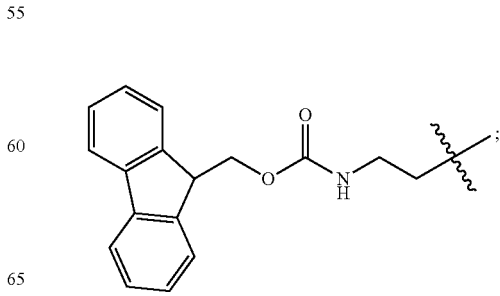

R'—X₃ is R', R'—CH=N—O—, R'—C(O)—NH—O—, or R'—(CH₂)₂—O—; and R' is H, H₂NO—, or phenyl-(C₁₋₆)alkyl.

In one embodiment, B is methyl. In another embodiment, B is

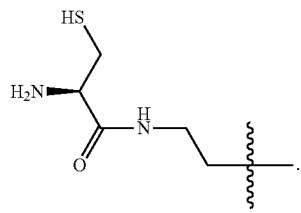 [SMILES: *CCNC(=O)[C@@H](N)CS]

In still another embodiment, B is

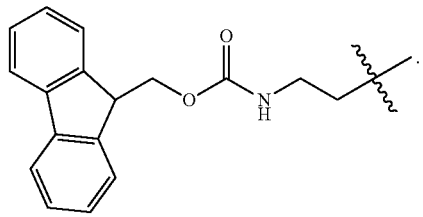 [SMILES: *CCNC(=O)OCC1c2ccccc2-c2ccccc21]

In a separate embodiment, R'—X₃ is R'—(CH₂)₂—O—; and R' is phenyl-(C₁₋₆)alkyl.

Certain exemplified compounds of Formula (b) include, but are not limited to, the compounds of Table 2 as follows:

TABLE 2

| | Expected ESI (M + H)⁺ | Observed ESI (M + H)⁺ |
|---|---|---| b-1 b-1A b-1A b-2

TABLE 2-continued
|  | Expected ESI (M + H)+ | Observed ESI (M + H)+ |
|---|---|---|
b-2A
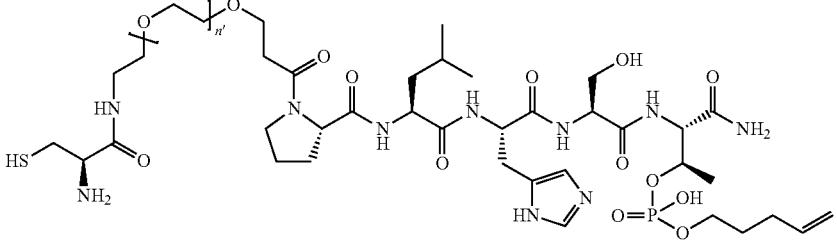
b-2A
b-3
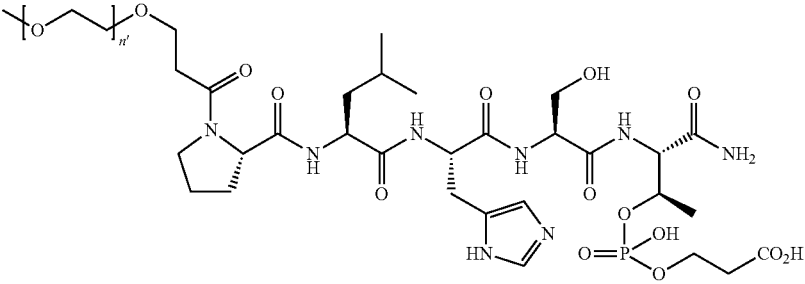
b-3
b-3A
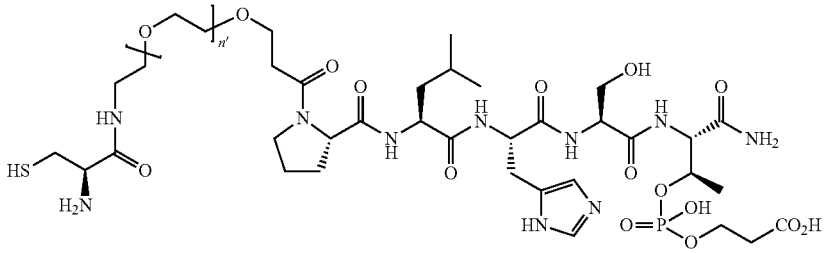
b-3A
b-4
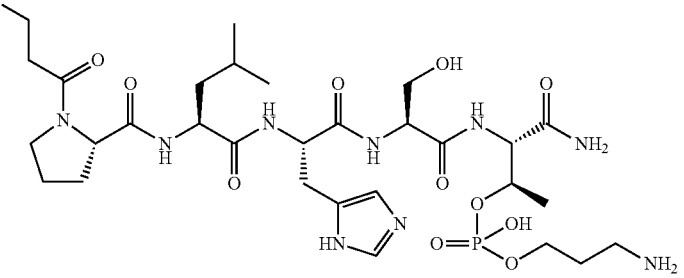
b-4
b-4A
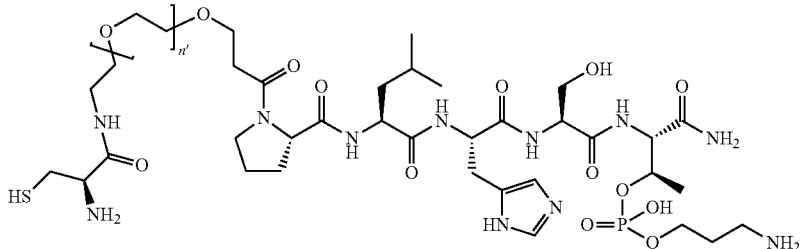
b-4A TABLE 2-continued
| | | Expected ESI (M + H)+ | Observed ESI (M + H)+ |
|---|---|---|---|
b-5
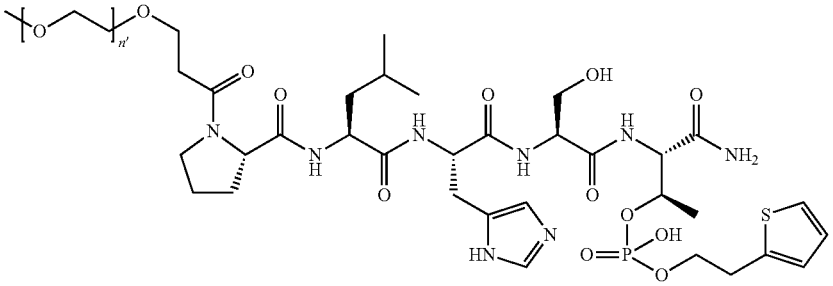
b-5A
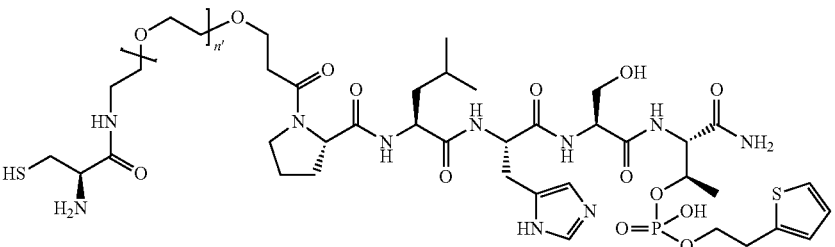
b-5A
b-6
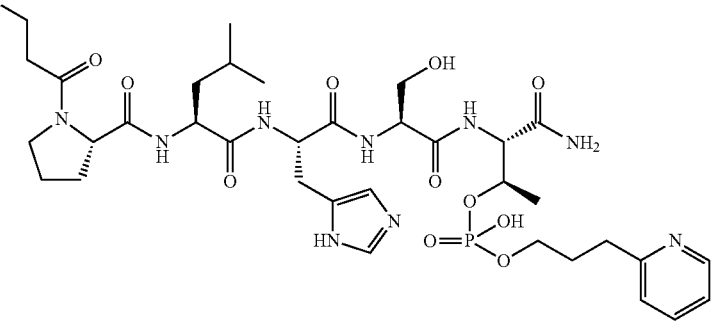
b-6A
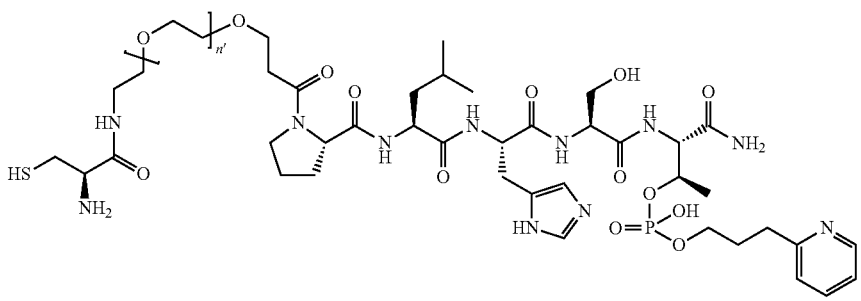
b-6A TABLE 2-continued

| | | Expected ESI (M + H)+ | Observed ESI (M + H)+ |
|---|---|---|---|
| b-7 | | | |
| b-7A | | | |
| b-8 | | | |
| b-8A | | | |
| b-9 | | | |

TABLE 2-continued
| | | Expected ESI (M + H)+ | Observed ESI (M + H)+ |
|---|---|---|---|
b-9A
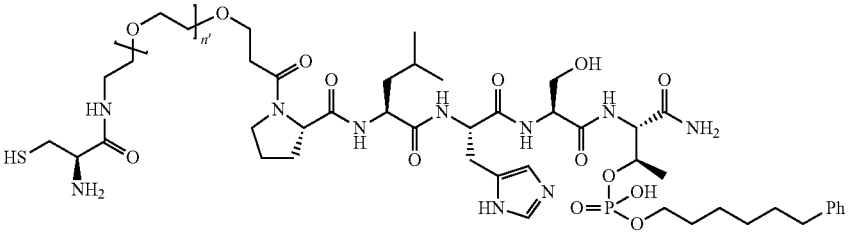
b-9A
b-10
b-10
b-10A
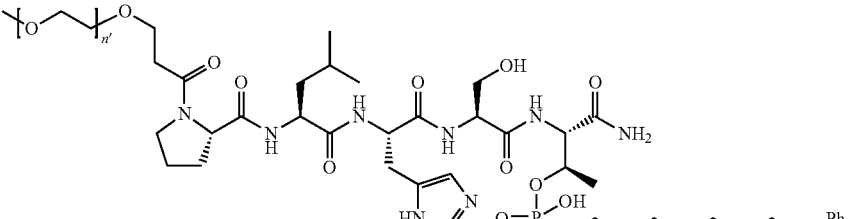
b-10A
b-11
b-11
b-11A
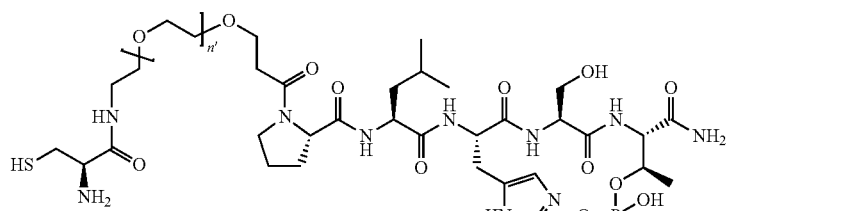
b-11A TABLE 2-continued
|  | Expected ESI (M + H)+ | Observed ESI (M + H)+ |
|---|---|---|
b-12
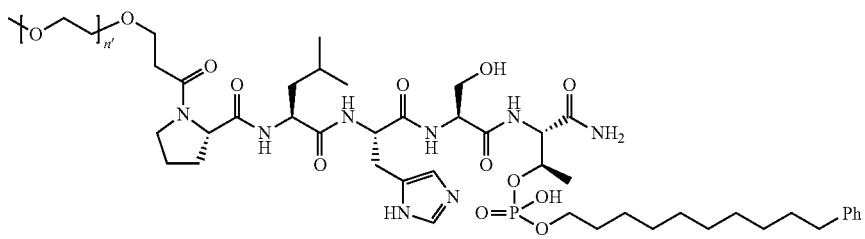
b-12
b-12A
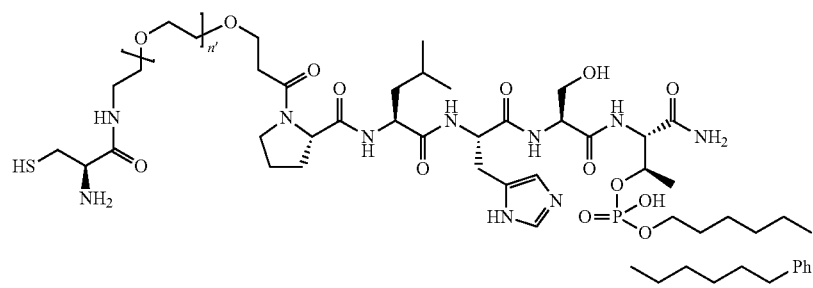
b-12A
b-13
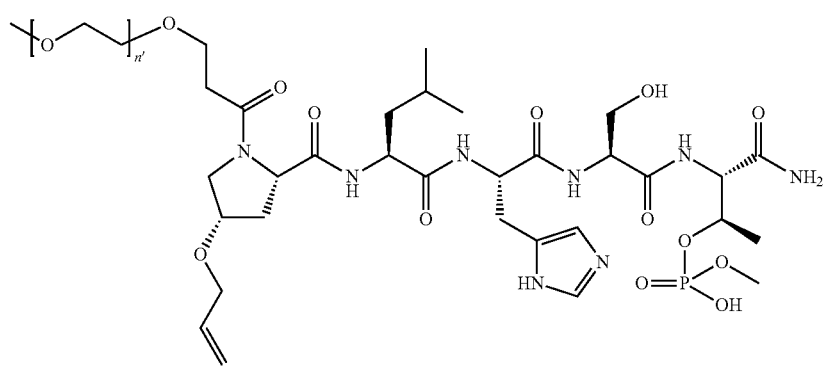
b-13

|  | Expected ESI (M + H)+ | Observed ESI (M + H)+ |
|---|---|---|
b-13A
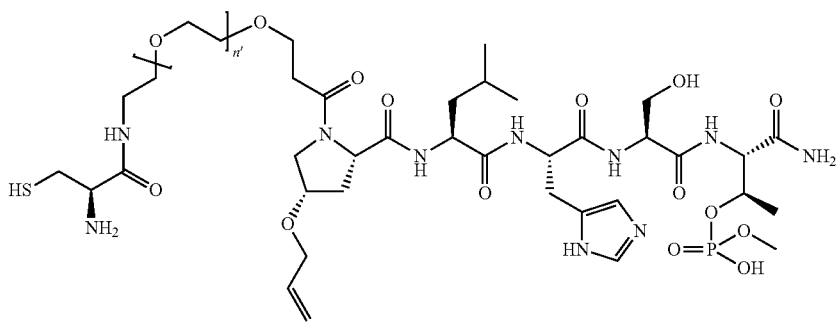
b-13A
b-14
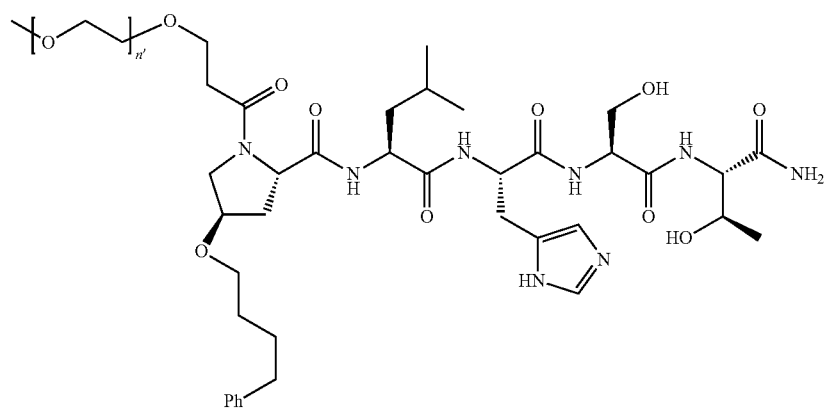
b-14
b-14A
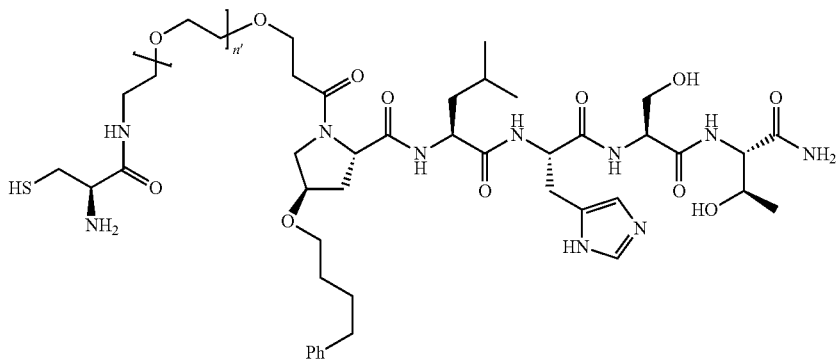
b-14A
n' is an integer from 5-8

Exemplified compounds of the invention also include compounds with the moiety

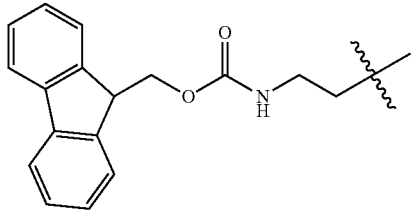 [SMILES: *CCNC(=O)OCC1c2ccccc2-c2ccccc21]

as the corresponding "B" group in the chemical structures as appears in the preceding table. As illustration, such compounds include the following structure:

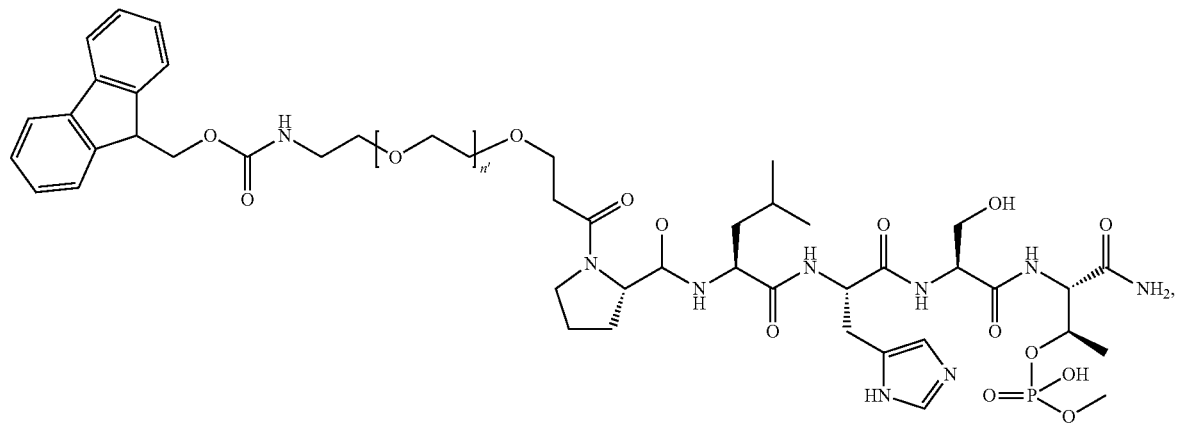

b-1A' wherein n' is an integer selected from 5-8. In certain embodiments, n' is 5.

In certain embodiments of Formula (IA), the compounds of the invention are compounds of Formula (c):

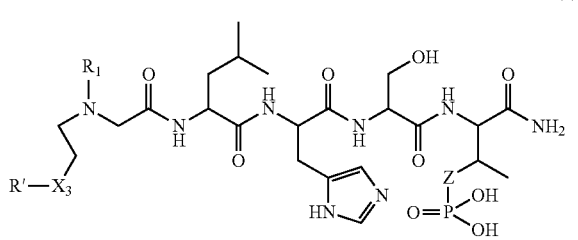

Formula (c)

wherein
Z is O, $CH_2$, or $CF_2$;
$R_1$ is

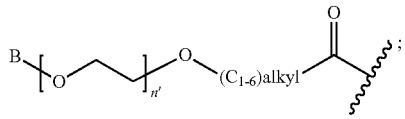

B is $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;
n' is an integer selected from 5-100;
R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl-; and
R' is H, amino-O—, $(C_{1-6})$alkyl-C(O)—, cycloalkyl, heterocyclic, aryl-$(C_{0-6})$alkyl, or heretoaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

or a pharmaceutically acceptable salt, solvate, hydrate, or stereoisomer thereof.

In one embodiment, Z is O. In another embodiment, Z is $CH_2$. In a separate embodiment, R' is aryl-$(C_{0-6})$alkyl, or heretoaryl-$(C_{1-6})$alkyl, wherein said aryl or heteroaryl moiety is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups.

In certain embodiments, R' is selected from the group of A-1, A-2, A-3, A-4, A-5, A-6, and A-7.

Certain exemplified compounds of Formula (c) include, but are not limited to, the compounds of Table 3 as follows:

TABLE 3
| | Expected ESI (M + H)+ | Observed ESI (M + H)+ |
|---|---|---|
| c-1 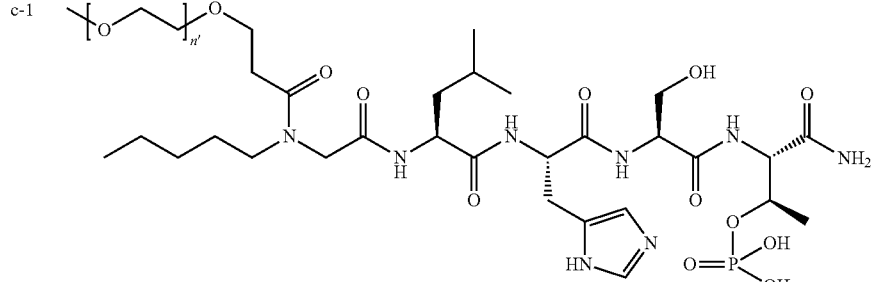 | | |
| c-1A 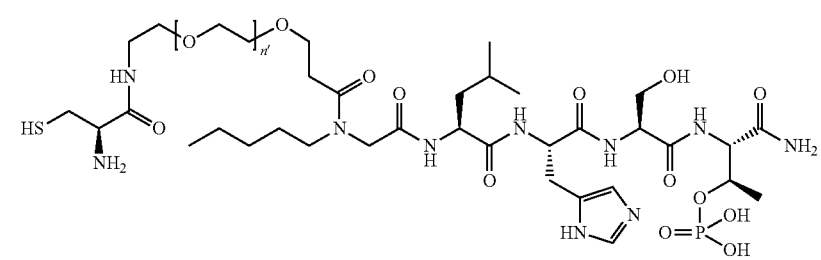 | | |
| c-2 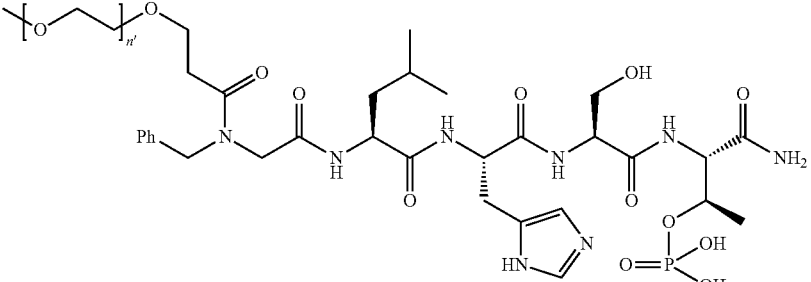 | 1345.7 | 1345.5 |
| c-2A 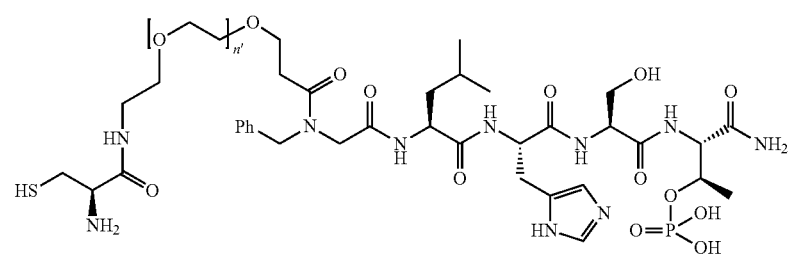 | | |

TABLE 3-continued

|  | | Expected ESI (M + H)+ | Observed ESI (M + H)+ |
| --- | --- | --- | --- | c-3 c-3A c-4 c-4A c-5

TABLE 3-continued

|  | Expected ESI (M + H)+ | Observed ESI (M + H)+ |
|---|---|---| c-5A c-6 c-6A c-7

TABLE 3-continued

| | Expected ESI (M + H)+ | Observed ESI (M + H)+ |
|---|---|---|
| c-7A 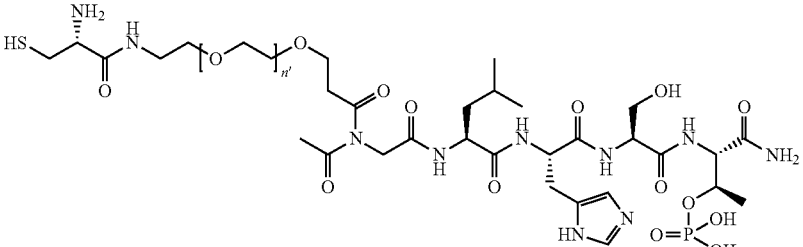 | | |
| c-7A | | | n' is an integer from 5-8

Exemplified compounds of the invention also include compounds with the moiety

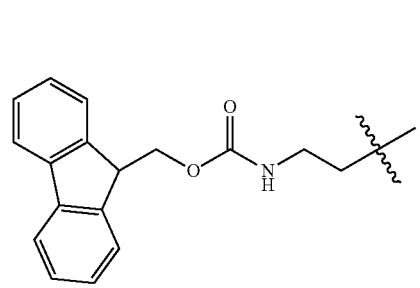 [SMILES: *CCNC(=O)OCC1c2ccccc2-c2ccccc21]

as the corresponding "B" group in the chemical structures as appears in the preceding table. As illustration, such compounds include the following structure:

Certain embodiments of the invention provide that the compound is a compound of Formula (IB):

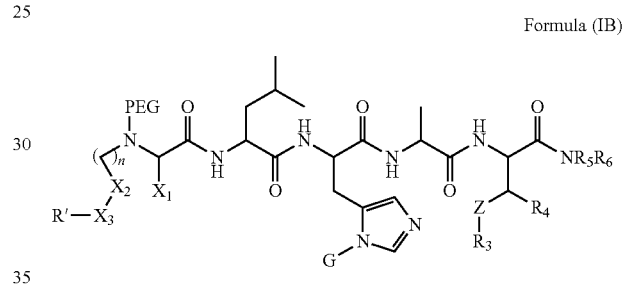

Formula (IB)

wherein
Z is O, $CH_2$, or $CF_2$;
n is 0, 1 or 2;

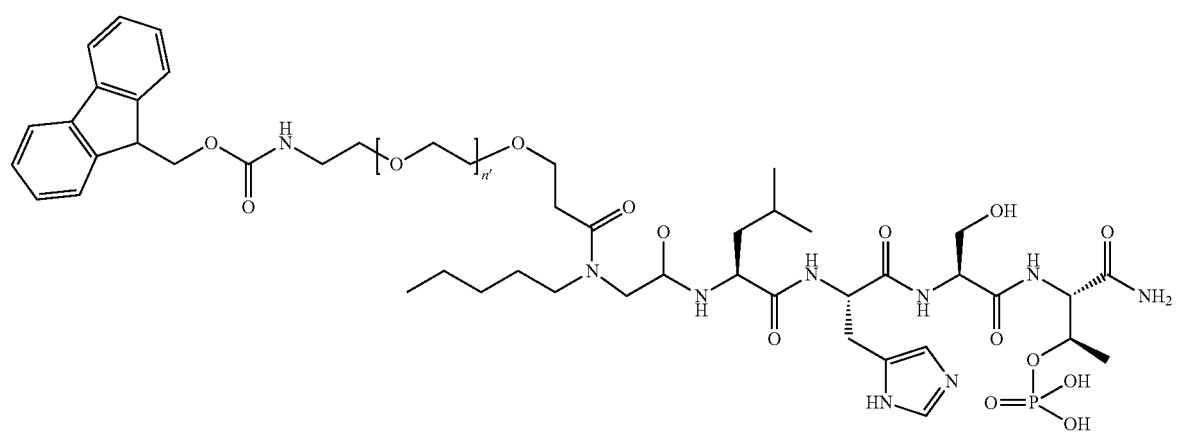

c-1A' wherein n' is an integer selected from 5-8. In certain embodiments, n' is 5.

$X_1$ is H; or $X_1$ and $X_2$, taken together with the bonds they are connected to, form a 5-membered heterocyclic ring;

$X_2$ is a bond or $CH_2$; or $X_1$ and $X_2$, taken together with the bonds they are connected to, form a 5-membered heterocyclic ring;

$R_3$ is H or $(X_4O)_2P(O)$—;

$R_4$ is H, or $(C_{1-6})$alkyl;

$R_5$ and $R_6$ are both H; or one of $R_5$ and $R_6$ is H, the other is $X_5$—O—$(C_{1-6})$alkyl or a glycine moiety; wherein $X_5$ is —N=$R_9$, and $R_9$ is derived from a sugar moiety;

R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl-;

R' is H, amino-O—, $(C_{1-6})$alkyl-C(O)—, cycloalkyl, heterocyclic, aryl-$(C_{0-6})$alkyl, or heretoaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$X_4$, for each occurrence independently, is H, $(C_{1-20})$alkyl, $(C_{1-20})$alkyl-Si—, aryl-$(C_{1-20})$alkyl-, alkenyl-$(C_{1-20})$alkyl, heteroaryl-$(C_{1-20})$alkyl-, $(C_{0-6})$alkoxy-carbonyl-$(C_{1-6})$alkyl, or amino$(C_{1-6})$alkyl, wherein each alkyl moiety as appear at the $X_4$ position is further optionally substituted by one or more hydroxyl or alkoxy groups; and G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino$(C_{1-20})$alkyl, aryl-$(C_{1-20})$alkyl, $(C_{1-20})$alkyl, or heretoaryl-$(C_{1-20})$alkyl, wherein each of alkyl, aryl and heretoaryl moieties is optionally substituted by one or more halogen, hydroxyl or alkoxy groups;

or a pharmaceutically acceptable salt, solvate, hydrate, or stereoisomer thereof.

In one embodiment of Formula (IB), PEG is

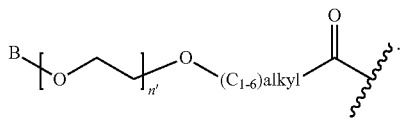

Certain embodiments provide that B is H, $(C_{1-6})$alkyl, or hydrosulfide-$(C_{1-6})$alkyl-C(O)—NH—$(C_{1-6})$alkyl, wherein each $(C_{1-6})$alkyl moiety as appears herein, independently, is further optionally substituted by an amino or N-Fmoc-amino group; and n' is an integer selected from 5-200.

In another embodiment, $X_1$ and $X_2$, taken together with the bonds they are connected to, form a 5-membered heterocyclic ring. In still another embodiment, $R_5$ and $R_6$ are both H.

In certain embodiments of Formula (IB), the compound of the invention is a compound of Formula (d)

Formula (d)

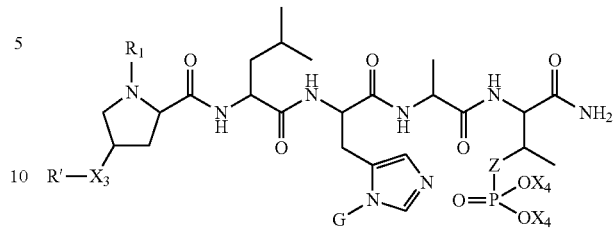

wherein

Z is O or $CH_2$;

$R_1$ is

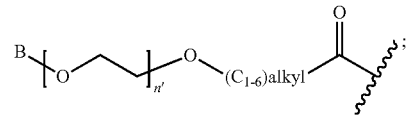

B is H, $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;

n' is an integer selected from 5-100;

R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl;

R' is H, $H_2NO$—, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$cycloalkyl, imidazolyl, quinolinyl, pyridinyl, pyrimidinyl, dioxo-pyrimidinyl, phenanthrenyl, or bicyclo[2.2.1]hept-2-enyl, wherein $R_3$ is further optionally substituted by one or more substituents selected from the group of halogen, $(C_{6-10})$aryl, heteroaryl, $(C_{1-6})$alkyl, $(C_{1-6})$alkoxy, hydroxyl, hydrosulfide, $(C_{1-6})$alkoxy-carbonyl, cyano, $(C_{6-10})$aryl-$(C_{1-6})$alkoxy, hydroxyl$(C_{1-6})$alkyl, trifluoromethyl, amino, and nitro;

$X_4$, for each occurrence independently, is H, aryl-$(C_{1-20})$alkyl-, or alkenyl-$(C_{1-20})$alkyl; and G is H, alkenyl-$(C_{1-20})$alkyl, or aryl-$(C_{1-20})$alkyl;

or a pharmaceutically acceptable salt, solvate, hydrate, or stereoisomer thereof.

In one embodiment of Formula (d), R'—$X_3$ is R'. In another embodiment, R'—$X_3$ is R'—$(C_{1-6})$alkyl. R' can be, for example, H, phenyl-$(C_{0-6})$alkyl, or imidazolyl, wherein $R_3$ is further optionally substituted.

In another embodiment, R' is selected from the group of A-1, A-2, A-3, A-4, A-5, A-6, and A-7.

Certain exemplified compounds of Formula (d) include, but are not limited to, the compounds of Table 4 as follows:

TABLE 4
| | | Expected ESI (M + H)+ | Observed ESI (M + H)+ |
|---|---|---|---|
| Cys-PEG-4j* (S/A) | 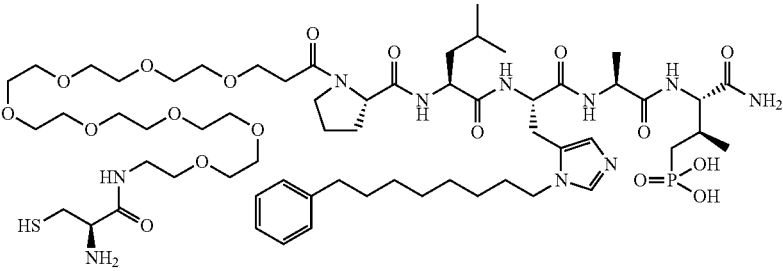 [SMILES: CC(C)C[C@H](NC(=O)[C@@H]1CCCN1C(=O)CCOCCOCCOCCOCCOCCOCCOCCOCCNC(=O)[C@@H](N)CS)C(=O)N[C@@H](Cc1cncn1CCCCCCCCc1ccccc1)C(=O)N[C@@H](C)C(=O)N[C@H](C(N)=O)[C@@H](C)CP(=O)(O)O] | 1329.7 | 1329.6 |
| PEG-1* (S/A) | 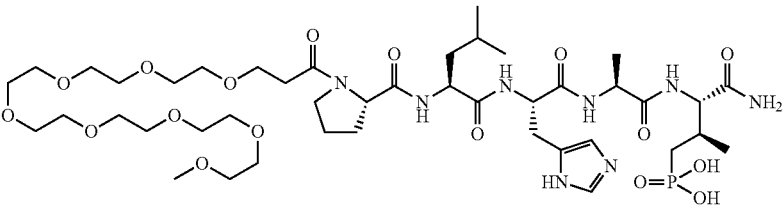 [SMILES: COCCOCCOCCOCCOCCOCCOCCOCCC(=O)N1CCC[C@H]1C(=O)N[C@@H](CC(C)C)C(=O)N[C@@H](Cc1cnc[nH]1)C(=O)N[C@@H](C)C(=O)N[C@H](C(N)=O)[C@@H](C)CP(=O)(O)O] | 1009.5 | 1009.2 |
| PEG-4j* (S/A) | 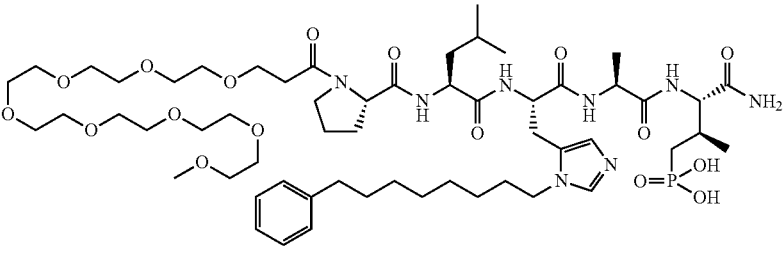 [SMILES: COCCOCCOCCOCCOCCOCCOCCOCCC(=O)N1CCC[C@H]1C(=O)N[C@@H](CC(C)C)C(=O)N[C@@H](Cc1cncn1CCCCCCCCc1ccccc1)C(=O)N[C@@H](C)C(=O)N[C@H](C(N)=O)[C@@H](C)CP(=O)(O)O] | 1197.7 | 1197.4 |
| d-1 | 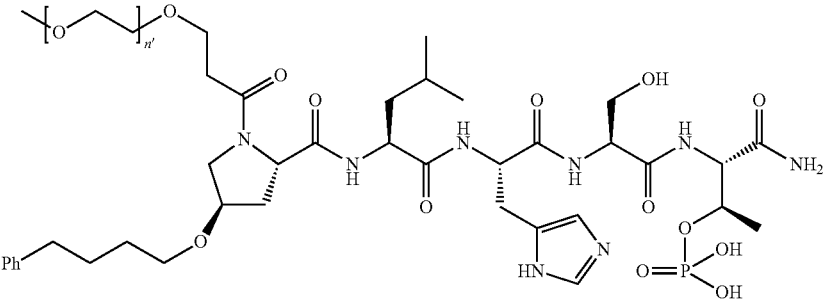 | | |
| d-1A | 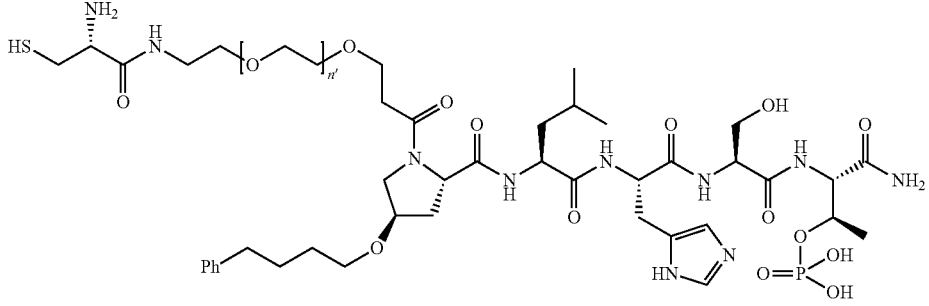 | | |
d-1
d-1A TABLE 4-continued

|  | Expected ESI (M + H)⁺ | Observed ESI (M + H)⁺ |
|---|---|---| d-2 d-2A d-3 d-3A

TABLE 4-continued

|  | Expected ESI (M + H)+ | Observed ESI (M + H)+ |
|---|---|---|

4j

[structure of compound 4j]

4j-A

[structure of compound 4j-A]

3j

[structure of compound 3j]

3j-A

[structure of compound 3j-A]

n' is an integer from 5-8

Exemplified compounds of the invention also include compounds with the moiety

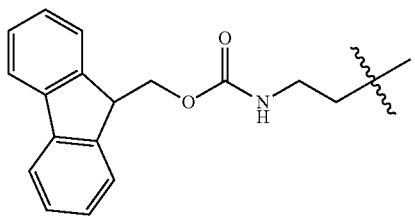 [SMILES: *CCNC(=O)OCC1c2ccccc2-c2ccccc21]

as the corresponding "B" group attached to the chemical structures as appears in the preceding table. In certain embodiments, n' is 5.

In certain embodiments of Formula (IB), the compound of the invention is a compound of Formula (e)

Formula (e)

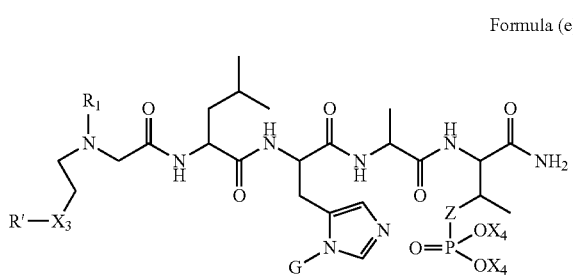

wherein
Z is O, $CH_2$, or $CF_2$;
$R_1$ is

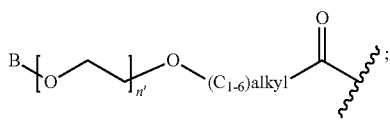

B is H, $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;

n' is an integer selected from 5-100;

R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl-;

R' is H, amino-O—, $(C_{1-6})$alkyl-C(O)—, cycloalkyl, heterocyclic, aryl-$(C_{0-6})$alkyl, or heteroaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$X_4$, for each occurrence independently, is H, $(C_{1-20})$alkyl, $(C_{1-20})$alkyl-Si—, aryl-$(C_{1-20})$alkyl-, alkenyl-$(C_{1-20})$alkyl, heteroaryl-$(C_{1-20})$alkyl-, $(C_{0-6})$alkoxy-carbonyl-$(C_{1-6})$alkyl, or amino$(C_{1-6})$alkyl, wherein each alkyl moiety as appear at the $X_4$ position is further optionally substituted by one or more hydroxyl or alkoxy groups; and G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino$(C_{1-20})$alkyl, aryl-$(C_{1-20})$alkyl, $(C_{1-20})$alkyl, or heteroaryl-$(C_{1-20})$alkyl, wherein each of alkyl, aryl and heretoaryl moieties is optionally substituted by one or more halogen, hydroxyl or alkoxy groups;

or a pharmaceutically acceptable salt, solvate, hydrate, or stereoisomer thereof.

In one embodiment of compounds of Formula (e), Z is $CH_2$. In another embodiment, G is H. In a separate embodiment, $X_4$ is H.

Certain exemplified compounds of Formula (e) include, but are not limited to, the compounds of Table 5 as follows:

TABLE 5

| | Expected ESI $(M + H)^+$ | Observed ESI $(M + H)^+$ |
|---|---|---| e-1 e-1

TABLE 5-continued

|  | Expected ESI (M + H)+ | Observed ESI (M + H)+ |
|---|---|---| e-1A

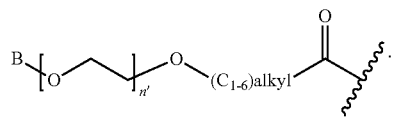

e-1A n' is an integer selected from 5-8

Exemplified compounds of the invention also include compounds with the moiety

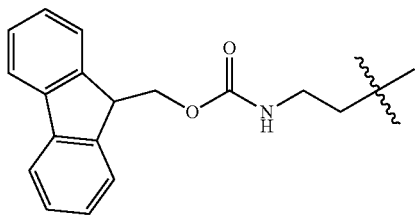 [SMILES: *CCNC(=O)OCC1c2ccccc2-c2ccccc21]

as the corresponding "B" group attached to the chemical structures as appears in the preceding table. In certain embodiments, n' is 5.

Other embodiments of compounds of Formula (I) provide that AA2 is Gln.

In certain embodiments, the compound of the invention is a compound of Formula (IC):

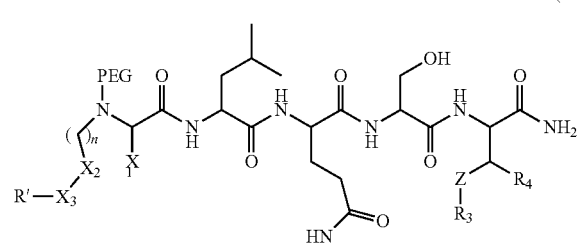
Formula (IC)

wherein

Z is O, $CH_2$, or $CF_2$;

n is 0, 1 or 2;

$X_1$ is H; or $X_1$ and $X_2$, taken together with the bonds they are connected to, form a 5-membered heterocyclic ring;

$X_2$ is a bond or $CH_2$; or $X_1$ and $X_2$, taken together with the bonds they are connected to, form a 5-membered heterocyclic ring;

$R_3$ is H or $(X_4O)_2P(O)$—;

$R_4$ is H, or $(C_{1-6})$alkyl;

$R'$—$X_3$ is $R'$, $R'$—CH=N—O—, $R'$—$(C_{1-6})$alkyl-O—, $R'$—C(O)—NH—O—, $R'$—$(C_{1-6})$alkyl-S—, or $R'$—$(C_{1-6})$alkyl-; and $R'$ is H, amino-O—, $(C_{1-6})$alkyl-C(O)—, cycloalkyl, heterocyclic, aryl-$(C_{0-6})$alkyl, or heretoaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

or a pharmaceutically acceptable salt, solvate, hydrate, or stereoisomer thereof.

In one embodiment of Formula (IC), PEG is

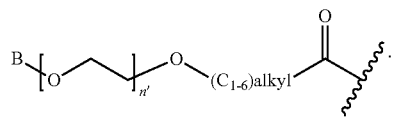

Certain embodiments provide that B is H, $(C_{1-6})$alkyl, or hydrosulfide-$(C_{1-6})$alkyl-C(O)—NH—$(C_{1-6})$alkyl, wherein each $(C_{1-6})$alkyl moiety as appears herein, independently, is further optionally substituted by an amino or N-Fmoc-amino group; and n' is an integer selected from 5-200.

In another embodiment, $X_1$ and $X_2$, taken together with the bonds they are connected to, form a 5-membered heterocyclic ring.

In certain embodiments, R' is H, $H_2NO$—, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$cycloalkyl, imidazolyl, quinolinyl, pyridinyl, pyrimidinyl, dioxo-pyrimidinyl, phenanthrenyl, or bicyclo[2.2.1]hept-2-enyl, wherein $R_3$ is further optionally substituted by one or more substituents selected from the group of halogen, $(C_{6-10})$aryl, heteroaryl, $(C_{1-6})$alkyl, $(C_{1-6})$alkoxy, hydroxyl, hydrosulfide, $(C_{1-6})$alkoxy-carbonyl, cyano, $(C_6$-10)aryl-$(C_{1-6})$alkoxy, hydroxyl$(C_{1-6})$alkyl, trifluoromethyl, amino, and nitro. R' can be, for example, one selected from the group of A-1 to A-48.

In one embodiment, $X_1$ is H, and $X_2$ is $CH_2$. In another embodiment, R' is selected from the group of A-1, A-2, A-3, A-4, A-5, A-6, and A-7.

Certain exemplified compounds of Formula (I) also include, but are not limited to, the compounds as follows:
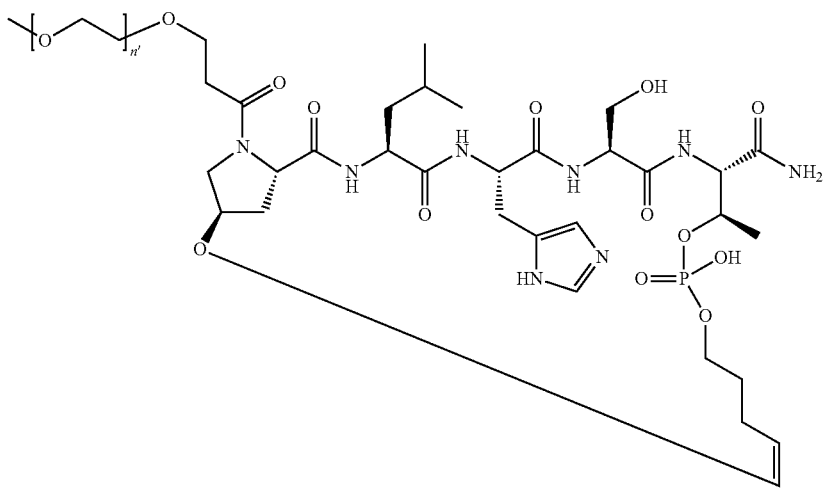
507
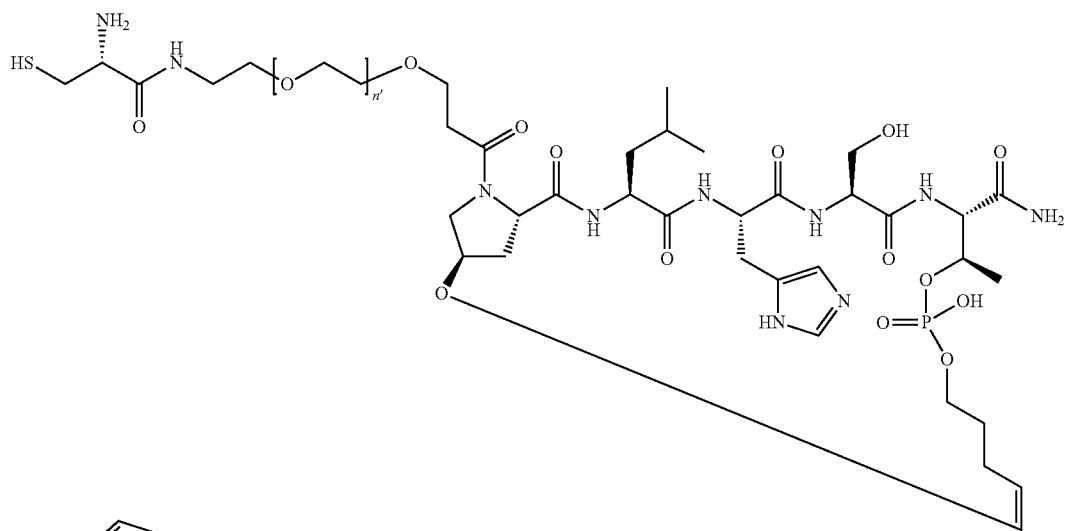
507-A
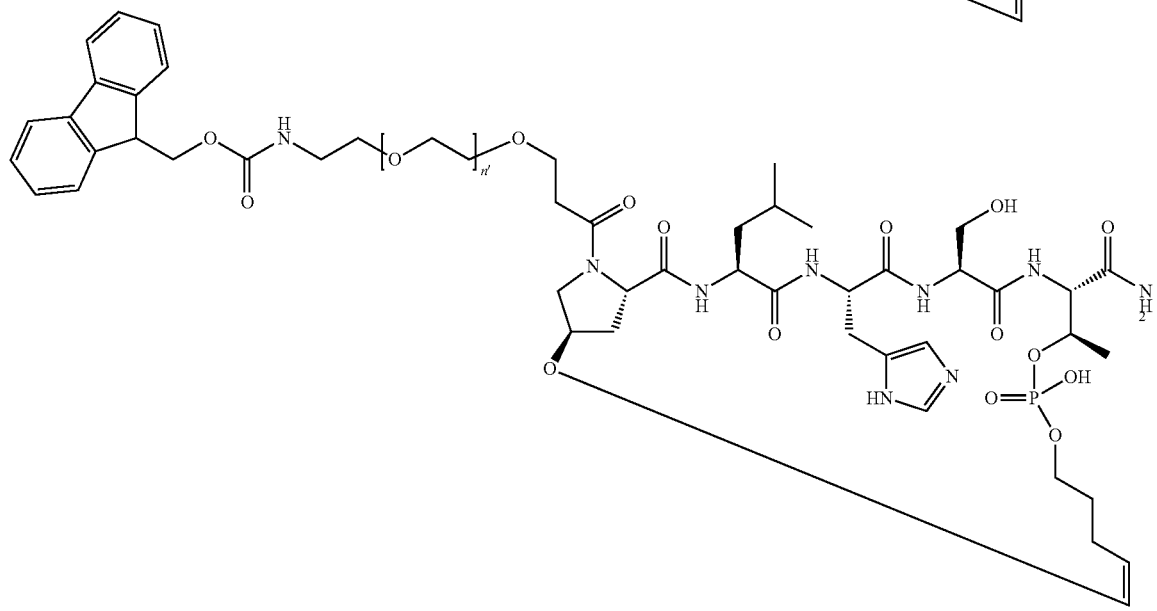
507-A' n' is independently 5, 6, 7, or 8 in the above structures. In certain embodiments, n' is 7. In another embodiment, n' is 5.

In certain embodiments of Formula (I), a compound of the invention is a compound of Structure (1)

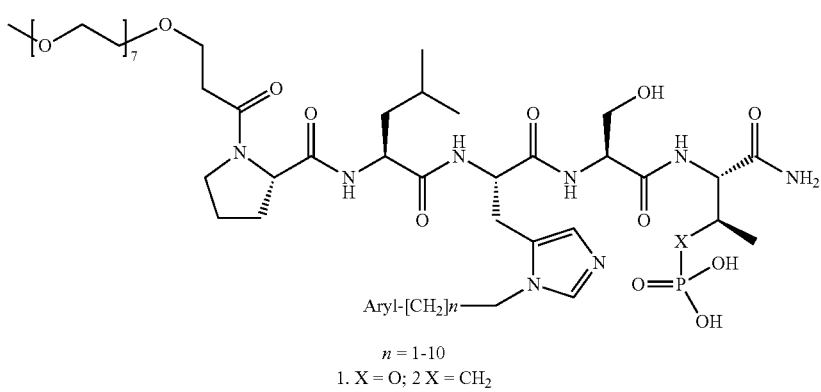

Structure (1)

$n = 1-10$
1. X = O; 2 X = CH$_2$ or a pharmaceutically acceptable salt, solvate, hydrate, or stereoisomer thereof.

In a particular embodiment, a compound of the invention is a compound of Structure (2)

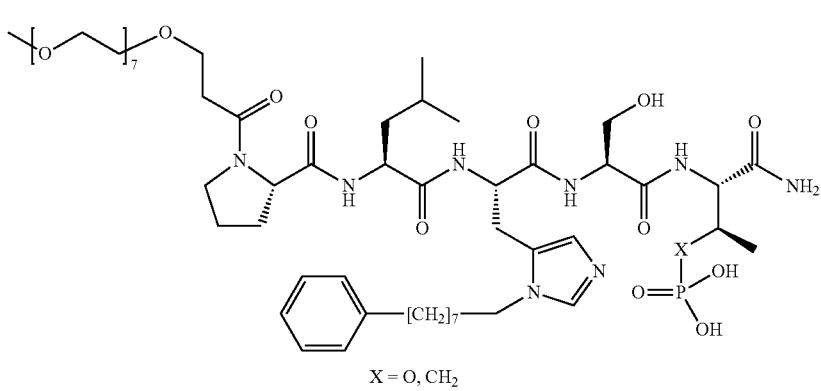

Structure (2)

X = O, CH$_2$ or a pharmaceutically acceptable salt, solvate, hydrate, or stereoisomer thereof.

Another aspect of the invention provides a compound of Formula (II):

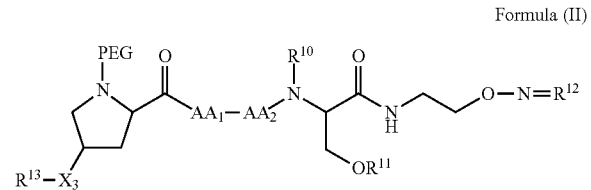

Formula (II)

wherein

PEG is a polyethylene glycol moiety or a derivative thereof;

$R^{10}$ is H or (C$_{1-6}$)alkyl-carbonyl;

$R^{11}$ is H or R$_9$O—;

$R_9$ is H, (C$_{1-6}$)alkyl-carbonyl, or (C$_{1-6}$)alkyl;

$R^{13}$—X$_3$ is $R^{13}$, $R^{13}$—CH=N—O—, $R^{13}$—(C$_{1-6}$)alkyl-O—, $R^{13}$—C(O)—NH—O—, $R^{13}$—(C$_{1-6}$)alkyl-S—, or $R^{13}$—(C$_{1-6}$)alkyl;

$R^{13}$ is H, amino-O—, (C$_{1-6}$)alkyl-C(O)—, (C$_{2-6}$)alkenyl, cycloalkyl, heterocyclic, aryl-(C$_{0-6}$)alkyl, or heretoaryl-(C$_{0-6}$)alkyl; wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$R^{12}$ is derived from a sugar moiety;

AA1 is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and AA2 is absent or an amino acid moiety selected from the group of His, Gln, Ala, Cys, Glu, Phe, Ile, Met, Asn, Ser, Thr, Val, and Tyr;

wherein each of the amino acid moieties for AA1 or AA2 is optionally substituted by aryl-(C$_{1-10}$)alkyl, heteroaryl-(C$_{1-10}$)alkyl, aryl-(C$_{1-10}$)alkyl-CH=N—O—, aryl-(C$_{1-10}$)alkoxy, aryl-(C$_{1-10}$)alkoxy, aryl-(C$_{1-10}$)alkyl-S—, aryl-(C$_{1-10}$)alkyl-C(O)—NH—O—, heteroaryl-(C$_{1-10}$)alkyl-C(O)—NH—O—, and wherein each aryl or heteroaryl moiety is further optionally substituted by one or more same or different substituents selected from the group of aryl, heteroaryl, alkenyl, alkyl, halogen, hydroxyl, amine, amide, carboxyl, ester groups;

or a pharmaceutically acceptable salt, solvate, hydrate, or stereoisomer thereof.

In certain embodiments, PEG is

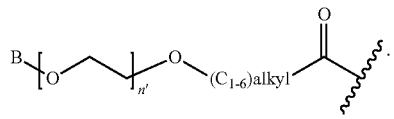

B can be, for example, H, $(C_{1-6})$alkyl, or hydrosulfide-$(C_{1-6})$alkyl-C(O)—NH—$(C_{1-6})$alkyl, wherein each $(C_{1-6})$ alkyl moiety as appears herein, independently, is further optionally substituted by an amino or N-Fmoc-amino group.

In one embodiment, n' is an integer selected from 5-200. In another embodiment, n' is an integer selected from 5-100.

In one embodiment, $R^{10}$ is H. In another embodiment, $R^{11}$ is H.

One embodiments provides that $R^{13}$—$X_3$ is $R^{13}$. $R^{13}$ can be, for example, H.

Certain exemplified compounds of Formula (II) include, but are not limited to, the compounds of Table 6 as follows:

TABLE 6

| | Expected ESI $(M + H)^+$ | Observed ESI $(M + H)^+$ |
|---|---|---|

FA512-1

FA512-1

FA512-A

FA512-1A

TABLE 6-continued
| | Expected ESI (M + H)+ | Observed ESI (M + H)+ |
|---|---|---|
FA511-1
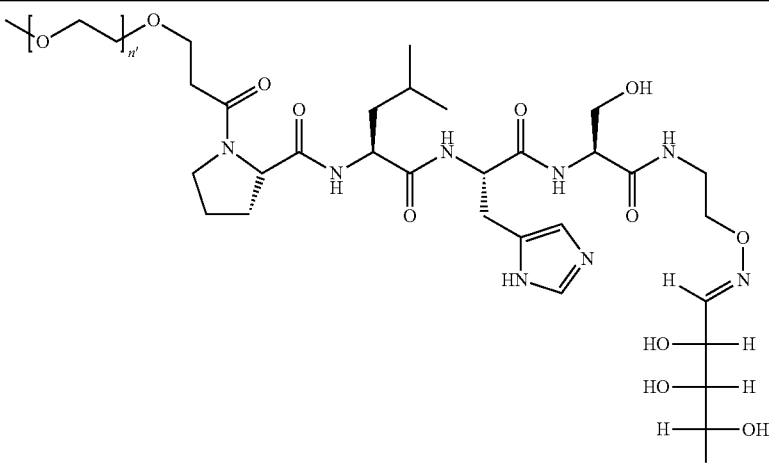
FA511-1
FA511-1A
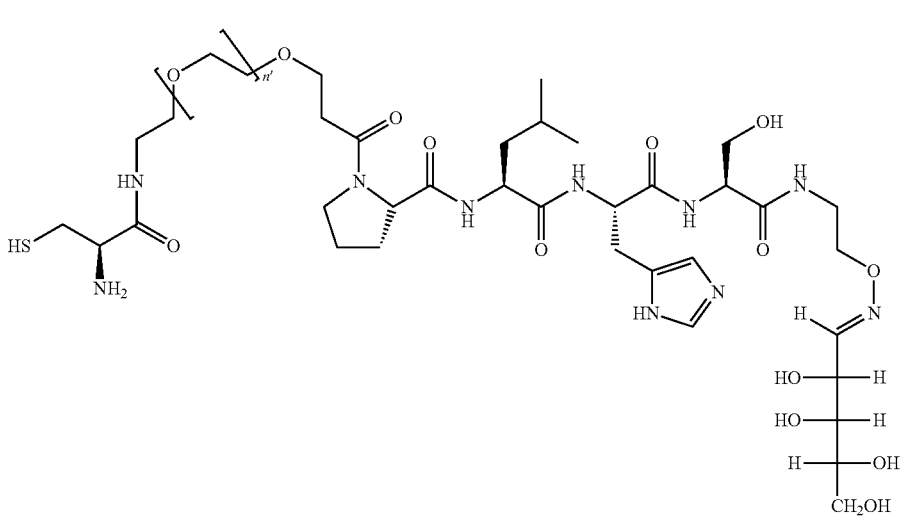
FA511-1A
FA510-1
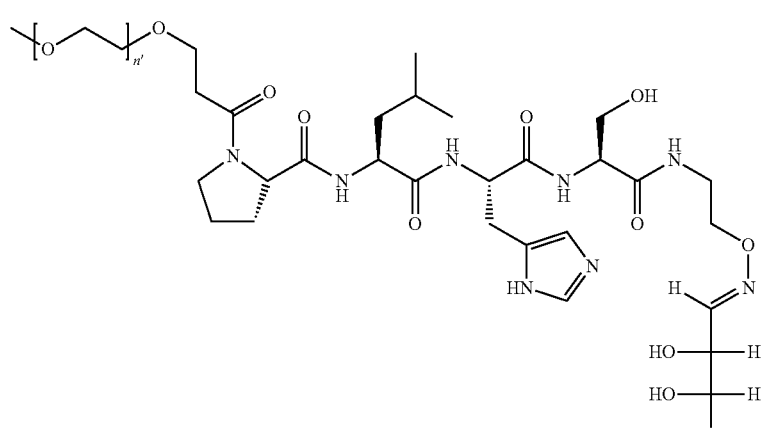
FA510-1

TABLE 6-continued

| | Expected ESI (M + H)+ | Observed ESI (M + H)+ |
|---|---|---|

FA510-1A

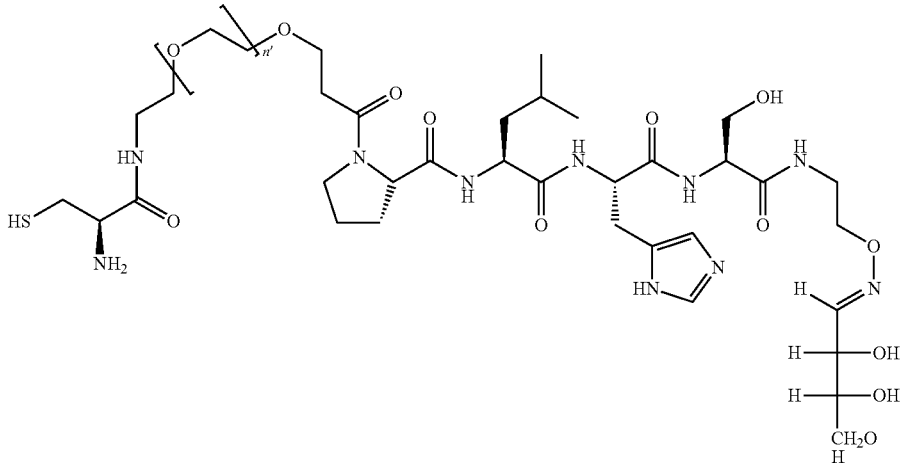

FA510-1A n' is an integer from 5-8

Exemplified compounds of the invention also include compounds with the moiety

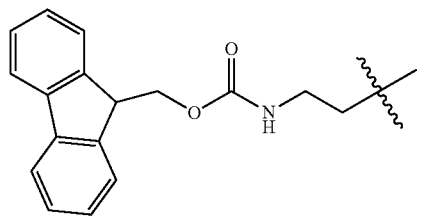 [SMILES: *CCNC(=O)OCC1c2ccccc2-c2ccccc21]

as the corresponding "B" group attached to the chemical structures as appears in the preceding table. In certain embodiments, n' is 5.

In certain embodiments, a compound of the invention is a compound of Structure (1)

Structure (1)

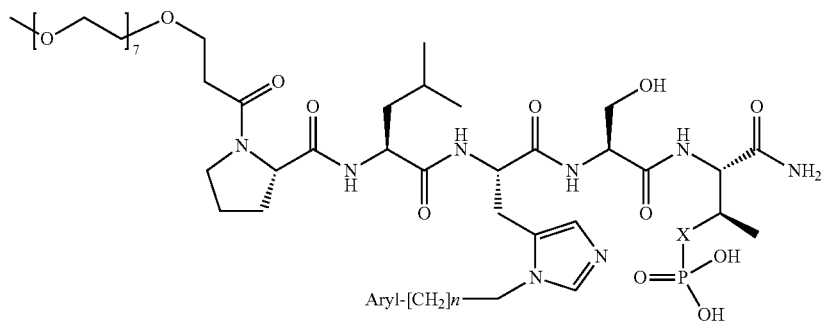

$n = 1\text{-}10$
1. X = O; 2 X = CH$_2$ or a pharmaceutically acceptable salt, solvate, hydrate, or stereoisomer thereof.

In a particular embodiment, a compound of the invention is a compound of Structure (2)

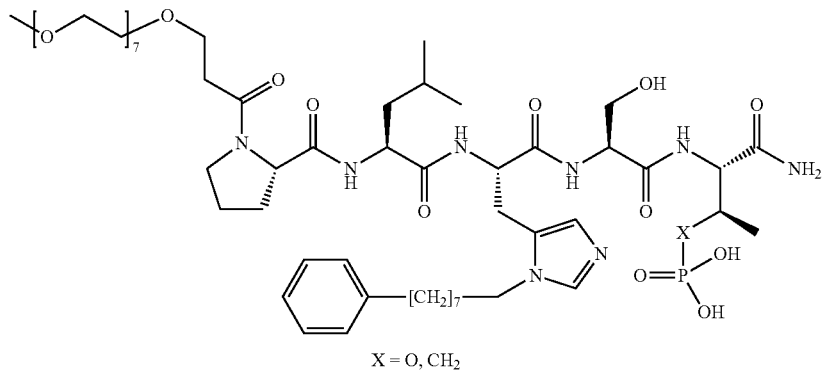

Structure (2)

X = O, CH₂ or a pharmaceutically acceptable salt, solvate, hydrate, or stereoisomer thereof.

In certain embodiments, exemplified compounds of the invention include, but are not limited to, the compounds of Table 7 as follows:

TABLE 7

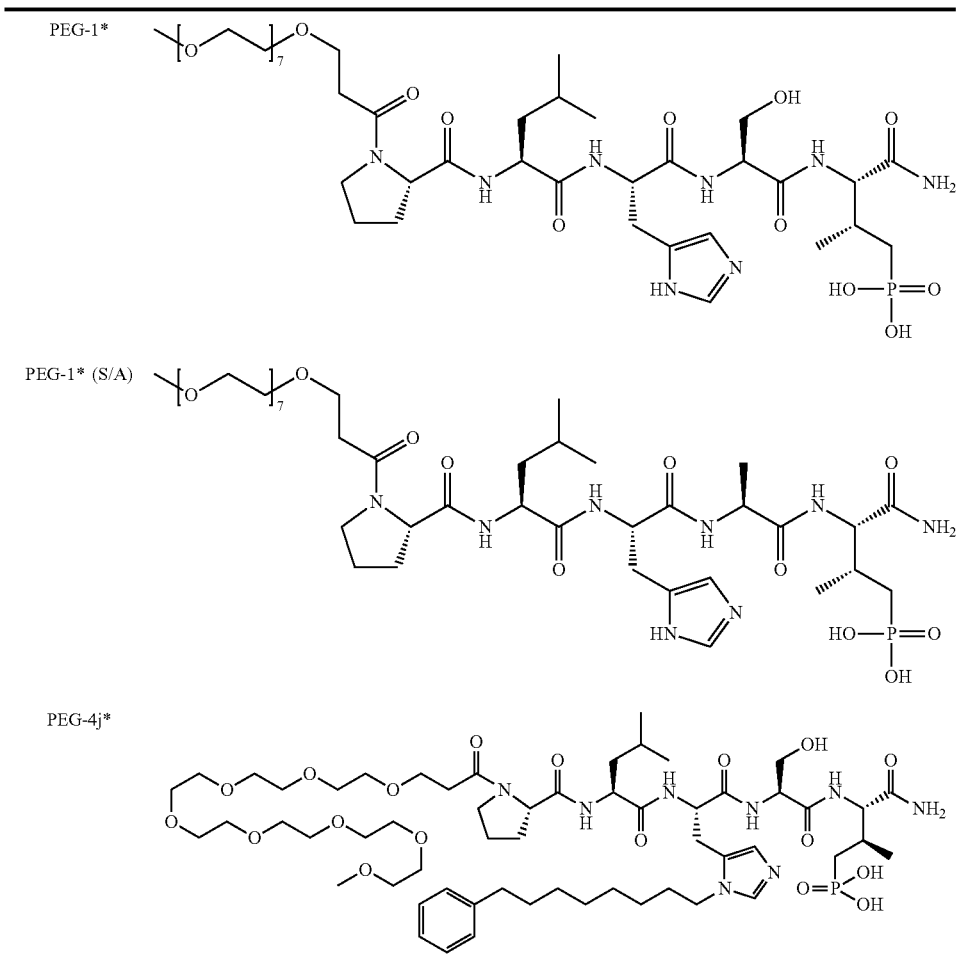

TABLE 7-continued

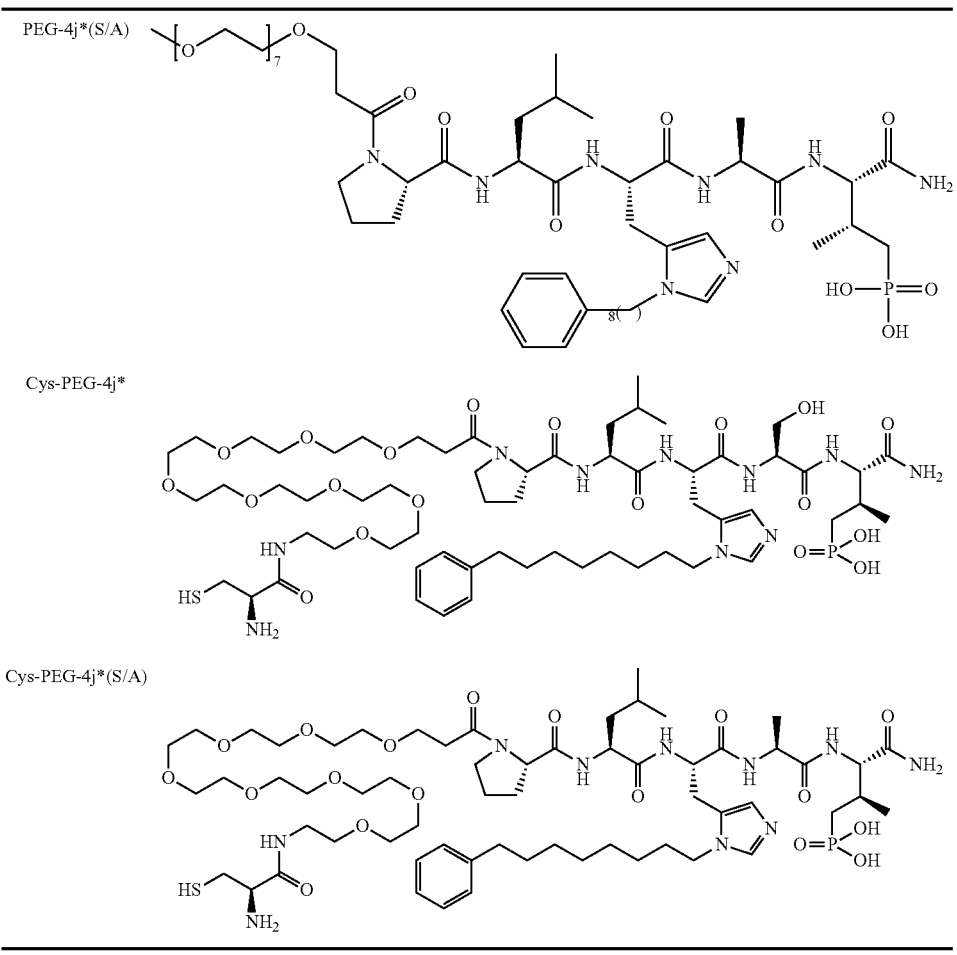

In another aspect, the invention provides a compound of formula III or IV:

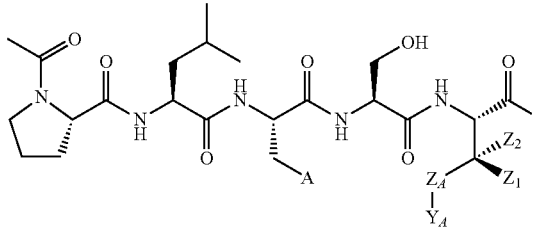
(III)

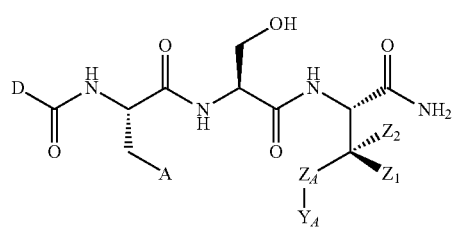
(IV)

wherein,

A is

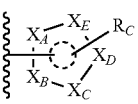

or $-(CH_2)_n-X-R_C$;

each of $X_A$, $X_B$, $X_C$, $X_D$, and $X_E$ are independently N or $CR_A(R_B)$; wherein at least one of $X_A$, $X_B$, $X_C$, $X_D$, and $X_E$ is N;

X is O, $S(O)_m$, $NR_M$, $NR_MC(O)$, $C(O)NR_M$, OC(O), or C(O)O;

$R_C$ is

$R_D$ is optionally substituted aryl or optionally substituted heteroaryl;

t is 1, 2, 3, 4, or 5;

each $R_A$ is independently H, optionally substituted alkyl, optionally substituted carbocyclic, optionally substituted heterocyclic, optionally substituted aryl, or optionally substituted heteroaryl;

each $R_B$ is independently absent, H, optionally substituted alkyl, optionally substituted carbocyclic, optionally substituted heterocyclic, optionally substituted aryl, or optionally substituted heteroaryl;

or any two of $R_A$ groups, together with the atoms to which each is attached, may form a fused carbocyclic, heterocyclic, aryl, or heteroaryl ring, wherein each is optionally substituted;

wherein each A is optionally further substituted with one or more of $R_D$; wherein each $R_D$ is independently alkyl, alkenyl, or alkynyl, each containing 0, 1, 2, or 3 heteroatoms selected from O, S, or N; carbocyclic, heterocyclic, aryl, or heteroaryl; each of which is optionally substituted; or halogen, amino, hydroxy, oxo, or cyano;

D is optionally substituted alkyl or optionally substituted alkoxy;

$Z_A$ is absent, O or $CR_A(R_B)$;

$Y_A$ is

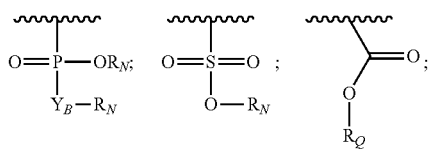

$Y_B$ is O or $CR_AR_A$;

each $Z_1$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

each $Z_2$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

or $Z_A$, $Y_A$, $Z_1$, and the atoms to which each is attached, form an optionally substituted heterocyclic or optionally substituted heteroaromatic ring;

each $R_N$ is independently H, optionally substituted alkyl, or optionally substituted alkoxy;

$R_Q$ is H, alkyl, benzyl, aryl, cycloalkyl, heterocycloalkyl, or heteroaryl, each of which is optionally substituted;

each $R_M$ is independently H or optionally substituted alkyl;

m is 0, 1, or 2; and n is 0, 1, 2, or 3;

wherein in formula I, if A is

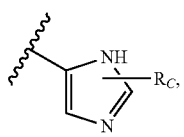

then —$Z_A$—$Y_A$ is not

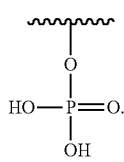

In one embodiment, A is pyrrolidine, pyrazolidine, imidazolidine, triazolidine, tetrazolidine, dihydropyrrole, dihydropyrazole, dihydrotriazole, pyrazole, or triazole; each of which is optionally substituted by $R_D$.

In another embodiment, A is

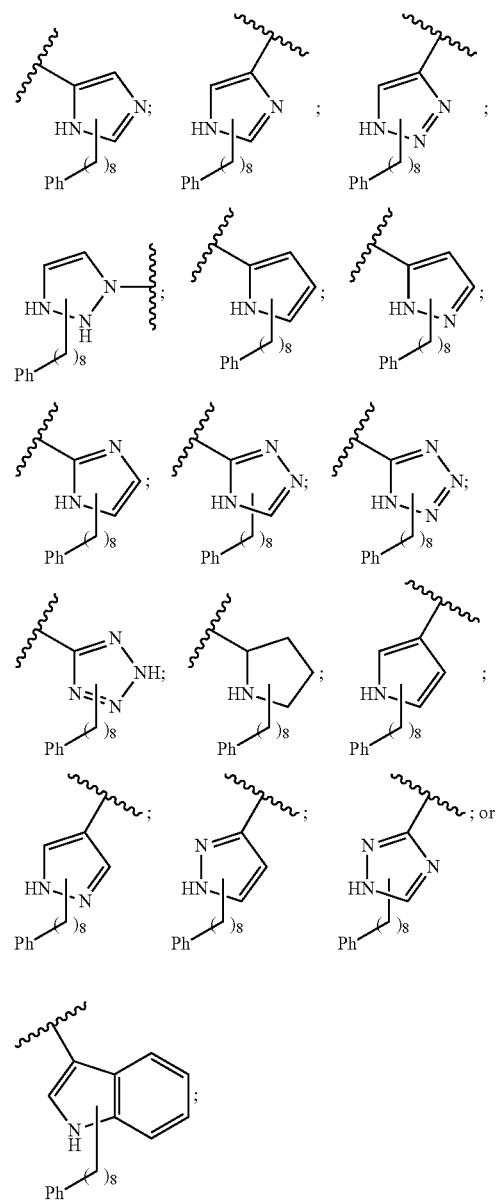

wherein each A is optionally substituted with one or more of $R_D$.

In other embodiments, A is

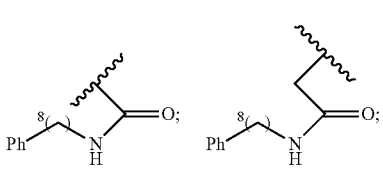

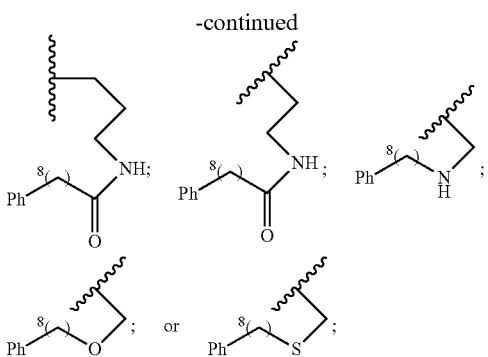

wherein each A is optionally substituted with one or more of $R_D$.

In another embodiment, the invention provides a compound of formula III:

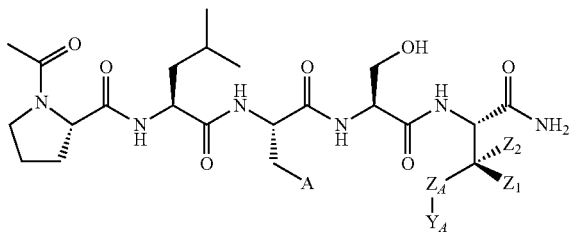

(III)

wherein,
A is

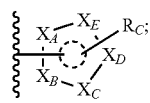

each of $X_A$, $X_B$, $X_C$, $X_D$, and $X_E$ are independently N or $CR_A(R_B)$; wherein at least one of $X_A$, $X_B$, $X_C$, $X_D$, and $X_E$ is N;

$R_C$ is

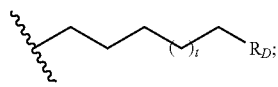

$R_D$ is optionally substituted aryl or optionally substituted heteroaryl;

t is 1, 2, 3, 4, or 5;

each $R_A$ is independently H, optionally substituted alkyl, optionally substituted carbocyclic, optionally substituted heterocyclic, optionally substituted aryl, or optionally substituted heteroaryl;

each $R_B$ is independently absent, H, optionally substituted alkyl, optionally substituted carbocyclic, optionally substituted heterocyclic, optionally substituted aryl, or optionally substituted heteroaryl;

or any two of $R_A$ groups, together with the atoms to which each is attached, may form a fused carbocyclic, heterocyclic, aryl, or heteroaryl ring, wherein each is optionally substituted;

wherein each A is optionally further substituted with one or more of $R_D$; wherein each $R_D$ is independently alkyl, alkenyl, or alkynyl, each containing 0, 1, 2, or 3 heteroatoms selected from O, S, or N; carbocyclic, heterocyclic, aryl, or heteroaryl; each of which is optionally substituted; or halogen, amino, hydroxy, oxo, or cyano;

$Z_A$ is O or $CH_2$;

$Y_A$ is

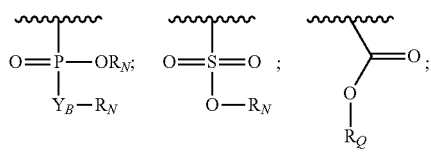

$Y_B$ is O or $CR_AR_A$;

each $Z_1$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

each $Z_2$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

or $Z_A$, $Y_A$, $Z_1$, and the atoms to which each is attached, form an optionally substituted heterocyclic or optionally substituted heteroaromatic ring;

each $R_1$ is independently H, optionally substituted alkyl, optionally substituted alkoxy;

$R_2$ is H, alkyl, benzyl, aryl, cycloalkyl, heterocycloalkyl, or heteroaryl, each of which is optionally substituted; and n is 0, 1, 2, or 3.

In certain embodiments, $Z_A$ is 0 or $CH_2$; and $Y_A$ is

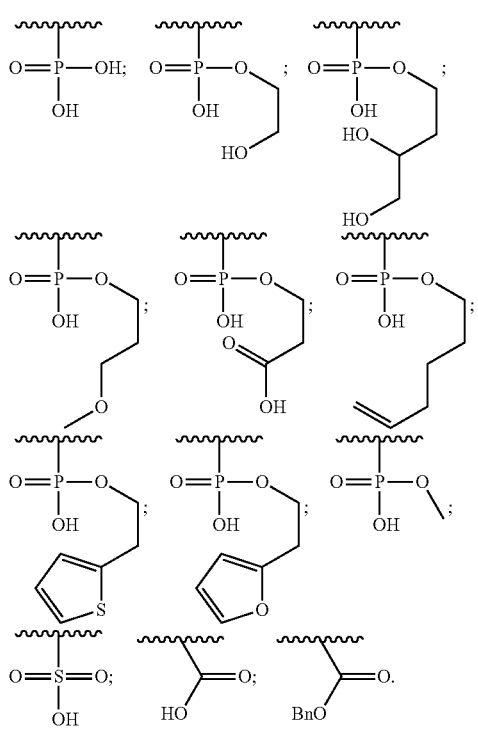

In various embodiments, $Z_A$, $Y_A$, $Z_1$, and the atoms to which each is attached, forms a 5-6 membered heterocyclic or heteroaryl ring, wherein at least one ring atoms is N, O, or S.

In a further embodiment, $Z_A$, $Y_A$, $Z_1$, and the atoms to which each is attached, is selected from pyridinyl, pyrimidinyl, furanyl, thienyl, pyrrolyl, pyrazolyl, pyrrolidinyl, morpholinyl, piperidinyl, piperazinyl, isoxazole, and imidazolyl, each of which is optionally substituted.

In a further embodiment, $Z_A$, $Y_A$, $Z_1$, and the atoms to which each is attached, is

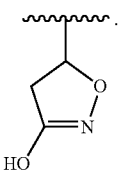

In various embodiments, A is

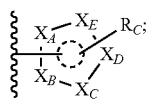

each of $X_A$, $X_B$, $X_C$, $X_D$, and $X_E$ are independently N or $CR_A(R_B)$; wherein at least one of $X_A$, $X_B$, $X_C$, $X_D$, and $X_E$ is N;

$R_C$ is

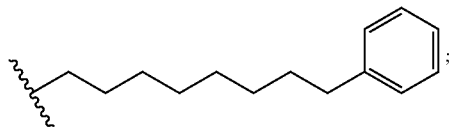 [SMILES: *CCCCCCCCc1ccccc1]

each $R_A$ is independently H or optionally substituted alkyl;

each $R_B$ is independently absent, H or optionally substituted alkyl;

or any two of $R_A$ groups, together with the atoms to which each is attached, may form a fused carbocyclic, heterocyclic, aryl, or heteroaryl ring, wherein each is optionally substituted.

In a further embodiment, A is

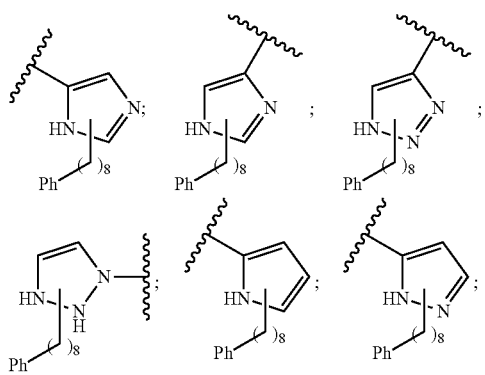

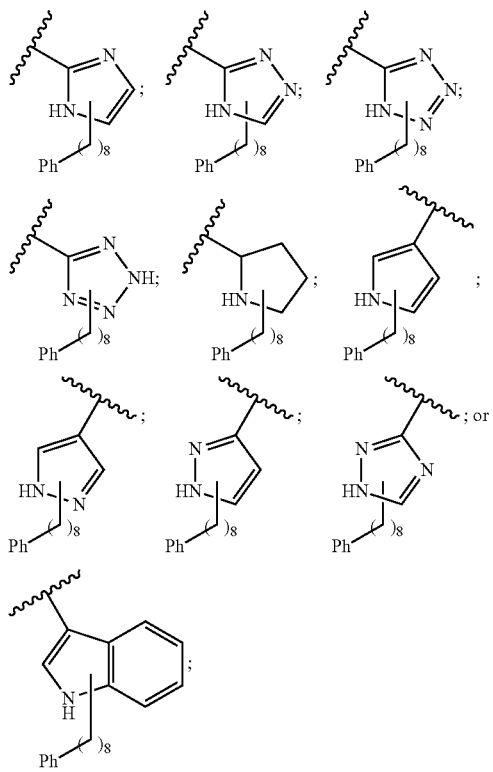

wherein each A is optionally substituted with one or more of $R_D$.

In certain embodiments, A is

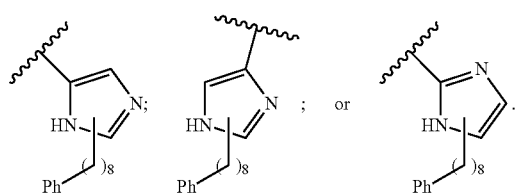

In another embodiment, the invention provides a compound of formula III:

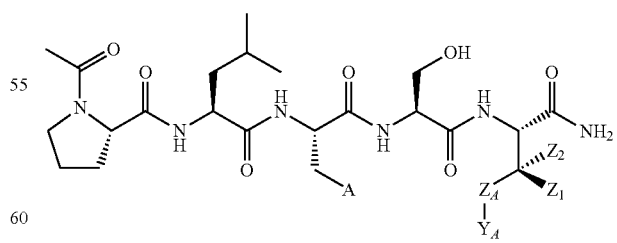

(III)

wherein,

A is $-(CH_2)_n-X-R_C$;

X is O, $S(O)_m$, $NR_M$, $NR_MC(O)$, $C(O)NR_M$, OC(O), or C(O)O;

$R_C$ is

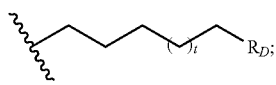

$R_D$ is optionally substituted aryl or optionally substituted heteroaryl;

t is 1, 2, 3, 4, or 5;

wherein each A is optionally further substituted with one or more of $R_D$; wherein each $R_D$ is independently alkyl, alkenyl, or alkynyl, each containing 0, 1, 2, or 3 heteroatoms selected from O, S, or N; carbocyclic, heterocyclic, aryl, or heteroaryl; each of which is optionally substituted; or halogen, amino, hydroxy, oxo, or cyano;

$Z_A$ is absent, O or $CH_2$;

$Y_A$ is

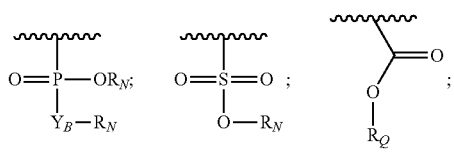

$Y_B$ is O or $CR_AR_A$;

each $Z_1$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

each $Z_2$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;

or $Z_A$, $Y_A$, $Z_1$, and the atoms to which each is attached, form an optionally substituted heterocyclic or optionally substituted heteroaromatic ring;

each $R_N$ is independently H, optionally substituted alkyl, or optionally substituted alkoxy;

$R_Q$ is H, alkyl, benzyl, aryl, cycloalkyl, heterocycloalkyl, or heteroaryl, each of which is optionally substituted;

each $R_M$ is independently H or optionally substituted alkyl;

m is 0, 1, or 2; and n is 0, 1, 2, or 3.

In certain embodiments, $Z_A$ is O or $CH_2$; and $Y_A$ is

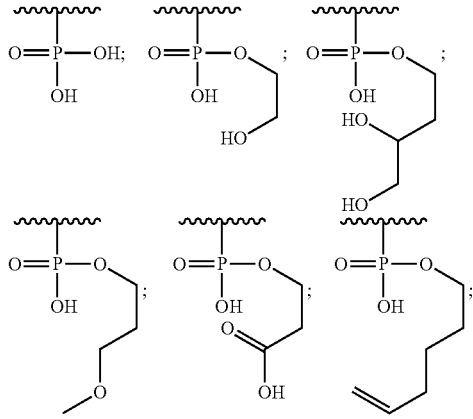

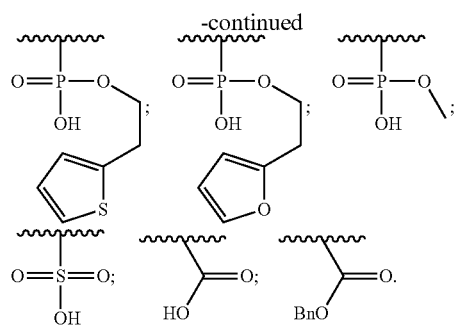

In various embodiments,

A is $-(CH_2)_n-X-R_C$;

X is O, $S(O)_m$, $NR_M$, $NR_MC(O)$, $C(O)NR_M$, OC(O), or C(O)O; and $R_C$ is

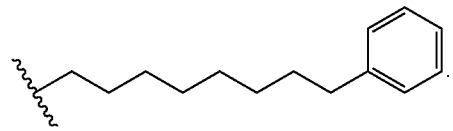 [SMILES: *CCCCCCCCc1ccccc1]

In a further embodiment, A is

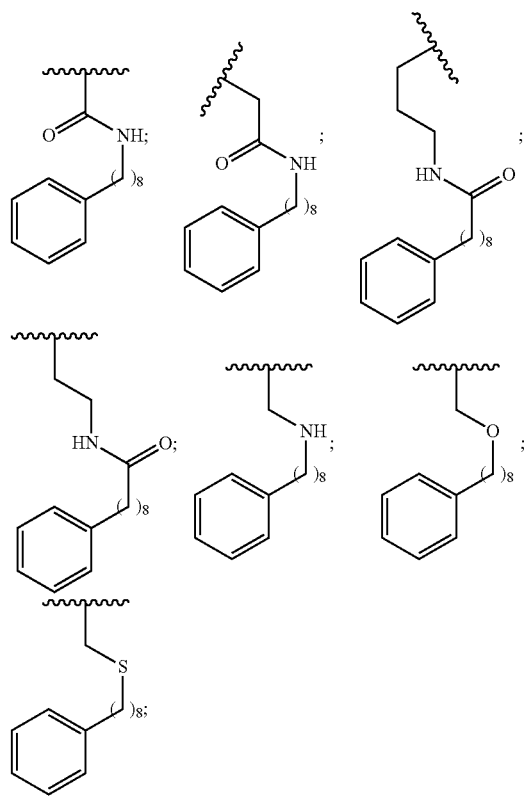

wherein each A is optionally substituted with one or more of $R_D$.

In other embodiments, the invention provides a compound of formula IV:

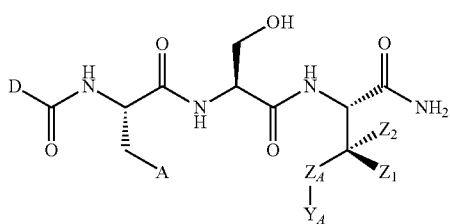

(IV)

wherein,
A is

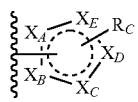

each of $X_A$, $X_B$, $X_C$, $X_D$, and $X_E$ are independently N or $CR_A(R_B)$; wherein at least one of $X_A$, $X_B$, $X_C$, $X_D$, and $X_E$ is N;
$R_C$ is

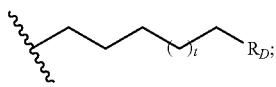

$R_D$ is optionally substituted aryl or optionally substituted heteroaryl;
t is 1, 2, 3, 4, or 5;
each $R_A$ is independently H, optionally substituted alkyl, optionally substituted carbocyclic, optionally substituted heterocyclic, optionally substituted aryl, or optionally substituted heteroaryl;
each $R_B$ is independently absent, H, optionally substituted alkyl, optionally substituted carbocyclic, optionally substituted heterocyclic, optionally substituted aryl, or optionally substituted heteroaryl;
or any two of $R_A$ groups, together with the atoms to which each is attached, may form a fused carbocyclic, heterocyclic, aryl, or heteroaryl ring, wherein each is optionally substituted;
wherein each A is optionally further substituted with one or more of $R_D$; wherein each $R_D$ is independently alkyl, alkenyl, or alkynyl, each containing 0, 1, 2, or 3 heteroatoms selected from O, S, or N; carbocyclic, heterocyclic, aryl, or heteroaryl; each of which is optionally substituted; or halogen, amino, hydroxy, oxo, or cyano;
D is optionally substituted alkyl or optionally substituted alkoxy;
$Z_A$ is absent, O or $CH_2$;
$Y_A$ is

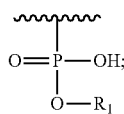

each $Z_1$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;
each $Z_2$ is independently H, alkyl, alkenyl, or alkynyl, each containing 0, 1, 2, or 3 heteroatoms selected from O, S, or N; carbocyclic, heterocyclic, aryl, or heteroaryl; each of which is optionally substituted;
or $Z_A$, $Y_A$, $Z_1$, and the atoms to which each is attached, form an optionally substituted heterocyclic or optionally substituted heteroaromatic ring;
each $R_N$ is independently H, optionally substituted alkyl, or optionally substituted alkoxy;
$R_Q$ is H, alkyl, benzyl, aryl, cycloalkyl, heterocycloalkyl, or heteroaryl, each of which is optionally substituted;
each $R_M$ is independently H or optionally substituted alkyl; and
n is 0, 1, 2, or 3.
In certain embodiments, $Z_A$ is O or $CH_2$; and $Y_A$ is

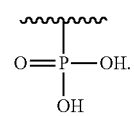

In other embodiments,
A is

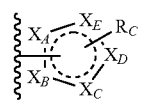

each of $X_A$, $X_B$, $X_C$, $X_D$, and $X_E$ are independently N or $CR_A(R_B)$; wherein at least one of $X_A$, $X_B$, $X_C$, $X_D$, and $X_E$ is N;
$R_C$ is

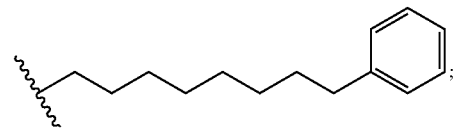 [SMILES: *CCCCCCCCc1ccccc1]

each $R_A$ is independently H or optionally substituted alkyl;
each $R_B$ is independently absent, H or optionally substituted alkyl;
or any two of $R_A$ groups, together with the atoms to which each is attached, may form a fused carbocyclic, heterocyclic, aryl, or heteroaryl ring, wherein each is optionally substituted.
In a further embodiment, A is

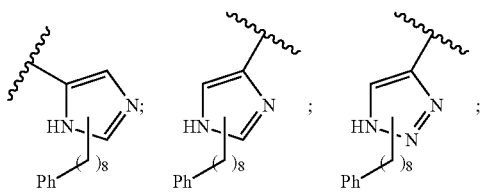

123
-continued
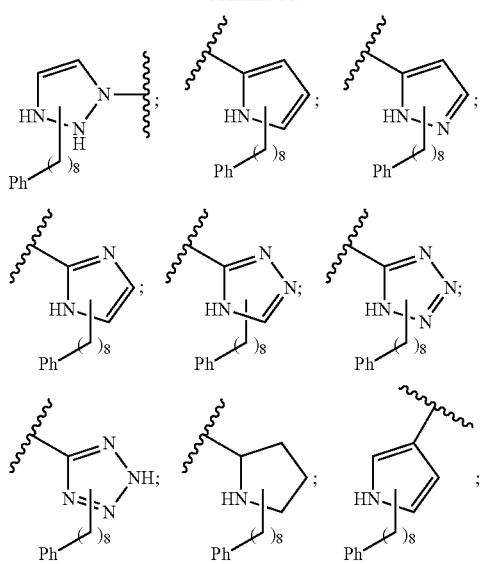
124
-continued
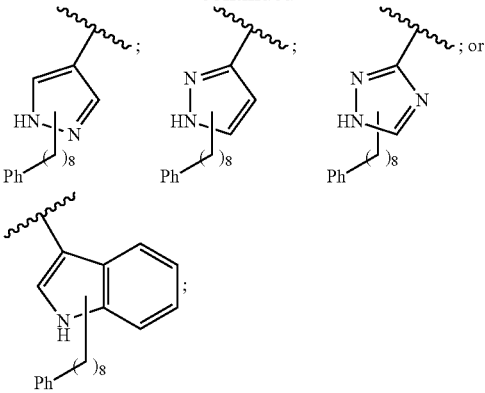
wherein each A is optionally substituted with one or more of $R_D$.
In certain embodiments, D is methyl or optionally substituted alkoxy, such as a PEG group.
In another aspect, the invention provides a compound selected from the following:
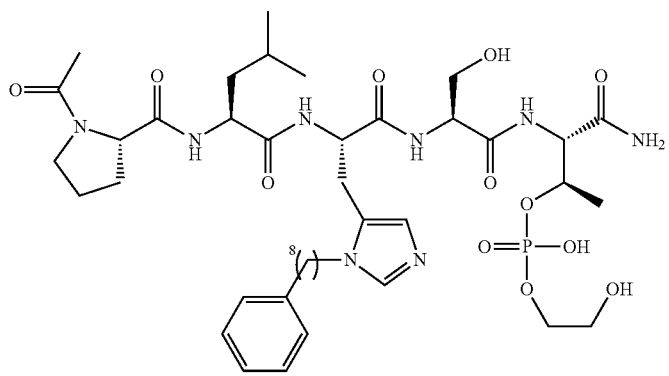
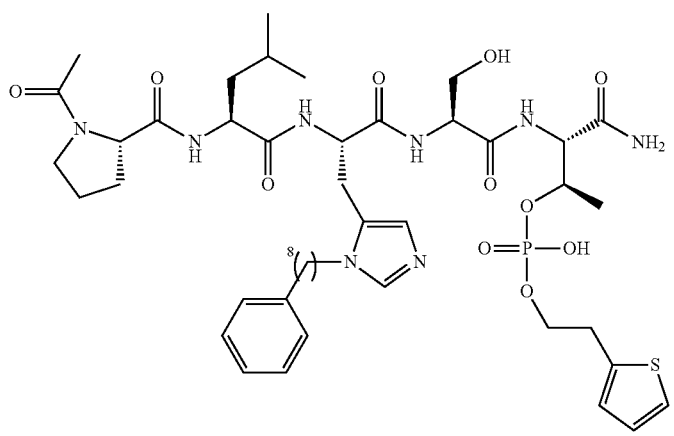

-continued
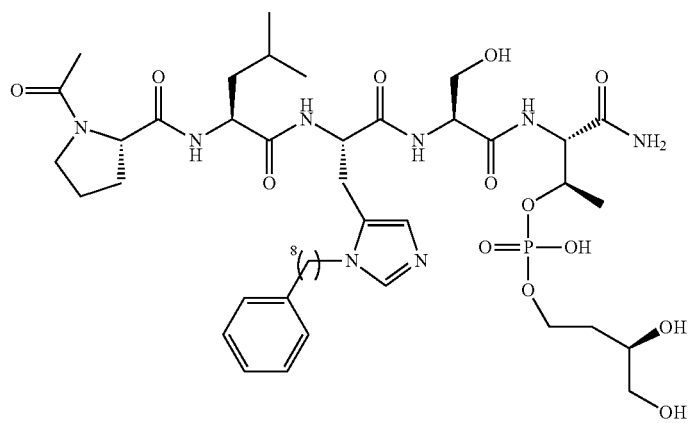
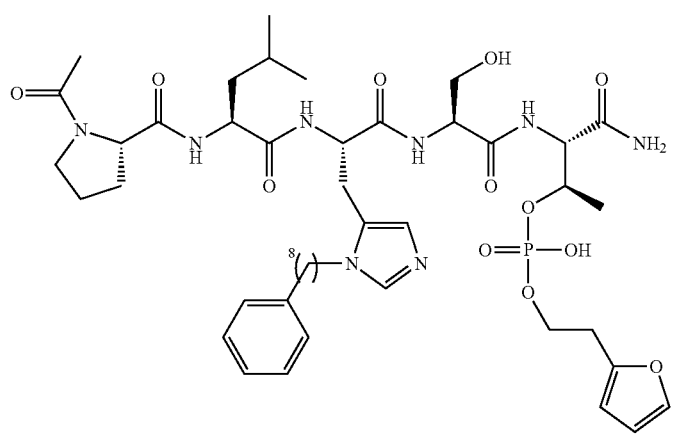
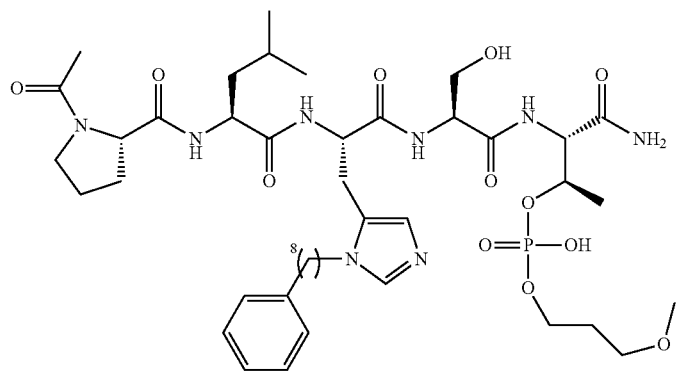
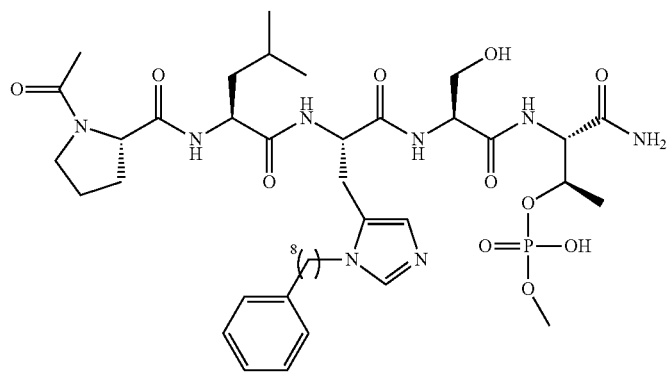

-continued
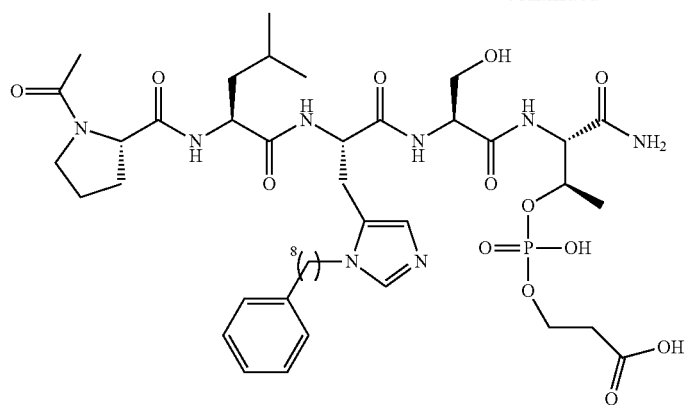
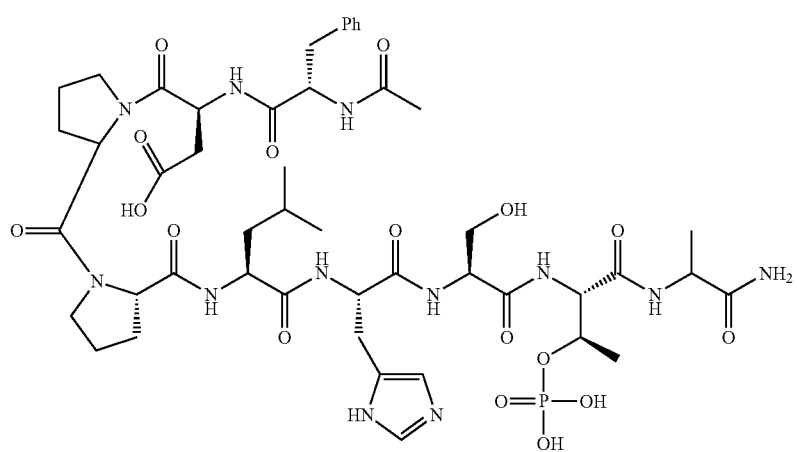
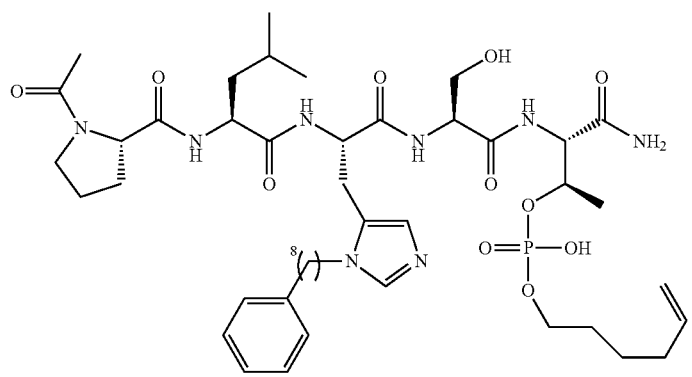
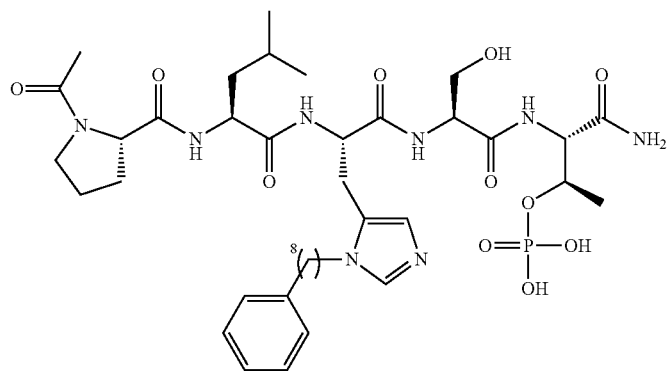

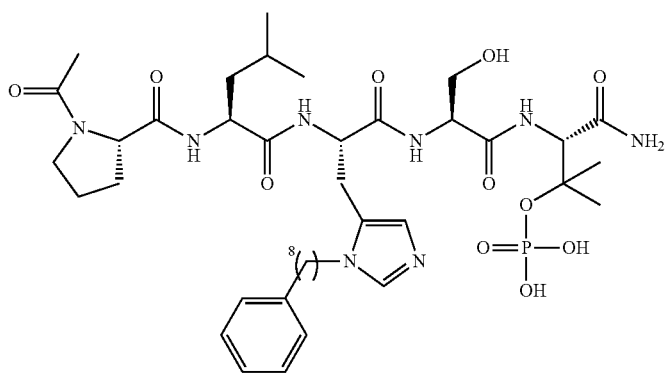
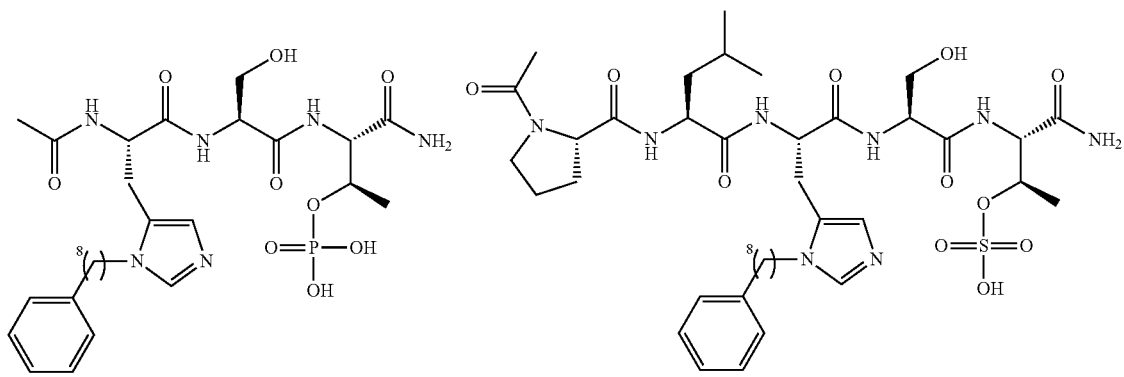
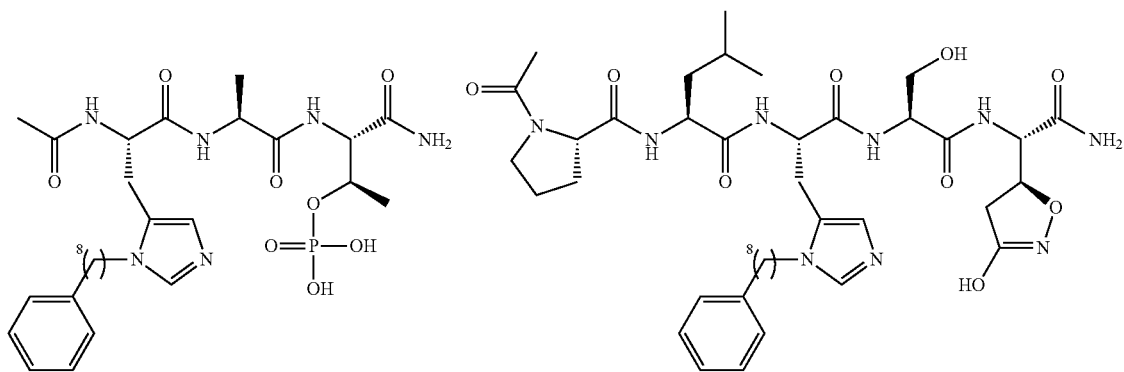
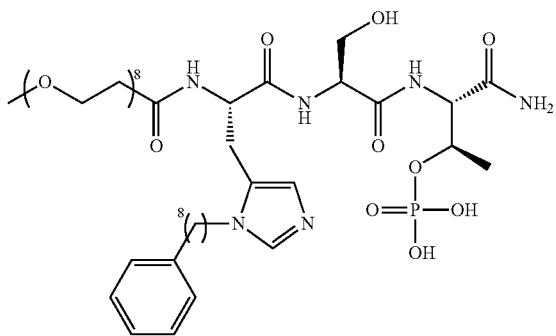

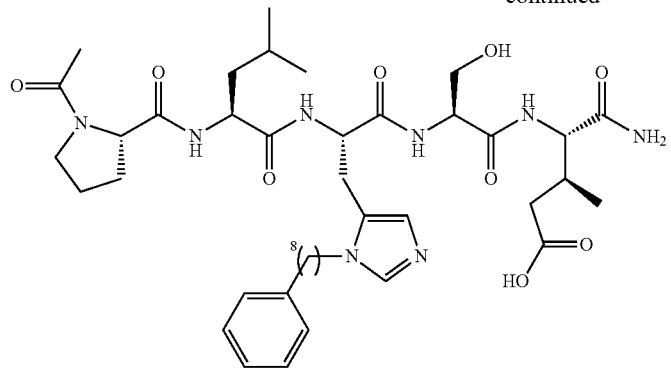
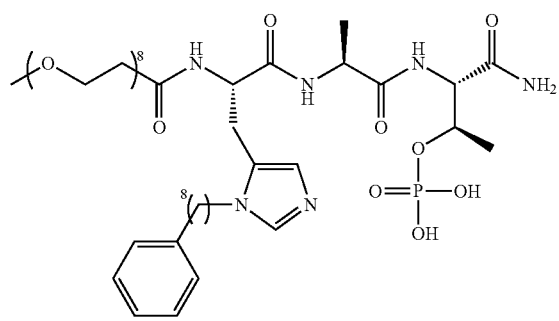
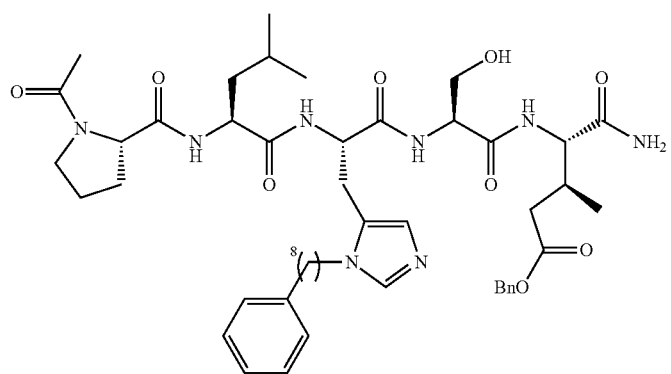
Compounds of the invention include, but are not limited to the following:
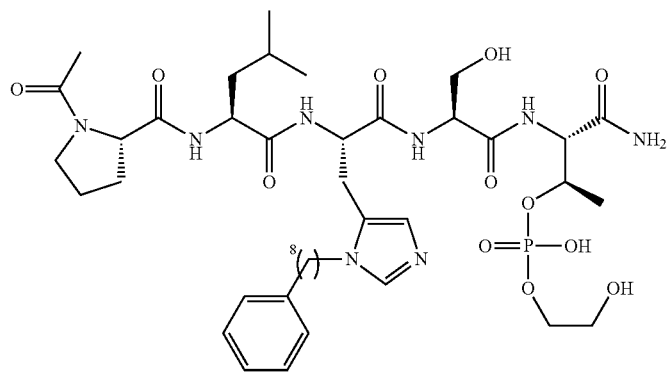

-continued
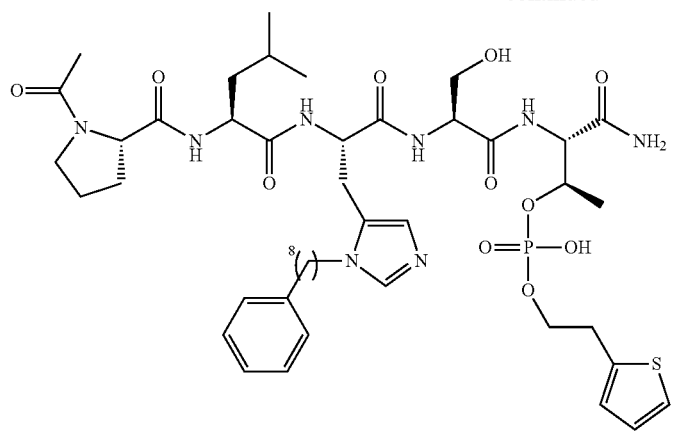
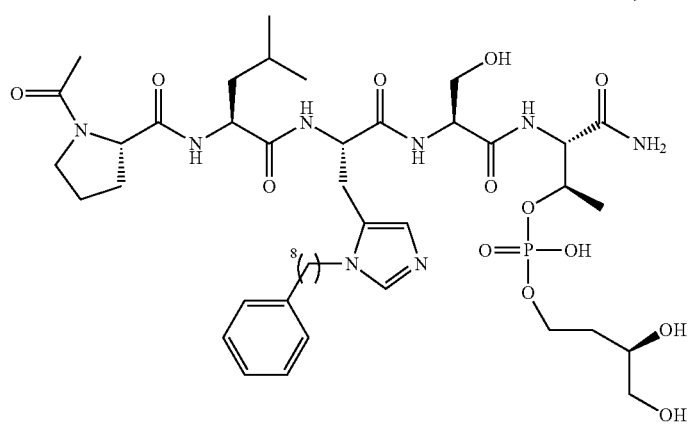
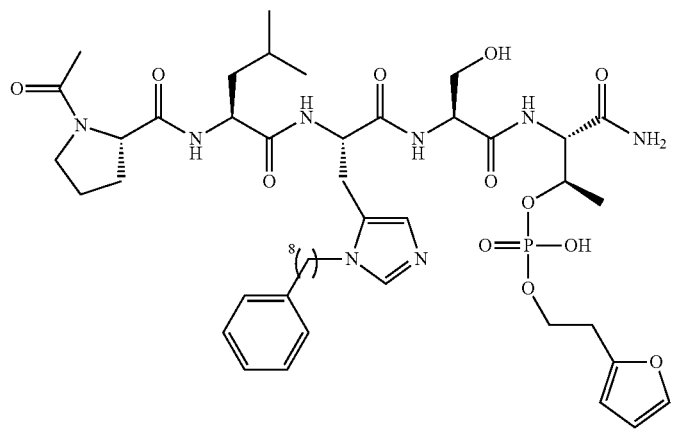
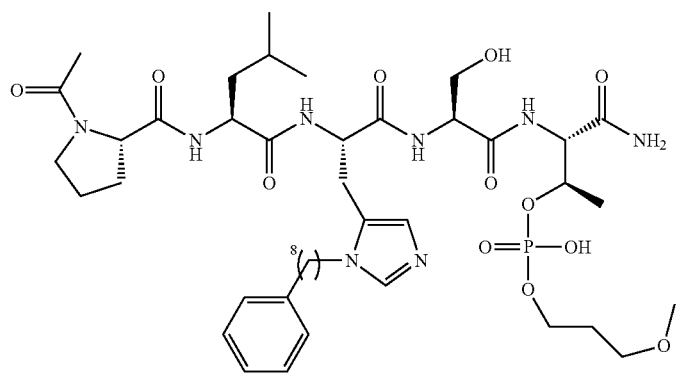

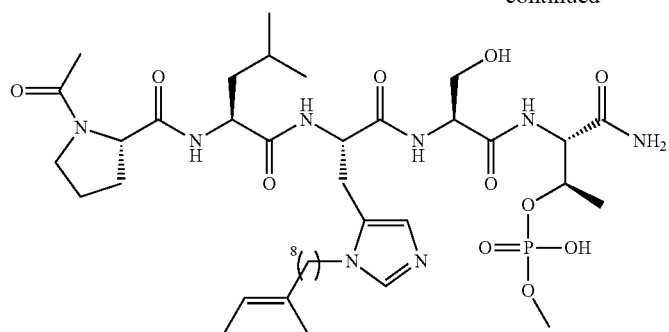
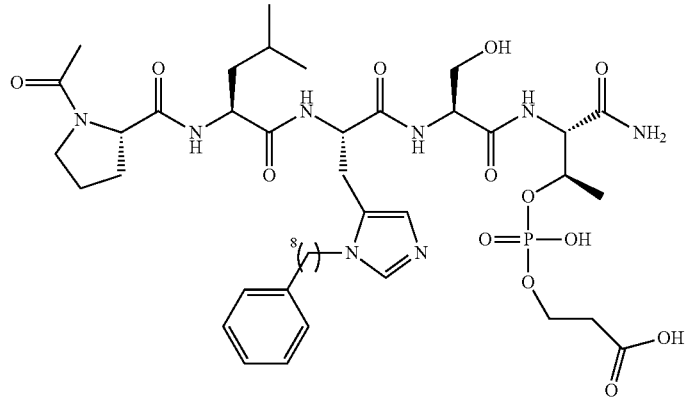
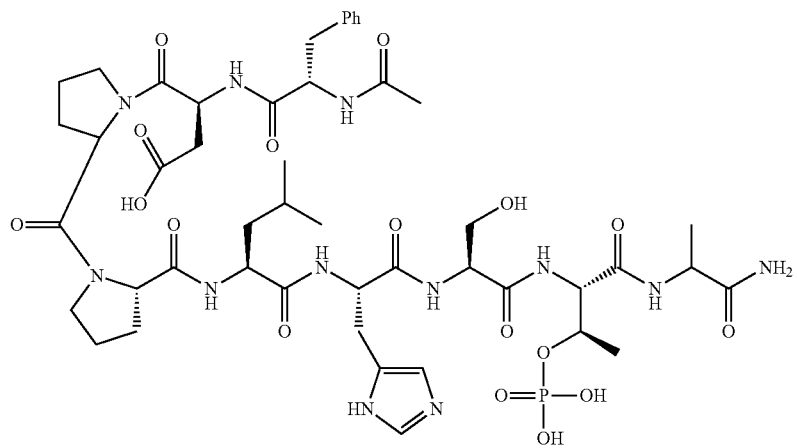
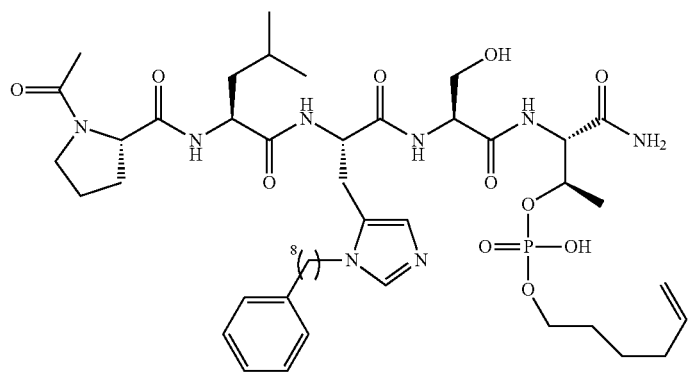

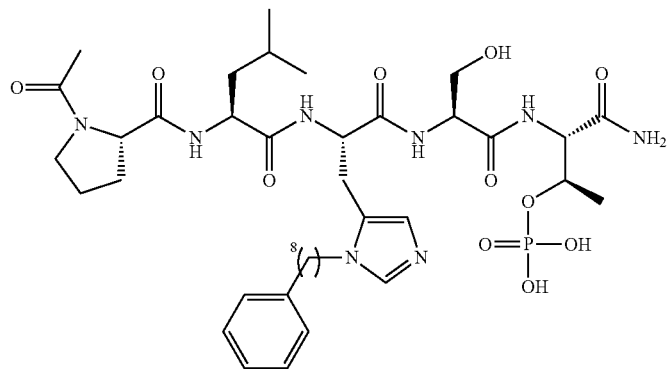
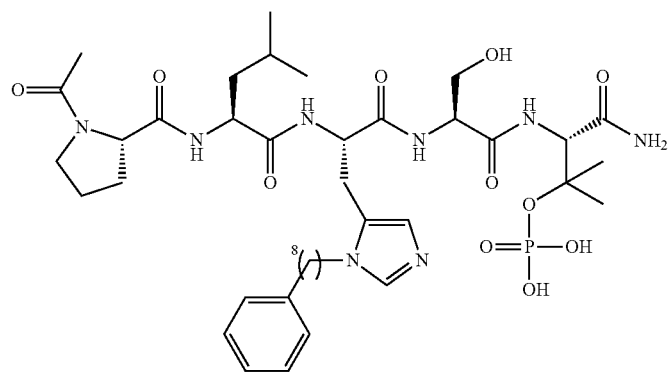
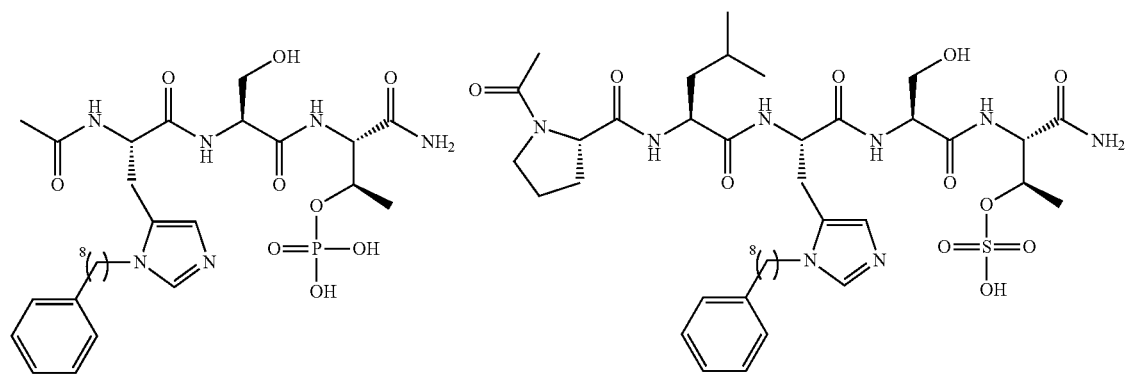
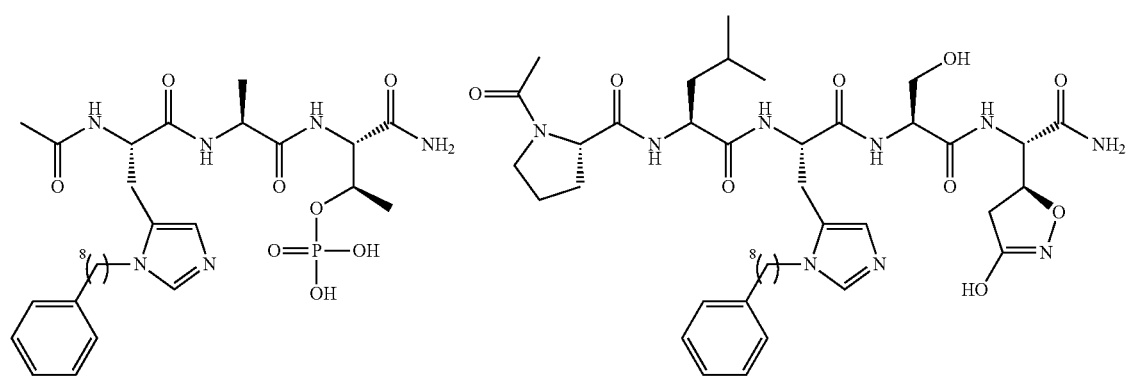

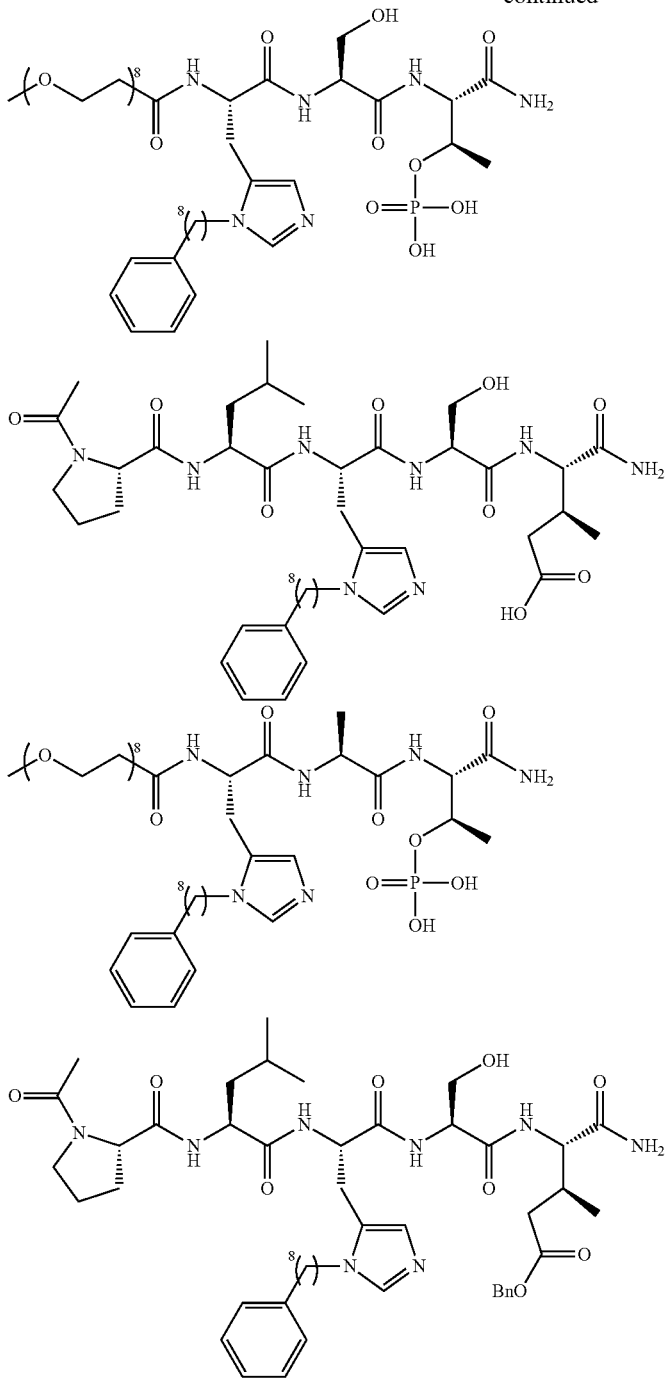

Another aspect is any compound delineated herein tagged with a HIV Tat sequence.

The invention provides method of making/preparing compounds of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$ $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), *Bioorganic and Medicinal Chemistry Letters*, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention.

Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

DESIGN OF THE COMPOUNDS OF THE INVENTION

The invention also provides methods of design and/or synthesis of the PEGylated peptides and methods of use thereof.

Over-expression of Plk1 induces neoplastic transformation of human cells, whereas interference with Plk1 function induces apoptosis in tumor cells but not in normal cells. Moreover, Plk1 over-expression is associated with aggressive disease stage and poor patient survival in various types of cancers. Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1 (Strebhardt, K. et al., Nat. Rev. Cancer 6, 321-330. (2006)). However, largely because of the structural similarities among the catalytic domains of all Plks and other related kinases, it has been difficult to generate Plk1-specific inhibitors. Thus, since the non-catalytic PBD is found only in the members of the Plk subfamily, development of novel inhibitors that target the PBD of Plk1 may prove to be an alternative strategy for selectively targeting Plk1.

While conducting studies on the interaction between Plk1 and its physiological binding target PBIP1, a minimal phosphopeptide derived from the Thr78 region of PBIP1 was identified that exhibits a high level of affinity and specificity for the Plk1 PBD. Testing of a non-hydrolyzable p-T78 mimetic peptide demonstrated that inhibition of the Plk1 PBD function results in a chromosome congression defect that leads to mitotic arrest and apoptotic cell death, as observed previously in cells expressing a dominant-negative PBD (Seong, Y. S. et al. J. Biol. Chem. 277, 32282-32293 (2002); & Hanisch, A. et al., Mol. Biol. Cell 17, 448-459 (2006)). Since interference with Plk1 function induces apoptosis in most tumor cells but not in normal cells, these findings demonstrate that inhibition of the PBD function is sufficient to interfere with cell proliferation activity of tumor cells. Furthermore, data presented here directly provide the proof-of-principle that specific inhibition of Plk1 PBD is achievable by a small mimetic peptide or its relevant compounds.

It has been demonstrated that SpT-dependent electrostatic interactions with His538 and Lys540 residues are critical for the interaction between optimal peptides (PMQSpTPL (SEQ ID NO: 4) and MQSpTPL (SEQ ID NO: 5)) and the Plk1 PBD12,13. Comparative in vitro binding studies and analyses of the phosphopeptide-binding pockets of PBDS+G and PBDS with PBDPL, PBDPP, and PBDLH revealed that, in addition to the SpT motif of the phosphopeptide that acts as a high affinity anchor, the N-terminal residues provide additional binding affinity and specificity to the Plk1 PBD through three distinct interactions. First, the polar contact between the carbonyl oxygen N-terminal to the Leu-3 of PLHSpT (SEQ ID NO: 1) or LHSpTA (SEQ ID NO: 3) and the guanidinium moiety of Arg516 of Plk1 PBD provides a molecular basis for a high affinity and specificity interaction. Second, docking of the N-terminal Pro-4 side chain into the pocket generated by the surrounding Trp414 and Phe535 offers additional affinity and likely another level of specificity to the interaction. Notably, the PBDs from both Plk2 and Plk3 possess Lys and Tyr residues at positions analogous to the Plk1 Arg516 and Phe535 residues, respectively, in Plk1, and, as a consequence, may fail to generate as favorable an environment to accommodate the N-terminal Pro residue. Third, peptide pull-down assays demonstrate that the His-2 residue adds another layer of Plk1 PBD specificity.

Besides each amino acid residue of the p-T78 peptide involved in defining the Plk1 binding affinity and specificity, the positions of the phosphopeptide and glycerol in the pocket, along with the network of water molecules that mediate contacts between the phosphopeptide and the PBD, suggest that both the glycerol and the network of water molecules surrounding the phosphopeptide could be important elements of the PBD recognition by phosphopeptides. Furthermore, the structures of the PBD$^{S+G}$, PBD$^S$, and PBD$^{PL}$ were remarkably similar, hinting that the other glycerol molecule and the sulfate anion occupying the phosphopeptide-binding cleft may substitute the role of the SpT dipeptide.

The collected data demonstrate that the Plk1 PBD-binding pocket accommodates (i) the core SpT motif, (ii) the N-terminal hydrophobic residue, (iii) glycerol, and (iv) a network of contacting water molecules. A combination of some or all of these four elements could be potentially used for targeted drug design. Better understanding of the PBD interaction as well as further isolation and development of PBD-binding agents would greatly facilitate the discovery of a new class of Plk1-specific anti-cancer therapeutic agents.

Figures 2, 10A:
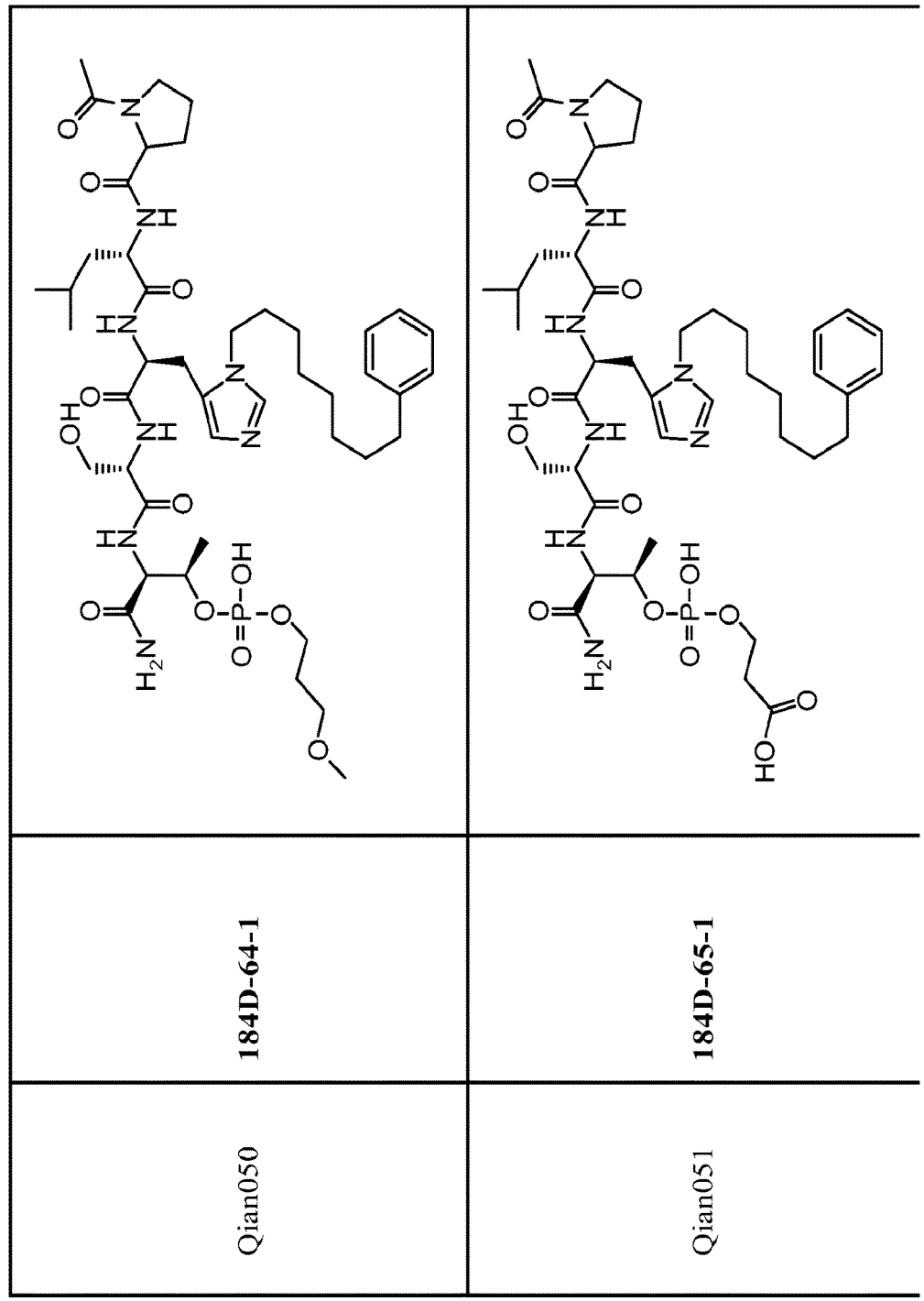
Figures 3, 10A:
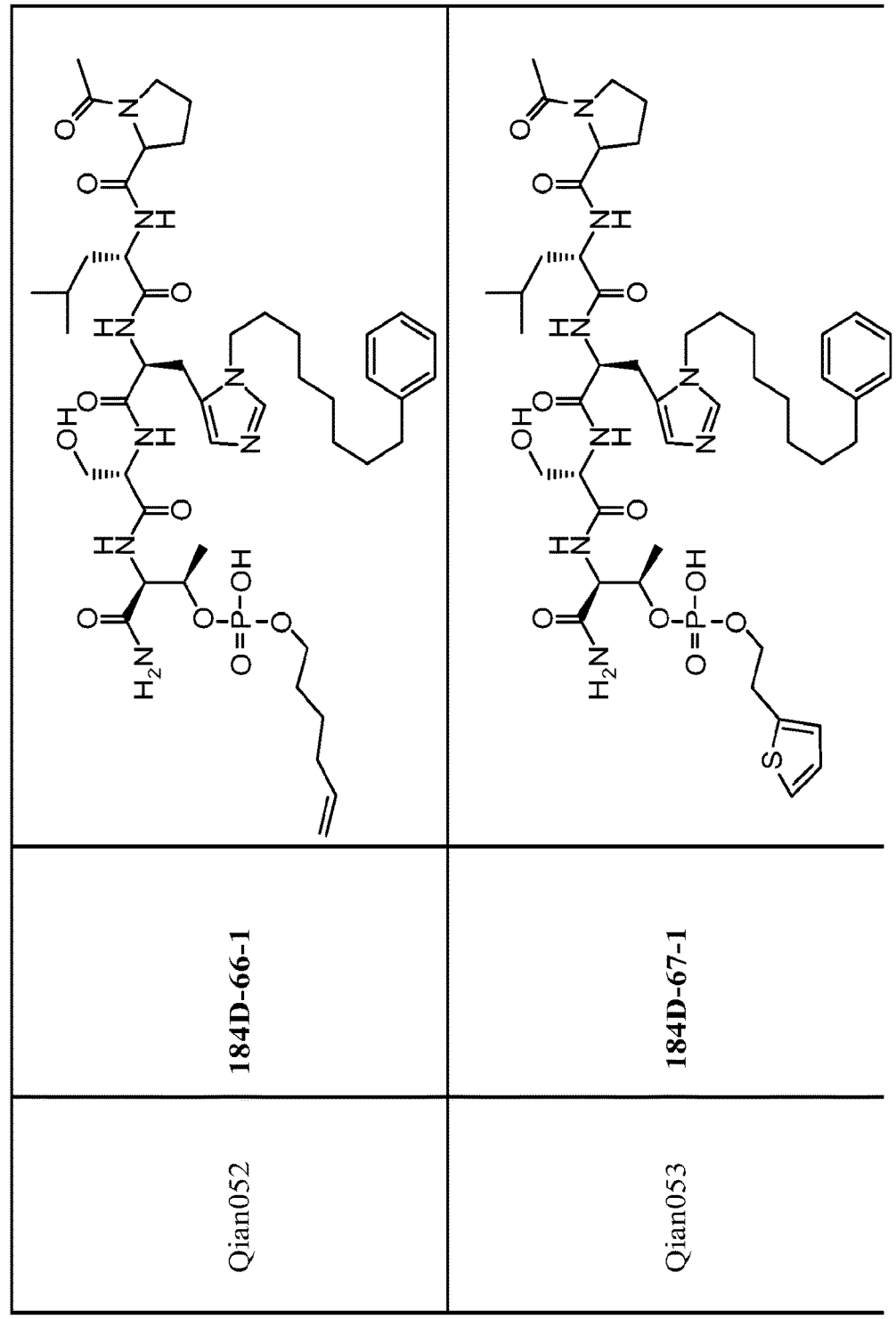
Figures 4, 10A:
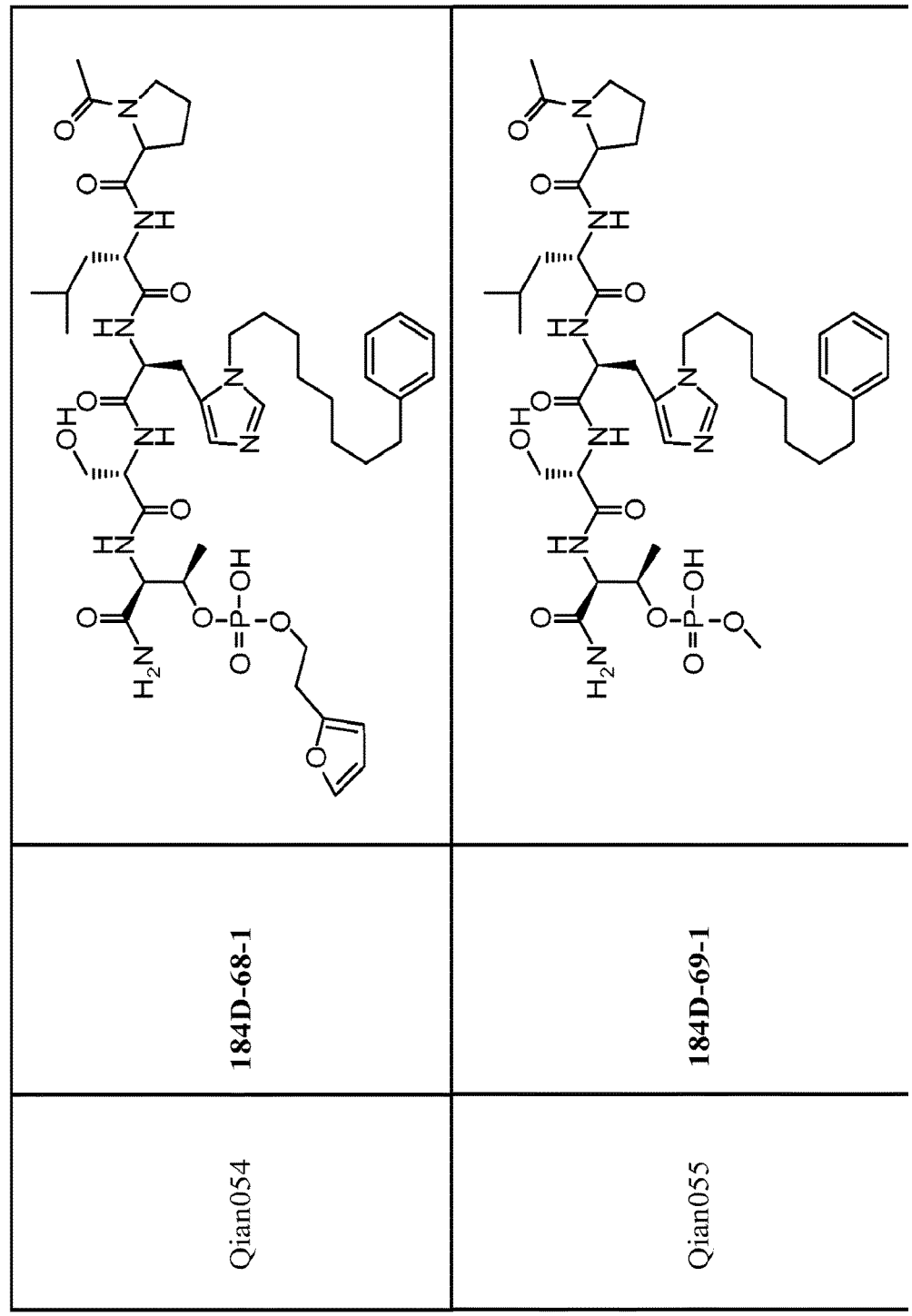
Figures 5, 10A:
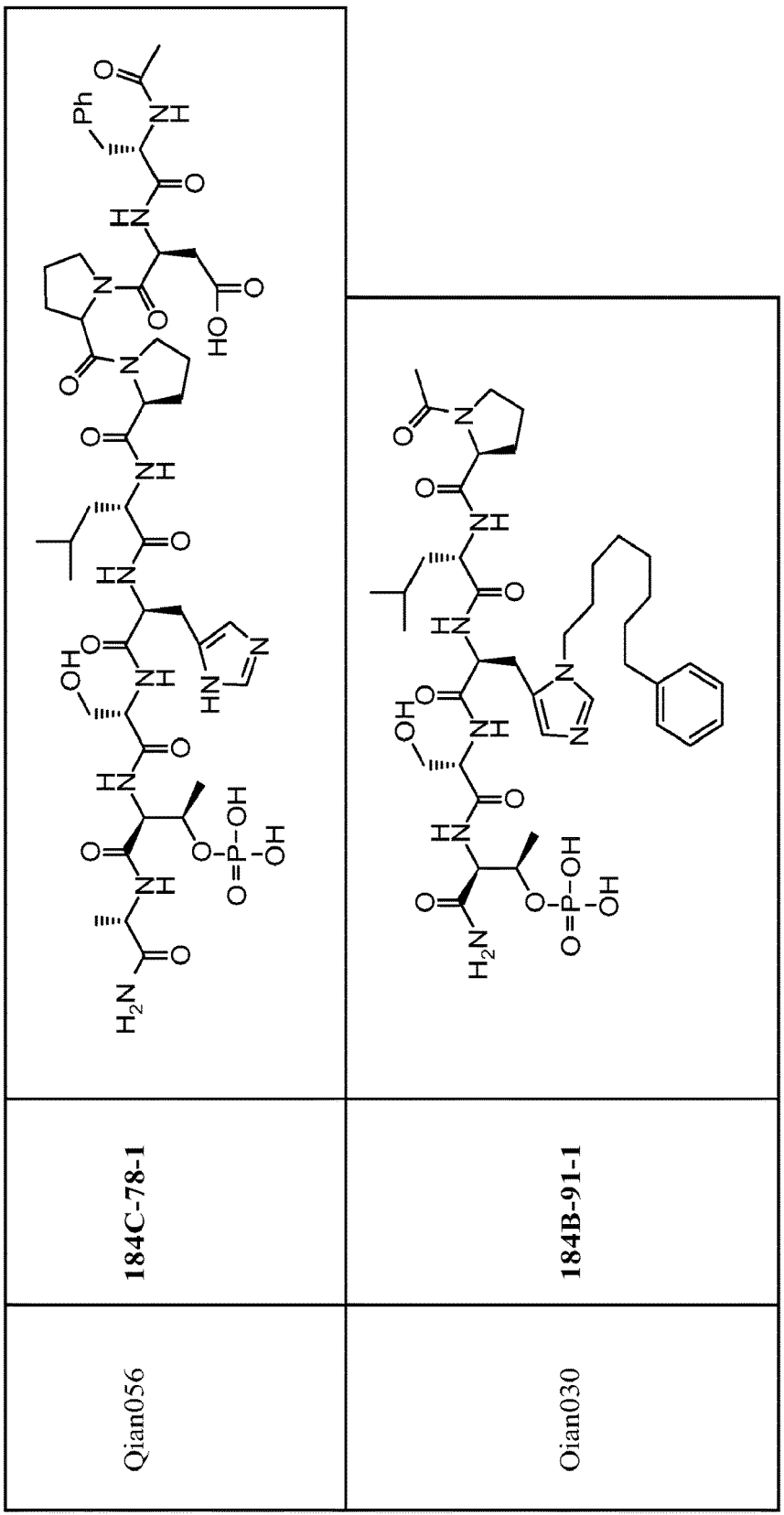
Figure 10B:
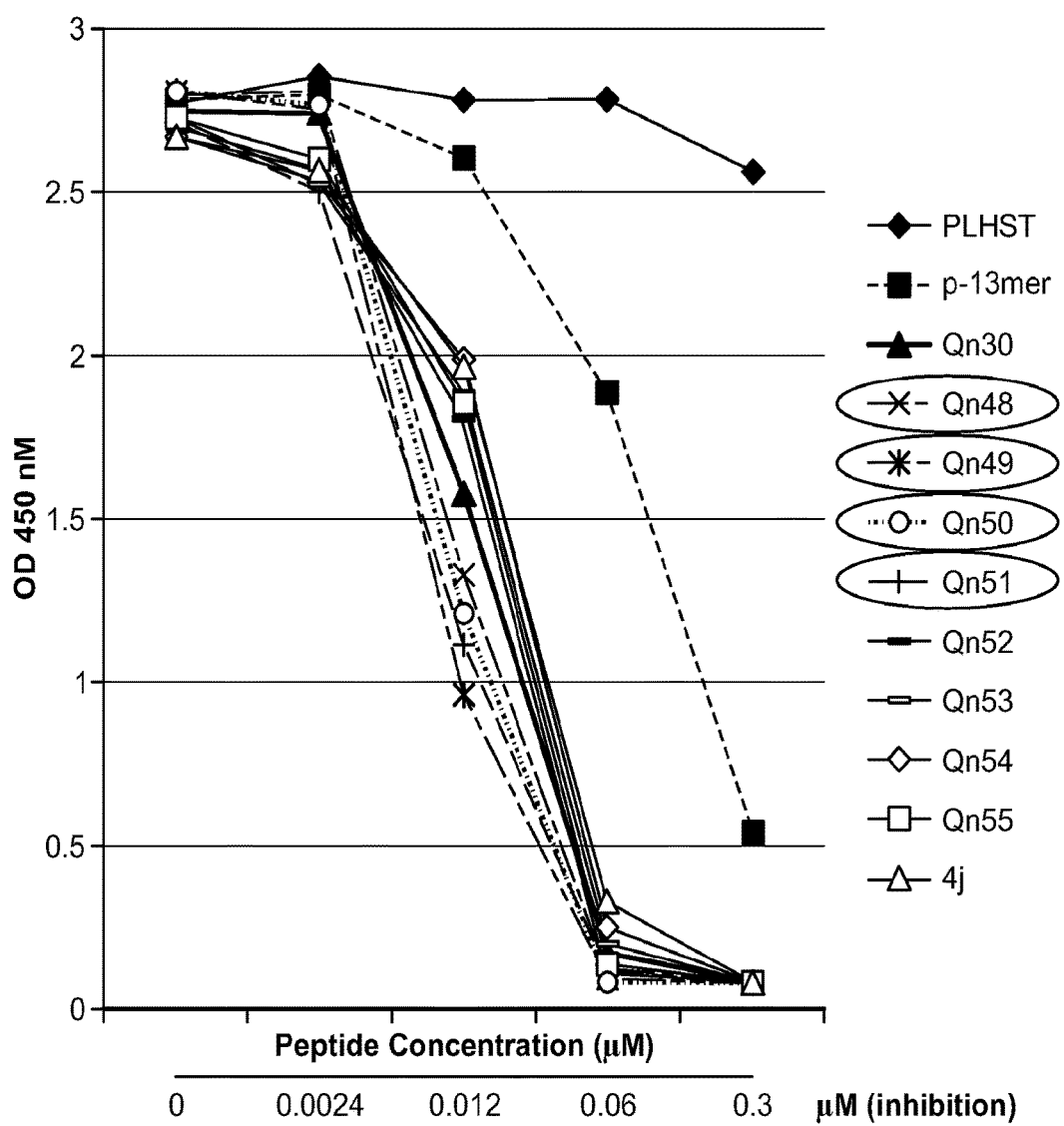
Figures 2, 11A:
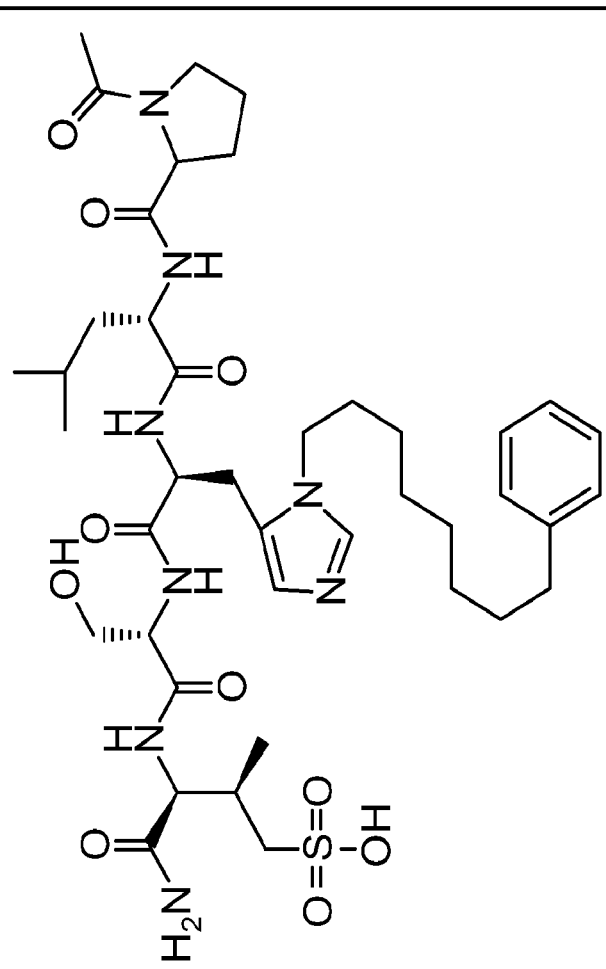
FIG. 11. A. Structures of pThr mimetics and peptides; B. Preliminary Plk1 binding data from an ELISA-based assay.
Figures 3, 11A:
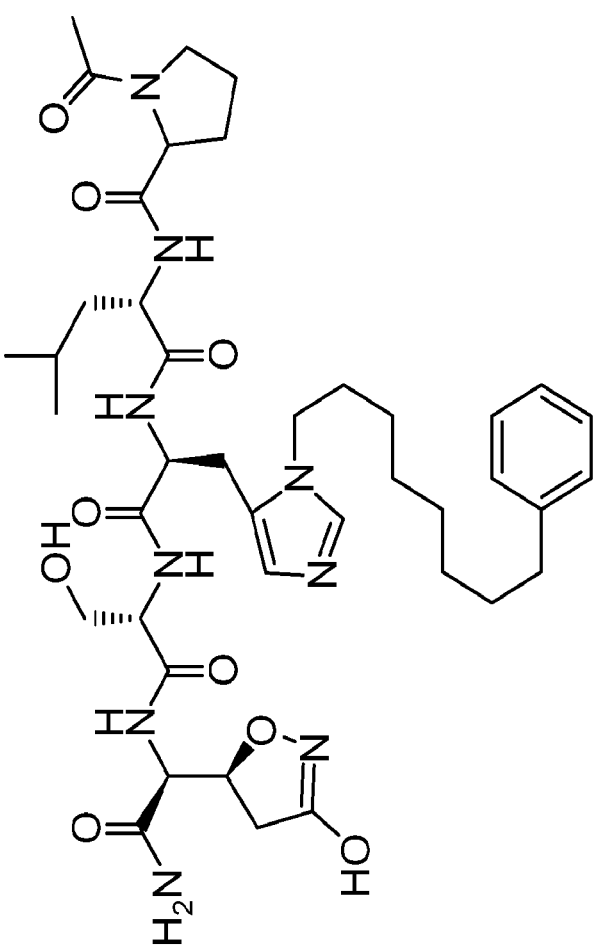
Figures 4, 11A:
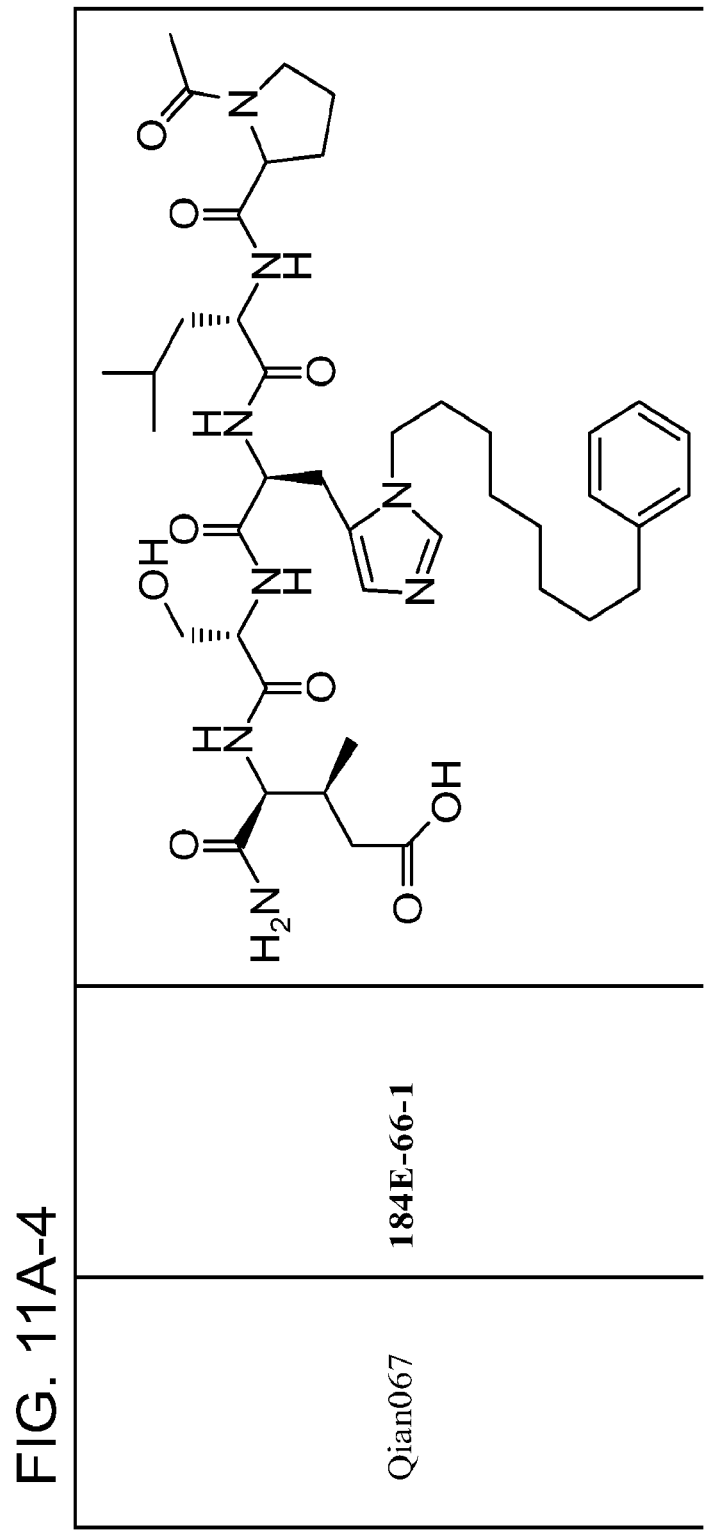
Figures 5, 11A:
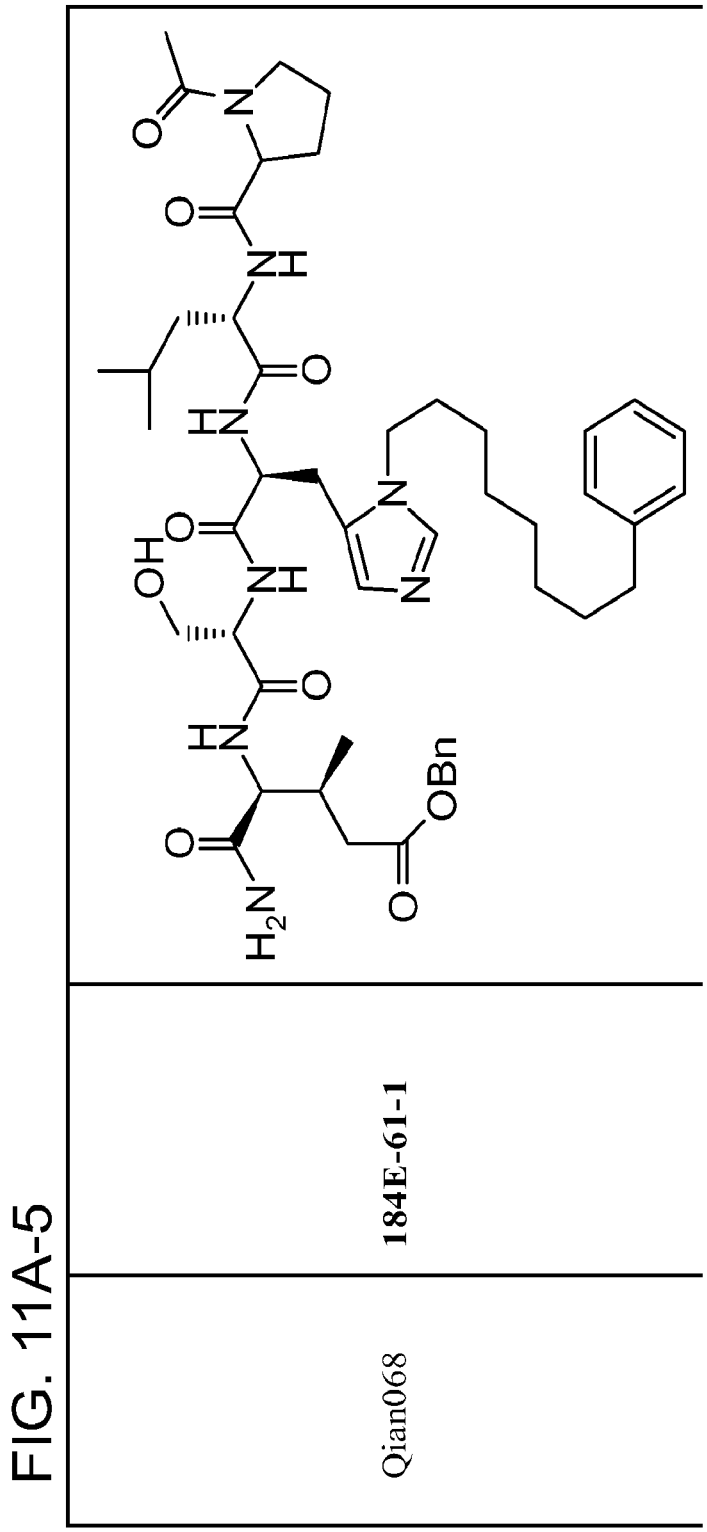
Figures 7, 11A:
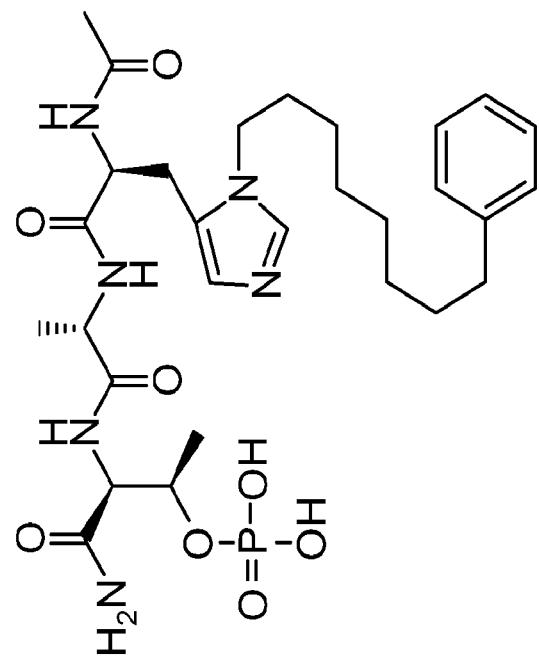
Figures 8, 11A:
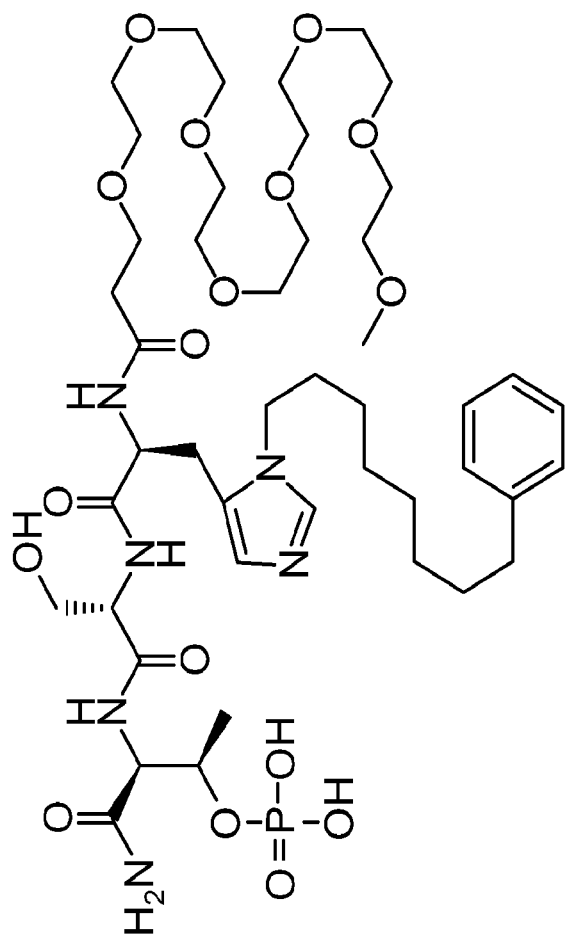
Figures 9, 11A:
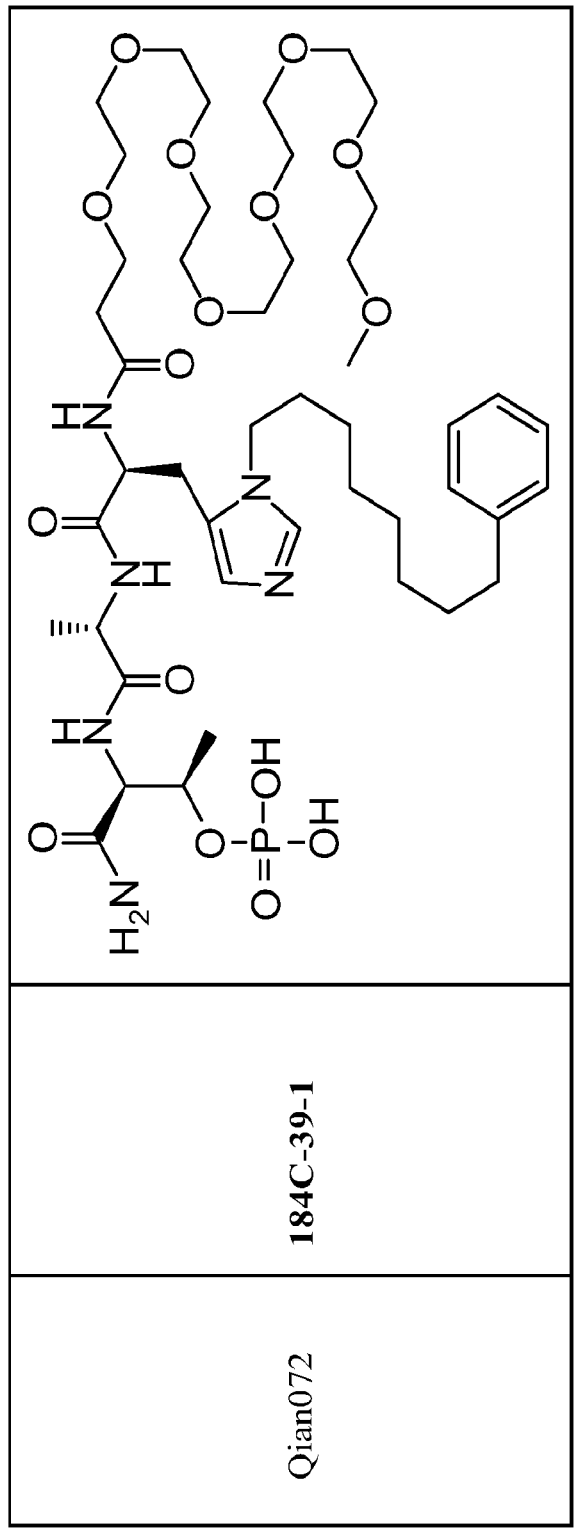
Figure 11B:
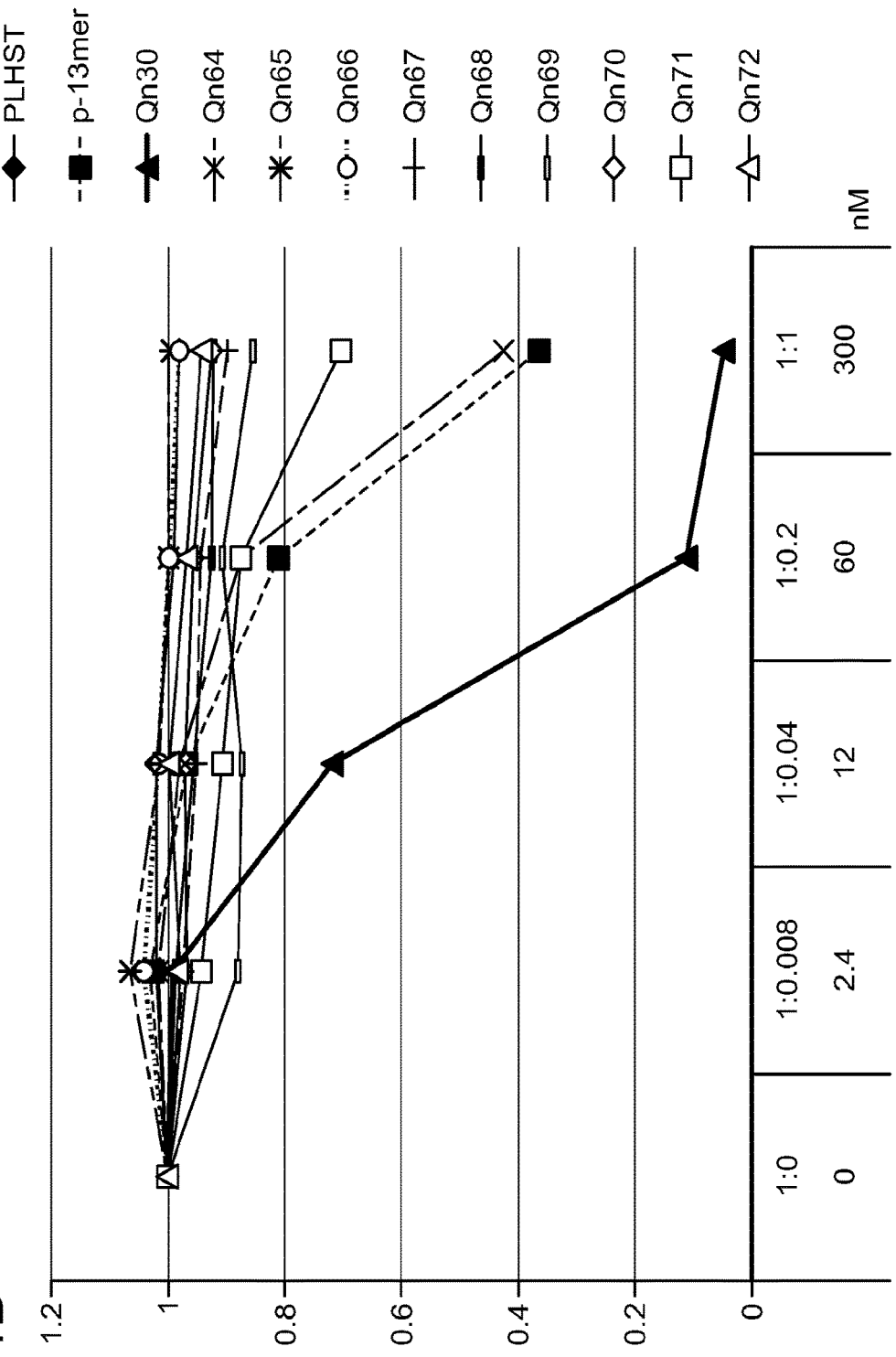

To unambiguously identify the site of the histidine alkylation and to understand the basis for the high binding affinity of Compound 4j:

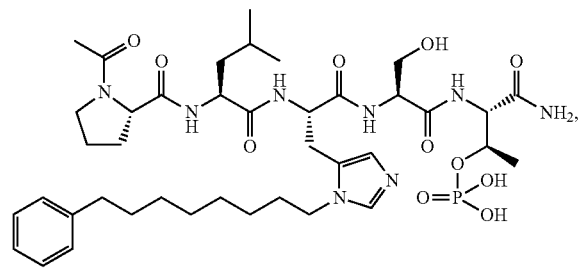 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)O]

the co-crystal structure of Plk1 PBD in complex with Compound 4j was solved (see FIG. 3).

This structure confirmed the earlier tandem MS results, showing that alkylation had occurred on the histidine residue. It also showed that the $C_6H_5(CH_2)_8$— group was attached to the $\delta^1$ nitrogen (N3) on the imidazole ring.

Figure 3A:
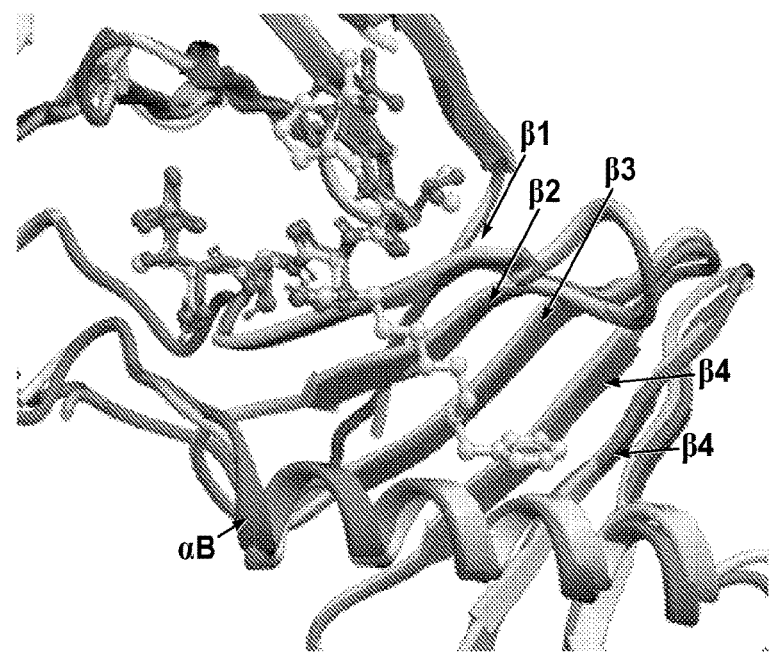
FIG. 3a-e. X-ray co-crystal structures of Plk1 PBD complexed with peptides 1 and 4j. (a) PBD in complex with 1 (PBD 3HIK; protein backbone and peptide shown) superimposed on the complex with 4j (protein backbone with peptide 4j). (b) The PBD•4j complex showing key protein residues (rendered as sticks) that interact with the His-$C_8H_{16}$-phenyl group. Hydrophobic contact regions of residue side chains are shaded, with the strength of interact indicated by stick thickness. (c) Comparison of PBD in complex with 1 and 4j for residues indicated in (b). $\Delta(\kappa_2)$ values are shown for residues Y417 and Y481, which undergo significant movement. The protein backbone is from the PBD•1 complex. (d, e) Electrostatic surfaces PBD in complex with 1 (d) and 4j (e) with coloring based on an arbitrary electrostatic potential scale. Graphics were generated using ICM Chemist Pro by Molsoft, Inc.
Figure 3B:
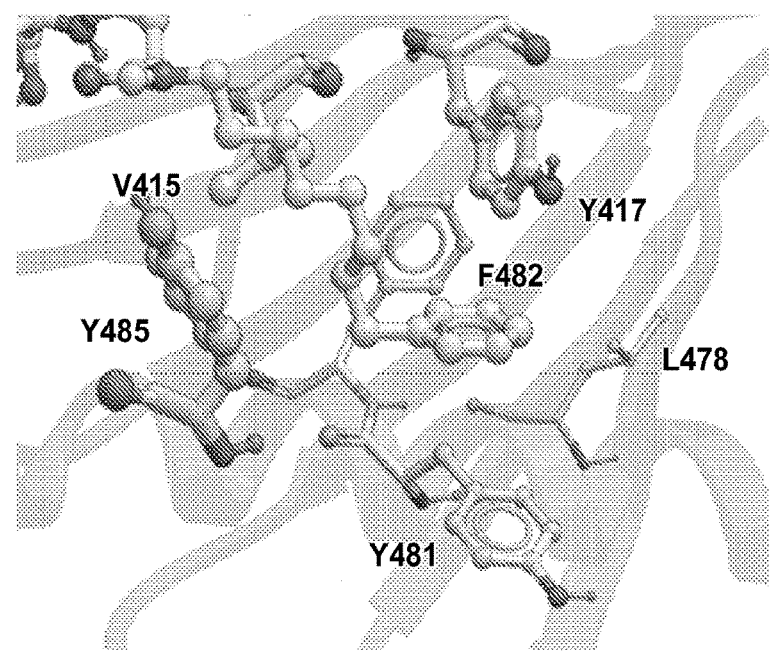
Figure 3C:
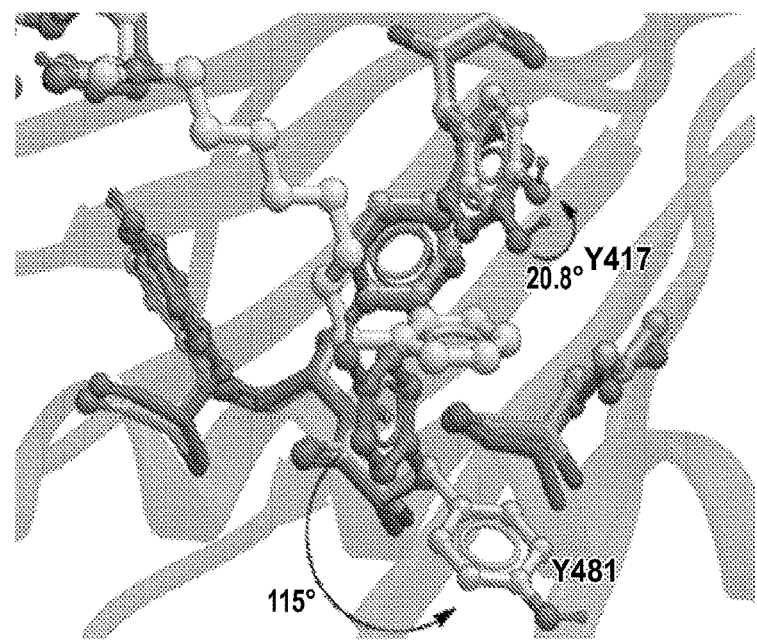
Figure 3D:
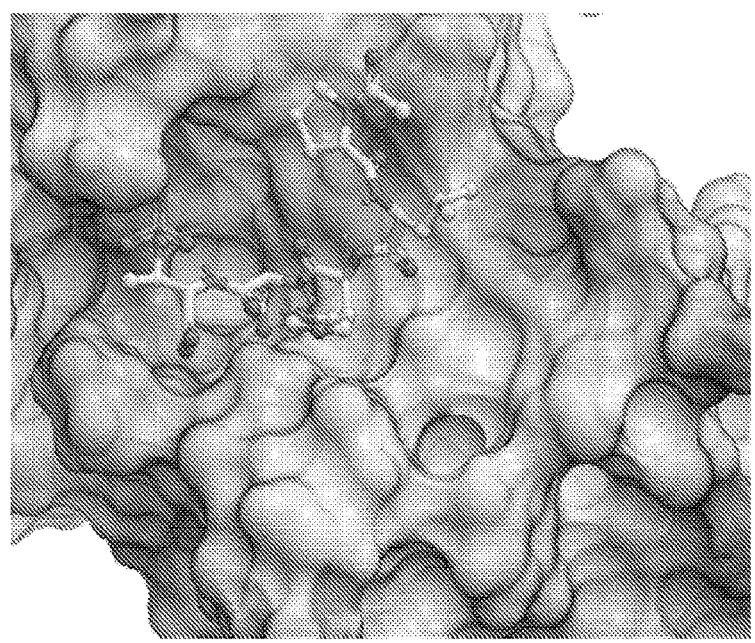
Figure 3E:
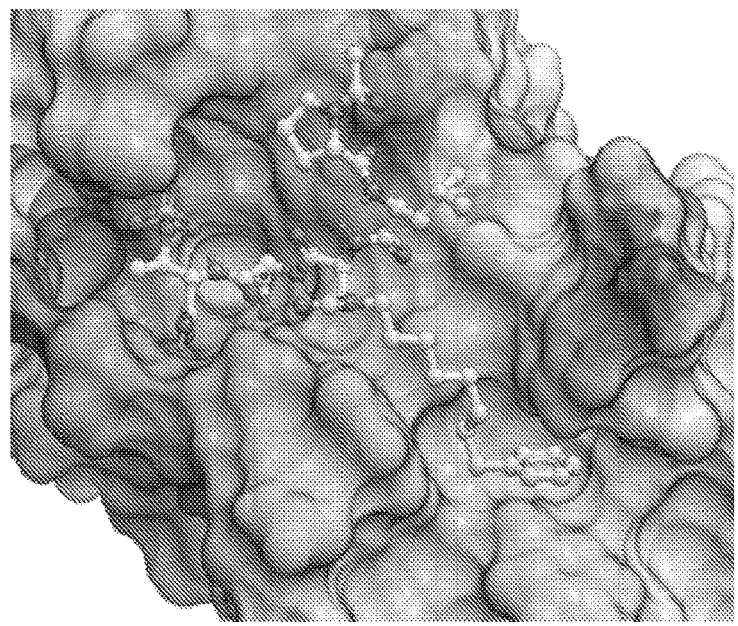

The PBD backbone in the PBD·4j complex was shown to be nearly superimposable with the backbone of the Plk1 PBD complexed to Compound 1 (PDB ID: 3HIK) (Yun et al., Nat. Struct. Mol. Biol. 16, 876-882 (2009)) (Differences in protein backbone occurred mainly in portions of the αβ helix. The binding orientation of the bound peptide 4j is also nearly superimposable with 1 in the 3HIK structure (see FIG. 3a). Differences in the two structures arise primarily from the binding of the $C_6H_5(CH_2)_8$— group of 4j, where the polymethylene chain extends from the histidyl imidazole ring and transverses laterally across a series of antiparallel β-sheets (β1-β4) of the PBD1 unit. Binding interactions occur in a well-formed hydrophobic channel whose floor is comprised proximally by V415 (arising from the β1 sheet) and distally by F482 (arising from the αβ helix) and whose opposing walls are defined by Y417 (arising from the β1 sheet) and Y485 (arising from the αβ helix). The terminus of the channel is formed by L478 and Y481 (arising from the αβ helix) (FIG. 3b). Formation of this binding channel required very little movement in the side chain orientations Y485 and F482 relative to the parent 3HIK structure and more pronounced, yet still modest movement in the side chain of Y417 (a change in $\kappa_3$ angle of 20.8°). However, the most dramatic movement occurred in the orientation of the Y481 aryl ring, which rotated downward by 1150 from a $\kappa_2$ angle of 44.5° in 3HIK to $\kappa_2$=159.50 in the 4j complex (FIG. 3c). This movement had profound effects on the topology of the protein surface, resulting in the revelation of a new binding channel, which had previously been occluded (compare FIGS. 3d and 3e). The formation of this hydrophobic channel was completely unanticipated based on previous crystal structures of peptide-ligated PBD.

It was found that microinjection of the Pmab-containing peptide 1* (structure shown below) into HeLa cells interferes with proper subcellular localization of Plk1 and induces apoptotic cell death as a result of prolonged mitotic arrest (Yun et al., Nat. Struct. Mol. Biol. 16, 876-882 (2009); and Seong et al. J. Biol. Chem. 277, 32282-32293 (2002)). However, direct incubation of 1* with cultured HeLa cells at up to 200 μM concentration failed to elicit a detectable cellular response (data not shown). This failure was potentially due to limited intracellular bioavailability arising from poor solubility and low membrane transport.

Figure 4A:
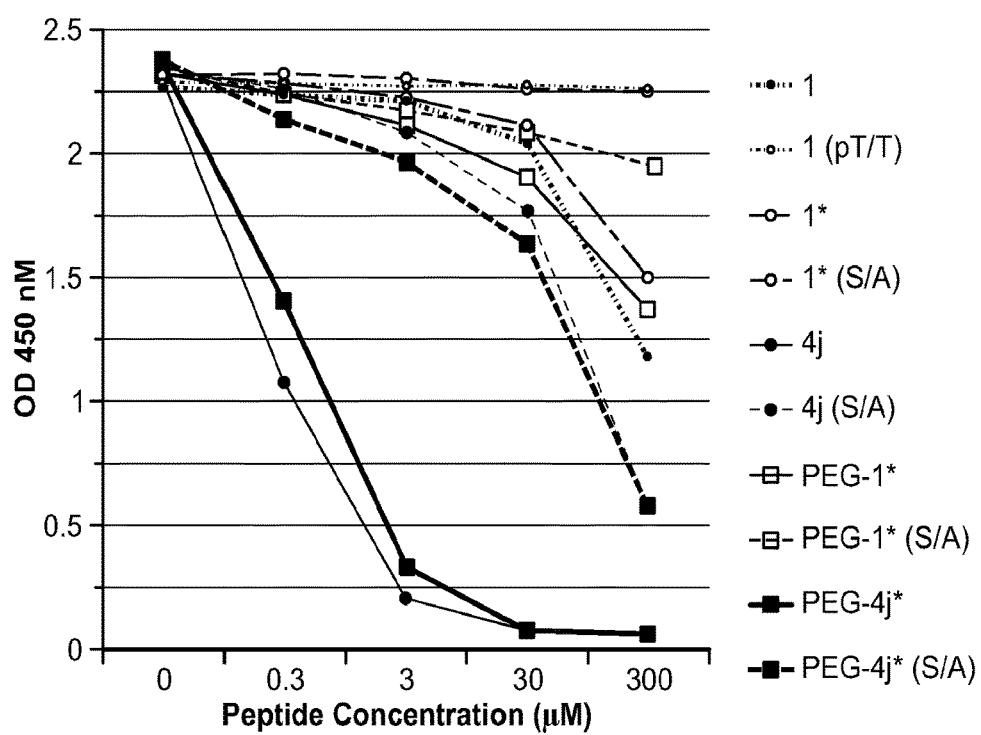
FIG. 4a-g. Specific inhibition of the function of Plk1 PBD by membrane-permeable PEG-4j*. (a) Inhibition of Plk1 PBD binding by the indicated peptides. (b) Mitotic 293A cell lysates expressing kinase-inactive Flag-Plk1 (K82M), Flag-Plk2 (K108M), or Flag-Plk3 (K52R) were mixed and then incubated with the indicated compounds cross-linked to the beads through an N-terminal Cys residue [for PEG-4j* and PEG-4j* (S/A)] or Cys-$(CH_2)_6$—CO linker [for 1, PLHST (SEQ ID NO: 11), 4j, and 4j (S/A)]. Precipitates were separated by 8% SDS-PAGE, immunoblotted with anti-Flag antibody, and stained with Coomassie (CBB). Numbers indicate the relative amounts of precipitated proteins.

Both the non-PEGylated (1* and 4j) and PEGylated forms (PEG-1* and PEG-4j*, respectively) exhibited similar levels of PBD-binding affinities in in vitro PBD inhibition assays (FIG. 4a). In certain embodiments, the PEGylated peptides of the invention have demonstrated activities in whole cell systems.

N-terminal PEGylation of short (5-mer) peptides did not deleteriously affect PBD-binding affinity, and that PEGylated peptides exhibited enhanced activity when given to cells in culture.

Polo-like kinases (Plks) are a conserved subfamily of Ser/Thr protein kinases that play pivotal roles in cell proliferation. Since Plk1 overexpression is closely associated with oncogenesis, Plk1 is considered an attractive target for anti-cancer therapy. The polo-box domain (PBD) uniquely found in the C-terminal non-catalytic region of Plks forms a phosphoepitope-binding module for protein-protein interaction. Provided herein is the identification of minimal phosphopeptides that specifically interacted with the PBD of Plk1, but not the two closely-related Plk2 and Plk3, with a high affinity. Comparative binding studies and analyses of the crystal structures of the Plk1 PBD in complex with a minimal phosphopeptide (PLHSpT (SEQ ID NO: 1)) or its derivative PPHSpT (SEQ ID NO: 2), LHSpTA (SEQ ID NO: 3), or no peptide revealed that the C-terminal SpT dipeptide functions as a high affinity anchor, whereas the N-terminal PLH residues are critical for providing both specificity and affinity to the PBD. Testing of minimal phospho-Thr mimetic peptides demonstrated that inhibition of the PBD of Plk1 is sufficient to induce mitotic arrest and apoptotic cell death. Thus, the mode of PLHSpT (SEQ ID NO: 1) binding to the PBD may provide an important template for designing anti-Plk1 therapeutic agents.

Also provided herein are high affinity analogues bearing non-natural amino acids as well as peptide-peptoid hybrids (containing N-alkylglycine residues).

Further provided herein are methods for the generation of stereoselective synthesis of protected phosphonate-based pThr mimetics and their application in the preparation of phosphatase-stable variants of these peptides.

The compositions and methods provided herein represent new approaches to the design and synthesis of PBD-binding antagonists that can lead to the development of further therapeutically relevant PBD-directed agents.

Overexpression of Plk1 induces neoplastic transformation of human cells, whereas interference with Plk1 function induces apoptosis in tumor cells but not in normal cells. Moreover, Plk1 overexpression is associated with aggressive disease stage and poor patient survival in various types of cancers. Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1. However, largely because of the structural similarities among the catalytic domains of all Plks and other related kinases, it has been difficult to generate Plk1-specific inhibitors. Thus, since the non-catalytic PBD is found only in the members of the Plk subfamily, development of novel inhibitors that target the PBD of Plk1 may prove to be an alternative strategy for selectively targeting Plk1.

While conducting studies on the interaction between Plk1 and its physiological binding target PBIP1, we identified a minimal phosphopeptide derived from the Thr78 region of PBIP1 that exhibits a high level of affinity and specificity for the Plk1 PBD. Testing of a non-hydrolyzable p-T78 mimetic peptide demonstrates that inhibition of the Plk1 PBD function results in a chromosome congression defect that leads to mitotic arrest and apoptotic cell death, as observed previously in cells expressing a dominant-negative PBD. Since interference with Plk1 function induces apoptosis in most tumor cells but not in normal cells, these findings suggest that inhibition of the PBD function is sufficient to interfere with cell proliferation activity of tumor cells. Furthermore, our results shown here directly provide the proof-of-principle that specific inhibition of Plk1 PBD is achievable by a small mimetic peptide or its relevant compounds.

It has been demonstrated that SpT-dependent electrostatic interactions with His538 and Lys540 residues are critical for the interaction between optimal peptides (PMQSpTPL (SEQ ID NO: 4) and MQSpTPL (SEQ ID NO: 5)) and the Plk1 PBD12,13. Comparative in vitro binding studies and analyses of the phosphopeptide-binding pockets of PBDS+G and PBDS with PBDPL, PBDPP, and PBDLH revealed that, in addition to the SpT motif of the phosphopeptide that acts as a high affinity anchor, the N-terminal residues provide additional binding affinity and specificity to the Plk1 PBD through three distinct interactions. First, the polar contact between the carbonyl oxygen N-terminal to the Leu-3 of PLHSpT (SEQ ID NO: 1) or LHSpTA (SEQ ID NO: 3) and the guanidinium moiety of Arg516 of Plk1 PBD provides a molecular basis for a high affinity and specificity interaction. Second, docking of the N-terminal Pro-4 side chain into the pocket generated by the surrounding Trp414 and Phe535 offers additional affinity and likely another level of specificity to the interaction. Notably, the PBDs from both Plk2 and Plk3 possess Lys and Tyr residues at positions analogous to the Plk1 Arg516 and Phe535 residues, respectively, in Plk1, and, as a consequence, may fail to generate as favorable an environment to accommodate the N-terminal Pro residue. Third, peptide pull-down assays demonstrate that the His-2 residue adds another layer of Plk1 PBD specificity, although the underlying mechanism is not clearly understood at present.

Besides each amino acid residue of the p-T78 peptide involved in defining the Plk1 binding affinity and specificity, the positions of the phosphopeptide and glycerol in the pocket, along with the network of water molecules that mediate contacts between the phosphopeptide and the PBD, suggest that both the glycerol and the network of water molecules surrounding the phosphopeptide could be important elements of the PBD recognition by phosphopeptides. Furthermore, the structures of the PBDS+$^G$, PBD$^S$, and PBD$^{PL}$ were remarkably similar, hinting that the other glycerol molecule and the sulfate anion occupying the phosphopeptide-binding cleft may substitute the role of the SpT dipeptide.

The results provided herein demonstrate that the Plk1 PBD-binding pocket accommodates (i) the core SpT motif, (ii) the N-terminal hydrophobic residue, (iii) glycerol, and (iv) a network of contacting water molecules. A combination of some or all of these four elements could be potentially used for targeted drug design. Better understanding of the PBD interaction as well as further isolation and development of PBD-binding agents would greatly facilitate the discovery of a new class of Plk1-specific anti-cancer therapeutic agents.

In another aspect, methods are provided for preparing peptide derivatives, wherein said method comprises using an orthogonally-protected N-alkyl histidine analogue as an intermediate. In certain embodiments, the orthogonally-protected N-alkyl histidine analogue is a compound of the following structure:

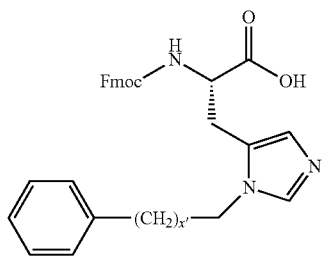

wherein x' is 0 or an integer selected from 1-20. It is believed that the use of the above orthogonally-protected N-alkyl histidine analogues in the synthetic schemes will result the final products (i.e., the peptide derivatives) in much higher yields.

Compositions, Methods, And Kits

The invention provides compositions including any of the compounds of the invention in a pharmaceutically acceptable carrier, for use, for example, for the preparation of a medicament. The medicament can be, for example, a medicament for the prevention, amelioration, or treatment of a hyperproliferative disorder such as cancer.

In still other embodiments, such compositions are labeled for the treatment of a hyperproliferative disorder such as cancer. In a further embodiment, the effective amount is effective to treat or prevent a hyperproliferative disorder such as cancer in a subject, as described herein.

In certain embodiments, the compounds of the invention can be used in methods for the prevention, amelioration, or treatment of a subject for a hyperproliferative disorder. Such methods can further include identification of a subject suffering from or suspected of suffering from a hyperproliferative disorder and/or monitoring the subject for prevention, amelioration, or treatment of a hyperproliferative disorder. In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

The compounds of the invention can also be used in methods for the prevention, amelioration, or treatment of a subject for acquired immunodeficiency syndrome (AIDS). In certain embodiments, the compounds of the invention can be tagged with a HIV Tat-sequence for inhibition of HIV budding.

In another aspect, the invention provides a method for preparing peptide derivatives, wherein said method comprises using an orthogonally-protected N-alkyl histidine analogue as an intermediate. In certain embodiments, the orthogonally-protected N-alkyl histidine analogue is a compound of the following structure:

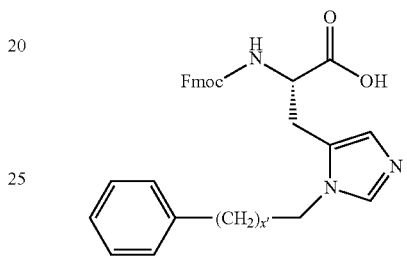

wherein x' is 0 or an integer selected from 1-20.

In an embodiment, the compound is administered to the subject using a pharmaceutically-acceptable formulation. In certain embodiments, these pharmaceutical compositions are suitable for oral or parenteral administration to a subject. In still other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. In certain embodiments, the subject is a mammal, e.g., a primate, e.g., a human.

The methods of the invention further include administering to a subject a therapeutically effective amount of a compound in combination with a pharmaceutically acceptable excipient. The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association a compound(s) with the carrier and, optionally, one or more accessory ingredients. In general, the formulations are prepared by uniformly and intimately bringing into association a compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants, such as wetting agents, emulsifying and suspending agents, sweetening, flavoring, coloring, perfuming and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound(s) include powders, sprays, ointments, pastes, creams, lotions, gels, solutions, patches and inhalants. The active compound(s) may be mixed under sterile conditions with a pharmaceutically-acceptable carrier, and with any preservatives, buffers, or propellants which may be required.

The ointments, pastes, creams and gels may contain, in addition to compound(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Transdermal patches have the added advantage of providing controlled delivery of a compound(s) to the body.

Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) in biodegradable polymers, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic to the patient. An exemplary dose range is from about 0.1 g to 20 milligram per kilogram of body weight per day (mg/kg/day) (e.g., 0.1 g/kg to 2 mg/kg, 0.3-3 µg/kg, 0.18-0.54 mg/kg). In other embodiments, the amount varies from about 0.1 mg/kg/day to about 100 mg/kg/day. In still other embodiments, the amount varies from about 0.001 µg to about 100 µg/kg (e.g., of body weight). Ranges intermediate to the above-recited values are also intended to be part of the invention.

The invention also provides methods including identification of a subject suffering from or suspected of suffering from a hyperproliferative disorder and/or monitoring the subject for prevention, amelioration, or treatment of a hyperproliferative disorder.

The invention provides kits for the treatment or prevention of a hyperproliferative disorder such as cancer. The kits contain at least one compound of the inventions and instructions for use. In one embodiment, the kit includes a therapeutic or prophylactic composition containing an effective amount of a compound of the invention in unit dosage form. The invention also provides kits having 2, 3, 4, 5, 6, 7, 8, 9, or 10 compounds of the invention.

As used herein, "kits" are generally understood to contain at least the non-standard laboratory reagents for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

In some embodiments, a compound of the invention is provided in combination with a conventional therapeutic agent. In other embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a compound of the invention is provided together with instructions for administering the compound to a subject having or at risk of developing neoplasia. The instructions will generally include information about the use of the composition for the treatment or prevention of neoplasia. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention further provides libraries including at least two compounds of the invention. "Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

Any compositions or methods provided herein can be combined with one or more of any of the other compositions and methods provided herein.

The practice of the present invention employs, unless otherwise indicated, conventional techniques that are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). Particularly useful techniques for particular embodiments will be discussed in the sections that follow.

In the Examples, the compound numbers refer to the compounds described in the Example. Efforts have been made to provide cross references to the same compound in other examples labeled with a different reference number.

The following non-limiting examples are illustrative of the invention.

EXAMPLES

I. Synthesis and Chemical Analysis of the Compounds of the Invention

A. Synthesis and Preparation

Compounds of the invention can be synthesized and/or prepared by methods described in this section, the examples, and the chemical literature.

1. General Procedures:

General.

All experiments involving moisture-sensitive compounds were conducted under dry conditions (positive argon pressure) using standard syringe, cannula, and septa apparatus. Solvents: All solvents were purchased anhydrous (Aldrich) and used directly.

HPLC-grade hexanes, EtOAc, CH2Cl2, and MeOH were used in chromatography. TLC: analytical TLC was performed on Analtech precoated plates (Uniplate, silica gel GHLF, 250 microns) containing a fluorescence indicator; NMR spectra were recorded using a Varian Inova 400 MHz spectrometer. The coupling constants are reported in Hertz, and the peak shifts are reported in the $\delta$ (ppm) scale. Low resolution mass spectra (ESI) was measured with Agilent 1200 LC/MSD-SL system, and high resolution mass spectra (ESI or APCI) was measured by UCR Mass Spectrometry Facility, Department of Chemistry, University of California, 3401 Watkins Dr., Riverside Calif., 92521. Optical rotations were measured on a Jasco P-1010 polarimeter at 589 nm. IR spectra were obtained neat with a Jasco FT-IR/615 spectrometer.

A) Solid-Phase Peptide Synthesis

Fmoc-Thr(PO(OBzl)OH)—OH and other Fmoc protected amino acids were purchased from Novabiochem. Peptides were synthesized on NovaSynTGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-diisopropylethylamine (DIPEA) (10.0 eq.) were used as coupling reagents. Amino terminal acetylation was achieved using 1-acetylimidazole. Finished resins were washed with N,N-dimethylforamide (DMF), methanol, dichloromethane and diethyl ether and then dried under vacuum (overnight). For the synthesis of Pmab-containing peptides, (2S,3R)-4-[di-(tert-butyl)-oxyphosphinyl]-N-Fmoc-L-valine was used in place Fmoc-Thr(PO(OBzl)OH)—OH (Liu, F. et al., *Tetrahedron* 65, 9673-9679 (2009)).

B) Derivatization on Solid-Phase Using Mitsunobu Reaction Conditions

Crude peptide resins (200 mg, 0.04 mmol) were swelled in dichloromethane (15 minutes) and then treated with triphenylphosphine (262 mg, 1.0 mmol), diethyl azidodicarboxylate (DEAD) (0.46 mL, 40% solution in toluene, 1.0 mol) and alcohols (for example, alcohols a-l; see below) (1.0 mmol) in dry dichloromethane at room temperature (2 h), then washed (dichloromethane), dried under vacuum (2 h) and cleaved by treatment with trifluoroacetic acid.

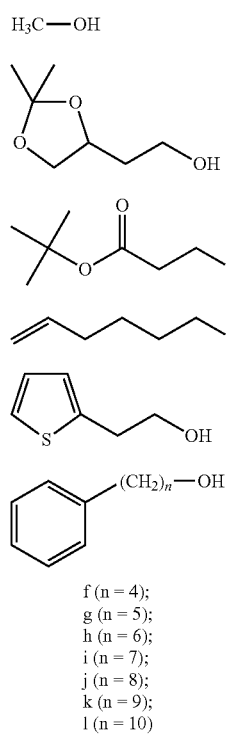

f (n = 4);
g (n = 5);
h (n = 6);
i (n = 7);
j (n = 8);
k (n = 9);
l (n = 10)

C) Peptide Cleavage and Purification

Peptide resins (200 mg) were cleaved by treatment with trifluoroacetic acid:triisbutylsilane:H$_2$O (90:5:5) (5 mL, 4 h). The resin was removed by filtrations and the filtrate was concentrated under vacuum, then peptide was precipitated by the addition of precipitated with diethyl ether and the precipitate washed with ether. The resulting solid was dissolved in 50% aqueous acetonitrile (5 mL) and purified by reverse phase preparative HPLC using a Phenomenex C$_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave the products as white powders.

D) Solid-Phase Synthesis of PEGylated Peptides

PEGylateptides were synthesized on NovaSyn® TGR resin (0.1 mmol resin was used for each peptide, Novabiochem, cat. no. 01-64-0060, loading 0.20-0.30 mmol/g) using standard Fmoc solid-phase protocols in a polypropylene column with a filter (Thermo Scientific. Cat. no. 29924, volume: 10 mL). For each coupling cycle, Fmoc protected amino acid (5.0 eq.), 1-O-Benzoriazole-N, N, N', N'-tetramethyl-uronium-hexafluoro-phosphate (HBTU) (5.0 eq.), hydroxybenzotriazole (HOBt) (5.0 eq.) and N, N-Diisopropylethylamine (DIPEA) (10 eq.) were used. Coupling proceeded for 2 hours at room temperature in N-Methyl-2-pyrrolidone (NMP, 4.0 mL), followed by DMF washing (3.0 mL×5). The resin was treated with 20% piperidine in N, N'-Dimethylformamide (4.0 mL) for 20 minutes at room temperature and washed (DMF, 3.0 mL×5) before the next coupling. The amino-terminus was acylated with m-dPEG®8-acid by reacting with HBTU (5.0 eq.), HOBt (5.0 eq.) and DIPEA (10.0 eq.) for 4 h at room temperature. The resin was washed with DMF (4.0 mL×5), methanol (4.0 mL×5), methylene chloride (4.0 mL×5) and diethyl ether (4.0 mL×5), then dried under vacuum (overnight).

E) Resin Cleavage and HPLC Purification of PEGylated Peptide Products

PEGylated peptides were cleaved from the resin (~200 mg) by treatment with trifluoroacetic acid:triisopropylsilane: H$_2$O (4.0 mL, 0.1 mL, 0.1 mL) for 4 hours at room temperature. The resin was removed by filtration and the filtrate was concentrated under vacuum, then precipitated with diethyl ether (5.0 mL), and the precipitate was washed with diethyl ether (5 mL×3). The resulting solid was dissolved in 50% aqueous acetonitrile (5 mL) and purified by reverse phase preparative HPLC using a Phenomenex C$_{18}$ column (21 mm dia×250 mm, cat. no: 00G-4436-P0). Lyophilization gave products as white powders.

F) X-ray Crystallography

Protein Purification and Crystallization.

Plk1 PBD protein (residues 371-603) was purified as previously described (Yun, S.-M. et al. *Nat. Struct. Mol. Biol.* 16, 876-882 (2009)). Crystals were grown using the hanging drop vapor diffusion method. PBD protein at 12 mg/mL in 10 mM Tris pH 8, 0.5 M NaCl, 10 mM DTT, 2% DMSO and 2 mM compound peptide 4j was mixed with an equal volume of reservoir solution consisting of 15% (w/v) PEG 3350, 0.1 M glycine pH 9, and 300 mM NaCl. Crystals appeared overnight and reached maximum size over several days.

Data Collection, and Structure Determination and Refinement.

Crystals were cryo-protected in 33.3% (w/v) PEG 3350, 500 mM NaCl, 0.1 M glycine pH 9, 2 mM peptide 4j, 2% DMSO and 10 mM DTT, and data were collected at 100 K on a Mar345 image plate detector with a Rigaku RU-300 home X-ray source. The data were processed with the HKL (Minor, W. et al. *Acta Crystallogr. D Biol. Crystallogr.* 62, 859-66 (2006)) and CCP4 software suites (*Acta Crystallogr. D Biol. Crystallogr.* 50, 760-3 (1994)). The structure was solved by molecular replacement using AmoRe (Navaza, J. *Acta Crystallogr. D Biol. Crystallogr.* 57, 1367-72 (2001)) using chain A of structure 3FVH (Yun, S.-M. et al. *Nat. Struct. Mol. Biol.* 16, 876-882 (2009)). (RCSB accession code) as a search model, and refined using PHENIX (Adams, P. D. et al. *Acta Crystallogr. D Biol. Crystallogr.* 66, 213-21) with manual fitting in XtalView (McRee, D. E. *J. Struct. Biol.* 125, 156-65 (1999)). The figure was created using Molscript (Kraulis, P. J. J. *Appl. Crystallogr.* 24, 946-950 (1991)) and PyMOL.

SUPPLEMENTARY TABLE 1

| Data Collection and Refinement Statistics | |
| --- | --- |
| PDB ID | XXXX |
| Space group | $P2_1$ |
| a (Å) | 35.3 |
| b (Å) | 51.2 |
| c (Å) | 58.0 |
| β | 101.0° |
| Resolution range (Å) | 15-1.55 |
| Average redundancy | 6.2 |
| Completeness[a] | 99.8% (98.3%) |
| $R_{sym}$[a] | 4.8 (19.7) |
| Average I/σ[a] | 31.7 (4.2) |
| R/$R_{free}$ (%) | 15.1/18.3 |

[a]Values for the highest resolution shell are shown in parentheses.

2. Synthetic Schemes And Examples

1.

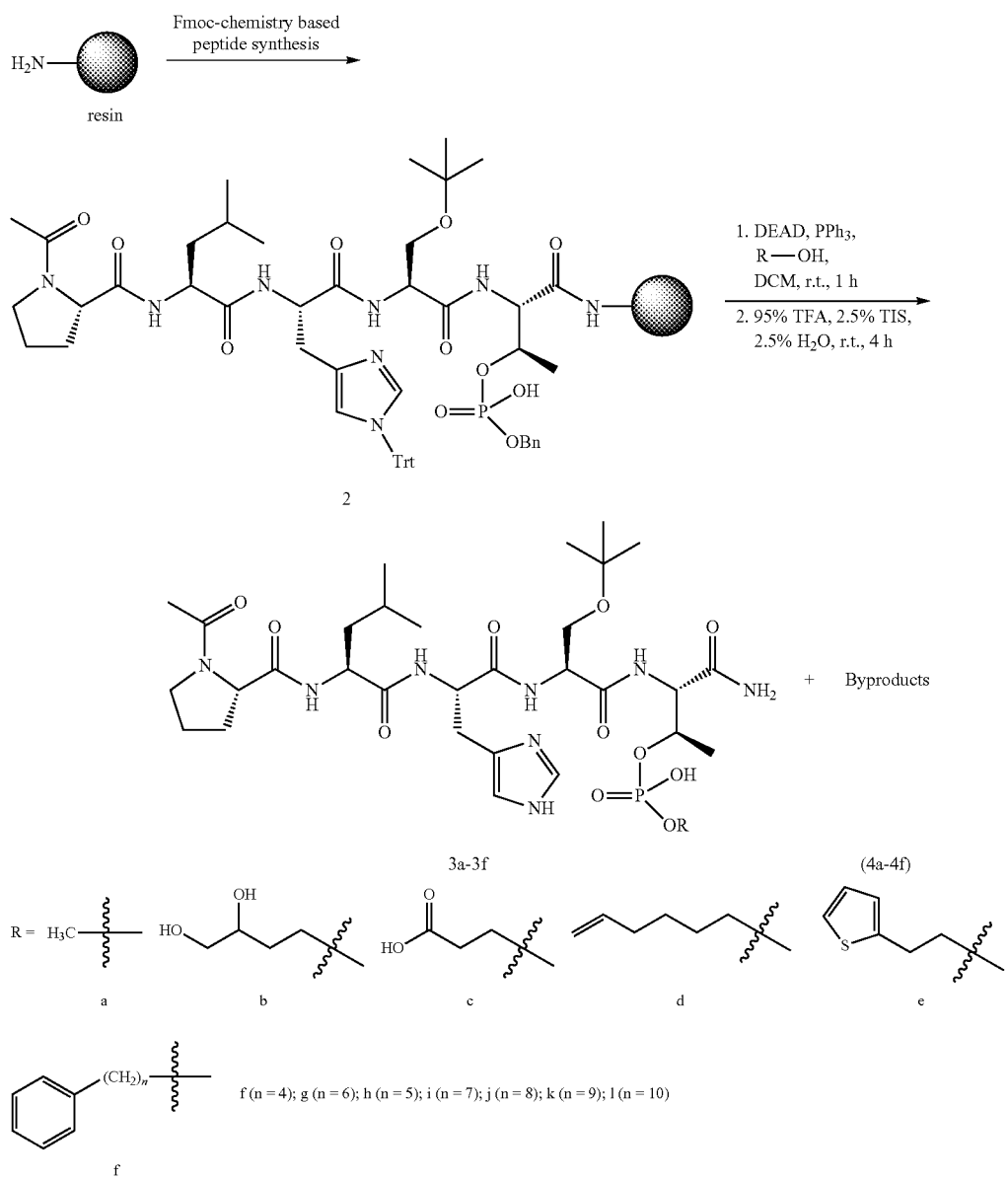

Mitsunobu coupling chemistries (Swamy et al., *Chem. Rev.* 109, 2551-2651 (2009)) were applied to precursor peptides bound to acid-sensitive solid-phase resin. These peptides bore global protection of all reactive heteroatoms, except for a single free phosphoryl hydroxyl group, which was the intended site of condensation with substrate alcohols. A variety of alcohols were employed for esterification, including short alkyl chains bearing terminal diol, carboxyl, alkenyl, thiofuranyl and phenyl substitutents (a-f, Scheme 1). Following Mitsunobu coupling, the peptides were cleaved from the resin under acidic conditions and the expected phosphodiesters (3a-3f) were obtained as the main reaction products. Unexpectedly, in each case a faster eluting (HPLC) minor byproduct of unknown structure (indicated as 4a-4f, FIG. 1) was obtained that exhibited a molecular weight identical to the expected product.

Byproduct (4f) from the first round of synthesis resulted from Mitsunobu esterification using 4-phenylbutaine-1-ol. Byproducts (4d and 4e) were also derived from alcohols having unsaturated groups tethered by alkyl chains. To explore the potential significance of this structural pattern, Mitsunobu esterification reactions were repeated using progressively longer n-alkyl-1-ols having terminal phenyl rings (g-l). As previously observed during the first round of synthesis, each expected phosphodiester product (3g-3l) was accompanied by the formation of faster eluting byproducts (indicated as 4g-4l, respectively).

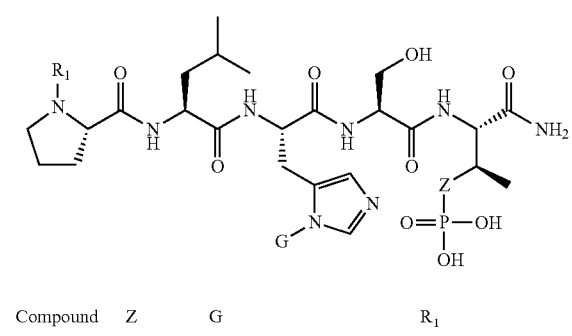

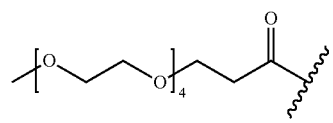

| Compound | Z | G | $R_1$ |
|---|---|---|---|
| 1 | O | H | Ac |
| 1* | $CH_2$ | H | Ac |
| (PEG)-1* | $CH_2$ | H | |
| 4j | O | Ph-$(CH_2)_8$— | Ac |
| (PEG)-4j* | $CH_2$ | Ph-$(CH_2)_8$— | |

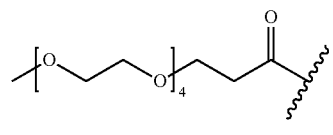

2. Synthesis of Orthogonally-Protected N-alkyl Histine-Analogues

Scheme 2

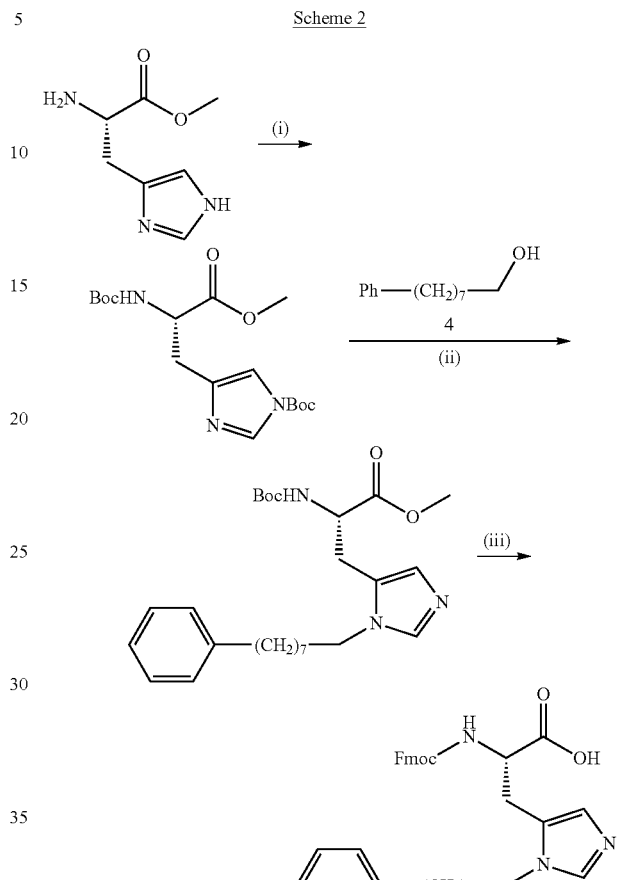

Reagents and Conditions: (i) $Et_3N$ (2.0 eq), $Boc_2O$ (2.0 eq), MeOH, room temp. 48 h (73% yield); (ii) 4 (1.1 eq), $Tf_2O$ (1.1 eq), DIPEA (1.1 eq), $CH_2Cl_2$, -75° C. to room temp., 16-18 h (60% yield); (iii) 1) $LiOH \cdot H_2O$ (2.0 eq),THF—$H_2O$ (v/v 4:1), 0° C. to room temp., 1 h; 2) 4M HCl in dioxane (10 eq), room temp., 1 h; (3)Fmoc—OSu (1.5 eq).

3. Library Synthesis

Taking advantage of the facile condensation of aminooxy functionality and carbonyl groups, aminooxy handles were incorporated into proteins consensus recognition sequences and used these for post-solid phase construction of peptide libraries bearing tethered components.

Based on the parent peptide "PLHSpT" (SEQ ID NO: 1) the amino-terminal proline was replaced by trans and cis-4-aminooxy proline 1 and 2 to provide the aminooxy-containing peptides 4 and 5. This approach allowed library diversification at this residue with maintenance of the parent proline pyrrolidine ring system as shown.

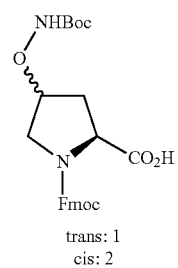

trans: 1
cis: 2

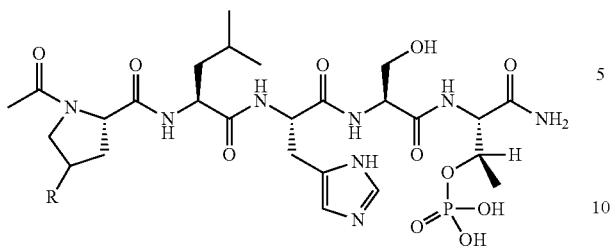

R = 2H, 3
R = trans-aminooxy-Pro, 4
R = cis-4-aminooxy-Pro, 5

Structure of protected 4-aminooxy prolines (1 and 2) and peptide products 4 and 5.

To rapidly explore a wide range of replacement functionality at the C-terminal position, the aminooxy-containing peptide 6 is prepared for post-solid-phase oxime diversification leading to products of type 7, which are amenable to direct biological evaluation without purification.

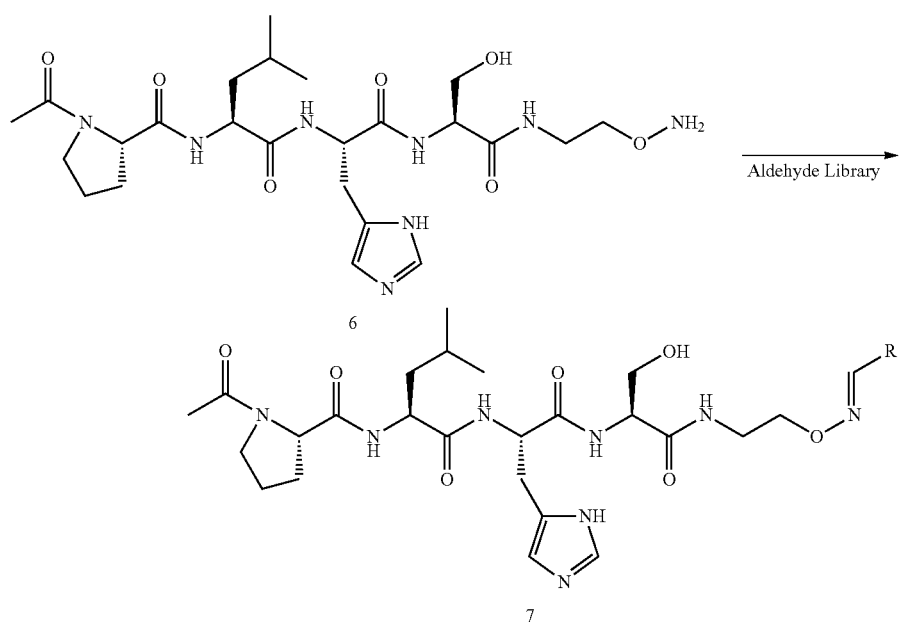

Oxime library approach to replacing the pThr residue.

Possible aldehydes for reaction with the oxime-containing peptide include, but are not limited to:

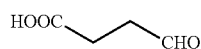
a

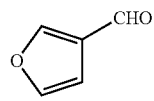
c

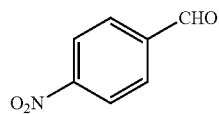
e

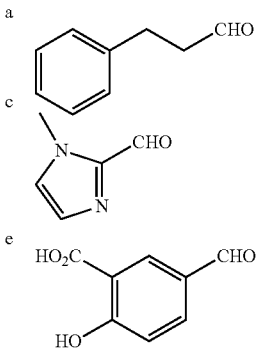

-continued
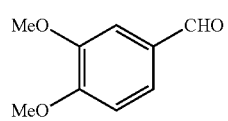 g 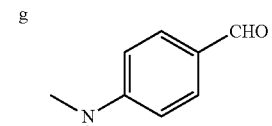 h
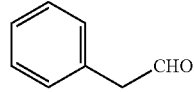 i 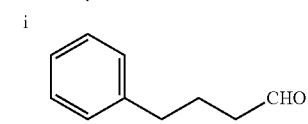 j
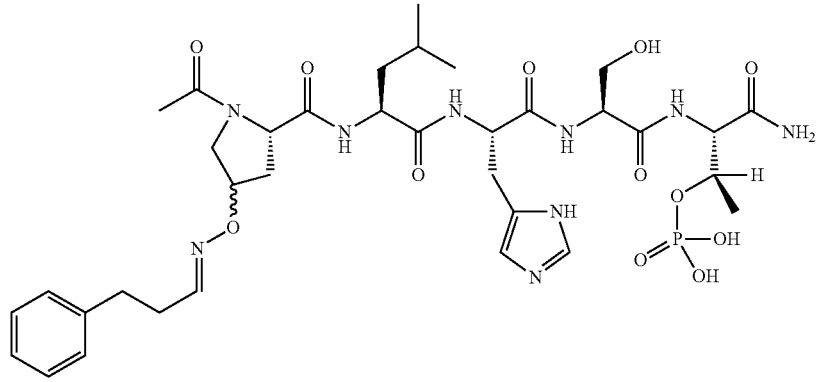
Trans-4-aminooxy-Pro: 4-b
Cis-4-aminooxy-Pro: 5-b
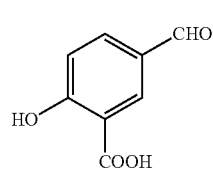 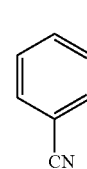 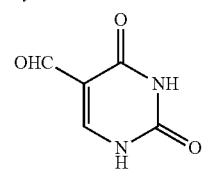 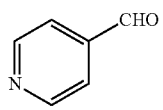 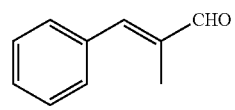
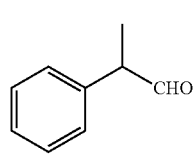 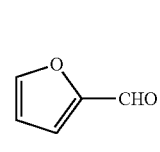 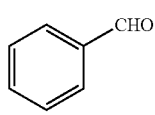 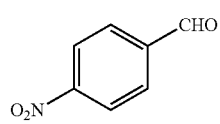 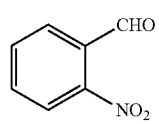
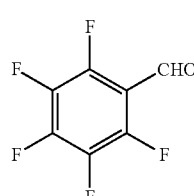 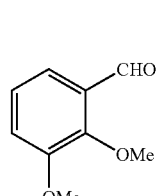 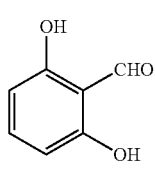 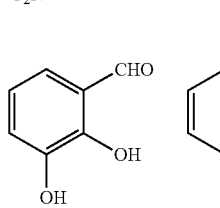 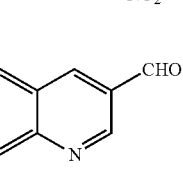
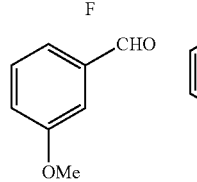 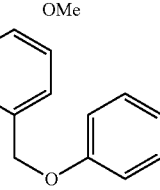 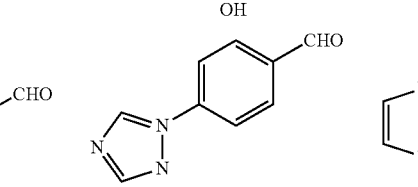 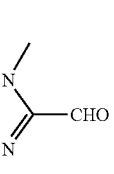
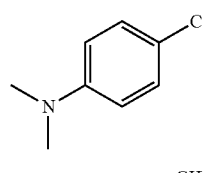 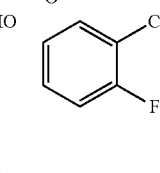 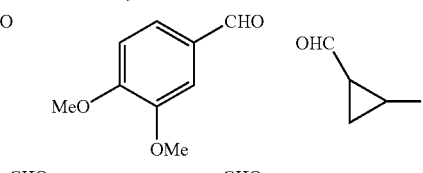 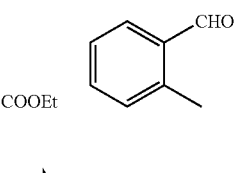
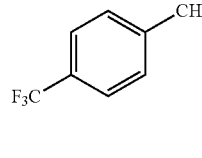 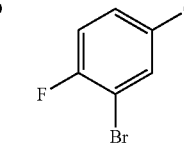 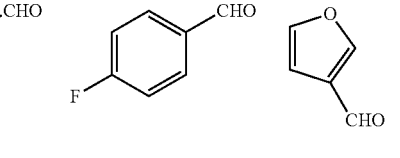 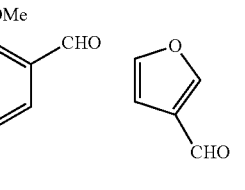 

-continued
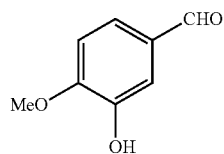 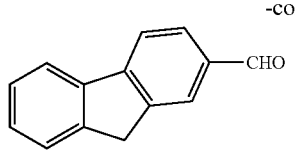 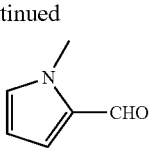 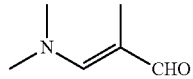
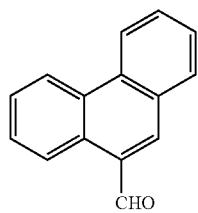 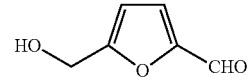 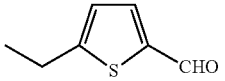 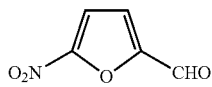
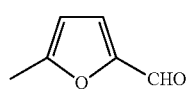 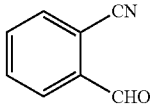 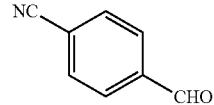
Oxime-containing peptides were prepared by conjugating peptides 4 or 5 with ten selected aldehdyes (Aldehyde a-j as shown above).
4. Preparation of Peptide-Peptoid Hybrid Using the "Sub-monomer Approach"
Scheme 3
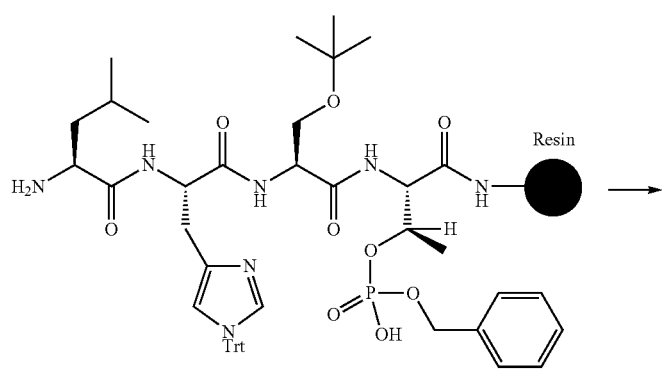
8
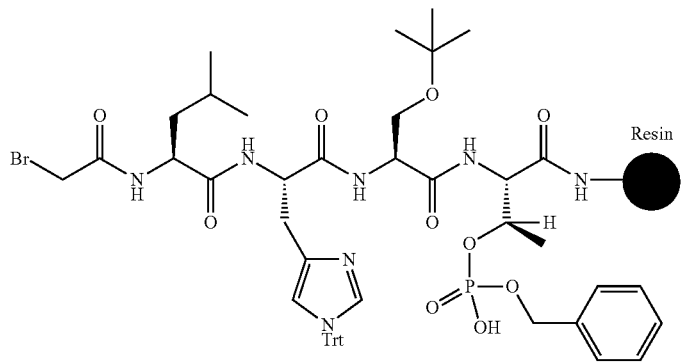
9

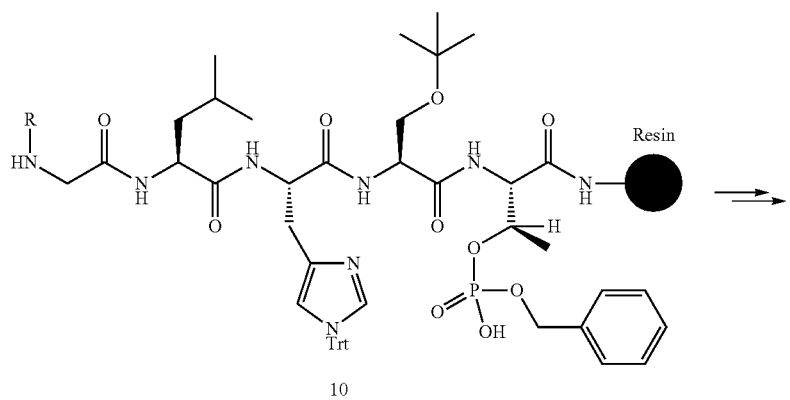
10
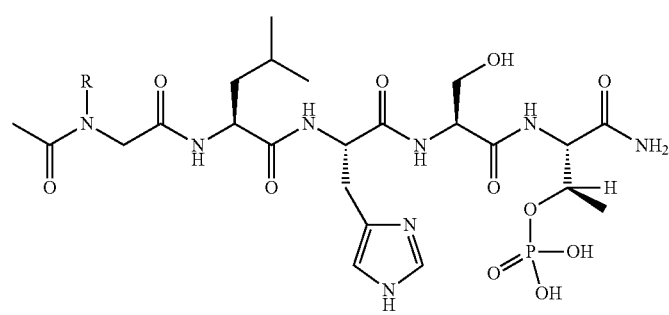
11
Amines that may be used to prepare hybrid 11 include, for example, compounds as follows:
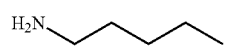
A
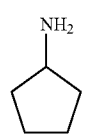
B
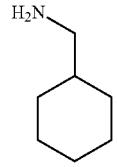
C
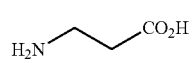
D
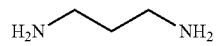
E
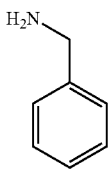
F
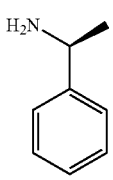
G
H
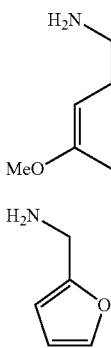
H
I -continued

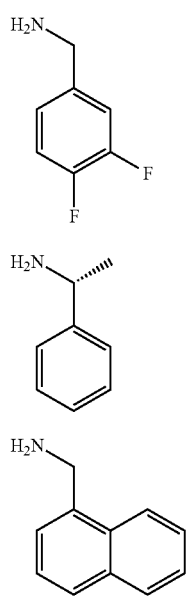

Structures of amines used to prepare peptide-peptoid hybrid 11 MALDI-TOF-MS for some peptoid-peptide hybrids 11 as prepared are shown in Table A.

TABLE A

MALDI-TOF-MS for the peptoid-peptide hybrids 11

R1 = H or acetyl

| | | Expected (M + H)+ | Observed (M + H)+ | | | Expected (M + H)+ | Observed (M + H)+ |
|---|---|---|---|---|---|---|---|
| 11A | Acetyl | 705.3 | 705.8 | 11-G | H | 697.3 | 697.6 |
| 11B | H | 661.3 | 661.5 | 11-H | Acetyl | 785.3 | 785.9 |
| 11C | Acetyl | 731.3 | 731.7 | 11-I | Acetyl | 715.3 | 715.9 |
| 11D | Acetyl | 707.3 | 707.4 | 11-G | Acetyl | 761.3 | 761.8 |
| 11E | Acetyl | 692.3 | 690.8 | 11-K | H | 697.3 | 698.0 |
| 11F | Acetyl | 725.3 | 725.4 | 11-L | H | 733.3 | 732.6 |

5. Preparation of Monocharged Phosphates and Cyclic Peptides

Scheme 4

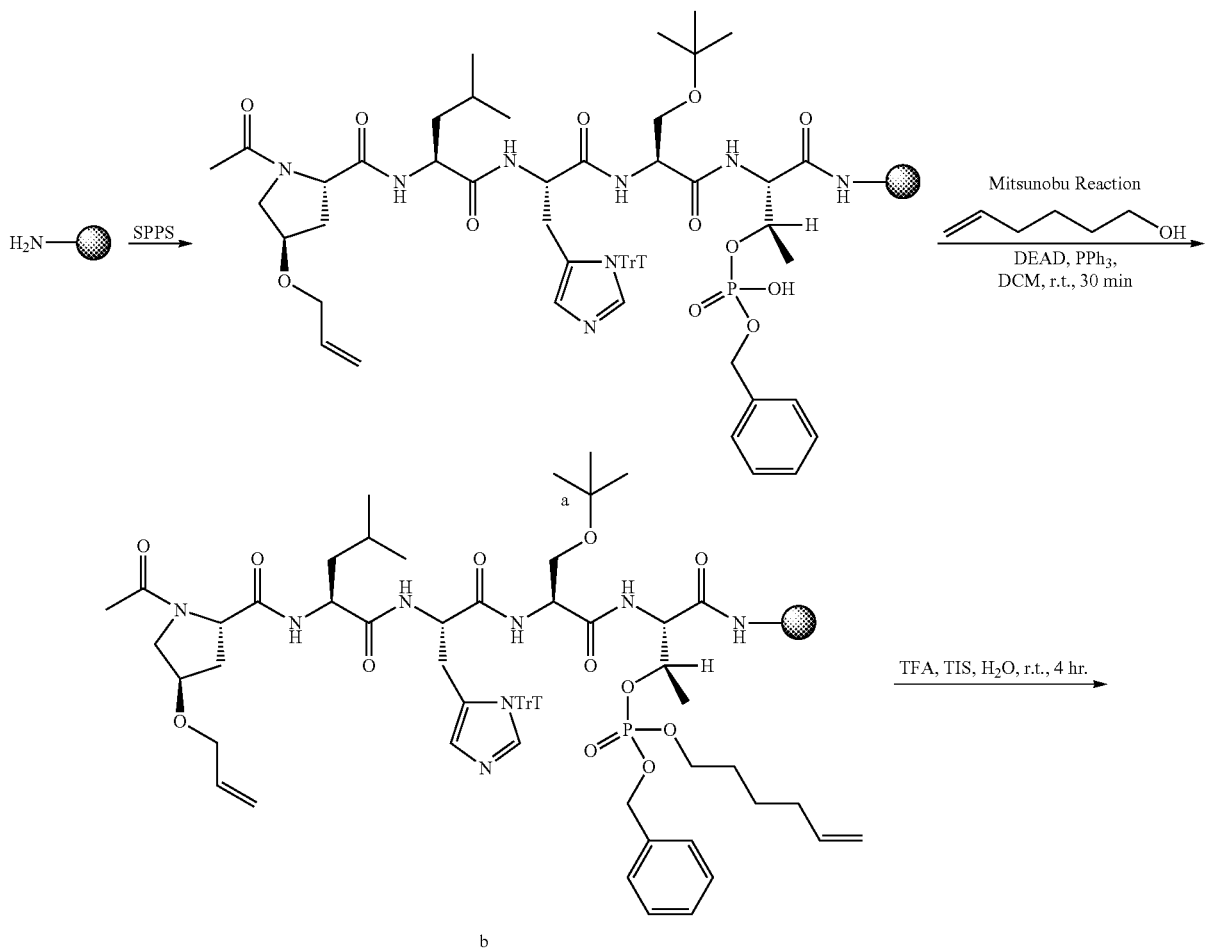

-continued

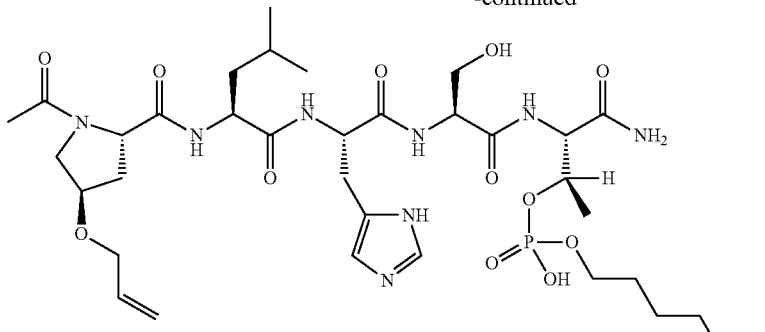

FA508: minor isomer;
FA509: major isomer;

RCM based ring closure
1. H-G II, DCE, r.t. overnight;
2. TFA, TIS, H₂O, r.t., 4 hr.

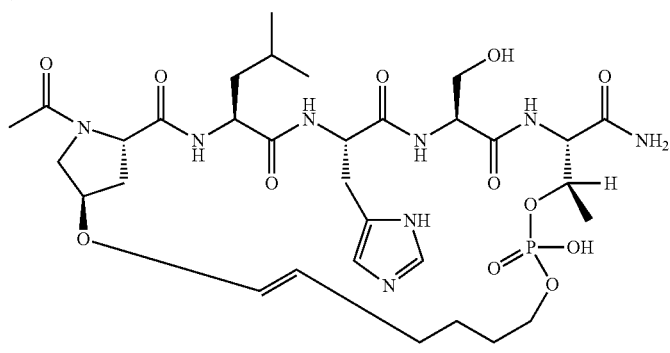

FA507

1. Mitsunobu Reaction: Resin 0.10 mmol was mixed with DEAD (0.46 mL, 40% solution in toluene, 1.0 mmol), PPh₃ (262 mg, 1.0 mmol) and alcohol (118 μL, 1.0 mmol) in DCM (2.50 mL), shaken gently at room temperature for 30 mins, then washed by DCM and DMF. 2. RCM based ring closure: Dried resin (0.05 mmol, 200 mg) was dissolved in DCE (3.0 mL), degassed by Argon for 3 mins, supplemented with Hoveyda-Grubbs generation II catalyst (10 mg), shaken gently overnight, and then washed by DCM.

Compounds that can be prepared in accordance with the above scheme include, but are not limited to, the compounds as follows:

-continued

FA506

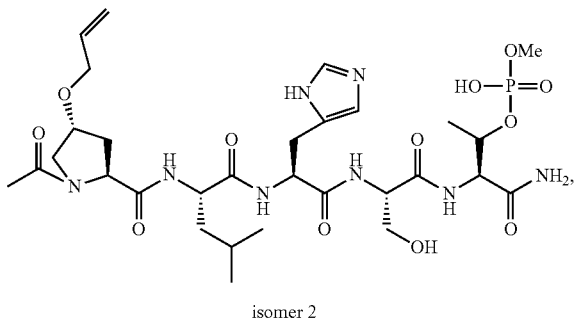

isomer 2

FA505

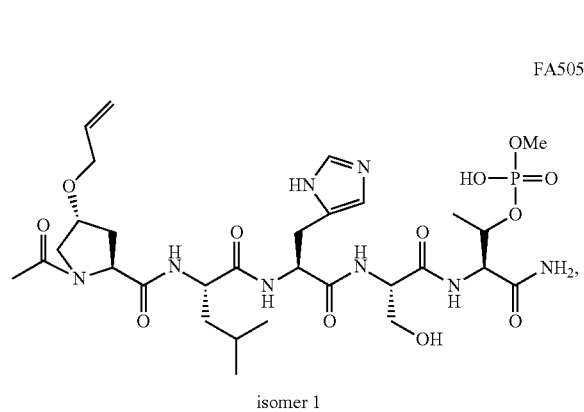

isomer 1

FA510

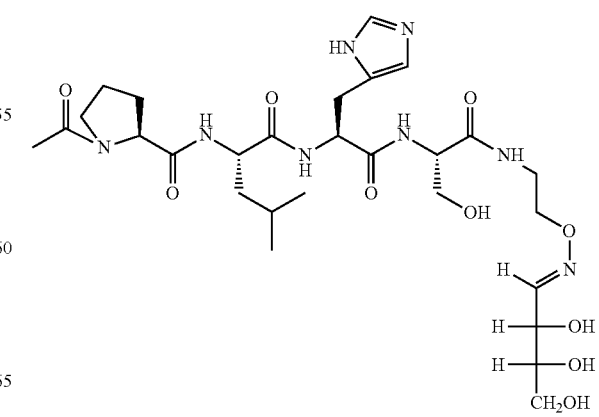

FA511

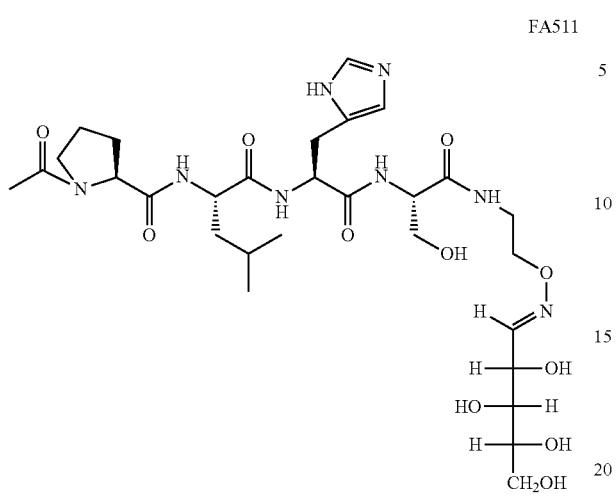

FA512

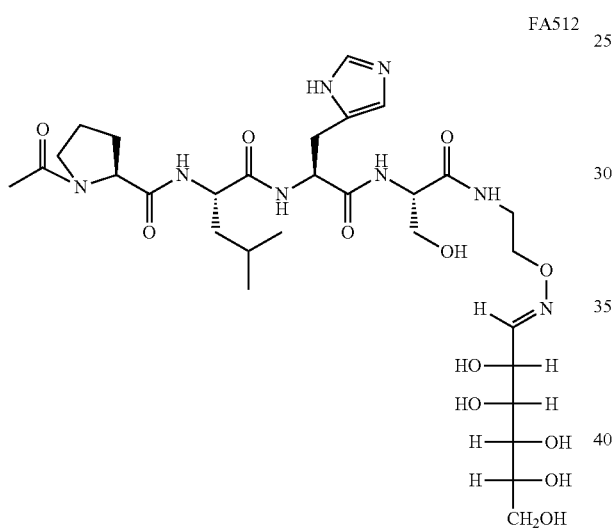

6. Synthetic Schemes for Preparation of Orthogonally Protected (2s, 3r)-2-Amino-3-Methyl-4-Phosphonobutyric Acid (Pmab) And Derivatives Scheme 5.

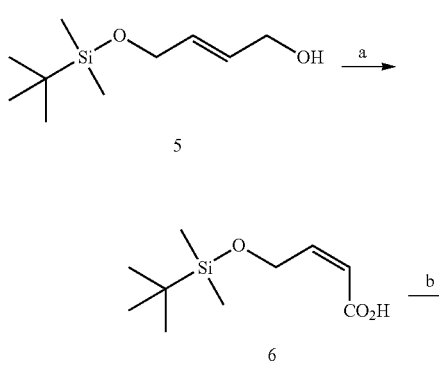

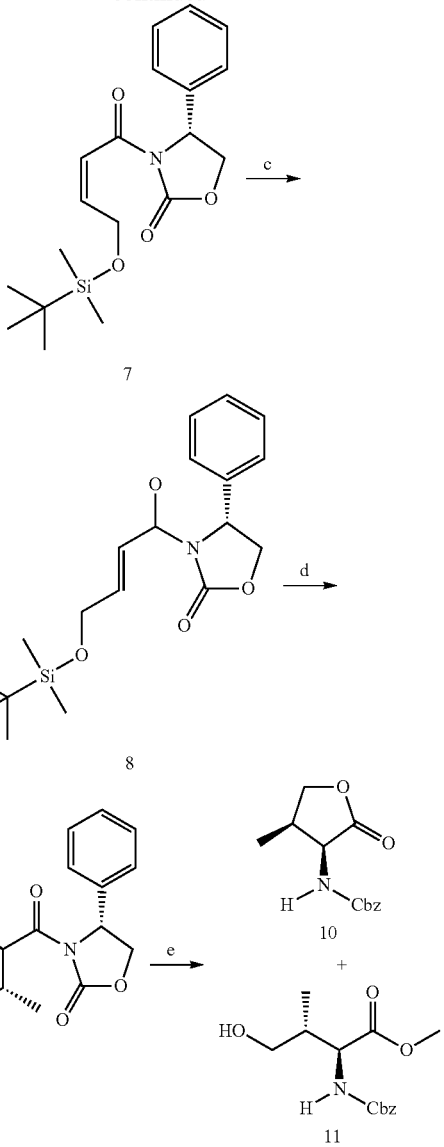

Reagents and conditions: (a) 1. Oxalyl chloride, DMSO, DCM, -78° C., 2 hrs; 2. NaClO$_2$, KH$_2$PO$_4$, 2-methyl-2-butene, tert-butanol and H$_2$O, rt, overnight, 97% for 2 steps. (b) 1. Trimethylacetyl chloride, triethylamine, THF, -78° C.-0° C., 20 min; 2. (R)-(+)-Phenyl-2-oxazolidinone lithium salt, THF, -78° C.-0° C., overnight, 100%. (c) Tributylphosphine, THF, rt, 1 hr, 84%. (d) 1. Methylmagnesium chloride, copper (I) bromide•dimethyl sulfide, dimethyl sulfide/THF, -78° C.-40° C., 2 hr; 2. NBS, -78° C., 1.5 hr; 3. NaN$_3$, DMF, 0° C., 2 hr, 79% for 2 steps. (e) 1. p-Toluenesulfonic acid monohydrate, MeOH, rt, 6 hr; 2. 1 atm H$_2$, 10% Pd•C (10%), MeOH/AcOH, rt, overnight; 3. Benzyl chloroformate, NaHCO$_3$, THF/H$_2$O, 0° C., 4 hr, 49% for 11 over 3 steps.

Stereoselective synthesis of orthogonally-protected Pmab (4) began with the Swern oxidation of tert-butyldimethylsilyl (TBDMS) mono-protected (2E)-2-butene-1,4-diol 5 followed by sodium chlorite oxidation. This provided acid 6 with Z-double bond geometry. Acid 6 was coupled with the Evan's chiral auxiliary, (4R)-4-phenyl-2-oxazolidinone and the Z-double bond geometry was isomerized by treatment with tri-n-butyl phosphine in THF to give the desired E-isomer (7). Both α and β stereogenic centers of 9 were constructed by a tandem sequence consisting of an asymmetric Cu(I)-catalyzed 1,4-Michael addition of methylmagnesium chloride followed by electrophilic α-bromination.

The crude (2R)-bromide was then converted to the corresponding (2S)-azide by nuclephilic SN2 replacement using sodium azide. A single (2S,3R)-diastereomer (9) was obtained by column chromatographic purification and crystallization. Assignment of absolute stereochemistries was based on well-established literature precedence (Navaza, J. Acta Cryst. A50, 157-163 (1994); Brunger, A. T. Nat. Protoc. 2, 2728-2733 (2007); & Adams, P. D. et al. Acta Crystallogr. D. Biol. Crystallogr. 58, 1948-1954 (2002). Removal of the TBDMS group by treatment with catalytic p-toluenesulfonic acid was followed by cyclization to release the Evan's auxiliary group and provide the 5-membered lactone. The azide was reduced by hydrogenation in a mixture of AcOH and MeOH and protected in situ to provide the lactone 10 as well as the ring-open alcohol 11 in a 1 to 4 ratio. Lactone 10 was further converted to 11.

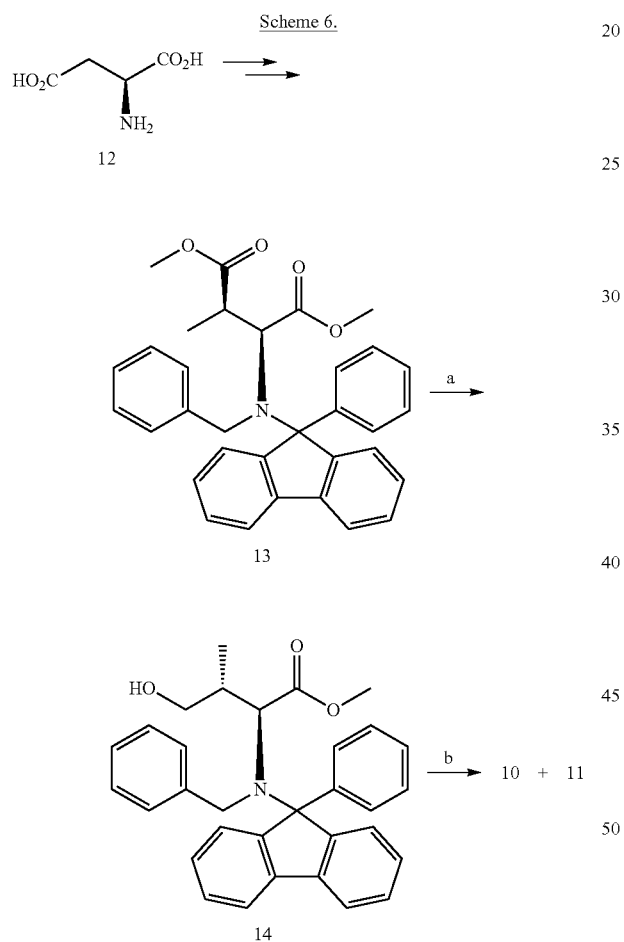

Reagents and conditions: (a) DIBAL, THF, -40° C.-0° C., 4 hr, 61%. (b) 1. 1 atm H₂, 10% Pd•C (10%), MeOH/AcOH, rt, overnight; 2. Benzyl chloroformate, NaHCO3, THF/H2O, 0° C., 4 hr.

Alcohol 11 can also be prepared from L-aspartic acid through the known bis-methyl ester 13. Selectively reduction of the γ-carboxyl of 13 using DIBAL provided the alcohol 14 (Scheme 6). Key to this reaction was the use of substrate concentrations less than 0.03 M. Similar to above, N-deprotection of 14 by hydrogenation in a mixture of AcOH and MeOH and subsequent Cbz protection gave the lactone 10 and the alcohol 11 in a 1 to 4 ratio.

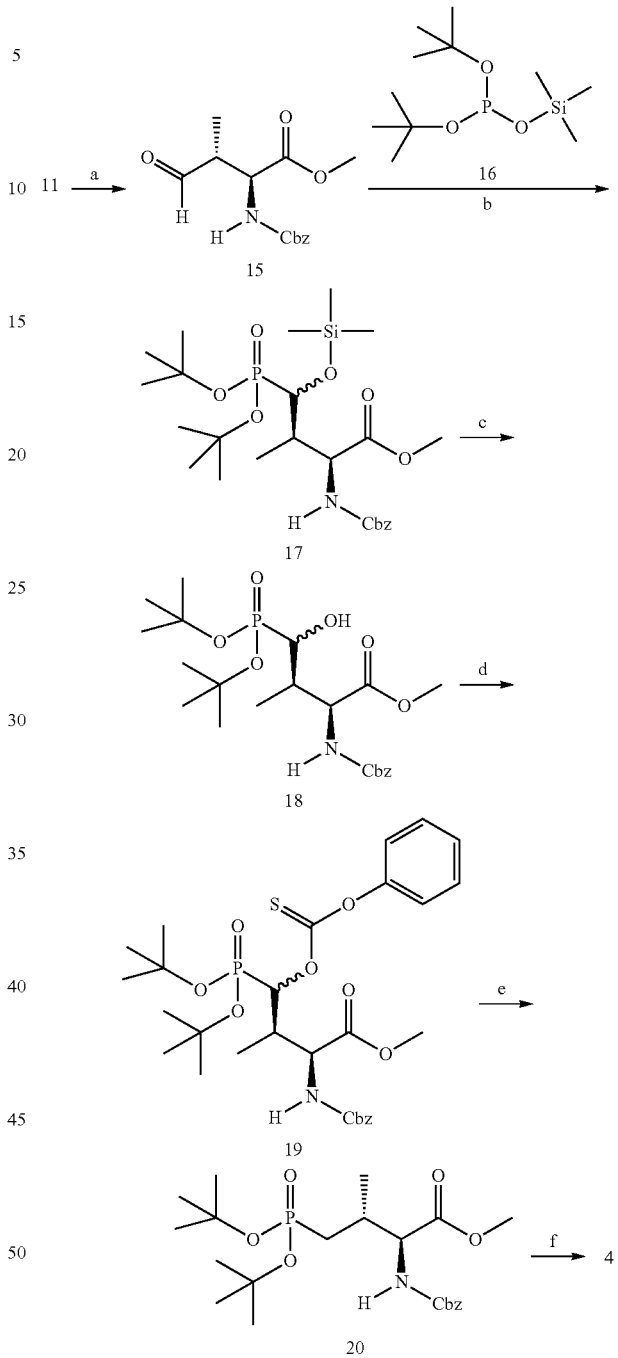

Reagents and conditions: (a) Oxalyl chloride, DMSO, DCM, -78° C., 2 hrs. (b) 16, DCM, rt, 3 hr. (c) citric acid, MeOH/H2O, rt, overnight, 88% over 3 steps. (d) O-phenylchlorothionoformate, DMAP (cat.) and N, N-diisopropylethylamine, DCM, r.t, overnight. (e) Tributyltin hydride, AIBN, toluene, 100° C., 20 min, 58% over 2 steps. (f) 1. LiOH, THF/H2O, rt, overnight; 2. 1 atm H₂, 10% Pd•C (10%), MeOH, rt, overnight; 3. FmocOSu, NaHCO₃, dioxane/H2O, rt, overnight, 100% over 3 steps.

Swern oxidation of alcohol 11 gave the corresponding aldehyde (15). This aldehyde was subjected to a phospho-Mukaiyama aldol reaction with freshly-prepared di-tert-butyltrimethylsilyl phosphite (17) to yield the aldehyde 17 (Scheme 7). Subsequent treatment with citric acid gave the free alcohol (18), which was derivatized as the phenylthiocarbonate 19 and subjected to Barton-McCombie deoxygenation to yield 20. Hydrolysis of the methyl ester, then hydrogenation and re-protection using Fmoc-OSu provided the orthogonally protected Pmab derivative 4 (see below):

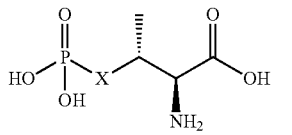

1 pThr: X = O
2 Pmab: X = CH$_2$
3 F$_2$Pmab: X = CF$_2$

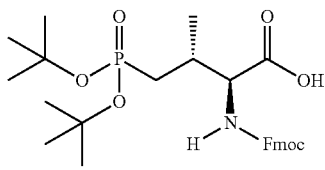

7. Design and Preparation of Pmab Derivatives

Stereoselective synthesis of (2S,3R)-4-[bis-(tert-butyloxy)phosphinyl]-2-[(9H-fluoren-9-ylmethoxy)carbonyl]amino-3-methylbutanoic acid [(N-Fmoc, O,O-(bis-(tert-butyl))-Pmab, 4; see above] as a hydrolytically-stable phosphothreonine mimetic bearing orthogonal protection compatible with standard solid-phase protocols. The synthetic approach used employs Evans' oxazolidinone for chiral induction.

Stereoselective synthesis of the pThr mimetic (2S,3R)-2-amino-3-methyl-4-phosphonobutanoic acid (Pmab, 2; see above) has been reported using Schollkopf's bislactim ether. This has provided derivatized Pmab bearing O,O-(bis-allyl) protection of the phosphonic acid group along with N-Fmoc protection (Hanisch, A. et al., Mol. Biol. Cell 17, 448-459. (2006)). Synthesis of the corresponding 4,4-difluoro analogue (F$_2$Pmab, 3; see above) bearing O,O-(bis-ethyl) phosphonic acid and N-Boc protection groups, has been approached using both (R)-isopropylideneglycerol as a chiral synthon and Oppolzer's sultam chiral auxiliary. This protection scheme would allow facile use in standard solid-phase protocols on acid-labile resins.

Application of Reagent 4 to the Synthesis of Polo Box Domain-Binding Peptides

The polo-like kinase 1 (Plk1) functions as an important mitotic regulator that phosphorylates serine and threonine residues. Its over-expression in a number of cancers and its association with poor prognosis have made it a potential anticancer therapeutic target. A main focus of Plk1 inhibitor development has been directed at the kinase catalytic domain. However, Plk1 contains modular C-terminal PBDs that bind specific phosphoserine and phosphothreonine-containing sequences to provide critical localization of Plk1. Competitive PBD binding antagonists could serve as inhibitors of Plk1 function that are distinct from kinase-directed agents. A starting point for the development of PBD-binding antagonists is given by short pThr-containing peptides modeled on consensus binding sequences derived from the p-Thr78 region (p-T78) of the PBD-binding protein, PBIP1. By examining various PBD-binding phosphpeptides, it has recently been shown that a 5-mer phosphopeptide "PLH-SpT" (SEQ ID NO: 1) (21) specifically interacts with the Plk1 PBD with high affinity ($K_d$=0.45 µM). In order to provide phosphatase-stable peptides for in vivo studies, F$_2$Pmab (3) was also incorporated into a 6-mer T78 peptide, "PLHSTA" (SEQ ID NO: 6), to give the corresponding peptide 25. (Note: The 6-mer sequence "PLHS-F$_2$Pmab-A" (SEQ ID NO: 7) (25) was synthesized due to inefficient synthesis of the 5-mer sequence, "PLHS-F$_2$Pmab" (SEQ ID NO: 8)). It was found that 25 showed much weaker PBD-binding affinity than the respective p-T78 peptide, "PLH-SpTA" (SEQ ID NO: 9), and it exhibited significant toxicity in cell-based experiments. The toxicity can potentially be attributed to the highly acidic CF$_2$PO$_3$H moiety. Therefore, using solid-phase techniques and standard Fmoc-based protocols, we employed reagent 4 to synthesize the Pmab-containing peptides 23 and 24.

8. Design and Synthesis of Pmab pThr Mimetics in Prodrug Form for Incorporation into Bioavailable PBD-Binding Peptides.

Pmab Analogue Synthesis.

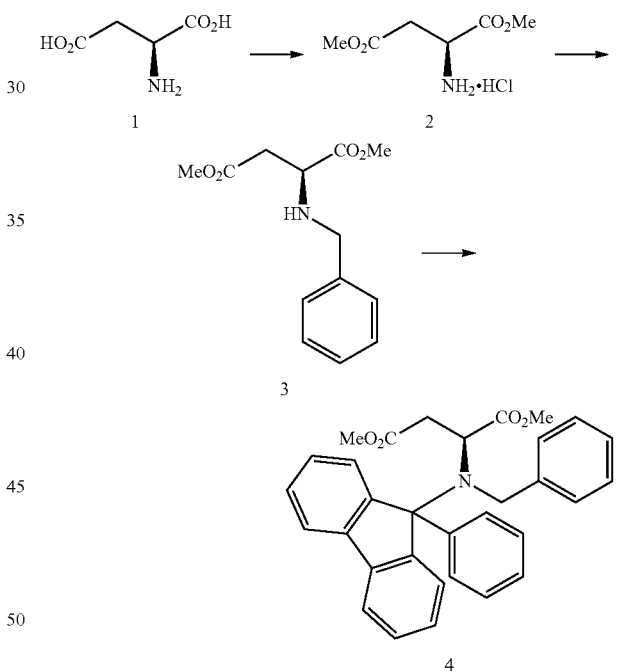

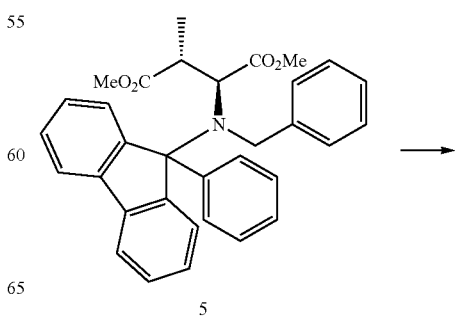

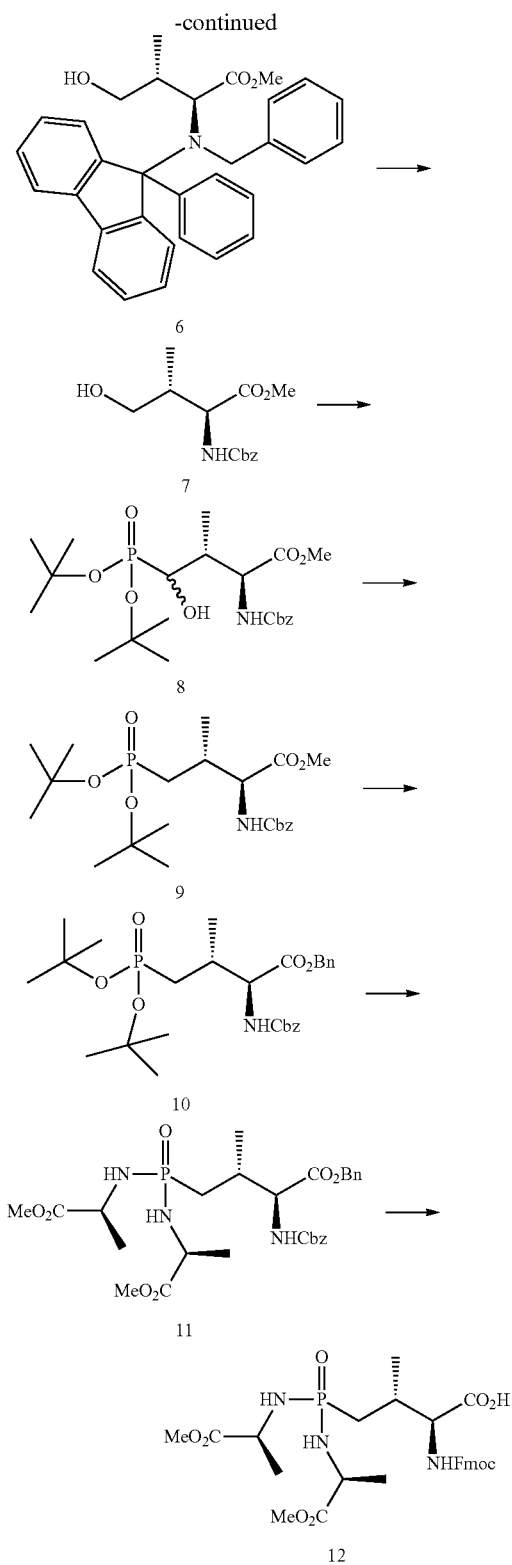

Preparation of Compound 10.

A mixture of 9 (180 mg, 0.39 mmol) and LiOH.H$_2$O (34 mg, 0.81 mg) in a mixture solvent of THF (3.0 mL) and H$_2$O (3.0 mL) was stirred at 0° C. to room temperature overnight, quenched by sat. NH$_4$Cl (50 mL), and extracted by EtOAc (150 mL). The EtOAc layer was washed (brine), dried (Na$_2$SO$_4$), and concentrated by rotary evaporator to an oil, which was dissolved in DMF (5.0 mL). NaHCO$_3$ (168 mg, 2.0 mmol), benzylbromide (120 µL, 1.0 mmol), and NaI (5 mg) were added to the above DMF solution. The resultant mixture was stirred at room temperature overnight, diluted by EtOAc (150 mL), washed (brine), dried (Na$_2$SO$_4$) and purified by silica gel column chromatography (hexanes: EtOAc) to gave 10 as a colorless oil (134 mg, 65% yield for 2 steps). $^1$H NMR (400 MHz, CDCl$_3$) δ 7.40-7.25 (m, 10H), 5.86 (d, J=8.4 Hz, 1H), 5.13-5.04 (m, 4H), 4.30 (dd, J=8.0, 6.4 Hz, 1H), 2.37 (m, 1H), 1.73 (m, 1H), 1.50-1.35 (m, 19H), 1.05 (d, J=6.8 Hz, 3H). $^{13}$C NMR (100 MHz, CDCl$_3$) δ171.4, 156.2, 142.3, 136.3, 135.1, 128.6, 128.5, 128.3, 128.1, 128.0, 110.4, 82.1, 67.3, 66.9, 59.6, 34.4, 33.8, 32.3, 31.9, 30.3, 24.1, 17.4. ESI (+VE) m/z: 556.3 (M+Na)$^+$.

Preparation of Compound 11.

Compound 10 (140 mg, 0.262 mmol) was treated by a solution of TFA (5.0 mL) in dichloromethane (5.0 mL) at room temperature for 2 hr. The solvent was removed by rotary evaporator, and the left residue was dissolved in toluene (10 mL) and concentrated again. The obtained residue was dried under high vacuum (oil pump) for 2 hr, then dissolved in dichloromethane (5.0 mL), and cooled to 0° C. Oxalyl chloride (0.20 mL, 2.30 mmol) was added to the above solution, followed by one drop of DMF. The mixture was stirred at room temperature for 2 hr, then concentrated by using rotary evaporator. In another flask, L-Alanine methyl ester hydrochloride (200 mg, 1.43 mmol) and DIPEA (0.80 mL) were dissolved in dichloromethane (4.0 mL) and cooled to 0° C., followed by the slow addition of the above-prepared phosphorus oxychloride solution in dichloromethane (2.0 mL). The resulted mixture was stirred at room temperature overnight, diluted by EtOAc (150 mL), washed(brine), dried (Na$_2$SO$_4$) and purified by silica gel column chromatography (hexanes:EtOAc) to gave 11 as a colorless oil (40 mg, 26% yield for 3 steps). $^1$H NMR (400 MHz, CDCl$_3$) δ 7.32-7.25 (m, 10H), 6.01 (d, J=7.6 Hz, 1H), 5.16 (s, 2H), 5.06 (s, 2H), 4.56 (dd, J=7.6, 4.8 Hz, 1H), 4.05-3.95 (m, 2H), 3.65 (s, 3H), 3.63 (s, 3H), 3.45 (brs, 1H), 3.20 (m, 1H), 2.45 (m, 1H), 1.85 (m, 1H), 1.65 (m, 1H), 1.33-1.28 (m, 6H), 0.97 (d, J=6.8 Hz, 3H). $^{13}$C NMR (100 MHz, CDCl$_3$) δ 175.1, 175.0, 171.0, 156.0, 136.2, 134.9, 128.7, 128.5, 128.1, 67.4, 67.0, 57.9, 52.2, 49.1, 48.2, 33.5, 32.2, 29.6, 21.2, 20.9, 17.6. ESI (+VE) m/z: 614.2 (M+Na)$^+$.

Preparation of Compound 12.

A mixture of compound 11 (60 mg, 0.102 mmol) and Pd/C (10%, 10 mg) in methanol was stirred under 1 atm hydrogen at room temperature for 5 hr. Pd/C was filtered off, the filtrate was concentrated and the left residue was dissolved in a mixture solvent of dioxane (3.0 mL) and H$_2$O (3.0 mL), followed by the addition of NaHCO$_3$ (42 mg, 0.51 mmol) and FmocOSu (76 mg, 0.204 mmol). The resulted mixture was stirred at room temperature overnight. Dioxane was removed by rotary evaporator, the left aqueous phase was washed by ether (50 mL×2), acidified to pH 3-4 by 1 N HCl, and extracted by EtOAc (100 mL). The EtOAc layer was washed (brine), dried (NaSO4) and evaporated to give analytical pure 12 as a white wax (50 mg, 83% yield for 2 steps), which was used directly for solid phase peptide synthesis without further purification. $^1$H NMR (400 MHz, CDCl$_3$) δ 7.71 (d, J=7.6 Hz, 2H), 7.55 (d, J=7.2 Hz, 2H), 7.37-7.33 (m, 2H), 7.28-7.23 (m, 2H), 5.96 (d, J=6.4 Hz, The preparation of compound 5 from L-Aspatic acid was conducted according to the literature (Humphrey, J. M.; Bridges, R. J.; Hart, J. A.; Chamberlin, A. R. *J. Org. Chem.* 1994, 59, 2467), these reactions are very re-producible in over 10 gram scale. The preparation of Pmab analogue 12 from compound 9 are described below.

1H), 4.71 (m, 1H), 4.34-4.31 (m, 2H), 4.18 (m, 1H), 4.10-3.95 (m, 2H), 3.66 (s, 6H), 2.50 (m, 1H), 2.00-1.85 (m, 2H), 1.45 (d, J=6.8 Hz, 3H), 1.35 (d, J=6.8 Hz, 3H), 1.01 (d, J=6.8 Hz, 3H). $^{13}$C NMR (100 MHz, CDCl$_3$) δ 174.7, 171.8, 155.8, 143.8, 141.2, 127.7, 127.0, 125.1, 120.0, 67.0, 60.4, 52.4, 49.1, 48.3, 47.1, 31.5, 29.7, 20.7, 14.1. ESI (−VE) m/z: 418.1 (M*−H)$^−$. ESI (+VE) m/z: 420.1 (M*+H)$^+$, 442.2 (M*+Na)$^+$.

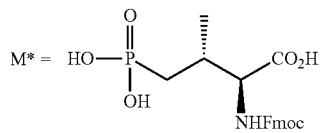

Chemical Formula: C$_{20}$H$_{22}$NO$_7$P
Exact Mass: 419.1134
Molecular Weight: 419.3649

9. Di-Amide Pro-Drug Peptide Synthesis

Peptides were synthesize on NovaSyn® TGR resin (Novabiochem, cat. no. 01-64-0060) using standard Fmoc solid-phase protocols in N-Methyl-2-pyrrolidone (NMP). Fmoc-Pro-OH, Fmoc-Leu-OH, Fmoc-His(Trt)-OH and Fmoc-Ser(tBu)-OH were purchased from Novabiochem and used. Pmab analogue 12 was coupled to the resin by using 12 (1.0 eq), HATU (1.0 eq.), HOBT (1.0 eq.) and DIPEA (2.0 eq.) in NMP, r.t., overnight. The following residue are coupled by using Fmoc protected amino acid (5.0 eq.), 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (5.0 eq.) in NMP, r.t, 2 hr. The N-terminal was acetylated by 1-Acetylimidazole. The final resin was washed with N, N-dimethylforamide (DMF), methanol, dichloromethane and ether then dried under vacuum (over night). Peptides were cleaved from resin (200 mg) by treatment with 5 mL of trifluoroacetic acid:triisbutylsilane:H$_2$O (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex C$_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 25 minutes at a flow rate of 10.0 mL/minute.

13

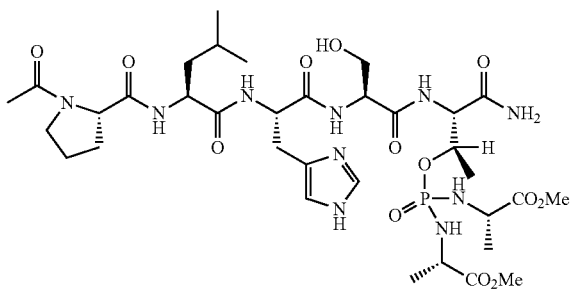

14

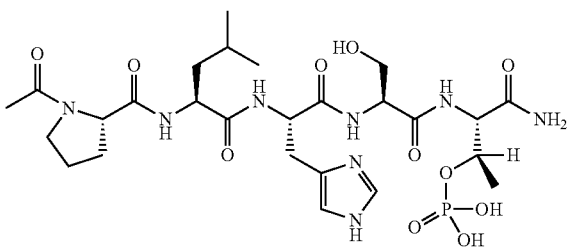

It turned out the 5% H$_2$O in the final cleavage conditions totally hydrolyzed the methyl ester, therefore released the L-alanine to give the free phosphate peptide 14.

10. Exemplified Peptide Synthesis:

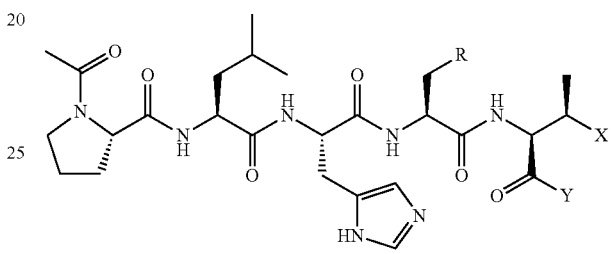

21 R = OH; Y = NH$_2$; X = OH
22 R = OH; Y = NH$_2$; X = O—PO(OH)$_2$
23 R = OH; Y = NH$_2$; X = CH$_2$—PO(OH)$_2$
24 R = H; Y = NH$_2$; X = CH$_2$—PO(OH)$_2$

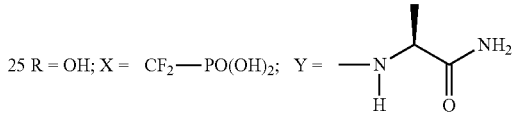

25 R = OH; X = CF$_2$—PO(OH)$_2$; Y =

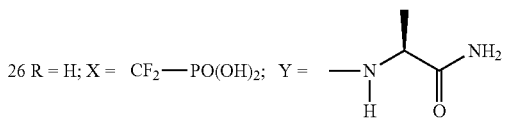

26 R = H; X = CF$_2$—PO(OH)$_2$; Y =

Fmoc-Thr(PO(OBzl)OH)—OH and other Fmoc protected amino acids were purchased from Novabiochem. Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. The N-terminal was acetylated by 1-Acetylimidazole. The final resin was washed with N, N-dimethylforamide (DMF), methanol, dichloromethane and ether then dried under vacuum (over night). Peptides were cleaved from resin (200 mg) by treatment with 5 mL of trifluoroacetic acid:triisbutylsilane:H$_2$O (90:5:5) (4 h). The resin was filtered off and the filtrate was concentrated under vacuum, then precipitated with ether and the precipitate washed with ether. The resulting solid was dissolved in 50% aqueous acetonitrile 5 mL) and purified by reverse phase preparative HPLC using a Phenomenex C$_{18}$ column (21 mm dia×250 mm, cat. no: 00G-4436-P0) with a linear gradient from 0% aqueous acetonitrile (0.1% trifluoroacetic acid) to 50% acetonitrile (0.1% trifluoroacetic acid) over 35 minutes at a flow rate of 10.0 mL/minute. Peptide 21: ESI (+VE) m/z: 595.3 (M+H)$^+$. Peptide 22: ESI (+VE) m/z:

675.3 (M+H)⁺. Peptide 23: ESI (+VE) m/z: 673.3 (M+H)⁺. Peptide 24: ESI (+VE) m/z: 657.3 (M+H)⁺. Analytical HPLC [By using Phenomenex $C_{18}$ column (4.60 mm dia× 250 mm, cat. no: 00G-4435-EO) with a linear gradient from 5% aqueous acetonitrile (0.1% trifluoroacetic acid) to 100% acetonitrile (0.1% trifluoroacetic acid) over 25 minutes at a flow rate of 1.0 mL/minute.] indicated the purity of peptide 21: 100%, peptide 22: 100%, peptide 23: 87%, peptide 24: 83%.

11. Peptides Containing Phosphate Monoesters and Arylalkyl-Histine-Containing PBD-Binding Peptides A structure-based rational design method based on the Mitsunobu reaction was used to make di-ester. The approach provides numerous advantages including, but not limited to, highly efficient library construction, resistance to phosphatase, and increased cell permeability.

Post-modification of the peptide on the resin gave two products 3 and 4 with the same molecular weight as about 1 to 4 ratio, the minor product 3 consistently gave higher potency than the major product 4.

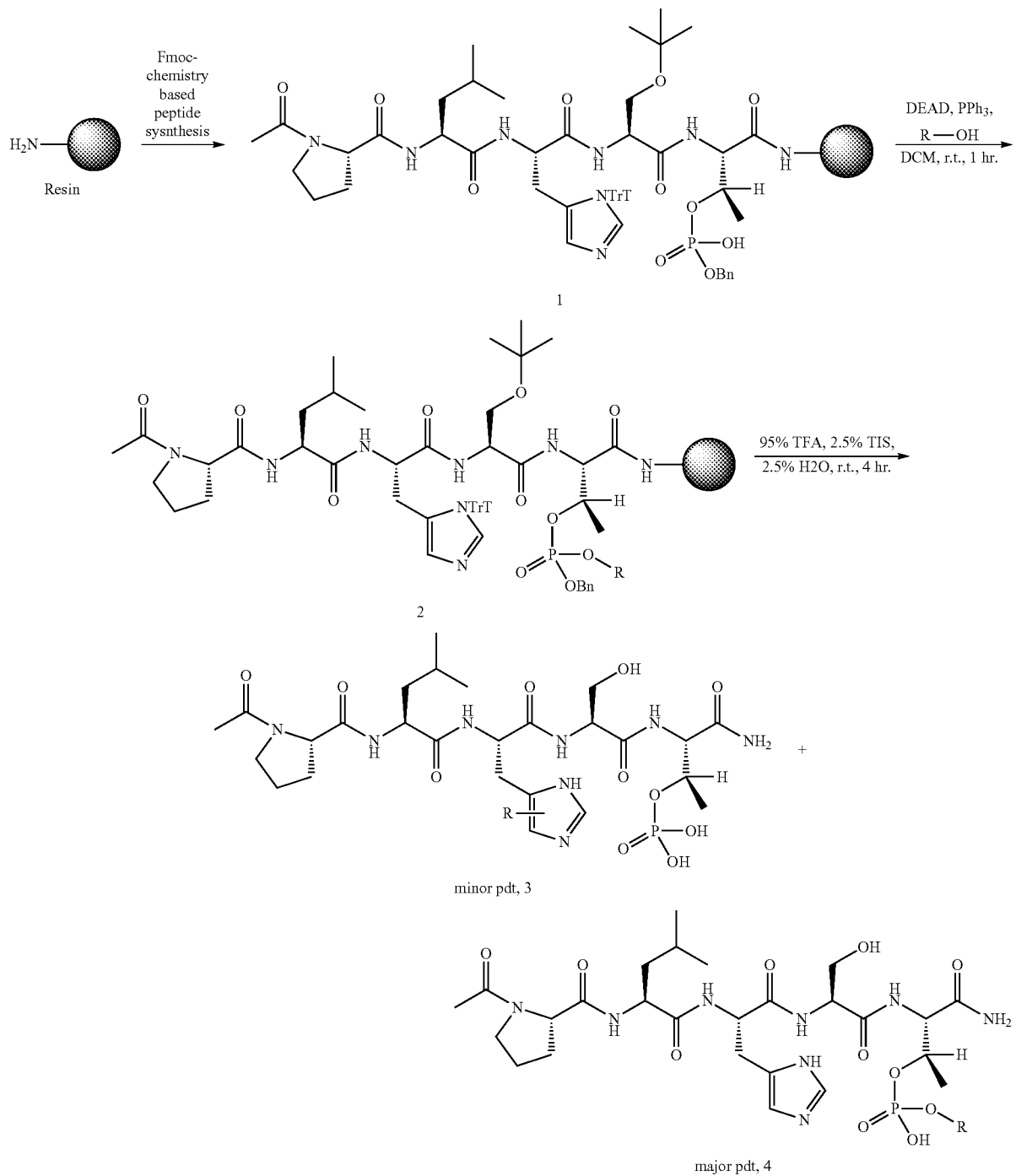

Post-modification on the solid phase by using Mitsunobu reaction.

MeOH a

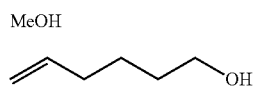 b

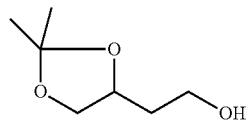 c

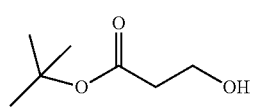 d

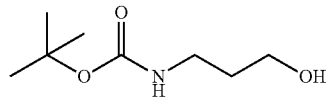 e

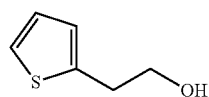 f

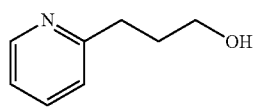 g

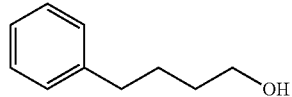 h

Initial alcohol library used prepare peptide 3 and 4.

Ph-(CH₂)₅—OH, i
Ph-(CH₂)₆—OH, j
Ph-(CH₂)₇—OH, k
Ph-(CH₂)₈—OH, l
Ph-(CH₂)₉—OH, m
Ph-(CH₂)₁₀—OH, n

Focused alcohol library to prepare peptide 3 and 4.

The S/A mutants of peptide 3l and 4l were also prepared and determined by ELISA. 5 gave 100-fold decreased binding compared to 3l, and 6 didn't show any activity.

5

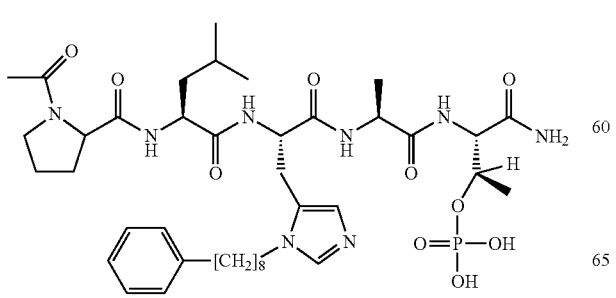

6

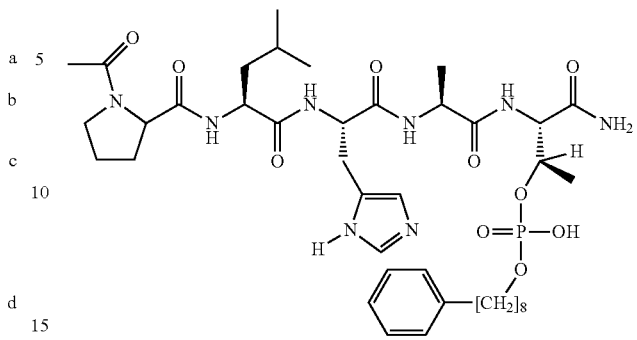

S/A mutants of peptide 3l and 4l, respectively.

12. Preparation of Proline Analogues:

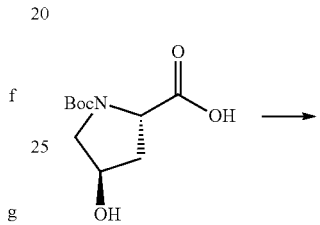

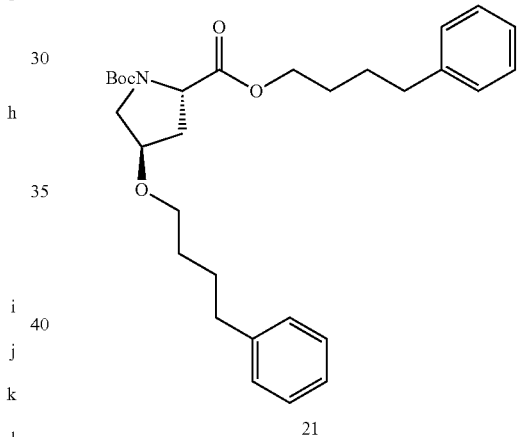

21

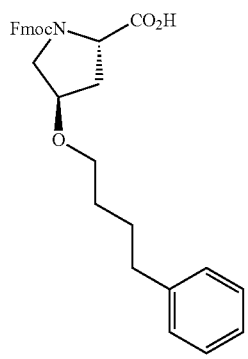

22

4-Phenyl-1-iodobutane was Prepared from 4-phenyl-1-butanol

To a suspension of sodium hydride (60% in mineral oil, 1.90 g, 47.5 mmol) in DMF (30 mL) at 0° C., was added a solution of Boc-L-hydroxyproline (5.0 g, 21.6 mmol) in DMF (30 mL) dropwisely during 5 min. The mixture was kept at 0° C. for another 15 min before the addition of 4-phenyl-1-iodobutane (16.9 g, 64.8 mmol), then stirred overnight from 0° C. to r.t.

The reaction was quenched by sat. NH₄Cl (50 mL), extracted with EtOAc (300 mL). The organic layer was washed, dried and purified by and column chromatography (hexanes:EtOAc) to yield 21 as a colorless oil (5.1 g, 48% yield). ¹H NMR (400 MHz, CDCl₃) δ 7.26-7.23 (m, 5H), 7.16-7.13 (m, 5H), 4.34 (dd, J=8.0, 6.4 Hz, 0.3H), 4.27 (t, J=7.6 Hz, 0.7H), 4.14-4.08 (m, 2H), 3.98 (m, 1H), 3.60-3.55 (m, 2H), 3.42-3.33 (m, 2H), 2.65-2.58 (m, 4H), 2.25 (m, 1H), 1.98 (m, 1H), 1.70-1.60 (m, 8H), 1.41 (s, 3.5H), 1.36 (s, 5.5H).

A mixture of 21 (5.00 g, 10.1 mmol) and LiOH monohydrate (848 mg, 20.2 mmol) in THF (30 mL), MeOH (10 mL) and H₂O (15 mL) was stirred at r.t. for 3 hr. The organic solvent was removed by rotary evaporator; the aqueous phase was washed with ether (50 mL×2), then acidified to pH 3-4 by 1N HCl, extracted with EtOAc (150 mL). The EtOAc layer was washed, dried (NaSO₄) and evaporated to a colorless oil, which was treated by a mixture of TFA (30 mL) and dichloromethane (30 mL) for 2 hr at r.t. The solvent was removed, and the left residue was dried under oil pump for 2 hr. This residue was dissolved in dioxane (30 mL) and H₂O (30 mL), followed by the addition of NaHCO₃ (4.20 g, 50.0 mmol) and FmocOSu (3.71 g, 11.0 mmol), and stirred at r.t. overnight. Dioxane was removed by rotary evaporator, the left aqueous was washed by ether (50 mL×20), acidified to pH 3-4 by 1 N HCl, extracted by EtOAc (200 mL). The EtOAc layer was washed (brine), dried (NaSO4) and evaporated to give analytical pure 22 as a thick oil (5.1 g, 100% yield). ¹H NMR (400 MHz, CDCl₃) δ 10.36 (brs, 1H), 7.74 (d, J=7.6 Hz, 1H), 7.68 (d, J=7.6 Hz, 1H), 7.57-7.46 (m, 2H), 7.40-7.22 (m, 7H), 7.18-7.12 (m, 2H), 4.49 (t, J=7.6 Hz, 0.5H), 4.45-4.32 (m, 2.5H), 4.24 (t, J=7.2 Hz, 0.5 Hz), 4.15-4.00 (m, 1.5H), 3.70 (m, 0.40H), 3.60-3.55 (m, 1.6H), 3.44-3.34 (m, 2H), 2.64-2.57 (m, 2H), 2.35 (m, 1H), 0.86 (m, 1H), 1.70-1.55 (m, 4H), 13C NMR (100 MHz, CDCl₃) δ 177.7, 176.5, 171.8, 159.1, 158.6, 155.9, 154.9, 143.7, 142.2, 141.3, 128.4, 128.3, 127.1, 119.9, 76.8, 76.2, 69.2, 68.0, 60.7, 58.1, 57.5, 52.0, 51.7, 47.1, 36.8, 35.6, 35.0, 29.3, 27.9, 21.0, 14.1.

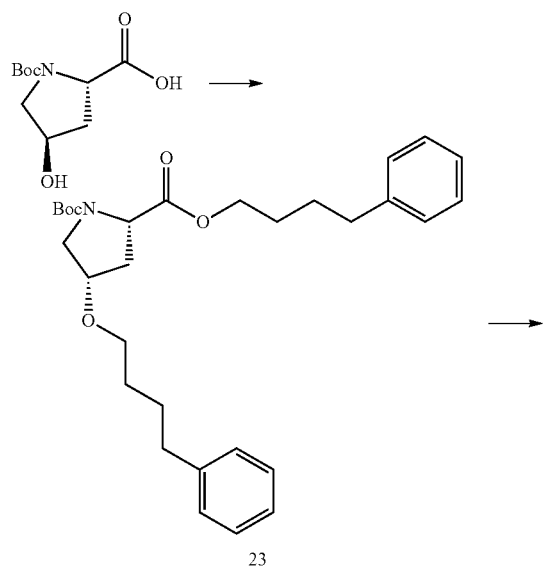

23

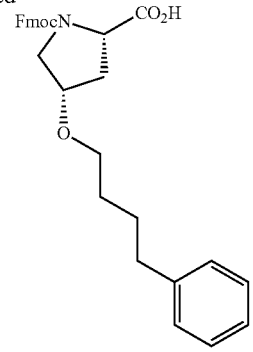

24

23 was prepared from N-Boc-cis-4-hydroxy-L-proline in 29% yield by using the same method described above for the preparation of 21. ¹H NMR (400 MHz, CDCl₃) δ 7.28-7.22 (m, 5H), 7.18-7.12 (m, 5H), 4.39 (dd, J=8.4, 3.6 Hz, 0.4H), 4.27 (dd, J=8.4, 4.0 Hz, 0.6H), 4.15-3.98 (m, 2H), 3.93 (m, 1H), 3.63 (m, 0.60H), 3.55 (dd, J=11.2, 5.2 Hz, 0.4H), 3.43 (ddd, J=18.4, 11.6, 3.2 Hz, 1H), 3.36-3.28 (m, 2H), 2.65-2.55 (m, 4H), 2.30-2.15 (m, 2H), 1.70-1.55 (m, 6H), 1.55-1.46 (m, 2H), 1.45 (s, 3.5H), 1.40 (s, 5.5H), 13C NMR (100 MHz, CDCl₃) δ 172.3, 172.0, 154.2, 153.8, 142.3, 142.1, 141.9, 128.3, 125.8, 79.9, 79.8, 77.4, 76.3, 68.9, 64.8, 57.8, 57.4, 52.0, 51.4, 36.2, 35.7, 35.4, 35.0, 29.4, 28.4, 28.3, 28.1, 27.9, 27.6.

24 was prepared from 23 in 30% yield by using the same method described above for the preparation of 22. ¹H NMR (400 MHz, CDCl₃) δ 8.70 (brs, 1H), 7.73 (d, J=7.6 Hz, 1H), 7.69 (d, J=7.2 Hz, 1H), 7.60-7.50 (m, 2H), 7.40-7.25 (m, 7H), 7.17-7.10 (m, 2H), 4.50-4.43 (m, 1.6H), 4.40-4.30 (m, 1.4H), 4.23 (m, 0.60H), 4.17 (m, 0.40H), 4.00 (m, 1H), 3.63-3.53 (m, 2H), 3.45 (m, 0.5H), 3.40-3.30 (m, 1.5H), 2.60-2.53 (m, 2H), 2.42 (m, 0.5H), 2.30 (m, 1H), 2.20 (m, 0.5H), 1.70-1.50 (m, 4H). ¹³C NMR (100 MHz, CDCl₃) δ 175.8, 174.5, 155.7, 143.9, 143.6, 142.3, 141.3, 128.3, 127.8, 127.0, 125.7, 125.0, 120.0, 76.3, 68.8, 67.8, 60.4, 58.1, 57.6, 52.2, 47.1, 36.0, 35.5, 34.1, 31.6, 29.1, 27.8, 25.4, 22.6, 21.0, 14.4.

13. Peptoid-Peptide Hybrid Synthesis Procedures.

Fmoc-Thr(PO(OBzl)OH)—OH and other Fmoc protected amino acids were purchased from Novabiochem. Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. After Leu was coupled and its amine group was freed, the resin was treated with bromoacetic acid (10.0 eq.), DIC (10.0 eq.) and DIPEA (20.0 eq.) in NMP for 30 mins. This resin was washed and treated with ~2.5 M individual amine in DMSO over night. The amine terminal was acetylated by acetylimidazole overnight, or by acetic anhydride (10.0 eq.), DIPEA (20.0 eq) in 1,2-dichloroethane 4 hr at rt. The final resin was washed with N, N-dimethylforamide (DMF), methanol, dichloromethane and ether then dried under vacuum (overnight). Peptides were cleaved from resin (200 mg) by treatment with 5 mL of trifluoroacetic acid:triisbutylsilane:H₂O (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute.

14. Post-Modification of the Peptides by Click Chemistry

Azides were obtained by treatment of the corresponding alcohols with methanesulfonyl chloride followed by sodium azide.

Copper Catalyzed Cyclization:

Dried resin 7 (100 mg) was suspended in acetonitrile (4.0 mL) and DMSO (1.0 mL) in a plastic tube, de-gassed by argon for 5 mins, and supplemented with DIPEA (10 µL), CuI (19 mg) and azide (10.0 eq.). The tube was sealed and shaked at room temperature overnight. The resin was washed with DMF, H2O, MeOH and ether, dried under high vacuum for 4 hr before cleavage.

Heat Driven Cyclization:

Dried resin 7 (100 mg) and azide (10.0 eq.) were mixed in DMF (2.0 mL) in a flask and heated to 100° C. for 2 days. The resulting resin was washed with DMF, methanol, dichloromethane and ether, and dried under high vacuum before cleavage. The products of copper catalyzed reaction were assigned as the 1,4-triazole products, the 1,5-triazole products were identified by comparing the HPLC retention times of the heat driven cyclization products with the 1,4-triazole product for copper catalyzed cyclization.

TABLE B

| Low resolution ESI-Mass Spec. | | | | |
|---|---|---|---|---|
| | Expected (M + H)+ | Observed (M + H)+ | Expected (M − H)− | Observed (M − H)− |

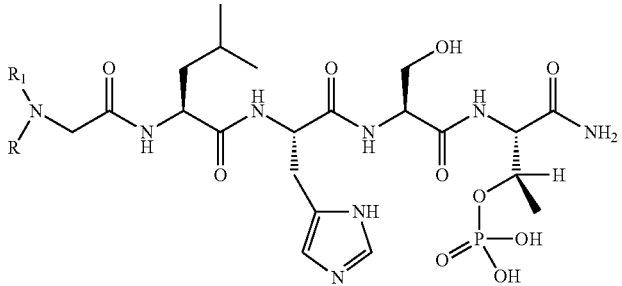

R1 = H or acetyl

| | | | |
|---|---|---|---|
| 4a | Acetyl | 705.3 | 705.8 |
| 4b | H | 661.3 | 661.5 |
| 4c | Acetyl | 731.3 | 731.7 |
| 4d | Acetyl | 707.3 | 707.4 |
| 4e | Acetyl | 692.3 | 690.8 |
| 4f | Acetyl | 725.3 | 725.4 |
| 4g | H | 697.3 | 697.6 |
| 4h | Acetyl | 785.3 | 785.9 |
| 4i | Acetyl | 715.3 | 715.9 |
| 4g | Acetyl | 761.3 | 761.8 |
| 4k | H | 697.3 | 698.0 |
| 4l | H | 733.3 | 732.6 |
| 4m | Acetyl | 739.3 | 739.2 |
| 4n | Acetyl | 753.3 | 753.3 |
| 4o | Acetyl | 767.3 | 767.2 |
| 4p | Acetyl | 781.4 | 781.3 |
| 4q | Acetyl | 795.4 | 795.3 |
| 4r | Acetyl | 809.4 | 809.4 |

| Compound number | Expected (M + H)+ | Observed (M + H)+ | Expected (M − H)− | Observed (M − H)− |
|---|---|---|---|---|
| 5 | 779.4 | 779.4 | 777.4 | 777.4 |
| 6 | 752.4 | 752.4 | 750.4 | 750.3 |
| 8 | 777.3 | 777.3 | | |
| 9 | 791.4 | 791.2 | | |
| 10 | 777.3 | 777.4 | 775.3 | 775.4 |
| 11 | 791.4 | 791.2 | | |
| 12 | 793.4 | 793.5 | 791.4 | 791.4 |
| 13 | 967.5 | 967.5 | 965.5 | 965.5 |
| 14 | 777.4 | 777.4 | 775.4 | 775.4 |
| 15 | 951.5 | 951.6 | | |

TABLE C

High resolution ESI-MS of selected peptoid-peptide hybrids.

| | Structure | Expected | Observed |
|---|---|---|---|
| 4a | 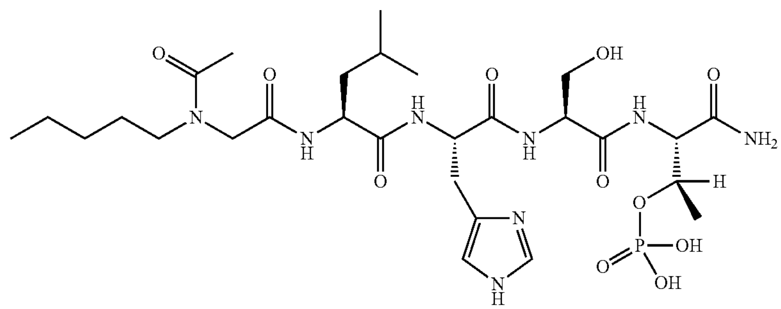 [SMILES: CCCCCN(CC(=O)N[C@@H](CC(C)C)C(=O)N[C@@H](Cc1c[nH]cn1)C(=O)N[C@@H](CO)C(=O)N[C@H](C(N)=O)[C@@H](C)OP(=O)(O)O)C(C)=O] | (M − H)⁻ C28H48N8O11P 703.3186 | (M − H)⁻ 703.3166 |
| 4f | 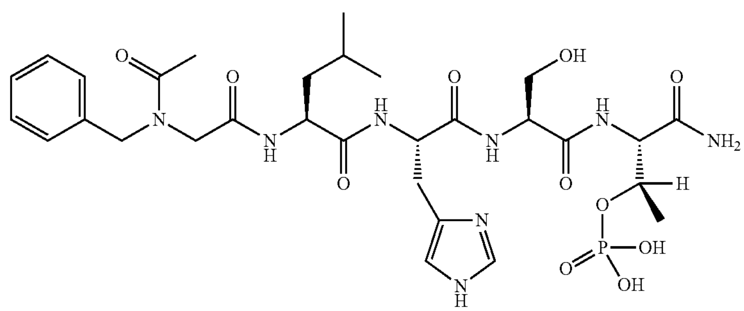 [SMILES: CC(=O)N(CC(=O)N[C@@H](CC(C)C)C(=O)N[C@@H](Cc1c[nH]cn1)C(=O)N[C@@H](CO)C(=O)N[C@H](C(N)=O)[C@@H](C)OP(=O)(O)O)Cc1ccccc1] | (M − H)⁻ C30H44N8O11P 723.2873 | 723.2846 |
| 4o | 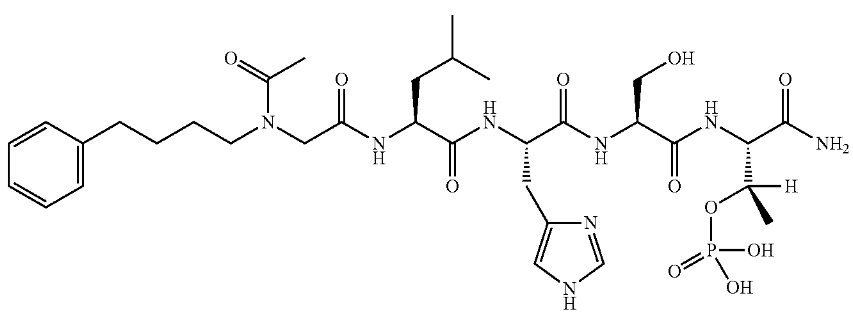 [SMILES: CC(=O)N(CCCCc1ccccc1)CC(=O)N[C@@H](CC(C)C)C(=O)N[C@@H](Cc1c[nH]cn1)C(=O)N[C@@H](CO)C(=O)N[C@H](C(N)=O)[C@@H](C)OP(=O)(O)O] | (M − H)⁻ C33H50N8O11P 765.3342 | 765.3328 |
| 4r | 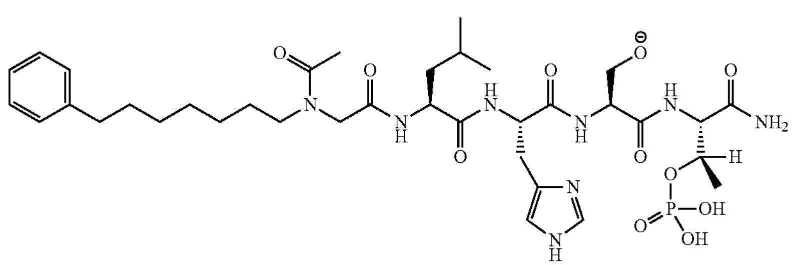 [SMILES: CC(=O)N(CCCCCCCc1ccccc1)CC(=O)N[C@@H](CC(C)C)C(=O)N[C@@H](Cc1c[nH]cn1)C(=O)N[C@@H](C[O-])C(=O)N[C@H](C(N)=O)[C@@H](C)OP(=O)(O)O] | (M − H)⁻ C36H56N8O11P 807.3812 | 807.3799 |
| 6 | 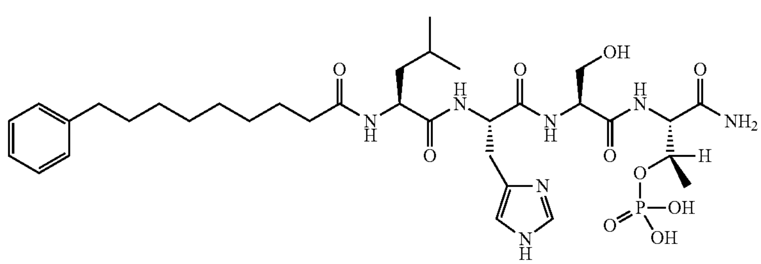 [SMILES: CC(C)C[C@H](NC(=O)CCCCCCCCc1ccccc1)C(=O)N[C@@H](Cc1c[nH]cn1)C(=O)N[C@@H](CO)C(=O)N[C@H](C(N)=O)[C@@H](C)OP(=O)(O)O] | (M − H)⁻ C34H53N7O10P 750.3597 | 750.3583 |

TABLE C-continued

High resolution ESI-MS of selected peptoid-peptide hybrids.

| | Structure | Expected | Observed |
|---|---|---|---|
| 12 | 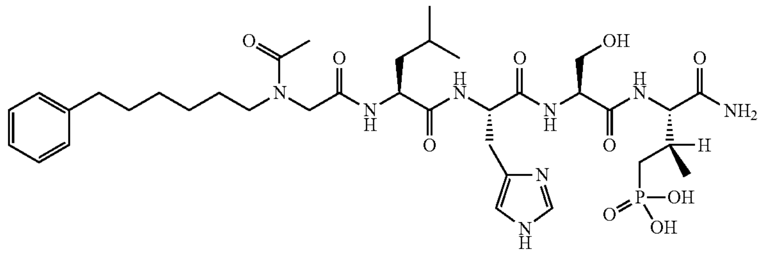 [SMILES: CC(=O)N(CCCCCCc1ccccc1)CC(=O)N[C@@H](CC(C)C)C(=O)N[C@@H](Cc1c[nH]cn1)C(=O)N[C@@H](CO)C(=O)N[C@H](C(N)=O)[C@@H](C)CP(=O)(O)O] | $(M + H)^+$ $C_{36}H_{58}N_8O_{10}P$ 793.4008 | 793.4021 |
| 14 | 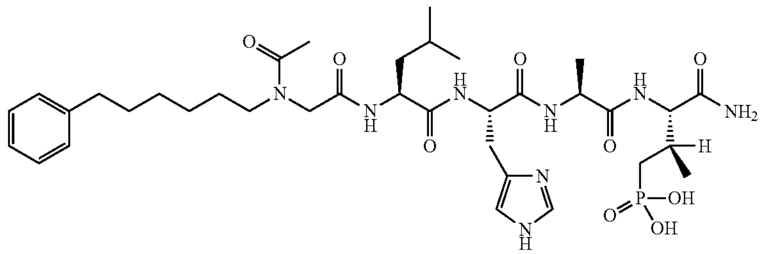 [SMILES: CC(=O)N(CCCCCCc1ccccc1)CC(=O)N[C@@H](CC(C)C)C(=O)N[C@@H](Cc1c[nH]cn1)C(=O)N[C@@H](C)C(=O)N[C@H](C(N)=O)[C@@H](C)CP(=O)(O)O] | $(M + H)^+$ $C_{36}H_{58}N_8O_9P$ 777.4059 | 777.4079 |

15. Synthesis of F₂Pmab-Containing Mimetic Peptide

Synthesis of 2-amino-4,4-difluoro-3-methyl-4-phosphobutanoic acid (F₂Pmab)-containing peptides were carried out by employing a tert-butoxycarbonyl (Boc)-based solid-phase method on 4-methylbenzhydrylamine (MBHA) resin as described previously. For peptide-based pull-down assays, peptides bearing the N-terminal Cys-(CH₂)₆ linker (1 mM stock) were cross-linked to the beads using SulfoLink Coupling gel (Pierce, Rockford, Ill.). An initial attempt to synthesize a 5-mer PLHS-F₂Pmab (SEQ ID NO: 8) mimetic peptide did not yield sufficient amounts because of an inefficient coupling of F₂Pmab to the resin. Thus, we synthesized a 6-mer F₂Pmab-containing peptide (PLHS-F₂Pmab-A (SEQ ID NO: 7)) and then examined its affinity and specificity to Plk1 in comparison to those of the corresponding p-T78 peptide.

16. Synthesis of PEGylated Peptides Tagged with HIV-Tat Sequence

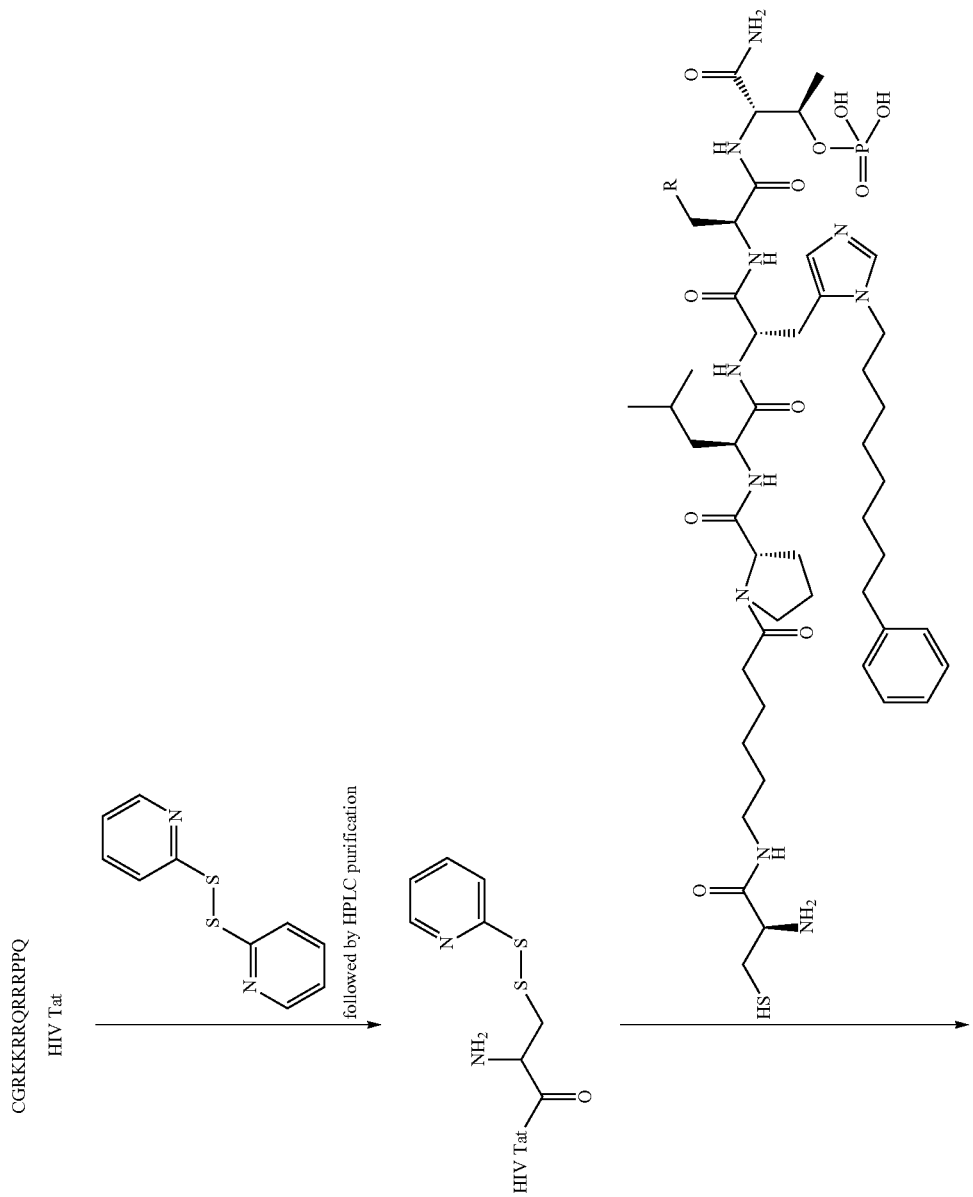

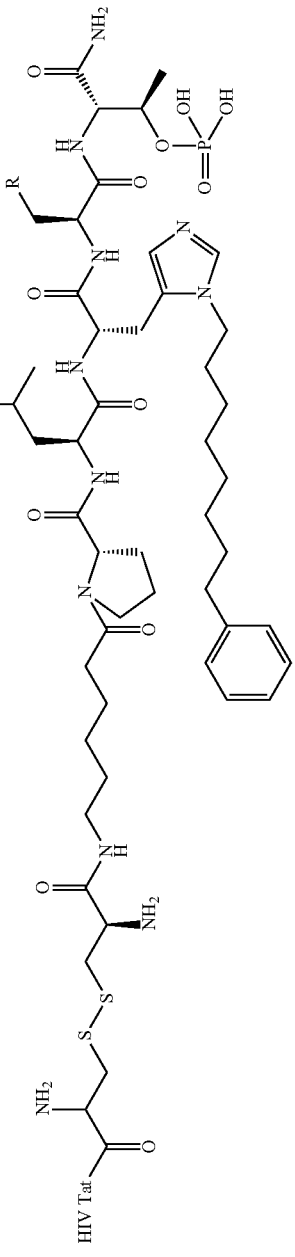
or
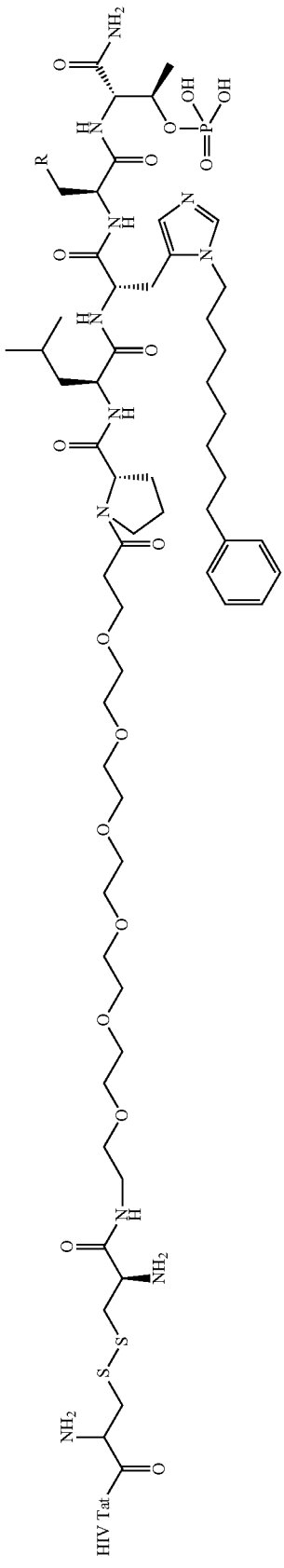

17. Detailed Synthetic Procedures and Supporting Data

(E)-4-[(Tert-butyldimethylsilyl)oxy]-2-buten-1-ol (5)

To a solution of (2E)-2-butene-1,4-diol (8.22 mL, 0.10 mol) and imidazole (8.50 g, 0.125 mol) in DMF (50 mL) at 0° C., was added ter-butyldimethylsilyl chloride (7.50 g, 0.050 mol) in several portions over 10 minutes. The resulting mixture was warmed to room temperature and stirred (2 h), then 5.50 (m, 2H), 4.18 (m, 2H), 4.09 (m, 2H), 2.76 (br, H), 0.83 (s, 9H), several 0.01 (s, 6H). 10 minutes. The resulting mixture was warmed to room temperature and stirred (2 h), then poured into $H_2O$ (200 mL) and extracted with EtOAc (2×150 mL). The organic layer was washed (brine), dried ($Na_2SO_4$) and purified by silica gel column chromatography (hexanes EtOAc) to yield 5 as a colorless oil (9.0 g, 89% yield). $^1H$ NMR (400 MHz, $CDCl_3$) δ 5.60-5.50 (m, 2H), 4.18 (m, 2H), 4.09 (m, 2H), 2.76 (br, 1H), 0.83 (s, 9H), 0.01 (s, 6H). $^{13}C$ NMR (100 MHz, $CDCl_3$) δ 136.3, 135.4, 64.8, 63.8, 31.1, 23.6.

Z-4-[[(1,1-Dimethylethyl)dimethylsilyl]oxy]-2-butenoic acid (6)

To a solution of oxalyl chloride (3.55 mL, 40.8 mmol) in $CH_2Cl_2$ (100 mL) at −78° C., was added a solution of DMSO (5.80 mL, 81.7 mmol) in $CH_2Cl_2$ (40 mL) and the mixture was stirred (15 minutes). Alcohol 5 (5.50 g, 27.2 mmol) in dry $CH_2Cl_2$ (40 mL) was added over 5 minutes, the mixture was stirred at −75° C. (2 h), then triethylamine (31 mL, 0.22 mol) was added. The mixture was warmed to room temperature, saturated $NH_4Cl$ (50 mL) was added, and then the mixture was extracted with $Et_2O$ (2×100 mL). The combined organic layers were washed (brine), dried ($Na_2SO_4$) and evaporated to yield the intermediate aldehyde as a pale yellow liquid. Without purification, a mixture of the aldehyde, potassium phosphate monobasic (5.55 g, 40.8 mmol) and 2-methyl-2-butene (14.4 mL, 136 mmol) in tert-butanol (150 mL) and $H_2O$ (30 mL) at 0° C. was supplemented with sodium chlorite (9.23 g, 81.6 mmol, 80% technical grade) in several portions over 10 minutes. The mixture was warmed to room temperature slowly and stirred (night). After cooling to 0° C., a solution of sodium bisulfate (31.8 g, 0.30 mol) in $H_2O$ (100 mL) was added slowly and the mixture was stirred (30 minutes) and extracted with EtOAc (2×150 mL). The combined organic layer was washed (brine), dried ($Na_2SO_4$) and purified by silica gel column chromatography (hexanes:EtOAc) to yield acid 6 as a colorless oil (5.70 g, 97% yield). $^1H$ NMR (400 MHz, $CDCl_3$) δ 6.40 (dt, J=11.6, 4.6 Hz, 1H), 5.68 (dt, J=12.0, 2.6 Hz, 1H), 4.65 (dd, J=4.6, 2.4 Hz, 2H), 0.83 (s, 9H), 0.00 (s, 6H). $^{13}C$ NMR (100 MHz, $CDCl_3$) δ 176.0, 159.7, 123.0, 67.1, 31.0, 23.0, 0.00. APCI (−VE) m/z: 215.2 (M−H)$^-$. HR-ESI MS cacld for $C_{10}H_{19}O_3Si$ (M−H)$^-$: 215.1109. Found: 215.1103.

(4R)-3-[(2Z)-[4-[(1,1-Dimethylethyl)dimethylsilyl] oxy]-1-oxo-2-buten-1-yl]-4-phenyl-2-oxazolidinone (7)

To a solution of acid 6 (6.0 g, 28.2 mmol) in THF (40 mL) at −78° C., was added triethylamine (4.00 mL, 28.2 mmol) followed by trimethylacetyl chloride (3.46 mL, 28.2 mmol) drop-wise. The mixture was warmed to 0° C. over 20 minutes, then the anhydride mixture was cooled to −78° C. Separately, to a solution of (R)-(+)-phenyl-2-oxazolidione (Aldrich) (4.60 g, 28.2 mmol) in THF (40 mL) at −78° C. was carefully added n-BuLi (2.50 M in THF, 11.3 mL, 28.2 mmol) and the mixture was stirred (30 minutes) then transferred to the anhydride solution at −78° C. The final reaction mixture was warmed to room temperature and stirred (over night). The mixture was diluted with EtOAc (200 mL), washed ($H_2O$ and brine), dried ($Na_2SO_4$), and purified by silica gel column chromatography (hexanes:EtOAc) to yield 7 as a colorless oil (10.2 g, 100% yield). $^1H$ NMR (400 MHz, $CDCl_3$) δ 7.36-7.20 (m, 5H), 7.10 (dt, J=11.6, 2.6 Hz, 1H), 6.50 (dt, J=12.0, 4.6 Hz, 1H), 5.44 (dd, J=8.8, 4.0 Hz, 1H), 4.68-4.59 (m, 3H), 4.22 (dd, J=8.8, 4.0 Hz, 1H), 0.85 (s, 9H), 0.00 (s, 6H). $^{13}C$ NMR (100 MHz, $CDCl_3$) δ 169.3, 160.6, 158.8, 144.3, 134.5, 134.0, 131.0, 122.0, 75.2, 67.9, 62.8, 31.1, 23.4, 0.00. ESI (+VE) m/z: 384.1 (M+Na)$^+$. HR-ESI cacld for $C_{19}H_{28}NO_4Si$ (M+Na)$^+$: 362.1782, Found: 362.1789.

(4R)-3-[(2E)-[4-[(1,1-Dimethylethyl)dimethylsilyl] oxy]-1-oxo-2-buten-1-yl]-4-phenyl-2-oxazolidinone (8)

To a solution of 7 (5.00 g, 13.9 mmol) in anhydrous THF (70 mL) at room temperature was added tributylphosphine (0.34 mL, 1.39 mmol). The resulting solution was stirred at room temperature (60 minutes), then diluted with EtOAc (200 mL), washed ($H_2O$ and brine), dried ($Na_2SO_4$), and purified by silica gel column chromatography (hexanes: EtOAc) to yield 8 as a white solid (4.20 g, 84% yield). $[\alpha]^{20}_D$ −54.5 (c 1.40, $CHCl_3$). mp. 79-81° C. $^1H$ NMR (400 MHz, $CDCl_3$) δ 7.48 (dt, J=15.2, 2.4 Hz, 1H), 7.30-7.21 (m, 5H), 7.02 (dt, J=15.2, 3.4 Hz, 1H), 5.39 (dd, J=8.6, 3.8 Hz, 1H), 4.60 (t, J=8.8 Hz, 1H), 4.28 (dd, J=3.4, 2.2 Hz, 2H), 4.17 (dd, J=8.8, 4.0 Hz, 1H), 0.85 (s, 9H), 0.00 (s, 6H). $^{13}C$ NMR (100 MHz, $CDCl_3$) δ 170.0, 159.0, 155.4, 144.5, 134.6, 134.1, 131.4, 124.1, 75.3, 68.1, 63.2, 31.3, 23.8, 0.00. IR (KBr) $v_{max}$: 2927, 2855, 1759, 1693, 1324, 1201, 1104, 951, 834, 715 cm$^{-1}$. ESI (+VE) m/z: 384.1 (M+Na)$^+$. HR-ESI cacld for $C_{19}H_{28}NO_4Si$ (M+Na)$^+$: 362.1782, Found: 362.1790.

(4R)-3-[(2S,3R)-[2-Azido-4[(1,1-dimethylethyl) dimethylsilyl]oxy]-3-methyl-1-oxo-butyl)]-4-phenyl-2-oxazolidinone (9)

To a solution of copper(I) bromide dimethyl sulfide complex (2.56 g, 12.45 mmol) in dimethyl sulfide (20 mL) and THF (30 mL) at −78° C. was added a solution of methylmagnesium chloride (3.0 M in THF, 5.50 mL, 16.4 mmol). The suspension was stirred at −78° C. (20 minutes), then warmed to 0° C. (20 minutes) and cooled to −78° C. The mixture was then transferred to a pre-cooled (−78° C.) solution of 8 (1.80 g, 4.98 mmol) in THF (16.0 mL) and $CH_2Cl_2$ (8.0 mL) using a cannula. The resulting mixture was kept at −78° C. (60 minutes) then warmed to −40° C. (60 minutes) and cooled again to −78° C. To the mixture was added a pre-cooled (−78° C.) solution of N-bromosuccinimide (4.45 g, 25.0 mmol) in THF (50 mL) and the mixture was stirred at −78° C. (90 minutes). The reaction was quenched by addition of saturated $NaHSO_3$ (50 mL), extracted with EtOAc (100 mL×2). The combined organic phase was washed ($H_2O$ and brine), dried ($Na_2SO_4$), and purified by silica gel column chromatography (hexanes: EtOAc) to yield the requisite α-bromo-containing intermediate as a white solid (1.93 g). To a solution of the α-bromo compound (1.93 g) in DMF (25 mL) at 0° C., was added sodium azide (1.00 g, 15.4 mmol) and the mixture was stirred (2 h). The mixture was diluted with EtOAc (150 mL), washed (H$_2$O and brine), dried (Na$_2$SO$_4$), and purified by silica gel column chromatography (hexanes:EtOAc) then crystallized (EtOAc:petroleum ether) to yield azide 9 as a white solid (1.65 g, 79% yield). [α]$^{20}_D$ −73.0 (c 1.10, CHCl$_3$). mp. 80-82° C. $^1$H NMR (400 MHz, CDCl$_3$) δ 7.40-7.30 (m, 5H), 5.49 (dd, J=8.8, 4.0 Hz, 1H), 5.17 (d, J=8.8 Hz, 1H), 4.75 (t, J=9.0 Hz, 1H), 4.34 (dd, J=8.8, 4.0 Hz, 1H), 3.65 (dd, J=10.2, 5.4 Hz, 1H), 3.48 (dd, J=10.2, 3.4 Hz, 1H), 2.14 (m, 1H), 0.89 (s, 9H), 0.83 (d, J=6.8 Hz, 3H), 0.03 (s, 3H), 0.00 (s, 3H). $^{13}$C NMR (100 MHz, CDCl$_3$) δ 175.7, 158.7, 143.9, 134.8, 134.6, 131.9, 75.7, 69.3, 66.7, 63.4, 43.5, 31.4, 23.8, 19.4, 0.00. IR (KBr) ν$_{max}$: 2930, 2359, 2106, 1786, 1710, 1206, 1097, 833, 778 cm$^{-1}$. ESI (+VE) m/z: 441.1 (M+Na)$^+$. HR-ESI MS cacld for C$_{20}$H$_{31}$N$_4$O$_4$Si (M+H)$^+$: 419.2109, Found: 419.2114.

[(3S,4R)-Tetrahydro-4-methyl-2-oxo-3-furanyl]-carbamic acid phenylmethyl ester (10) and (2S,3R)-4-hydroxy-N-(phenylmethoxycarbonyl)-L-valine methyl ester (11)

To a solution of 9 (600 mg, 1.44 mmol) in MeOH (20 mL) at room temperature was added p-toluenesulfonic acid monohydrate (14 mg, 0.07 mmol). The solution was stirred at room temperature (6 h), then diluted with EtOAc (150 mL), washed (H$_2$O and brine), dried (Na$_2$SO$_4$), and purified by silica gel column chromatography (hexanes:EtOAc) to yield the intermediate azide-containing lactone as a colorless liquid (270 mg, containing a small amount EtOAc). $^1$H NMR (400 MHz, CDCl$_3$) δ 4.36 (dd, J=8.8, 6.4 Hz, 1H), 4.26 (d, J=7.2 Hz, 1H), 4.02 (dd, J=9.2, 4.0 Hz, 1H), 2.75 (m, 1H), 1.13 (d, J=7.2 Hz, 3H). A suspension of the this lactone and Pd*C (10%, 60 mg) in MeOH (9.0 mL) and acetic acid (1.0 mL) was stirred under H$_2$ (1 atmosphere) at room temperature (overnight). The catalyst was removed by filtration though a celite pad under argon and the filtrate was concentrated. The residue was re-dissolved in THF (10.0 mL) containing H$_2$O (10 mL) and then cooled to 0° C. To this was added benzyl chloroformate (0.32 mL, 2.25 mmol) and NaHCO$_3$ (840 mg, 10.0 mmol) and the mixture was stirred (4 h). The mixture was diluted with EtOAc (150 mL), washed (H$_2$O and brine), dried (Na$_2$SO$_4$), and purified by silica gel column chromatography (hexanes:EtOAc) to yield 10 as a white crystalline solid (90 mg, 25% yield over 3 steps) and 11 as a viscous colorless oil (250 mg, 49% yield over 3 steps). For (10): mp. 125-127° C. $^1$H NMR (400 MHz, CDCl$_3$) δ 7.40-7.30 (m, 5H), 5.33 (m, 1H), 5.10 (s, 2H), 4.53 (t, J=6.8 Hz, 1H), 4.35 (dd, J=9.2, 5.2 Hz, 1H), 4.05 (d, J=9.2 Hz, 1H), 2.92 (m, 1H), 0.95 (d, J=7.2 Hz, 3H). $^{13}$C NMR (100 MHz, CDCl$_3$) δ 174.5, 156.1, 135.9, 128.5, 128.3, 128.1, 72.4, 67.3, 54.5, 34.1, 12.7. ESI (+VE) m/z: 272.1 (M+Na)$^+$. HR-ESI cacld for C$_{13}$H$_{16}$NO$_4$ (M+H)$^+$: 250.1074, Found: 250.1081.

For (11): $^1$H NMR (400 MHz, CDCl$_3$) δ 7.29-7.28 (m, 5H), 5.98 (d, J=8.4 Hz, 1H), 5.04 (s, 2H), 4.34 (m, 1H), 3.65 (s, 3H), 3.54 (dd, J=11.2, 4.4 Hz, 1H), 3.44 (dd, J=11.2, 6.0 Hz, 1H), 2.92 (s, 1H), 2.14 (m, 1H), 0.92 (d, J=7.2 Hz, 3H). ESI (+VE) m/z: 304.2 (M+Na)$^+$. HR-ESI MS cacld for C$_{14}$H$_{20}$NO$_5$ (M+H)$^+$: 282.1336, Found: 282.1343.

(2S,3R)-4-hydroxy-N-(9-Phenylfluoren-9-yl)-N-benzyl-L-valine methyl ester (14)

To a solution of 13 (4.00 g, 7.91 mmol) in anhydrous THF (260 mL) at −40° C., was added DIBAL (1.0 M in Hexanes, 19.8 mL, 19.8 mmol). The mixture was stirred for 4 hr (−40° C.-0° C.) before cooled down to −78° C., quenched by acetone (10 mL), warmed to r.t., stirred with 1 N KH$_2$PO$_4$ (500 mL) and sodium potassium tartrate (30.0 g) overnight, filtered through the celite. The filtrate was extracted with EtOAc, washed (H$_2$O and brine), dried (Na$_2$SO$_4$), and purified by silica gel column chromatography (hexanes:EtOAc) to yield alcohol 14 as a white wax (2.30 g, 61% yield, quantitative yield based on recovered starting material) and recycled 13 as a white wax (1.60 g). $^1$H NMR (400 MHz, CDCl$_3$) δ 7.76-7.60 (m, 8H), 7.35-7.20 (m, 10H), 4.70 (AB, J$_{AB}$=13.6 Hz, 1H), 4.38 (AB, J$_{AB}$=13.6 Hz, 1H), 3.84 (dd, J=10.8, 3.6 Hz, 1H), 3.33 (dd, J=10.8, 6.4 Hz, 1H), 3.04 (d, J=8.4 Hz, 1H), 2.93 (s, 3H), 1.40 (m, 1H), 0.34 (d, J=6.8 Hz, 3H). $^{13}$C NMR (100 MHz, CDCl$_3$) δ 171.7, 148.3, 144.8, 144.0, 142.0, 141.3, 139.7, 129.7, 128.6, 128.4, 128.0, 127.7, 127.3, 127.2, 127.1, 127.0, 125.3, 120.2, 80.3, 65.5, 63.3, 50.6, 36.3, 14.2. ESI (+VE) m/z: 478.2 (M+H)$^+$. HR-ESI MS cacld for C$_{32}$H$_{32}$NO$_3$ (M+H)$^+$: 478.2377, Found: 478.2385.

(2S,3R)-4-[Di-(tert-butyl)-oxyphosphinyl]-4-hydroxy-N-phenylmethoxycarbonyl)-L-valine methyl ester (18)

To a solution of oxalyl chloride (0.96 mL, 10.1 mmol) in CH$_2$Cl$_2$ (40 mL) at −78° C., was added a solution of DMSO (1.60 mL, 20.2 mmol) in CH$_2$Cl$_2$ (5 mL) and the mixture was stirred (15 minutes). To this was added alcohol 11 (0.63 g, 2.24 mmol) in dry CH$_2$Cl$_2$ (5 mL) over 5 minutes and the mixture was stirred at −75° C. (2 h). triethylamine (8.40 mL, 53.8 mmol) was added and the mixture was warmed to room temperature. To this was added saturated NH$_4$Cl (50 mL) and the mixture was extracted with Et$_2$O (100 mL×2) and the combined organic phase was washed (brine), dried (Na$_2$SO$_4$), and purified by silica gel column chromatography (hexanes:EtOAc). Aldehyde 15 was obtained as a viscous colorless oil (450 mg, 96% yield based on recovered starting material) along with starting alcohol 11 (160 mg). To a solution of di-tert-butyl phosphite (0.30 mL, 1.50 mmol) and triethylamine (0.21 mL, 1.50 mmol) in CH$_2$Cl$_2$ (5 mL) at 0° C., was added chlorotrimethylsilane (0.19 mL, 1.50 mmol) and the mixture was stirred (5 minutes) and then transfer to a solution of aldehyde 15 (300 mg, 1.08 mmol) in CH$_2$Cl$_2$ (5 mL) at room temperature and the mixture was stirred (3 h). The mixture was diluted with EtOAc (150 mL), washed (brine), dried (Na$_2$SO$_4$) and concentrated. The resulting crude silyl-protected 17 was re-dissolved in MeOH (10 mL), to this was added H$_2$O (1.0 mL) and citric acid (200 mg) and the mixture was stirred at room temperature (over night). The mixture was diluted with EtOAc (200 mL), washed (saturated NaHCO$_3$ and brine), dried (Na$_2$SO$_4$) and purified by silica gel column chromatography (hexanes:EtOAc) to yield 18 as a white wax epimeric at the γ-carbon (450 mg, 88% yield). $^1$H NMR (400 MHz, CDCl$_3$) δ 7.30-7.29 (m, 5H), 6.30 (d, J=8.0 Hz, 0.7H), 5.30 (m, 0.3H), 5.10-5.05 (m, 2H), 4.30 (m, 0.7H), 4.09 (m, 0.3H), 3.75-3.55 (m, 4H), 2.51 (m, 0.7H), 1.51-1.40 (m, 18H), 1.15-1.00 (m, 3H). $^{13}$C NMR (100 MHz, CDCl$_3$) δ 172.3, 156.7, 136.4, 128.4, 128.0, 70.5, 68.8, 67.3, 66.8, 59.8, 53.9, 53.1, 52.2, 36.6, 35.4, 30.3, 24.1, 14.7, 11.5, 9.4. ESI (+VE) m/z: 496.2 (M+Na)$^+$. HR-ESI MS cacld for C$_{22}$H$_{36}$NO$_8$NaP (M+Na)$^+$: 496.2071, Found: 496.2065.

(2S,3R)-4-[Di-(tert-butyl)-oxyphosphinyl]-N-(phenylmethoxycarbonyl)-L-valine methyl ester (20)

A solution of alcohol 18 (250 mg, 0.53 mmol), 0-phenylchlorothionoformate (215 μL, 1.60 mmol), 4-(dimethylamino) pyridine (DMAP) (15 mg, 0.20 eq.) and N,N-diisopropylethylamine (363 μL, 2.10 mmol) in anhydrous CH$_2$Cl$_2$ (8.0 mL) was stirred at room temperature (overnight). The mixture was diluted with EtOAc (100 mL), washed (sat. NaHCO$_3$ and brine), dried (Na$_2$SO$_4$) and purified by silica gel column chromatography (hexanes:EtOAc) to give the intermediate thiocarbonate 19 as a pale brown wax (225 mg). Crude 19 was dissolved in toluene (10 mL) and to this was added tributyltin hydride (0.42 mL, 1.59 mmol) and azobisisobutyronitrile (AIBN) (one spatula tip). The mixture was maintained at 100° C. (20 minutes), then cooled to room temperature and concentrated under vacuum. The residue was purified by silica gel column chromatography (hexanes:EtOAc) to give 20 as viscous colorless oil (140 mg, 58% yield for 2 steps). [α]$^{20}$$_D$+2.4 (c 0.85, CHCl$_3$). $^1$H NMR (400 MHz, CDCl$_3$) δ 7.27-7.20 (m, 5H), 5.80 (d, J=8.4 Hz, 1H), 5.07 (AB, J$_{AB}$=12.4 Hz, 1H), 5.02 (AB, J$_{AB}$=12.4 Hz, 1H), 4.23 (m, 1H), 3.67 (s, 3H), 2.33 (m, 1H), 1.69-1.10 (m, 20H), 1.05 (d, J=6.8 Hz, 3H). $^{13}$C NMR (100 MHz, CDCl$_3$) δ 172.1, 156.2, 136.3, 128.4, 128.1, 82.1, 66.9, 59.4, 52.2, 32.2, 30.3, 29.6, 27.8, 26.8, 17.5, 13.5. IR (KBr) ν$_{max}$: 2976, 1720, 1535, 1322, 1252, 975 cm$^{-1}$. ESI (+VE) m/z: 480.3 (M+Na)$^+$. HR-ESI MS cacld for C$_{22}$H$_{36}$NO$_7$NaP (M+Na)$^+$: 480.2122, Found: 480.2126.

(2S,3R)-4-[Di-(tert-butyl)-oxyphosphinyl]-N-[(9H-fluoren-9-ylmethoxy)carbonyl]-L-valine (4)

To a solution of 20 (140 mg, 0.31 mmol) in THF (3.0 mL) and H$_2$O (3.0 mL) at 0° C., was added LiOH.H$_2$O (26 mg, 0.62 mmol) and the mixture was stirred room temperature (over night). The THF was removed by rotary evaporation and the residual aqueous phase was neutralized by addition of saturated aqueous NH$_4$Cl (20 mL) and extracted with EtOAc (3×50 mL). The combined organic extract was washed with H$_2$O (50 mL), brine (50 mL), dried (Na$_2$SO$_4$) and concentrated. The resulting residue was dissolved in MeOH (20 mL) and hydrogenated (1 atmosphere H$_2$) over 10% Pd.C (40 mg) at room temperature (over night). The catalyst was removed by filtration and the filtrate was concentrated. The resulting residue was dissolved in dioxane (5.0 mL) and H$_2$O (5.0 mL) and 9-fluorenylmethyl-succinimidyl carbonate Fmoc-OSu (173 mg, 0.465 mmol) and NaHCO$_3$ (62 mg, 0.62 mmol) were added and the mixture was stirred at room temperature (over night). The reaction mixture was neutralized by addition of saturated NH$_4$Cl (20 mL) and extracted with EtOAc (3×50 mL). The combined EtOAc layer was washed with H$_2$O (50 mL), brine (50 mL), dried (Na$_2$SO$_4$) and purified by silica gel column chromatography (CH$_2$Cl$_2$: MeOH) to yield 4 as a white wax (166 mg, quantitative yield over 3 steps). [α]$^{20}$$_D$+16.5 (c 0.65, CHCl$_3$). $^1$H NMR (400 MHz, DMS)-d6) δ 7.88 (d, J=7.6 Hz, 2H), 7.70 (d, J=7.2 Hz, 2H), 7.41 (t, J=7.4 Hz, 2H), 7.31 (t, J=7.6 Hz, 2H), 4.30-4.19 (m, 4H), 3.84 (m, 1H), 2.31 (m, 1H), 1.80-1.55 (m, 2H), 1.42 (s, 18H), 0.96 (d, J=6.4 Hz, 3H). $^{13}$C NMR (100 MHz, CDCl$_3$) δ 155.8, 143.9, 140.7, 127.6, 127.0, 125.1, 120.0, 80.7, 65.4, 60.5, 46.7, 31.5, 30.0, 16.9. ESI (+VE) m/z: 554.2 (M+Na)$^+$. HR-ESI MS cacld for C$_{28}$H$_{38}$NO$_7$NaP (M+Na)$^+$: 554.2278, Found: 554.2277.

Example 1. Peptides Containing Phosphate Monoesters and Arylalkyl-Histine-Containing PBD-Binding Peptides Post-Mistunobu reaction conditions were used to make mono-ester peptide combined with arylalkyl-Histidine. Through Solid phase peptide synthesis, resin bound 5-mer peptide 1 was obtained. After on-resin Mistunobu reaction and cleavage step, the peptides 3 containing different monoester could be synthesized and used for biological evaluation.

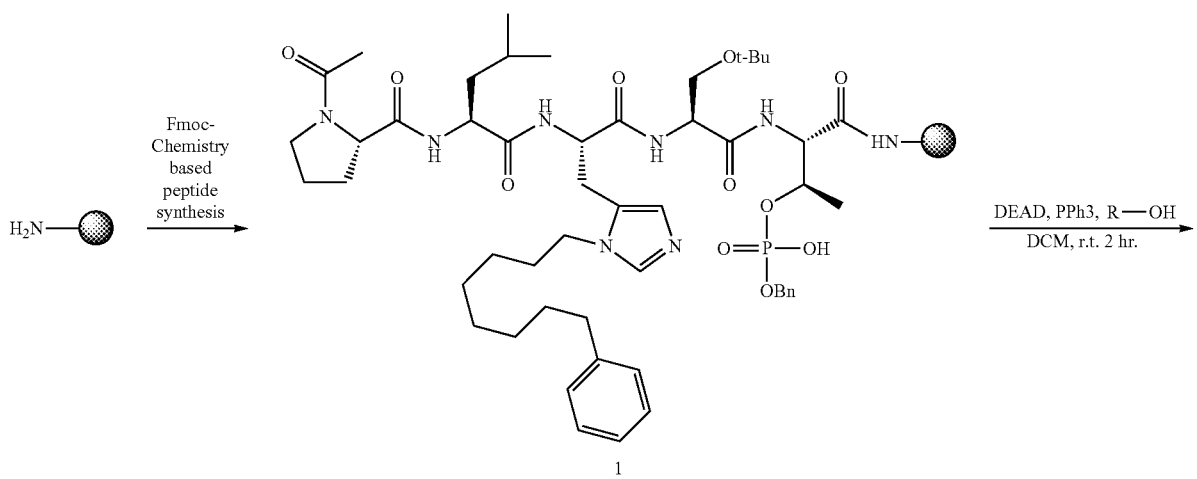

-continued
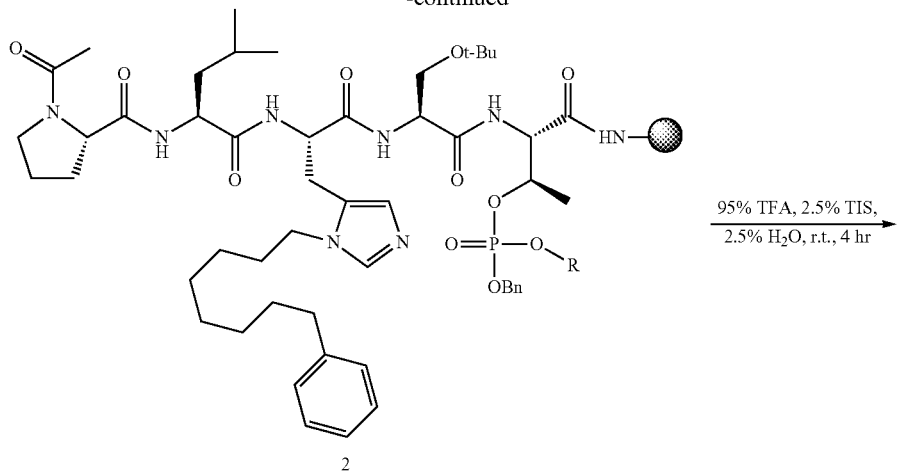
2
95% TFA, 2.5% TIS, 2.5% H₂O, r.t., 4 hr →
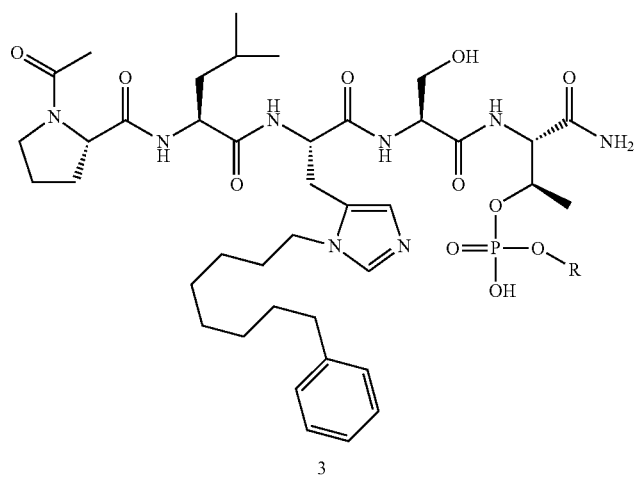
3
Post-modification on the solid phase by using Mitsunobu reaction.
The alcohol library is provided below:
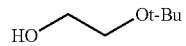
a
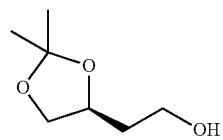
b
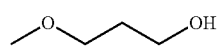
c
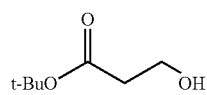
d
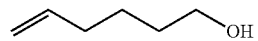
e
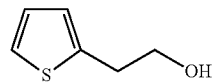
f
-continued
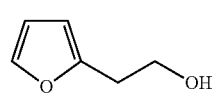
g
MeOH
h
i
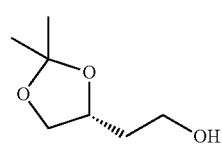
i
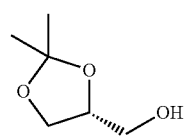
j
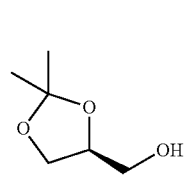
k

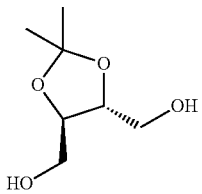

Initial alcohol library used prepare peptide 3

Relative to parent peptide (R=H), very little loss of affinity was observed for any of the mono-anionic esters and astoundingly, for seven derivatives (3a-3d, and 3i-3j); greater affinity was found than for the parent di-anionic peptide.

Peptide Synthesis Procedures.

Fmoc-Thr(PO(OBzl)OH)—OH and other Fmoc protected amino acids were purchased from Novabiochem. Fmoc-His ($N^{\pi}$—$(CH2)_8$Ph)-OH was synthesized through our previous published paper [*J. Org. Chem*, 2011, 76, 8885.] Peptides were synthesize on NovaSyn® TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-Diisopropylethylamine (DIPEA) (10.0 eq.) were used as coupling reagents. The N-terminal was acetylated by 1-Acetylimidazole. Finally the resin was washed with N,N-dimethylforamide (DMF), methanol, dichloromethane and ether, and then dried under vacuum (overnight).

Post-Modification of the Peptide by Mitsunobu Reaction.

The above resin (200 mg, 0.04 mmol) was swelled in dichloromethane for 15 mins, treated by triphenylphosphine (262 mg, 1.0 mmol), DEAD (0.46 mL, 40% solution in toluene, 0.10 mol) and alchohol a-l (0.10 mmol) in dry dichloromethane for 2 hr at r.t., washed by dichloromethane, dried under vacuum for 2 hr before cleavage.

Peptide Cleavage and Purification.

Peptides were cleaved from resin (200 mg) by treatment with 5 mL of trifluoroacetic acid:triisbutylsilane:$H_2O$ (90:5:5) (4 h). The resin was filtered off and the filtrate was concentrated under vacuum, then precipitated with ether and the precipitate washed with ether. The resulting solid was dissolved in 50% aqueous acetonitrile (5 mL) and purified by reverse phase preparative HPLC using a Phenomenex $C_{18}$ column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave the product as white powders.

| | Low resolution ESI-Mass Sepc. | | |
| --- | --- | --- | --- |
| Entry | Structure | Expected $(M + H)^+$ | Observed $(M + H)^+$ |
| 3a | 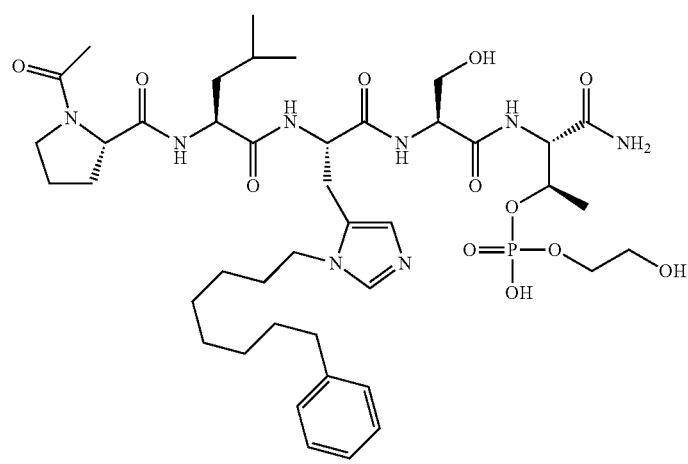 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OCCO] | 907.5 | 907.4 |

-continued
| | | Low resolution ESI-Mass Spec. | |
|---|---|---|---|
| Entry | Structure | Expected (M + H)+ | Observed (M + H)+ |
| 3b | 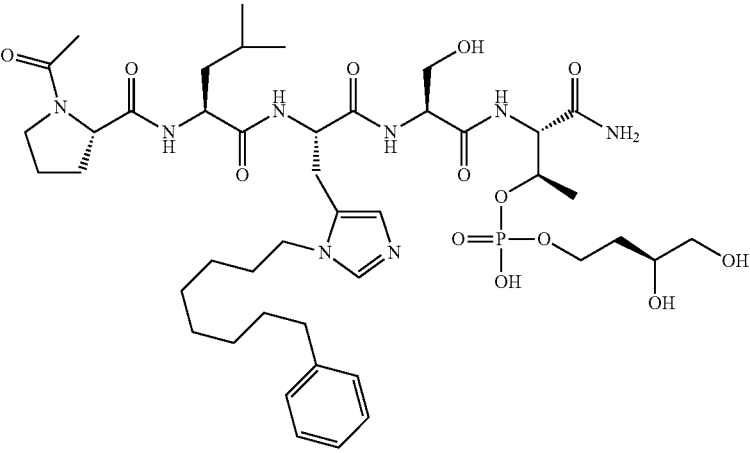 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OCC[C@H](O)CO] | 951.5 | 951.4 |
| 3c | 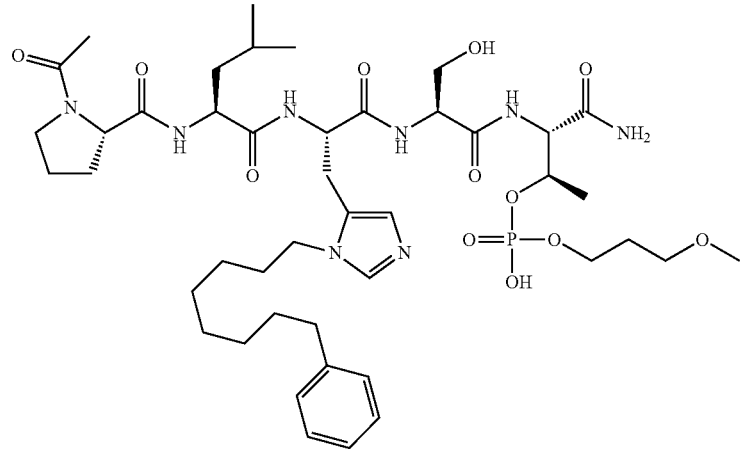 [SMILES: COCCCOP(=O)(O)O[C@H](C)[C@H](NC(=O)[C@H](CO)NC(=O)[C@H](Cc1cncn1CCCCCCCCc1ccccc1)NC(=O)[C@H](CC(C)C)NC(=O)[C@@H]1CCCN1C(C)=O)C(N)=O] | 935.5 | 935.4 |
| 3d | 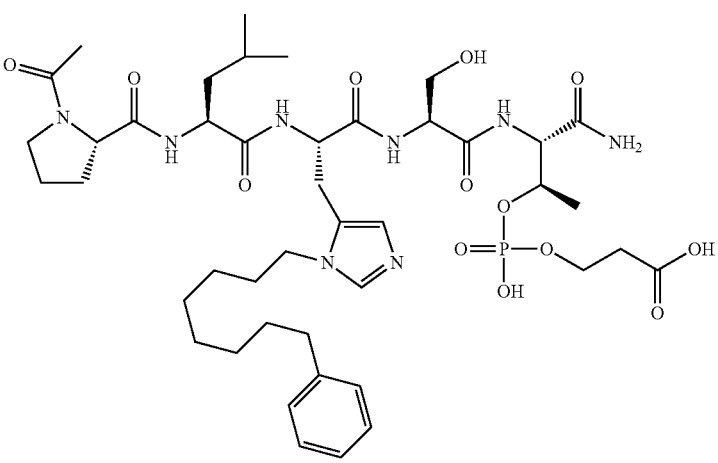 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OCCC(=O)O] | 935.5 | 935.4 |

-continued

| | | Low resolution ESI-Mass Spec. | | |
|---|---|---|---|---|
| Entry | Structure | | Expected (M + H)+ | Observed (M + H)+ |
| 3e | | | 945.5 | 945.4 |
| 3f | | | 973.5 | 973.3 |
| 3g | | | 957.5 | 957.4 |

-continued
Low resolution ESI-Mass Spec.
| Entry | Structure | Expected (M + H)+ | Observed (M + H)+ |
|---|---|---|---|
| 3h | 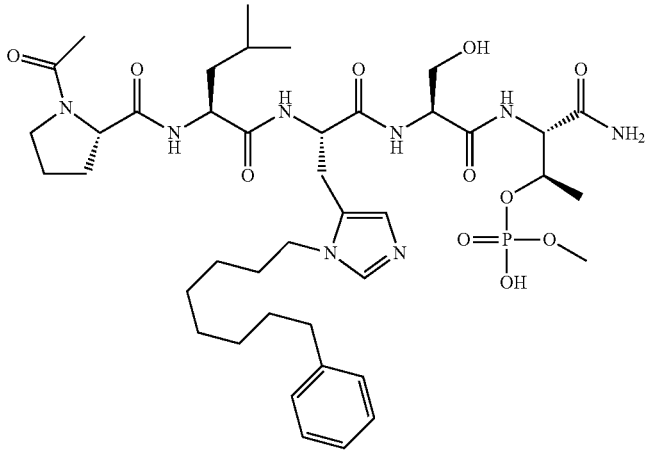 [SMILES: COP(=O)(O)O[C@H](C)[C@H](NC(=O)[C@H](CO)NC(=O)[C@H](Cc1cncn1CCCCCCCCc1ccccc1)NC(=O)[C@H](CC(C)C)NC(=O)[C@@H]1CCCN1C(C)=O)C(N)=O] | 877.5 | 877.3 |
| 3i | 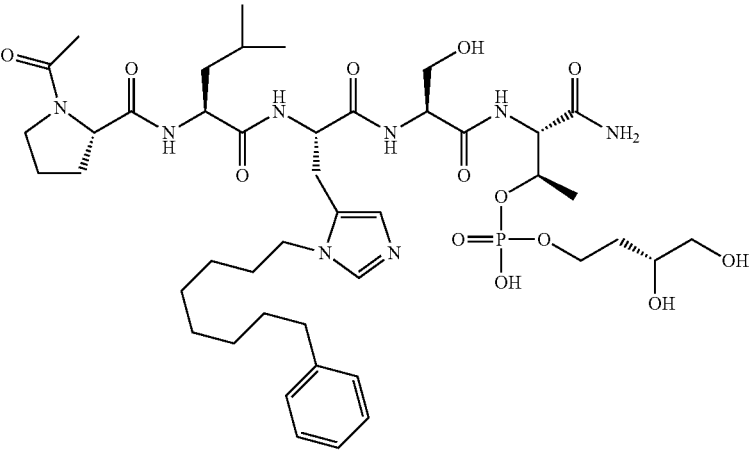 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OCC[C@@H](O)CO] | 951.5 | 951.4 |
| 3j | 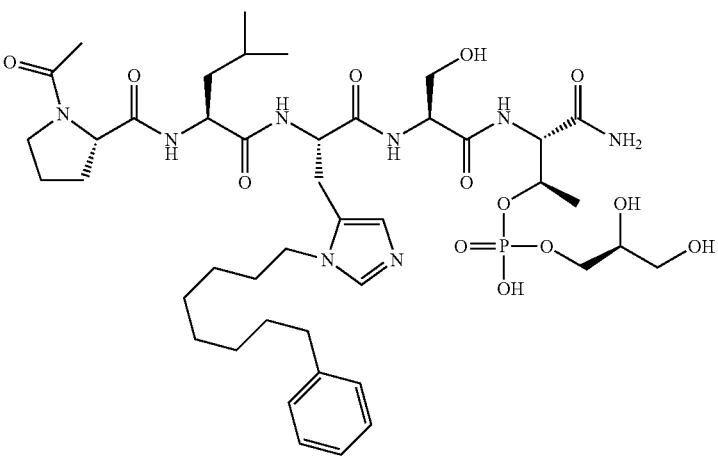 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OC[C@@H](O)CO] | 937.5 | 937.4 |

-continued

Low resolution ESI-Mass Spec.

| Entry | Structure | Expected (M + H)+ | Observed (M + H)+ |
|---|---|---|---|
| 3k | 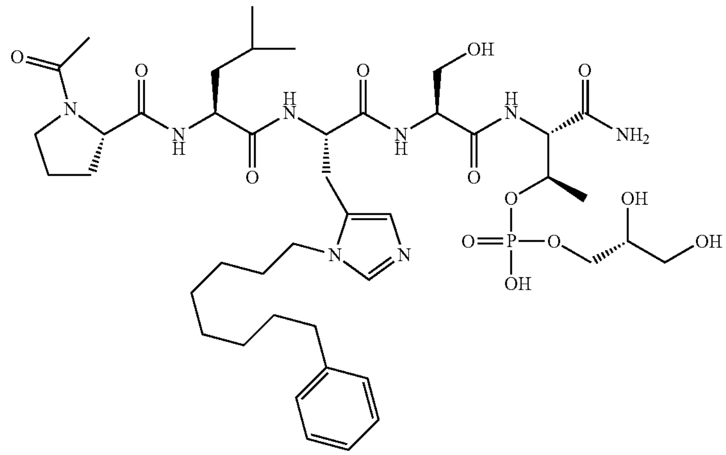 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OC[C@H](O)CO] | 937.5 | 937.4 |
| 3l | 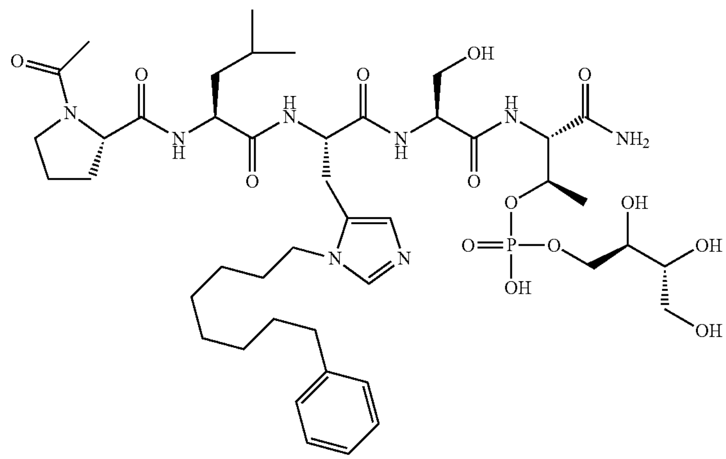 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)OC[C@@H](O)[C@H](O)CO] | 967.5 | 967.4 |

II. Biological Examples

A: Materials and Methods
Methods
Peptide-Binding, GST-PBD Pull-Down, and ELISA-Based PBD-Binding Inhibition Assays.

Peptide binding and GST-PBD pull-down assays were performed as described previously (15). An ELISA-based PBD-binding inhibition assay was carried out using an immobilized biotinylated 9-mer p-T78 peptide {Biotin-C—(CH$_2$)$_6$—(CH$_2$)$_6$-DPPLHSpTAI-NH$_2$ (SEQ ID NO: 10)} and the cellular lysates expressing HA-EGFP-Plk1.

Isothermal Titration Calorimetry Analyses.

The calorimetric titrations were carried out using purified recombinant PBDs (for Plk1 and Plk2) from bacterial cells and the indicated peptides. Further details are presented in Online Supplemental Materials.

Crystallization, Data Collection, and Refinement.

All initial crystallization screens for the Plk1 PBD-PLH-SpT (SEQ ID NO: 1) complex were performed on an Art Robbins Phoenix Liquid Handling System using Index (Hampton Research, Aliso Viejo, Calif.) and PEGs (Qiagen, Valencia, Calif.) crystallization kits. All subsequent crystals were grown using the hanging-drop vapor diffusion method at room temperature. PBD and the kinase domain of Plk1 were concentrated to ~30 mg/ml in buffer A (20 mM Tris-Cl, pH 8.0, 500 mM NaCl, 3 mM DTT). The phosphopeptide Ac-PLHSpT (SEQ ID NO: 1) was dissolved in buffer A. The phosphopeptide and PBD were added in 2:1 stoichiometric ratio, respectively, and the final concentration was adjusted to ~15 mg/ml. Crystals of this complex were grown by adding 1 μl of this complex to 1 μl of well solution (0.2 M di-potassium phosphate, 20% w/v PEG 3350). The complex between PBD and kinase domain was formed similarly using a 1:1 stoichiometric ratio, and 0.2 M lithium sulfate monohydrate, 0.1 M Bis-Tris, pH 5.5, 25% w/v PEG 3350 as the well solution. Crystals formed within one week and were soaked for 5 minutes in mother liquor constituted with 20% v/v glycerol prior to flash-freezing in liquid nitrogen. The complex of PBD and Ac-PLHSpT (SEQ ID NO: 1) crystallized in the space group P2$_1$2$_1$2$_1$ (a=35.19 Å, b=65.76 Å, c=104.11 Å). The kinase domain of Plk1 precipitated and PBD crystallized in the space group P2$_1$ (a=35.29 Å, b=102.29 Å, c=68.55 Å, β=93.24°).

Crystals of the Plk1 PBD-PPHSpT (SEQ ID NO: 2) complex were obtained in a similar fashion using a well solution of 0.1 M MES buffer (pH 6.0) containing 15% PEG 3350. The crystals were soaked for 5 minutes in the mother liquor constituted with 15% v/v glycerol, 10 mM DTT and 2 mM of the phosphopeptide Ac-PPHSpT (SEQ ID NO: 2) prior to freezing in liquid nitrogen. This complex crystallized in the space group $P2_12_12_1$ (a=35.44 Å, b=66.50 Å, c=105.82 Å). All data were collected at 100K. The data for PBD, and PBD in complex with Ac-PLHSpT (SEQ ID NO: 1) were collected at the SER-CAT beamline 22-ID, at the Advanced Photon Source (APS), on a MAR 300CCD detector. The data for the complex of PBD and Ac-PPHSpT (SEQ ID NO: 2) were collected at APS beamline 24-ID-C at 100 K. All data were processed and scaled using the HKL2000 package20. Phasing of the data was done by molecular replacement using a previously published structure (PDB ID; 1UMW). The structures were refined independently of each other with the program REFMAC521 and CNS1.122. Model building was performed using Coot (23) and XtalView (24) (Table 4).

Crystals of the Plk1 PBD-LHSpTA (SEQ ID NO: 3) complex were grown by hanging drop vapour diffusion using 1 µl of protein solution (12 mg/ml in 10 mM Tris-Cl, pH 8.0, 0.5 M NaCl, 10 mM DTT, 2 mM Ac-LHSpTA-NH$_2$ (SEQ ID NO: 3) peptide) mixed with 1 µl of well solution consisting of 32.5% PEG 2000 MME, 0.1 M Tris-Cl, pH 8.5, 0.2 M trimethyl-amine N-oxide. Crystals grew overnight at room temperature. For data collection, a crystal was looped from the drop and flash frozen by direct transfer to a cryostream at 100 K. Data were collected with a rotating anode home source on a Rigakgu R-axis IV detector and processed using the HKL2000 package20. A molecular replacement solution was found with AMoRe (25). Initial refinement was done with CNS 1.2126 with manual model fitting using XtalView (24). The final rounds of refinement were completed in PHENIX 1.3 (27) with the addition of riding hydrogens.

Peptide Pull-Down Assay:

Peptide pull-down assays were carried out essentially as described previously (Yun, S.-M. et al. *Nat. Struct. Mol. Biol.* 16, 876-882 (2009). To study Plk1 PBD-binding specificity, p-T78 peptide or its derivatives were cross-linked to beads using SulfoLink Coupling Gel (Pierce, Rockford, Ill.) via either an N-terminal Cys-(CH$_2$)$_6$—CO linker [PLHSpT (SEQ ID NO: 1), PLHST (SEQ ID NO: 11), 4j, and 4j (S/A)] or an N-terminal Cys residue conjugated to PEG moiety [PEG-4j* and PEG-4j* (S/A)]. Mitotic lysates expressing Plk1-3 were prepared from 293T cells transfected with Flag-Plk1 (K82M), Flag-Plk2 (K108M) or Flg-Plk3 (K52R) (a gift of Wei Dai, New York University School of Medicine, NY) and treated with 200 ng/ml of nocodazole for 16 h. After incubating the cell lysates prepared in TBSN buffer {20 mM Tris-Cl (pH8.0), 150 mM NaCl, 0.5% Np-40, 5 mM EGTA, 1.5 mM EDTA, 20 mM p-nitrophenylphosphate and protease inhibitor cocktail (Roche, Nutley, N.J.)} with the bead-immobilized ligands for 2 h at 4° C., the ligand-associating proteins were precipitated, washed, boiled in sodium dodecyl sulfate (SDS) sample buffer, separated by 8% SDS-polyacrylamide gel electrophoresis (PAGE), and then subjected to immunoblotting analysis with anti-Flag antibody and the enhanced chemilunimescence (ECL) detection system (Pierce). The same membrane was also stained with Coomassies (CBB). Signal intensities were quantified using Image J program.

Peptide and GST-PBD Pull-Down Assays.

For Plk1 pull-down assays with immobilized peptides, we used total lysates prepared from mitotic HeLa cells. HeLa cells contain no mutations in Plk1 coding sequence and the level of Plk1 expression is high (2). Cells treated with 200 ng/ml of nocodazole for 16 h were lysed in TBSN buffer {20 mM Tris-Cl (pH8.0), 150 mM NaCl, 0.5% NP-40, 5 mM EGTA, 1.5 mM EDTA, 0.5 mM Na$_3$VO$_4$, 20 mM p-nitrophenyl phosphate, and protease inhibitor cocktail (Roche, Nutley, N.J.)}, and then clarified by centrifugation at 15,000×g for 20 min at 4° C. The resulting lysates were incubated with bead-immobilized peptides (40 µM per binding) for 2 h, precipitated, washed, and then boiled in sodium dodecyl sulfate (SDS) sample buffer to elute the associated proteins. Samples were separated by 10% SDS-polyacrylamide gel electrophoresis (PAGE), and then either stained with silver or transferred to PVDF membrane for immunoblotting analysis with anti-Plk1 antibody using the enhanced chemiluminescence (ECL) detection system (Pierce).

To investigate the binding specificity of p-T78 peptides to various Plks, Flag-Plk1 (K82M), Flag-Plk2(K108M)3 or Flag-Plk3(K52R) (a gift of Wei Dai, New York University School of Medicine, NY) construct was first transfected into HeLa cells. Cellular lysates were prepared as above, mixed, and then incubated in TBSN buffer with the immobilized peptides indicated.

To determine whether PLHSpT (SEQ ID NO: 1) binds to the phosphate pincer cleft of the PBD, bead-immobilized PLHSpT (SEQ ID NO: 1) or the respective non-phospho PLHST (SEQ ID NO: 11) control peptide was incubated with soluble control GST, GST-PBD, or GST-PBD(H538A K540M)4 for 2 h, washed, and then precipitated fraction was analyzed.

For p-Cdc25C pull-down assays, either bead-bound GST-PBD or the corresponding GST-PBD(H538A K540M) mutant was incubated with mitotic HeLa lysates in TBSN buffer supplemented with 2 mM DTT. To test the ability of the indicated peptides to compete the PBD-p-Cdc25C interaction, lysates were pre-incubated with GST-PBD for 1.5 h prior to the addition of the indicated peptides. Lysates were then incubated for additional 1.5 h, washed in the binding buffer, and then analyzed. For competition of the interaction between p-Cdc25C and endogenous Plk1, mitotic lysates were prepared in TBSN and incubated with the indicated peptides for 1 h before subjecting to immunoprecipitation with anti-Plk1 antibody.

ELISA-Based PBD-Binding Inhibition Assay.

A biotinylated p-T78 peptide was first diluted with 1× coating solution (KPL Inc., Gaithersburg, Md.) to the final concentration of 0.3 µM, and then 100 µl of the resulting solution was immobilized onto a 96-well streptavidin-coated plate (Nalgene Nunc, Rochester, N.Y.). The wells were washed once with PBS plus 0.05% Tween20 (PBST), and incubated with 200 µl of PBS plus 1% BSA (blocking buffer) for 1 h to prevent non-specific binding. Mitotic 293A lysates expressing HA-EGFP-Plk1 were prepared in TBSN buffer (~60 µg total lysates in 100 µl buffer), mixed with the indicated amount of the competitors (p-T78 peptide and its derivative compounds), provided immediately onto the biotinylated peptide-coated ELISA wells, and then incubated with constant rocking for 1 h at 25° C. Following the incubation, ELISA plates were washed 4 times with PBST. To detect bound HA-EGFP-Plk1, the plates were probed for 2 h with 100 µl/well of anti-HA antibody at a concentration of 0.5 µg/ml in blocking buffer and then washed 5 times. The plates were further probed for 1 h with 100 µl/well of HRP-conjugated secondary antibody (GE Healthcare, Piscataway, N.J.) at a 1:1,000 dilution in blocking buffer. The plates were washed 5 times with PBST and incubated with 100 µl/well of 3,3',5,5'-tetramethylbenzidine (TMB) solution (Sigma, St. Louis, Mo.) as a substrate until a desired absorbance was reached. The reactions were stopped by the addition of 100 µl/well of stop solution (Cell Signaling Technology, Danvers, Mass.). The optical density (O.D.) was measured at 450 nm by using an ELISA plate reader (Molecular Devices, Sunnyvale, Calif.).

Cell Culture, Analysis of the Cell Proliferation and Aberrant Mitotic Population, and Indirect Immunofluorescence Microscopy:

HeLa cervical carcinoma cell line CCL2, 293A and 293T cells were cultured as recommended by the American Type Culture Collection (Manassas, Va.), were cultured as recommended by American Type Culture Collection (Manassas, Va.). To prepare mitotic 293A cells expressing HA-EGFP-Plk1, cells were infected with adenovirus expressing HA-EGFP-Plk1 and arrested with 200 ng/ml of nocodazole for 16 h. To analyze the effect of the indicated compounds in cultured cells, logarithmically growing HeLa cells were treated with 200 µM of the indicated compounds for 24 h (a sufficient amount of time to enrich mitotically-arrested cells), treated with Hoechst 33342 for 10 min, and then fixed with 4% paraformaldehyde.

In a separate experiment, HeLa cells were arrested with 2.5 mM thymidine for 16 h and released into fresh medium. Four hours after release, cells were treated with 200 µM of the compounds, harvested at the indicated time points, and then analyzed. Indirect immunofluorescence studies were performed as described previously (Liu, F. et al. Tetrahedron 65, 9673-9679 (2009)), using anti-Plk1 (Santa Cruz Biotechnologies, Santa Cruz, Calif.) and anti-α-tubulin (Sigma) antibodies followed by Texas red (red) and Alexa Fluor 488 (green)-conjugated secondary antibodies, respectively. Confocal images were acquired using a Zeiss LSM510 system mounted on a Zeiss Axiovert 100 M microscope (Carl Zeiss MicroImaging, Inc., Thornwood, N.Y.).

Isothermal Titration Calorimetry Analyses.

The calorimetric titrations were performed on a VP-ITC titration calorimeter (Microcal, Inc., Northampton, Mass.). In a typical experiment, 5 l aliquots of a phosphorylated peptide were injected from a 250 l syringe into a rapidly mixing (300 rpm) solution of Plk1 PBD (cell volume=1.3472 ml). Control experiments involved injecting identical amounts of the peptide solution into buffer without Plk1 PBD. The concentrations of Plk1 PBD were 0.033-0.052 mM, and those of the peptides were 0.145-0.365 mM, all concentration values determined by amino acid analysis. Titrations were carried out at 25° C. in 20 mM Tris-Cl (pH 7.5), 100 mM NaCl, 3 mM DTT. The isotherms, corrected for dilution/buffer effects, were fit using the Origin ITC Analysis software according to manufacturer's protocols. A nonlinear least-square method was used to fit the titration data and to calculate the errors. Consistent with the structural data, a 1:1 stoichiometry was assumed and the data were fit to a one-site binding model. From the binding curve, values for enthalpy and binding affinity were extracted. Thermodynamic parameters were calculated using $\Delta G=-RT\ln Ka$, $\Delta G=\Delta H-T\Delta S$.

Cloning, Protein Expression, and Purification.

Two forms of Plk1 PBD (residues 326-603 and residues 367-603) were expressed as fusion constructs with an N-terminal $His_6$-DsRed tag (SEQ ID NO: 12) in a vector based on pDEST-527 (Addgene, Cambridge, Mass.). Another form of Plk1 PBD (residues 371-603) was expressed with an N-terminal $His_6$-MBP tag (SEQ ID NO: 12) in a vector based on pET-28a (Novagen, Madison, Wis.). A TEV protease cleavage site was engineered between the tag and PBD. The vectors were expressed in either E. coli BL21(DE3)pLysS or Rosetta 2 cells (Novagen) with similar yield. Cells were grown to an optical density of 0.4 at 30° C. with vigorous shaking. The cultures were cooled to 20° C., induced by addition of IPTG to a final concentration of 0.4 mM, and incubated for 12 h. The cells were harvested and the pellets were frozen prior to lysis. All subsequent purification was done at 4° C. The frozen pellets were thawed in buffer A (20 mM Tris-Cl, pH 8.0, 500 mM NaCl, 3 mM DTT) and lysed by addition of 4% v/v BugBuster 10× protein extraction reagent (Novagen) and 0.1 mg/ml of DNase I (Sigma). The lysate was centrifuged at 40000×g for 30 minutes to pellet the cell debris and filtered through a 0.2 µm filter. The lysate was loaded onto HisTrap HP columns (Amersham Biosciences, Piscataway, N.J.) with 100 mM imidazole, washed with 100 mM imidazole in buffer A, and eluted with 500 mM imidazole in buffer A. The peaks containing the fusion protein were digested with TEV protease (1:100 molar ratio) overnight by dialysis against buffer A. The digestion was reloaded onto HisTrap HP column without imidazole, washed with buffer A, and eluted with 80 mM imidazole in buffer A. A HiLoad 16/60 Superdex 75 gel filtration column (Amersham) equilibrated with buffer A was used as the final step in purification. Full length PBD was dialyzed against a low salt buffer (20 mM Tris-Cl, pH 7.5, 100 mM NaCl, 3 mM DTT), and used in calorimetry experiments. The truncated forms of PBD were used for crystallography. The kinase domain of Plk1 (residues 1-337) was purified in the same manner. $His_6$-MBP ("$His_6$" disclosed as SEQ ID NO: 12) constructs were purified by Ni metal affinity chromatography, loaded on to an amylose-agarose column, and then eluted with 50 mM maltose in a buffer {10 mM Tris (pH 8), 0.5 M NaCl, 2 mM DTT}. The resulting protein was digested with TEV protease to cleave the tag, flowed through Ni column, and then finally subjected to gel filtration. The PBD of human Plk2 (residues 373 to 685) was cloned as a MBP fusion with a TEV protease cleavage site and purified as the same fusion with PBD of Plk1.

Cell Culture and Microinjection.

HeLa cells were cultured as subconfluent monolayers under the conditions recommended by American Type Culture Collection (Manassas, Va.). To acutely inhibit the Cdc2 kinase activity, HeLa cells arrested with 200 ng/ml of nocodazole for 16 h were treated with 200 nM of BMI-1026 for 10 min. No mitotic exit was observed during the period of 10 min BMI-1026 treatment. For microinjection experiments with the Pmab-containing mimetic peptides, cells were arrested for 16 h with 2.5 mM thymidine (Sigma) and released into fresh medium. Two hours after release from the S phase block, the indicated peptides (2.5 mM stock in PBS) were microinjected into the cells using Eppendorf® Transjector 5246 (Eppendorf®, Westbury, N.Y.) at the 150 hPa pressure level and the 0.5 second injection time. All the cells in a single grid were injected and then further incubated to monitor cell cycle progression. For microinjection experiments with the $F_2$Pmab-containing mimetic peptides, cells were arrested with 2.5 mM thymidine for 16 h twice with a 9 h release interval, and then released into fresh medium. Seven hours after release from the G1/S phase block, the indicated peptides (4 mM stock in PBS) were microinjected similarly as above. Where indicated, peptides containing the final concentration of 30 ng/µl of pEGFP-C1 vector (Clontech®, Mountain View, Calif.) were used to visualize the injected cells.

To determine the level of Plk1 delocalization by the microinjected PLHS-Pmab (SEQ ID NO: 19) peptide, cells were released for 5 h from the single thymidine (S phase) block and then microinjected. Four hours after microinjection, cells were fixed and subjected to immunostaining analyses as described below.

Similar methods were used for the experiments shown in FIG. 16 using the peptides indicated. HeLa cells were arrested at the G1/S boundary by double thymidine treatment and released into fresh medium. Six hours after release, the cells were microinjected with a mixture of 3 mM of peptides 21, 23 or 24 and 30 ng/μL of pEGFP-C1 vector and the cells were then photographed 15 h after G1/S release. Co-injected EGFP plasmid provided a convenient marker to identify the microinjected cells.

Electroporation.

For the purpose of investigating a long term effect of the peptide, a 6-mer Biotin-conjugated p-T78 mimetic peptide {Biotin-(CH)$_6$—PLHS-F$_2$Pmab-A-NH$_2$ (SEQ ID NO: 7)} was electroporated into asynchronously growing HeLa cells using a Bio-Rad® Gene Pulser (Bio-Rad® Laboratories, Hercules, Calif.) at 250 μFD and 300 V. Cells were then incubated for 2 days, fixed, and then subjected to immunostaining analysis.

Indirect Immunofluorescence and Confocal Microscopy.

Indirect immunostaining was carried out as described previously (5) using anti-Plk1 antibody (Santa Cruz Biotechnologies, Santa Cruz, Calif.) and anti-CREST antiserum (Cortex Biochem, San Leandro, Calif.). All the appropriate secondary antibodies were purchased from Jackson ImmunoResearch Laboratories, Inc. (West Grove, Pa.). Biotinylated F$_2$Pmab-positive cells were detected by co-staining with FITC-conjugated Streptavidin (Invitrogen®, Carlsbad, Calif.). Chromosomes were visualized with 4',6-diamidino-2-phenylindole (DAPI) (Sigma). Digital images were collected with a Zeiss LSM510 confocal microscope. For the quantification of the fluorescence signal intensities, images of unsaturated fluorescence signals were acquired with the same laser intensity at 512×512 pixels and 12-bit resolution. Fluorescence intensities for localized signals were determined after subtracting the background signal intensities using Zeiss AIM confocal software.

Example 1: Preparation of pT Phosphodiesters and Assessment of PBD-Binding Activity Mitsunobu coupling chemistries (Swamy et al., *Chem. Rev.* 109, 2551-2651 (2009)) were applied to precursor peptides bound to acid-sensitive solid-phase resin to provide a library of phosphodiesters (see FIG. 1). Following Mitsunobu coupling, the peptides were cleaved from the resin under acidic conditions and the expected phosphodiesters (3a-3f) were obtained as the main reaction products. Unexpectedly, in each case a faster eluting (HPLC) minor byproduct of unknown structure (indicated as 4a-4f, FIG. 1) was obtained that exhibited a molecular weight identical to the expected product.

Figure 6:
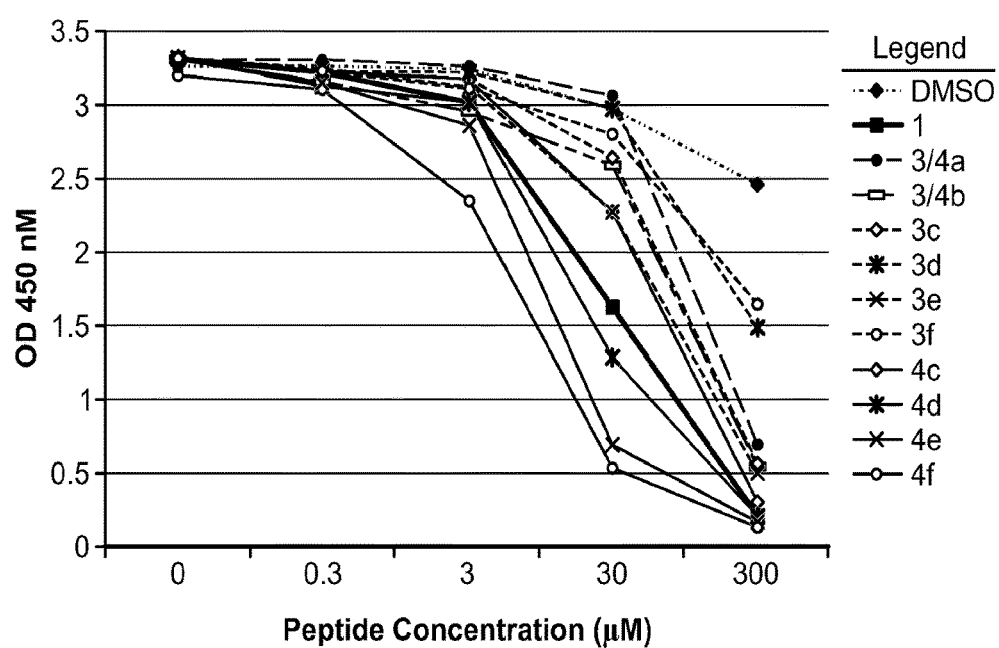
FIG. 6 Results from an ELISA-based Plk-1 PBD binding inhibition assays; OD stands for optical density.
Figure 7:
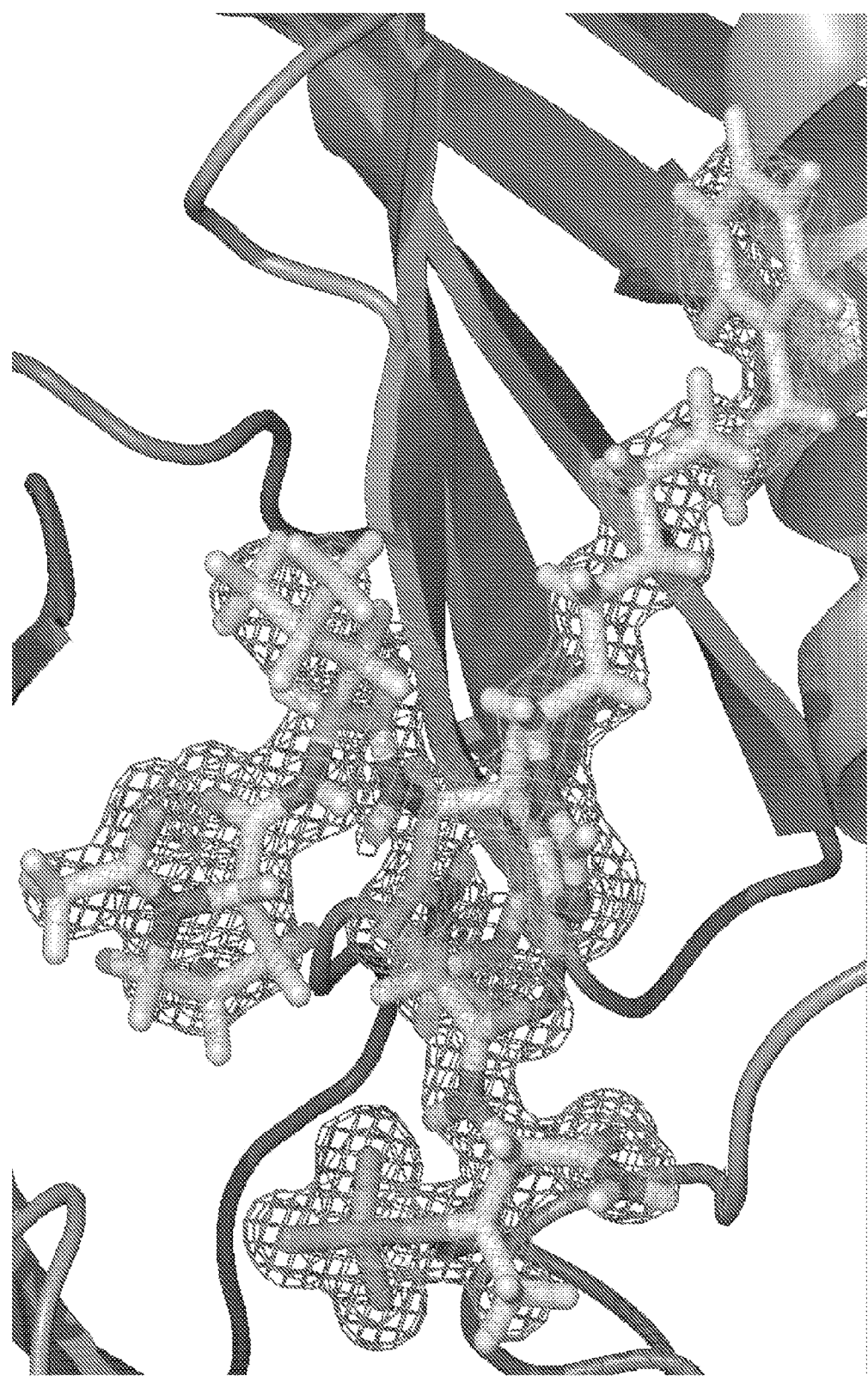
FIG. 7 SigmaA weighted 2Fo-Fc electron density map contoured at 1σ and 1.55 Å resolution around peptide ligand 4j (stick rendering).

When the Plk1 PBD binding affinities of the synthetic products were evaluated using an ELISA-based 96-well assay (Yun, S.-M. et al. *Nat. Struct. Mol. Biol.* 16, 876-882 (2009)), all expected phosphodiester products (3a-3f) displayed measurable affinity, with the greatest affinity being shown by the thiofuranyl derivative (3e). With the exception of 4a and 4b, which were tested as mixtures with the corresponding 3a and 3b, it was found that the reaction byproducts (4c-4f) uniformly showed significantly higher affinity than their corresponding phosphodiester counterparts, with byproducts 4d, 4e and 4f showing higher affinity than the parent phosphoryl peptide 1 (FIG. 6).

The highest affinity byproduct (4f) from the first round of synthesis resulted from Mitsunobu esterification using 4-phenylbutaine-1-ol. The next highest affinities were shown with byproducts (4d and 4e) that were also derived from alcohols having unsaturated groups tethered by alkyl chains. To explore the potential significance of this structural pattern, Mitsunobu esterification reactions were repeated using progressively longer n-alkyl-1-ols having terminal phenyl rings (g-l, FIG. 1).

Figure 2A:
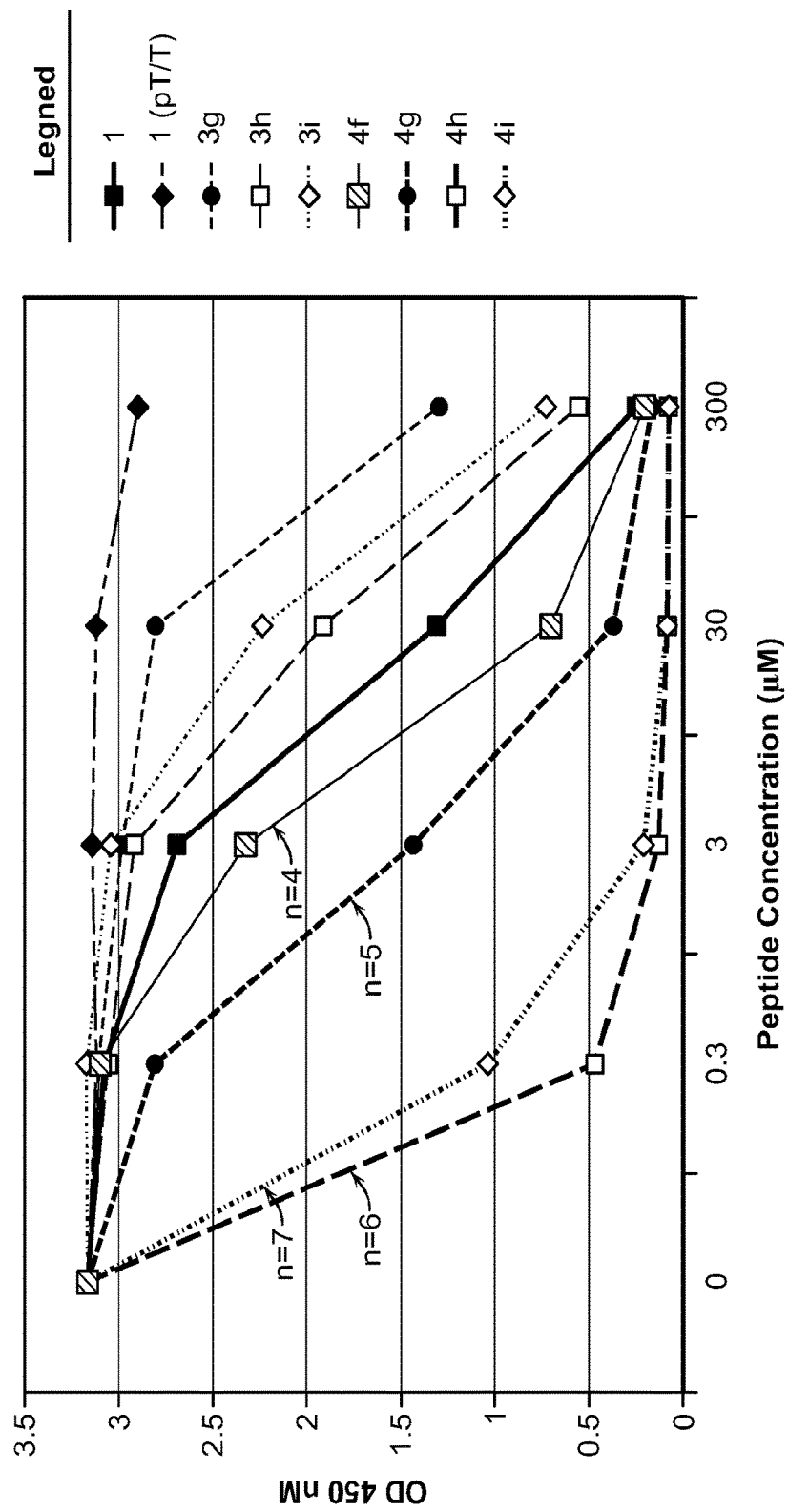
FIG. 2a-c. Inhibition of Plk1 PBD by various PLHSpT (SEQ ID NO: 1)-derived compounds. (a-c) ELISA-based PBD inhibition assays were performed essentially as described in the Methods using HA-EGFP-Plk1-expressing mitotic 293A cell lysates. Slight differences in the inhibition curves among the graphs are due to the differences in development time. Optical densities (O.D.) for each sample were measured at 450 nm by using an ELISA plate reader.
Figure 2B:
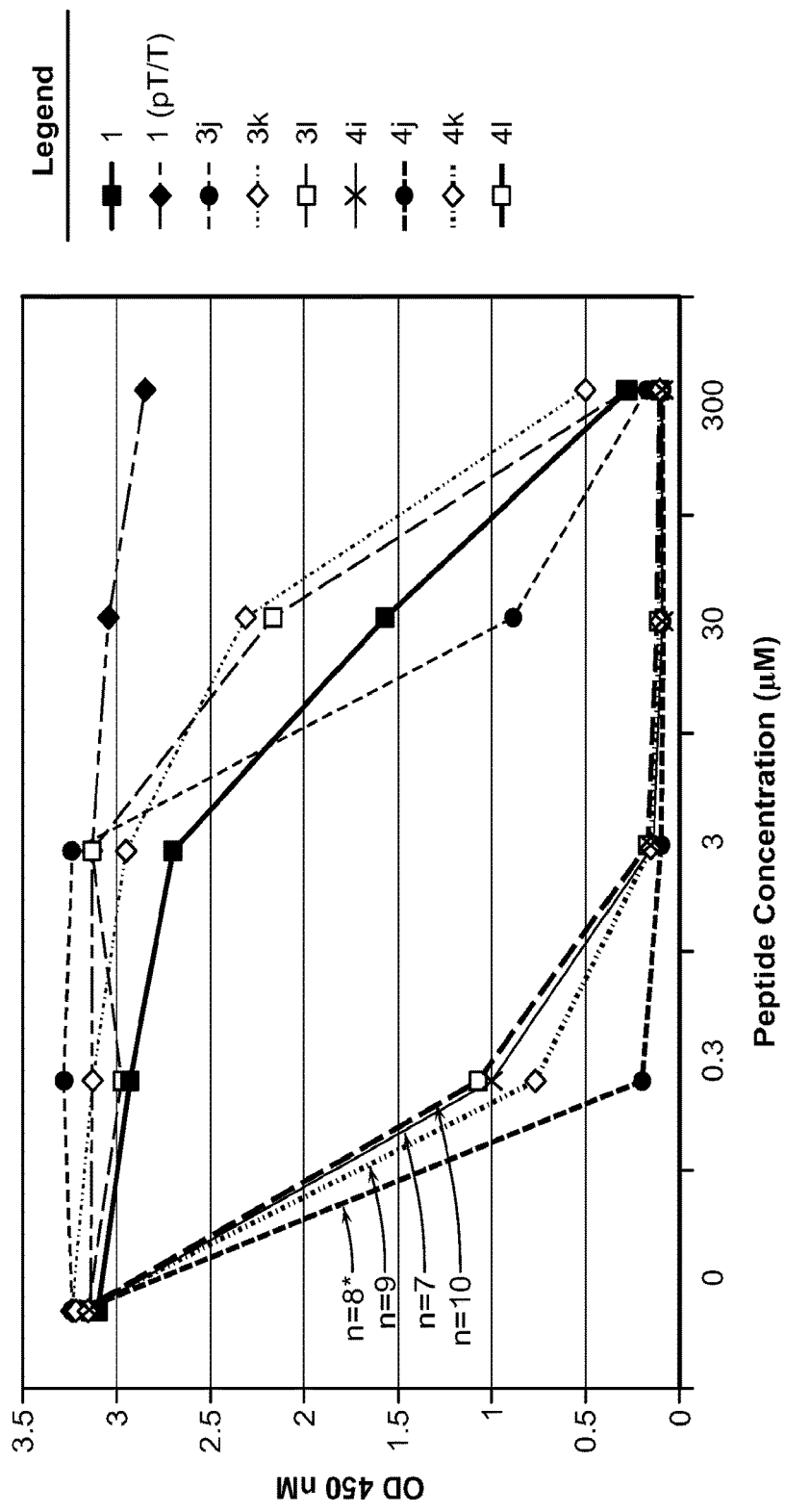

As previously observed during the first round of synthesis, each expected phosphodiester product (3g-3l) was accompanied by the formation of faster eluting byproducts (indicated as 4g-4l, respectively). The Plk1 PBD binding affinity of the phosphodiester product with a chain length of n=8 (3j) bound with affinity equal to or slightly greater than the parent peptide 1 (FIG. 2a-2c). This addressed our original inquiry whether phosphoryl dianionic charge is an absolute requirement, by demonstrating that mono-anionic ligands could exhibit good affinity. However, a more significant result of this work was the formation of minor reaction byproducts (4g-4l) that exhibited much higher affinity than the intended parent phosphodiesters (3g-3l). Starting from an initial alkyl chain length of n=4 (4f), the affinities of the byproducts increased roughly with lengthening of the alkyl chain (with the exception of n=6 and n=7; see also FIG. 2) and reached a maximum for n=8 (4j). Chain extension beyond this length was accompanied by a reduction in binding affinity (4k, 4l). The affinity of the most potent analogue (4j) exceeded that of 1 by approximately three orders-of-magnitude (1, IC$_{50}$=13 μM; 4j, IC$_{50}$=18 nM) (FIG. 2).

The inventors prepared the corresponding S/A mutants of 3j and 4j [3j (S/A) and 4j (S/A), respectively] and observed that a significant loss of affinity occurred for the S/A mutant peptides (FIG. 2c). Failure to completely eliminate the PBD-binding affinity of 3j and 4j by the S/A mutation as has been demonstrated previously (Elia, A. E. H. et al., *Science* 299, 1228-1231 (2003)) could be attributable to the presence of substantially increased Ser-independent interactions. This demonstrated strongly that binding of 3j and 4j was specific in nature.

Example 2: Identification of High Affinity Side Products as Histidine Adducts

In order to identify the structure of the highest affinity byproduct (4j), tandem MS analyses were performed on both 4j and its associated phosphodiester product (3j) (FIGS. 8 and 9) (see also Tables D and E).

Tandem MS studies were undertaken to clarify the site of C$_6$H$_5$C$_8$H$_{16}$-adduct addition in peptides 3j and 4j. Mass spectrometry data were acquired on an Agilent 6520 Accurate-Mass Q-TOF LC/MS System, (Agilent Technologies, Inc., Santa Clara, Calif.) equipped with a dual electro-spray source, operated in the positive-ion mode. Separation was performed on Zorbax 300SB-C18 Poroshell column (2.1 mm×75 mm; particle size 5 m). The analytes were eluted with solvent system 0.1% formic acid in H$_2$O/0.1% formic acid in acetonitrile at a flow rate of 1 ml/min with a 5 to 100% organic gradient over 4 minutes and holding organic for 1 minute. The instrument was used in either full-scan TOF mode or product ion scan (MS/MS) mode. MS source parameters were set with a capillary voltage of 4 kV, the fragmentor voltage of 175 V and skimmer 65 V. The gas temperature was 350° C., drying gas flow 12 L/min and nebulizer pressure 55 psig. High purity nitrogen was used as a collision gas. Data were acquired at high resolution (1,700 m/z), 4 GHz. TOF-MS mass spectra were recorded across the range 100-1600 m/z. Q-TOF-MS/MS experiments were carried out in the range 50-1000 m/z with a scan rate of 1.4 spectra/s with collision energy of 35 V. Data acquisition and analysis were performed using MassHunter Workstation Software (version B.02.00). To maintain mass accuracy, an internal mass calibration solution, containing reference ions m/z 121.050873 and m/z 922.009798, was infused continuously during the LC/MS runs.

Figure 8:
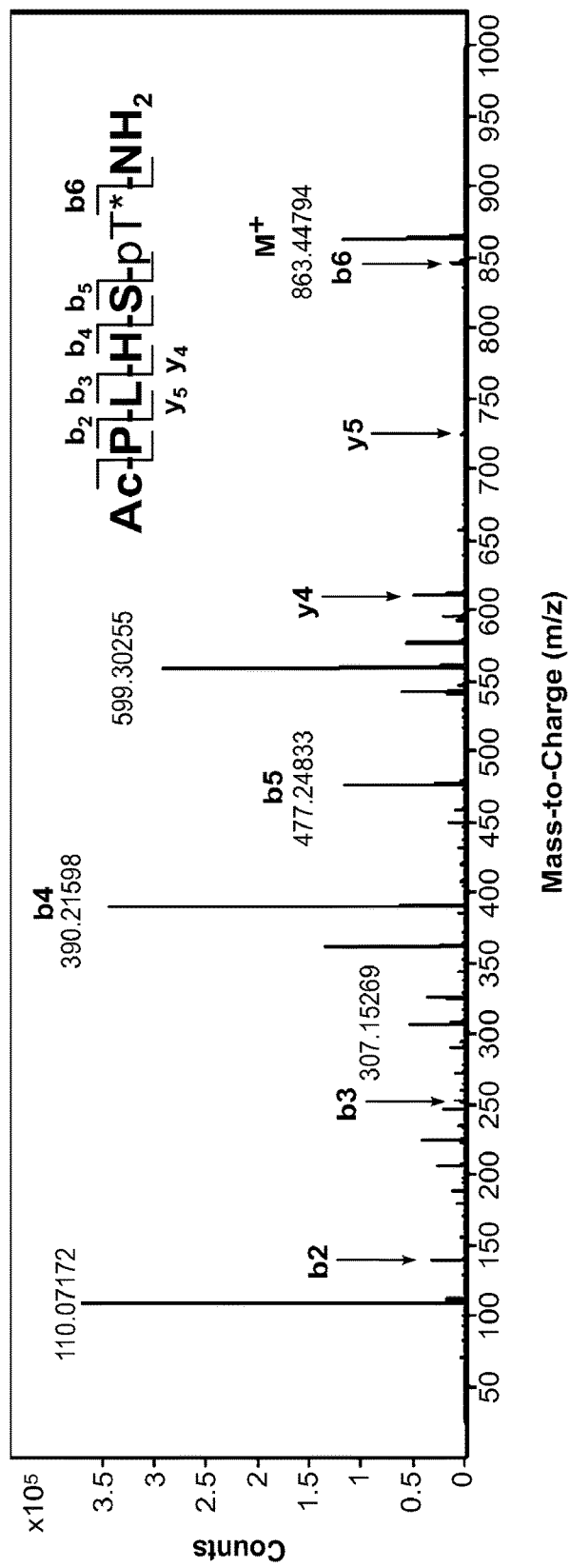
FIG. 8 MS-MS spectrum of peptide 3j (SEQ ID NO: 1)
Figure 9:
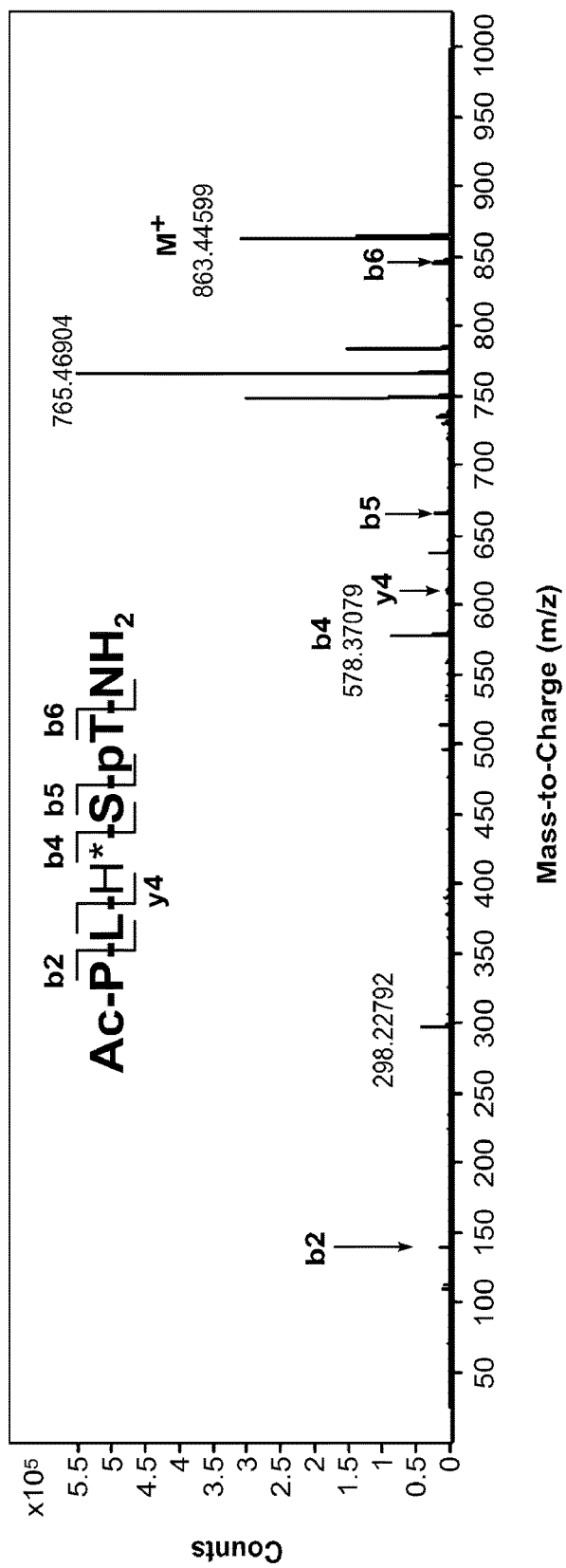
FIG. 9. MS-MS spectrum of peptide 4j (SEQ ID NO: 1)
Figure 10A:
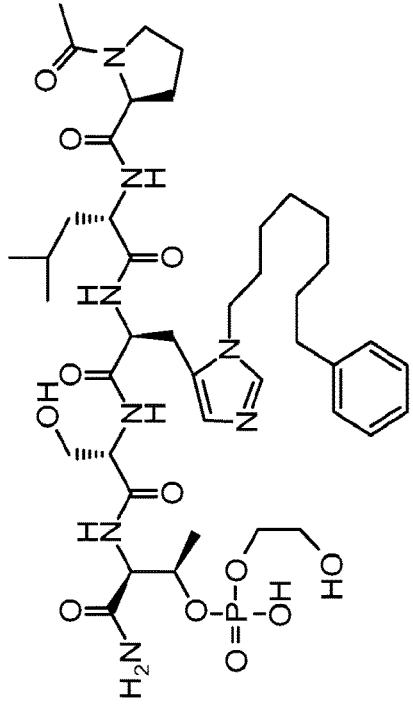
FIG. 10. A. Structures of pThr mimetics having reduced anionic charge with preliminary Plk1 PBD-binding data; B. Preliminary Plk1 binding data from an ELISA-based assay.
FIG. 10b discloses "PLHST" as SEQ ID NO: 11

Fragmentation of peptides typically occurs sequentially along the peptide backbone at the sites of the carboxamide groups. For each residue starting from the N-terminal end of the peptide, fragments are given sequential alphabetical designations starting with "a"; for example, a1, b1, c1 for residue 1; a2, b2, c2 for residue 2, etc as shown in FIG. 8. In similar fashion starting from the C-terminal end of the peptide, fragments for each residue are designated alphabetically starting from "z" as shown in the Figure. The most commonly observed ions are of the "a", "b" and "y" type. For peptide 3j the MS-fragments were consistent with the $C_6H_5C_8H_{16}$-adduct being on the pThr residue, with key fragments being $b_6$+H, $b_5$ and $y_2$ (see the Table below). For peptide 4j, fragmentation was consistent with the $C_6H_5C_8H_{16}$-adduct being on the His residue, with key fragments being b4 and y4. It should be noted that the data did not indicate the site of adduct attachment on the His residue.

As had been anticipated, the mass spectral data for 3j was consistent with the intended phosphodiester. However, it was found that the fragmentation of the byproduct 4j was best explained by placement of the $C_6H_5(CH_2)_8$— group on the histidine residue. The histidine side chain consists of a (1H-imidazol-4-yl) ring that presents two nitrogen atoms as potential sites of alkylation. It was not possible from the tandem MS data to determine on which of the two histidine nitrogens alkylation had occurred.

TABLE D

MS-MS Fragmentation for Peptide 3j

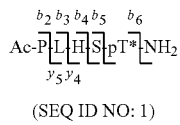

(SEQ ID NO: 1)

| Fragment | Structure | Formula | Theoretical | Observed |
|---|---|---|---|---|
| M + H | 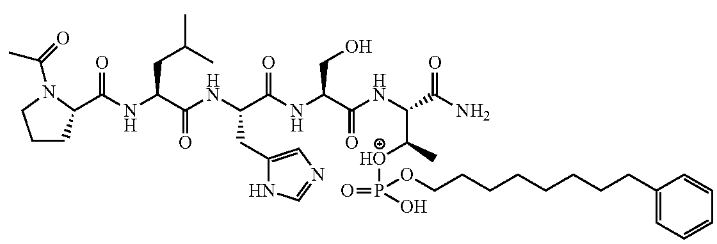 [SMILES: CC(=O)N1CCC[C@H]1C(=O)N[C@@H](CC(C)C)C(=O)N[C@@H](Cc1cnc[nH]1)C(=O)N[C@@H](CO)C(=O)N[C@H](C(N)=O)[C@@H](C)[OH+]P(=O)(O)OCCCCCCCCc1ccccc1] | $C_{40}H_{63}N_8O_{11}P$ | 863.44267 | 863.44794 |
| $b_6$ + H | 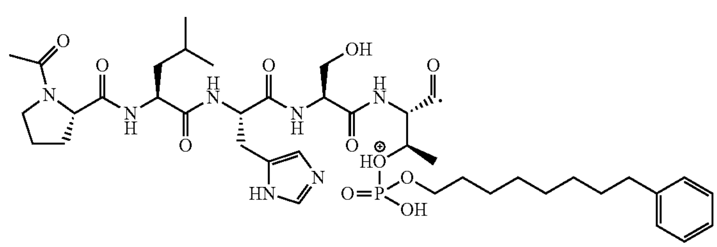 [SMILES: CC(=O)N1CCC[C@H]1C(=O)N[C@@H](CC(C)C)C(=O)N[C@@H](Cc1cnc[nH]1)C(=O)N[C@@H](CO)C(=O)N[C@H](C=O)[C@@H](C)[OH+]P(=O)(O)OCCCCCCCCc1ccccc1] | $C_{40}H_{62}N_7O_{11}P^{\cdot+}$ | 847.42394 | 846.42713 |
| $b_5$ | 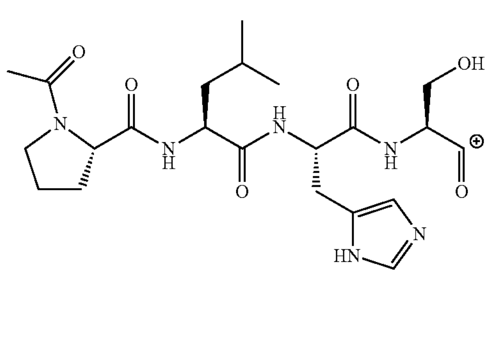 [SMILES: CC(=O)N1CCC[C@H]1C(=O)N[C@@H](CC(C)C)C(=O)N[C@@H](Cc1cnc[nH]1)C(=O)N[C@H]([C+]=O)CO] | $C_{22}H_{33}N_6O_6^+$ | 477.24561 | 477.24833 |

TABLE D-continued
MS-MS Fragmentation for Peptide 3j
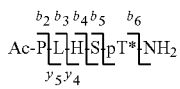
(SEQ ID NO: 1)
| Fragment | Structure | Formula | Theoretical | Observed |
|---|---|---|---|---|
| $b_4$ | 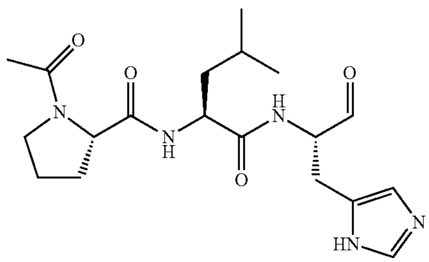 [SMILES: CC(=O)N1CCC[C@H]1C(=O)N[C@@H](CC(C)C)C(=O)N[C@H](C=O)Cc1cnc[nH]1] | $C_{19}H_{28}N_5O_4^+$ | 390.21358 | 390.21598 |
| $b_3$ | 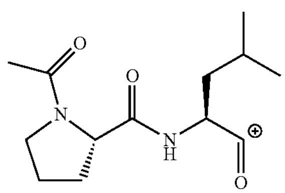 [SMILES: CC(=O)N1CCC[C@H]1C(=O)N[C@H]([C+]=O)CC(C)C] | $C_{13}H_{21}N_2O_3^+$ | 53.15467 | 253.15603 |
| $b_2$ | 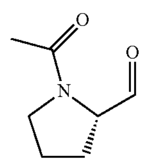 | $C_7H_{10}NO_2^+$ | 140.07060 | 140.07086 |
| $y_4$ | 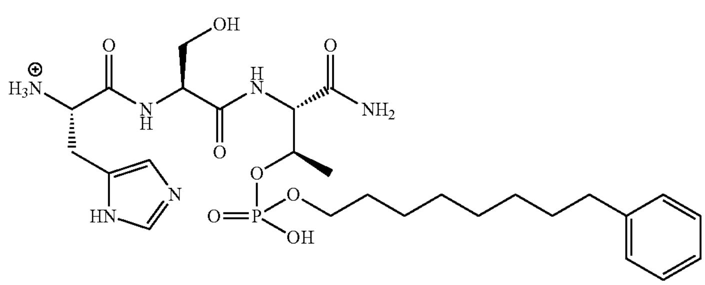 [SMILES: C[C@@H](OP(=O)(O)OCCCCCCCCc1ccccc1)[C@H](NC(=O)[C@H](CO)NC(=O)[C@@H]([NH3+])Cc1cnc[nH]1)C(N)=O] | $C_{27}H_{44}N_6O_8P$ | 611.29528 | 611.29517 |
| $y_5$ | 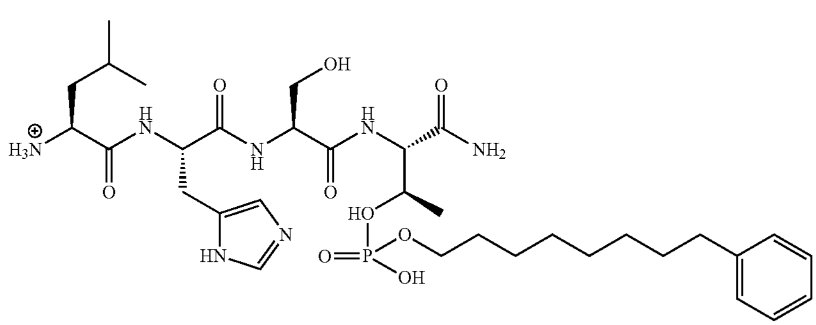 [SMILES: CC(C)C[C@H]([NH3+])C(=O)N[C@@H](Cc1cnc[nH]1)C(=O)N[C@@H](CO)C(=O)N[C@H](C(N)=O)[C@@H](C)OP(=O)(O)OCCCCCCCCc1ccccc1] | $C_{33}H_{55}N_7O_9P$ | 724.37934 | 724.37812 |

TABLE E
MS-MS Fragmentation for Peptide 4j
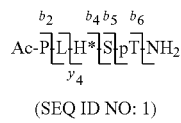
(SEQ ID NO: 1)
| Fragment | Structure | Formula | Theoretical | Observed |
|---|---|---|---|---|
| M + H | 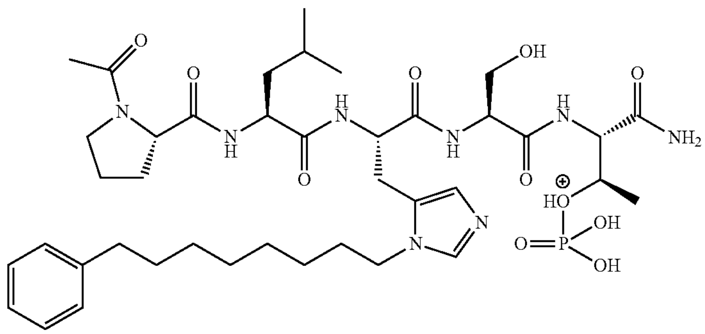 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)[OH+]P(=O)(O)O] | $C_{40}H_{64}N_8O_{11}P^+$ | 863.44267 | 863.4460 |
| $b_6$ + H | 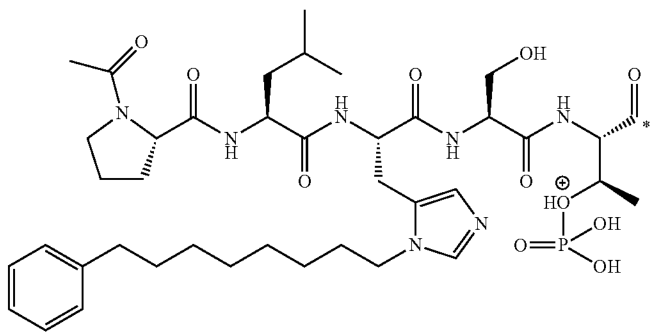 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C=O)[C@@H](C)[OH+]P(=O)(O)O] | $C_{40}H_{62}N_7O_{11}P^{\bullet+}$ | 847.42394 | 847.4252 |
| M + H − $H_3PO_4$ + $H_2O$ | 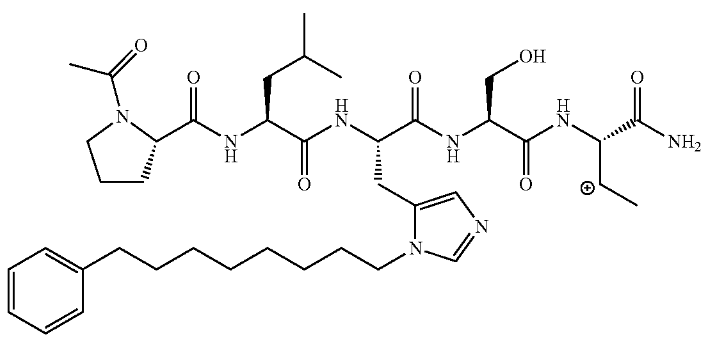 | $C_{40}H_{63}N_8O_8^+$ | 783.47634 | 783.4790 |
| M + H − $H_3PO_4$ | 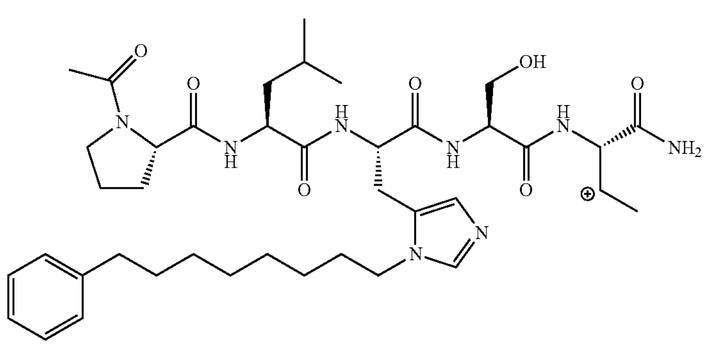 | $C_{40}H_{61}N_8O_7^+$ | 765.46577 | 765.4690 |

TABLE E-continued
MS-MS Fragmentation for Peptide 4j
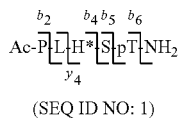
(SEQ ID NO: 1)
| Fragment | Structure | Formula | Theoretical | Observed |
|---|---|---|---|---|
| $b_6 + H - H_3PO_4$ | 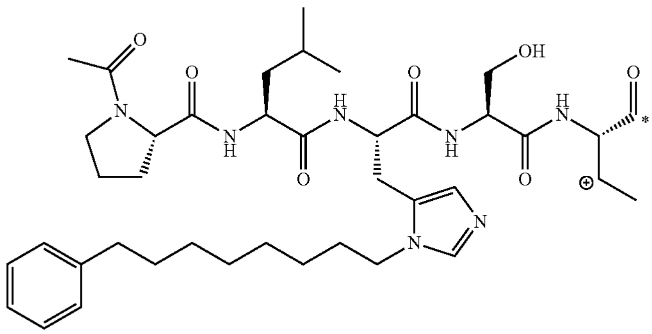 | $C_{40}H_{59}N_7O_7^{\bullet+}$ | 749.44705 | 749.4485 |
| $b_5$ | 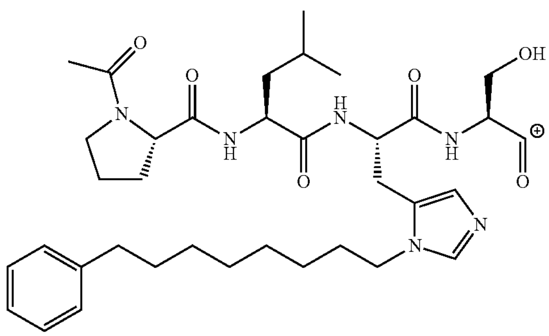 [SMILES: CC(=O)N1CCC[C@H]1C(=O)N[C@@H](CC(C)C)C(=O)N[C@@H](Cc1cncn1CCCCCCCCc1ccccc1)C(=O)N[C@H]([C+]=O)CO] | $C_{36}H_{53}N_6O_6^+$ | 665.40211 | 665.4032 |
| $a_5$ | 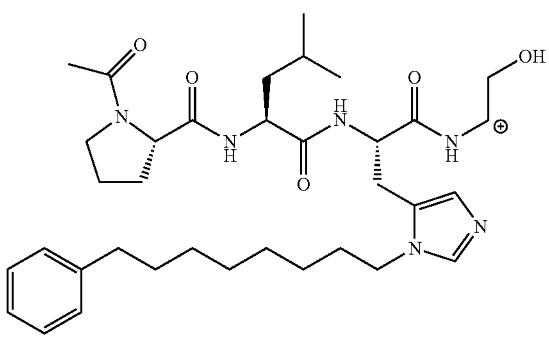 | $C_{35}H_{53}N_6O_5^+$ | 637.40720 | 637.4081 |
| $y_4$ | 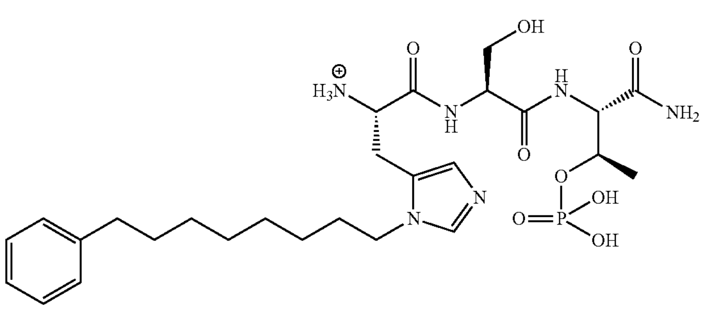 [SMILES: C[C@@H](OP(=O)(O)O)[C@H](NC(=O)[C@H](CO)NC(=O)[C@@H]([NH3+])Cc1cncn1CCCCCCCCc1ccccc1)C(N)=O] | $C_{27}H_{44}N_6O_8P^+$ | 611.29528 | 611.2970 |

TABLE E-continued

MS-MS Fragmentation for Peptide 4j

Ac-P[L]H*[S]pT]NH₂
  b₂  b₄b₅  b₆
      y₄

(SEQ ID NO: 1)

| Fragment | Structure | Formula | Theoretical | Observed |
|---|---|---|---|---|
| b₄ | | $C_{33}H_{48}N_5O_4^+$ | 578.37008 | 578.3708 |
| y₄ − H₃PO₄ | | $C_{27}H_{41}N_6O_4^+$ | 513.31838 | 513.3198 |
| a₄ − b₃ | | $C_{19}H_{28}N_3^+$ | 298.22777 | 298.2279 |
| b₂ | | $C_7H_{10}NO_2^+$ | 140.07060 | 140.0700 |

Example 3: Identification of the Site of Histidine Alkylation and Discovery of a New PBD-Binding Mode To unambiguously identify the site of the histidine alkylation and to understand the basis for the high binding affinity of 4j, the co-crystal structure of Plk1 PBD in complex with 4j was solved (FIG. 3). This structure confirmed the earlier tandem MS results, showing that alkylation had occurred on the histidine residue. It also showed that the $C_6H_5(CH_2)_8$— group was attached to the $\delta^1$ nitrogen (N3) on the imidazole ring.

The PBD backbone in the PBD•4j complex was shown to be nearly superimposable with the backbone of the previously reported Plk1 PBD complexed to 1 (PDB ID: 3HIK) (Yun, S.-M. et al. Nat. Struct. Mol. Biol. 16, 876-882 (2009)). Differences in protein backbone occurred mainly in portions of the αβ helix. The binding orientation of the bound peptide 4j is also nearly superimposable with 1 in the 3HIK structure (FIG. 3a).

Differences in the two structures arise primarily from the binding of the $C_6H_5(CH_2)_8$— group of 4j, where the polymethylene chain extends from the histidyl imidazole ring and transverses laterally across a series of antiparallel β-sheets (β1-β4) of the PBD1 unit. Binding interactions occur in a well-formed hydrophobic channel whose floor is comprised proximally by V415 (arising from the β1 sheet) and distally by F482 (arising from the αβ helix) and whose opposing walls are defined by Y417 (arising from the β1 sheet) and Y485 (arising from the αβ helix). The terminus of the channel is formed by L478 and Y481 (arising from the αβ helix) (FIG. 3b). Formation of this binding channel required very little movement in the side chain orientations Y485 and F482 relative to the parent 3HIK structure and more pronounced, yet still modest movement in the side chain of Y417 (a change in $\kappa_3$ angle of 20.8°).

However, the most dramatic movement occurred in the orientation of the Y481 aryl ring, which rotated downward by 1150 from a $\kappa_2$ angle of 44.50 in 3HIK to $\kappa_2$=159.50 in the 4j complex (FIG. 3c). This movement had profound effects on the topology of the protein surface, resulting in the revelation of a new binding channel, which had previously been occluded (compare FIGS. 3d and 3e). The formation of this hydrophobic channel was completely unanticipated based on previous crystal structures of peptide-ligated PBD.

Example 4: Peptide Modification for Enhancement of Cellular Bioavailability and Inhibition of Plk1 PBD Function It was demonstrated that microinjection of the Pmab-containing peptide 1* (FIG. 1b) into HeLa cells interferes with proper subcellular localization of Plk1 and induces apoptotic cell death as a result of prolonged mitotic arrest (Yun, S.-M. et al. Nat. Struct. Mol. Biol. 16, 876-882 (2009) & Seong, Y.-S. et al., J. Biol. Chem. 277, 32282-32293 (2002)). However, direct incubation of 1* with cultured HeLa cells at up to 200 μM concentration failed to elicit a detectable cellular response (data not shown; see also below). This failure was potentially due to limited intracellular bioavailability arising from poor solubility and low membrane transport.

Figure 1B:
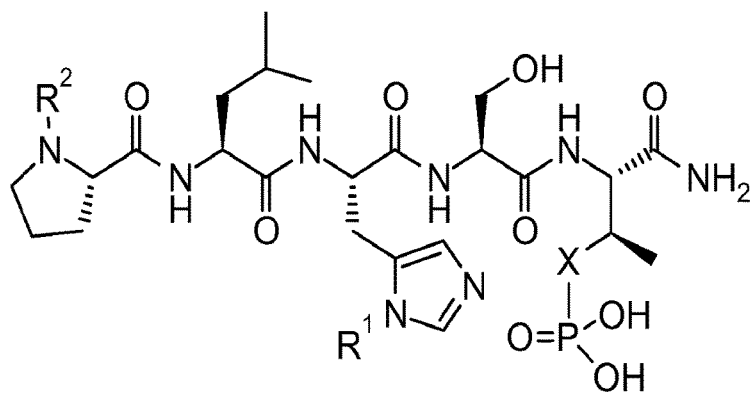
Figure 1:
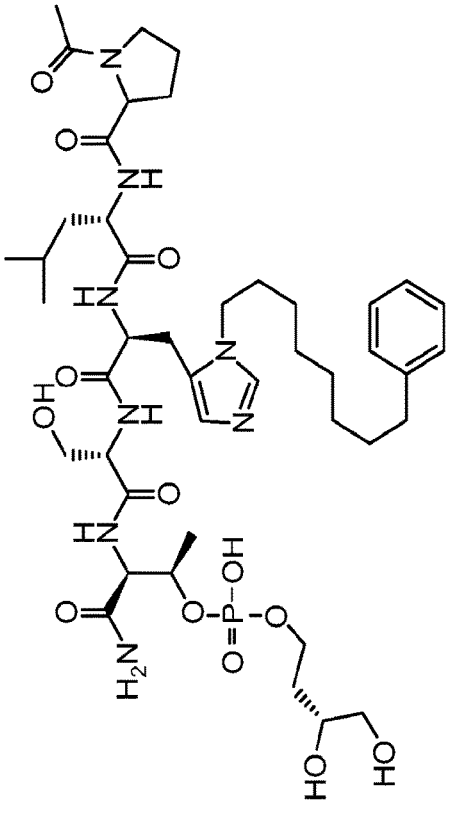

Since 4j exhibited almost three orders of magnitude higher PBD-binding affinity than 1. In order to examine whether 4j exhibits anti-Plk1 activity in cultured cells, the corresponding non-hydrolyzable form of 4j conjugated with an N-terminal polyethyleneglycol (PEG) (ie, PEG-4j*; FIG. 1b) were generated to increase the bioavailability, PEGylation was applied to the N-terminus of the indicated compounds (FIG. 1b). It was observed that both the non-PEGylated (1* and 4j) and PEGylated forms (PEG-1* and PEG-4j*, respectively) exhibited similar levels of PBD-binding affinities in in vitro PBD inhibition assays (FIG. 4a).

Figure 4B:
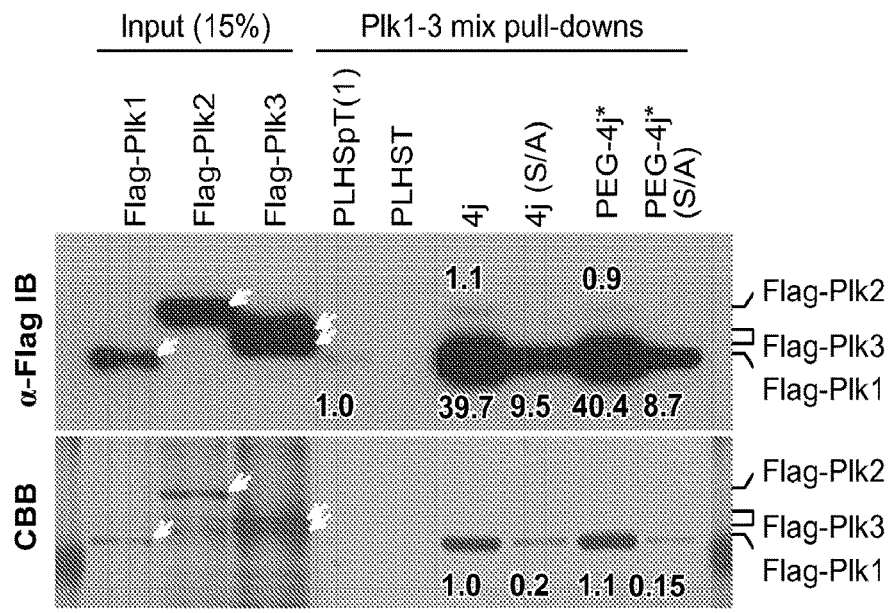

To test the specificity of the PEGylated compounds, an N-terminal Cys residue was introduced onto the PEG moiety and then cross-linked the Cys residue to beads. Non-PEGylated parental forms were also cross-linked via an N-terminal Cys-containing linker. Results showed that both 4j and its PEGylated and non-hydrolyzable form, PEG-4j* interacted with Plk1 approximately 40-fold better than the parent 1 in PBD pull-down assays using transfected 293T cells (FIG. 4b). Strikingly, both 4j and PEG-4j* failed to significantly interact with Plk2 or Plk3, indicating that PEGylation did not compromise the level of Plk1 specificity. Binding was PBD-specific, since the corresponding 4j (S/A) and PEG-4j* (S/A) mutants showed at least 4-5 fold loss of affinity under these pull-down conditions (FIG. 4b).

Figure 4C:
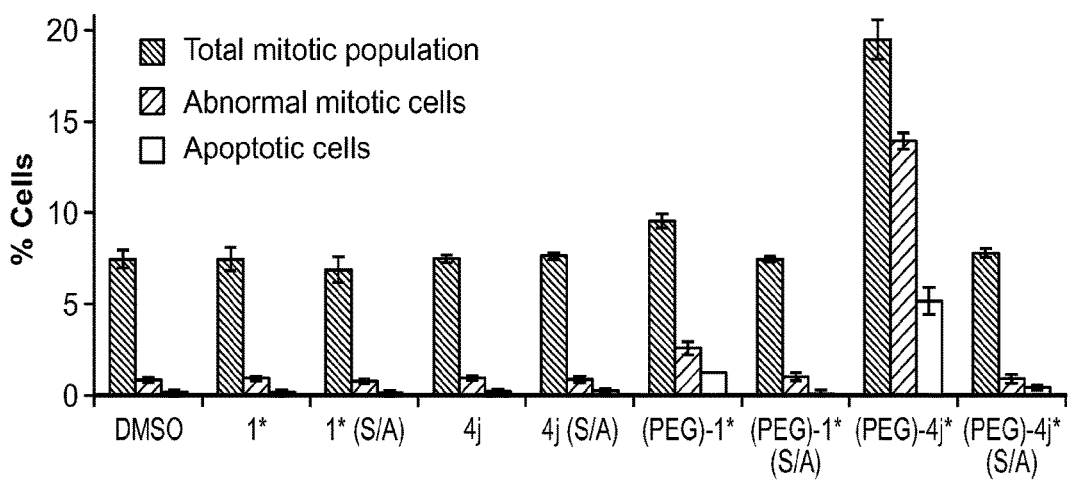
Figure 4D:
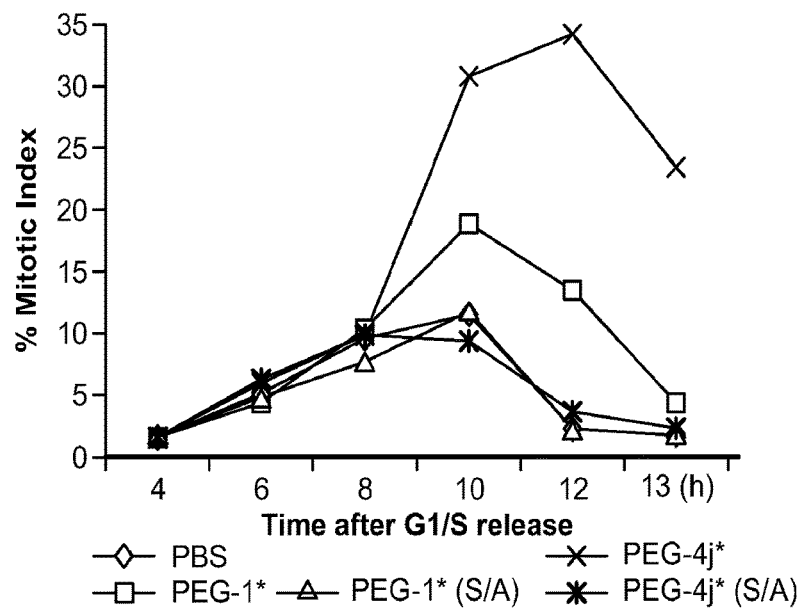
Figure 4F:
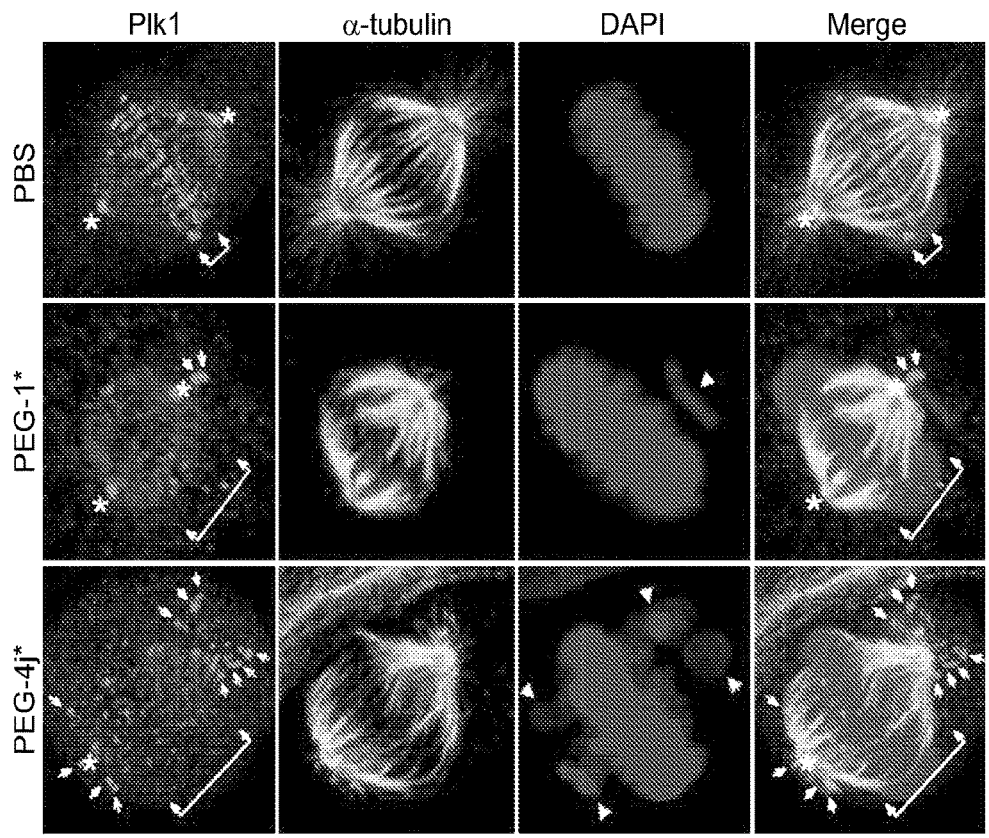
Figure 4E:
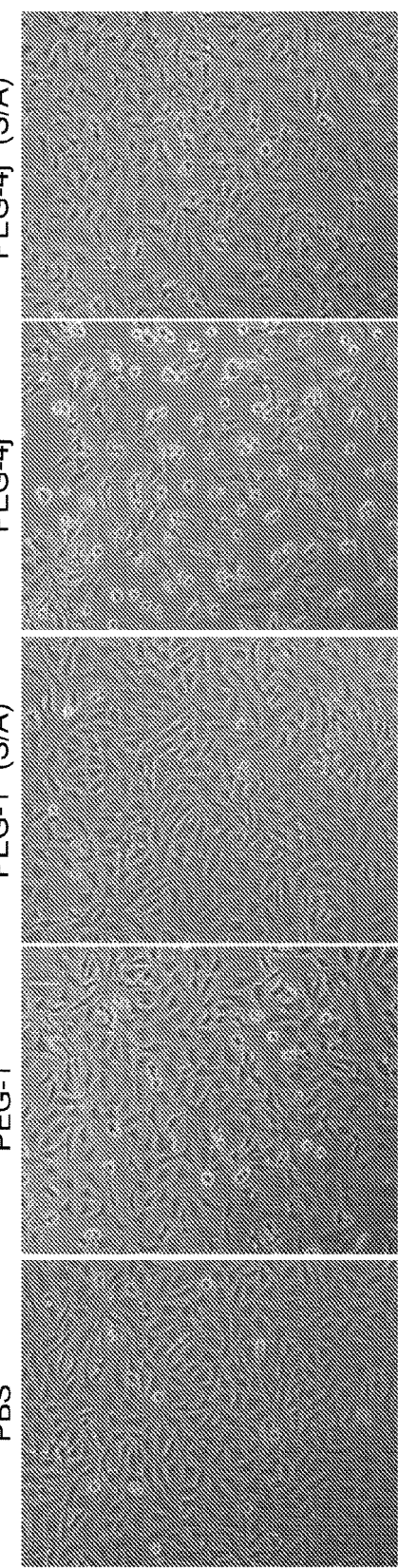

Consistent with the above observations, direct treatment of HeLa cells with 200 μM of PEG-4j* effectively induced mitotic arrest and apoptotic cell death, whereas PEG-4j* (S/A) did not (FIG. 4c-e). As a consequence of the increasing level of apoptotic cell death following mitotic arrest, the number of arrested cells shrank at later time points. Notably, PEG-1*, but not PEG-1* (S/A) also induced a weak but significant level of mitotic arrest under these conditions.

Figure 4G:
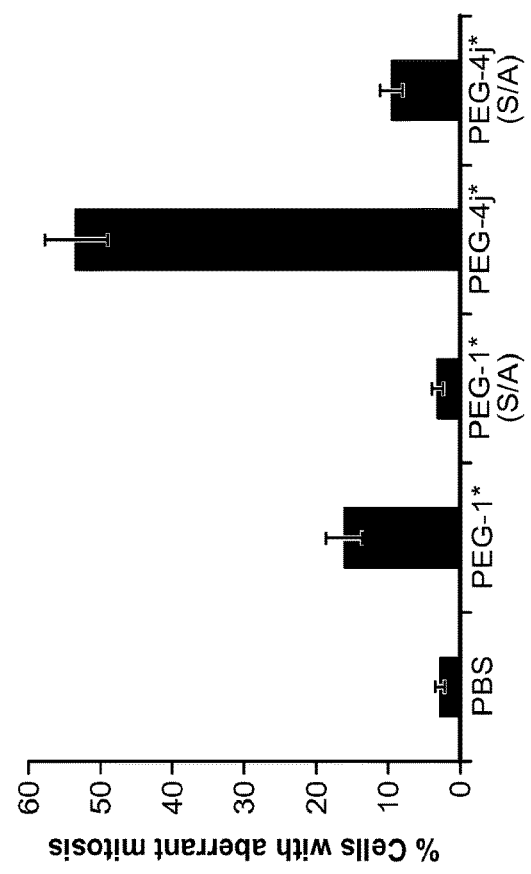
Figure 5:
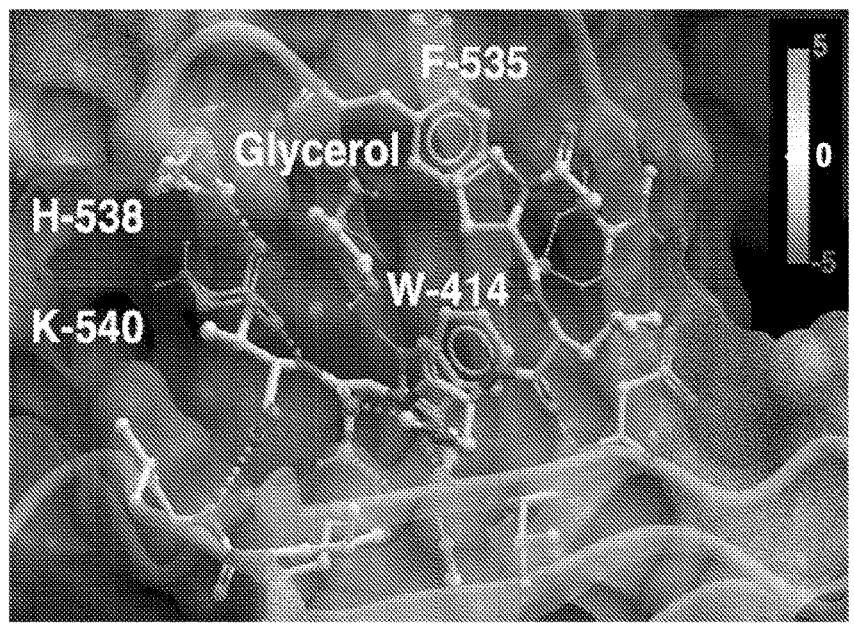
FIG. 5 X-ray crystal structure of PLHSpT (SEQ ID NO: 1) (1) bound to the Plk-1 PBD (PBD: 3HIK). A semi-transparent surface is shown with coloring based on an arbitrary electrostatic potential scale. The protein backbone is rendered in wide ribbon format and the peptide as well as key protein residues are rendered as thick sticks and colored by atom. Key hydrogen bonds are indicated in by dots. A molecule of glycerol observed in the crystal structure proximal to the pT phosphoryl group is explicitly indicated. The Figure was generated using ICM Chemist Pro software by Molsoft, Inc.

In contrast, non-PEGylated 1* and 4j failed to generate a detectable level of cellular effect, even though their PBD inhibitory activities were comparable to those of their respective PEGylated forms (FIG. 4a and FIG. 4b). These findings underscore the importance of PEGylation in the induction of cellular response. As would be expected if the observed mitotic arrest was the result of inhibition of the function of PBD, treatment of HeLa cells with PEG-4j*, but not with PEG-4j* (S/A), induced drastic Plk1 delocalization from centrosomes and kinetochores, and severe misaligned chromosomes (FIG. 4f-g and data not shown) (Ahonen, L. J. et al. Curr. Biol. 15, 1078-1089 (2005)). Closely correlating with the degree of PBD binding, PEG-1*, but not the PEG-1* (S/A) mutant, induced only mild Plk1 delocalization with a moderate level of misaligned chromosomes.

Example 5. Identification of Minimal p-T78 Peptides that Bind to the PBD of Plk1

PBIP1/MLFIIP/KLIP1/CENP-50/CENP-U (PBIP1 hereafter) was isolated as a PBD-interacting protein critical for Plk1 localization to the centromeres and for proper chromosome segregation. Further investigation on the Plk1-PBIP1 interaction shows that the PBD of Plk1 binds to the T78 region of PBIP1 in a phospho-dependent manner. To better understand the binding nature of Plk1 PBD to the S77-p-T78 motif, various p-T78 peptides for in vitro binding analyses were synthesized. Consistent with the previous observation, a bead-immobilized 10-mer or 14-mer phospho-T78 (p-T78) peptide, but not the respective non-phospho forms, precipitated Plk1 from mitotic HeLa cells as the major binding protein. To determine a minimal sequence of the T78 motif that is sufficient for the interaction, a systematic deletion analysis starting from the 10-mer p-T78 peptide (PLHSpTAIYAD (SEQ ID NO: 13)) was carried out and the ability of each resulting peptide to bind to Plk1 was tested. Surprisingly, removal of all the amino acid residues C-terminal to the p-T78 residue did not diminish the level of Plk1 binding, suggesting that these C-terminal residues after p-T78 are dispensable for the PBD binding. Further N-terminal deletion analyses of PLHSpT (SEQ ID NO: 1) showed that LHSpT (SEQ ID NO: 14) lacking the N-terminal Pro possessed a greatly diminished (~7 fold) binding affinity to Plk1, while HSpT lacking both the Pro and Leu residues did not exhibit any significant level of binding. These data suggest that PLHSpT (SEQ ID NO: 1) binds to Plk1 as efficiently as the initial 10- or 14-mer p-T78 peptide and that, besides the SpT dipeptide, the N-terminal Pro-Leu motif is critically required to provide an additional level of affinity to the PBD.

To eliminate the bias of the deletion scheme that was followed, the question of whether other 5-mer peptides encompassing the SpT motif efficiently bind to Plk1 was also tested. Interestingly, LHSpTA (SEQ ID NO: 3), which lacks the N-terminal Pro but bears the C-terminal Ala, bound to Plk1 almost as efficiently as PLHSpT (SEQ ID NO: 1), suggesting that loss of the N-terminal Pro can be largely compensated by the addition of the C-terminal Ala. However, HSpTAI, lacking both Pro and Leu but instead bearing two additional C-terminal residues following the SpT motif, bound to Plk1 only weakly, thus underlining the importance of the Leu-3 residue in the absence of the Pro-4 residue. A high level of interaction between LHSpTA (SEQ ID NO: 3) and PBD was somewhat unexpected, because previous data showed that the Pro, Cys, and Gly residues are selected for the residue at the p-Thr+1 position 13. Among the 4-mers, both LHSpT (SEQ ID NO: 14) and HSpTA (SEQ ID NO:

15) bound to Plk1 better than SpTAI (SEQ ID NO: 16), suggesting that the central PBD-binding motif in the T78 region of PBIP1 is built around the core sequences of LHSpT (SEQ ID NO: 14) and HSpTA (SEQ ID NO: 15). Consistent with the strong binding affinity of the p-T78 peptides, comparative binding studies between a short form of the previously characterized optimal PBD-binding peptide (MQSpTPL (SEQ ID NO: 5))13 and the analogous p-T78 peptide (LHSpTAI (SEQ ID NO: 17)) showed that the binding affinity of the latter is equivalent to that of the former.

Example 6: A Specific and High Affinity Binding Between Minimal p-T78 Peptide and the Plk1 PBD Next, the specificity of the minimized p-T78 peptides against Plk1 PBD was tested. Because of the distinct binding nature of Plk4 PBD, Plk4 was not included in these analyses. The results showed that, similar to the initial 14-mer peptide, minimized p-T78 peptides specifically precipitated Plk1 from lysates containing similar levels of Plk1, Plk2, and Plk3. In contrast, the 6-mer optimal MQSpTPL (SEQ ID NO: 5) peptide precipitated Plk2 with ~27% efficiency of Plk1 precipitation under the same conditions, suggesting that it possesses a significantly lower Plk1 specificity than PLHSpT (SEQ ID NO: 1). Consistent with this notion, MQSpTPL (SEQ ID NO: 5) but not the p-T78 peptides, precipitated Plk2 from the HeLa lysates expressing Plk2 alone. Remarkably, although much shorter in length than the initial 14-mer peptide, a minimal p-T78 peptide, PLHSpT (SEQ ID NO: 1), exhibited an undiminished Plk1 specificity and precipitated Plk1 as the only major binding protein from the total HeLa lysates. Another 5-mer, LHSpTA (SEQ ID NO: 3), also displayed a similar but somewhat reduced level of Plk1 affinity. These observations suggest that elements critical for Plk1-binding affinity and specificity reside within these minimal sequences. Further examination with PLHSpT (SEQ ID NO: 1) showed that it specifically bound to GST-fused PBD (GST-PBD), but only weakly to the corresponding GST-PBD(H538A, K540A) phosphate pincer mutant, indicating that an intact phosphoepitope-binding module is required for the PLHSpT (SEQ ID NO: 1)-Plk1 PBD interaction.

Next, out isothermal titration calorimetry analyses were carried out with recombinant Plk1 PBD and quantified the binding parameters of the minimal p-T78 peptides. Among the minimal peptides tested, a 5-mer PLHSpT (SEQ ID NO: 1) mediated the best binding contacts with the PBD ($\Delta H=-14.5$ kcal/mol), although it exhibited an equivalent binding affinity overall (Kd~0.45 µM) with another 5-mer peptide, LHSpTA (SEQ ID NO: 3). Under the same conditions, the synthetic optimal 6-mer peptide, MQSpTPL (SEQ ID NO: 5), bound to PBD with a Kd of 0.534 µM (Table 1), a value similar to those of the 5-mer p-T78 peptides. The two other 6-mer peptides (PLHSpTA (SEQ ID NO: 9) and LHSpTAI (SEQ ID NO: 17)) displayed slightly higher affinities than the 5-mer peptides, whereas the 4-mers (LHSpT (SEQ ID NO: 14) and HSpTA (SEQ ID NO: 15)) exhibited much lower affinities (Table 1).

To test the specificity of binding of the above peptides, calorimetry binding experiments were conducted with recombinant Plk2 PBD. Saturable binding was not observed and, as a result of the lack of a binding curve in all cases, values for binding enthalpy or binding affinity could not be extrapolated. However, a clear difference in the initial heats of interaction of the peptides was observed above the limits of detection (1 kcal/mol) of the instrument. The two minimal p-T78 peptides, PLHSpT (SEQ ID NO: 1) and LHSpTA (SEQ ID NO: 3), exhibited virtually no interactions with Plk2 (only baseline heats were detected), whereas MQSpTPL (SEQ ID NO: 5) titrated into Plk2 PBD produced initial heats of −1.68 kcal/mol. These results further corroborate the specificity of the minimal p-T78 peptides for Plk1 over Plk2.

Example 7: p-T78 Peptide Disrupts the PBD-Cdc25C Interaction

The minimal p-T78 peptides were examined to determine if they have the capacity to interfere with the interaction between Plk1 PBD and its physiological binding target, phospho-Cdc25C (p-Cdc25C). In agreement with the previous finding, GST-PBD precipitated p-Cdc25C, but not the unphosphorylated form, from mitotic HeLa cells. Addition of PLHSpT (SEQ ID NO: 1), but not the respective non-phosphopeptide, into the mitotic lysates disrupted the pre-formed PBD-p-Cdc25C complex in both a phospho- and concentration-dependent manner. LHSpT (SEQ ID NO: 14) also interfered with the PBD-p-Cdc25C interaction, although it was much less effective than PLHSpT (SEQ ID NO: 1).

In a separate experiment, it was found that LHSpTA (SEQ ID NO: 3) disrupted the pre-formed PBD-p-Cdc25C complex nearly as efficiently as PLHSpT (SEQ ID NO: 1), whereas both LHSpT (SEQ ID NO: 14) and HSpTA (SEQ ID NO: 15) disrupted the complex weakly. Consistent with these observations, PLHSpT (SEQ ID NO: 1), but not the corresponding non-phosphorylated peptide, disrupted the in vivo Plk1-p-Cdc25C interaction efficiently. The data demonstrate that p-T78 peptides interrupt the interaction between the PBD and its binding targets by competitively binding to the PBD.

Example 8: The Binding Nature of the Plk1 PBD

Since PLHSpT (SEQ ID NO: 1) exhibited a high affinity and specificity to Plk1 PBD, the binding nature of this peptide to the PBD was investigated to determine the interactions critical for Plk1 specificity, especially on its N-terminus. To this end, the crystal structures of the Plk1 PBD in complex with the phosphopeptides PLHSpT (SEQ ID NO: 1) (hereon referred to as PBD$^{PL}$) and PPHSpT (SEQ ID NO: 2) (PBD$^{PP}$; to examine the importance of the N-terminal residue for the interaction) were solved at 1.7 Å and at 2.3 Å resolution, respectively. Additionally, an attempt was made to crystallize a complex by mixing the PBD (without phosphopeptide) and the kinase domain, each expressed and purified separately. However, the kinase domain precipitated and only the PBD was found in a diffraction quality crystal. This novel crystal form contained two PBD molecules per asymmetric unit, referred to as PBD$^{S+G}$ (with sulfate and glycerol) and PBD$^S$ (with sulfate only) for chains A and B, respectively. Several strong peaks of positive difference density were found in the Fo-Fc maps for PBD$^{PL}$, PBD$^{S+G}$, and PBD$^S$, which could not be interpreted as water molecules. These peaks were modeled as sulfate, glycerol, and ethylene glycol molecules. PBD$^{PL}$ contained a glycerol molecule in the phosphopeptide-binding cleft, occupying a cavity formed by the phosphopeptide, two water molecules, and PBD.

The three hydroxyl groups of this glycerol molecule were involved in hydrogen bonding with the backbone carbonyls of the phosphopeptide and PBD, the phosphate group of p-Thr, and one of the water molecules. PBD$^{S+G}$ and PBD$^S$ contained a sulfate anion in the same pocket, in the region normally occupied by the phosphate of p-Thr. The choice of modeling the density in this pocket as sulfate instead of phosphate stemmed from the presence of 0.3 M lithium sulfate in the crystallization media. $PBD^{S+G}$ contained a glycerol molecule in the phosphopeptide-binding cleft. This glycerol molecule was located at the −1 position, normally occupied by the Ser residue when a phosphopeptide is in the binding cleft. The L2 loop in $PBD^S$ is much less ordered than in the $PBD^{S+G}$ structure. Analysis of contacts with symmetry-related molecules showed that this difference in the degree of order observed in the L2 region is likely caused by crystal packing. Notably, the structures for the $PBD^{S+G}$, $PBD^S$, and $PBD^{PL}$ were remarkably similar among themselves, raising the possibility that the glycerol molecule and the sulfate anion are capable of mimicking the role of the SpT dipeptide in the PBD binding.

Example 9: The Role of the N-Terminal Residues of p-T78 Peptide for Plk1 Binding Affinity and Specificity Close inspection of the structure of the PLHSpT (SEQ ID NO: 1)-PBD complex revealed that, in addition to the previously described SpT-dependent interactions (Cheng, K. Y. et al., EMBO J. 22, 5757-5768. (2003); & Elia, A. E. et al. Cell 115, 83-95 (2003)), the N-terminal Pro residue is crucial for providing additional stability to the PBD binding by engaging in two discrete yet interconnected interactions. The carbonyl oxygen of the N-terminal Pro residue was in polar contact (i.e., hydrogen-bonding interaction) with the guanidinium moiety of Arg516, while the pyrrolidine ring of the Pro residue enhanced the interaction by docking into a shallow hydrophobic pocket generated by the surrounding Trp414 and Phe535. The importance of the latter interaction with the Pro-binding pocket was manifest by the observation that LHSpT (SEQ ID NO: 14), which can still form the polar contact with Arg516 through the carbonyl oxygen N-terminal to the Leu-3 residue, exhibited ~50-fold weaker binding than PLHSpT (SEQ ID NO: 1).

The critical role of the N-terminal Pro residue in PBD binding was directly demonstrated in experiments with PPHSpT (SEQ ID NO: 2). Here, the N-terminal Pro at the −4 position of PPHSpT (SEQ ID NO: 2) was flipped out of the Pro-binding pocket and was unable to generate the polar contact and hydrophobic interactions because the Pro-3 residue locks the backbone of the phosphopeptide in a conformation opposite to that of PLHSpT (SEQ ID NO: 1). The effect of removal of the N-terminal Pro from the Pro-binding pocket and loss of the polar contact with the guanidinium moiety of Arg516 was reflected in the drastically diminished (20-fold) binding affinity of PPHSpT (SEQ ID NO: 2) to Plk1. In a separate experiment, a Pro-4 to Met-4 mutant, MLHSpT (SEQ ID NO: 18), exhibited a greatly diminished level of Plk1 PBD binding, further highlighting the importance of the Pro-4 residue in stably binding into the pocket. Consistent with these observations, the Pro-4 residue in PMQSpTPL (SEQ ID NO: 4) docked into the Pro-binding pocket 13, while, in the absence of the N-terminal Pro-4, the side chain of the N-terminal unacetylated (i.e., free amine) Met-3 in MQSpTPL (SEQ ID NO: 5) extended into the Pro-binding pocket.

It is noteworthy that LHSpTA (SEQ ID NO: 3) also exhibited a high level of Plk1 PBD binding affinity and specificity even in the absence of the Pro-4 residue. Analyses of the crystal structure of the Plk1 PBD in complex with LHSpTA (SEQ ID NO: 3) ($PBD^{LH}$) revealed that, similar to the Leu-3 of PLHSpT (SEQ ID NO: 1), the N-terminal Leu-3 side chain of LHSpTA (SEQ ID NO: 3) was directed into an intramolecular cavity and did not appear to be involved in interactions with the surrounding PBD residues. The N-terminal acetyl carbonyl of LHSpTA (SEQ ID NO: 3) was also in polar contact with Arg516, thus substituting the interaction engaged by the carbonyl oxygen of the Pro-4 of PLHSpT (SEQ ID NO: 1). Unlike Plk1, both Plk2 and Plk3 possess the Lys residue (Lys607 and Lys568, respectively) at the position analogous to the Plk1 Arg516, suggesting that the observed polar contact is Plk1-specific. Since both PLHSpT (SEQ ID NO: 1) and LHSpTA (SEQ ID NO: 3) exhibit a high level of Plk1 PBD-binding specificity, this polar contact between the carbonyl oxygen N-terminal to the Leu-3 and the guanidinium moiety of the Arg516 is likely one of the major determinants of Plk1 PBD specificity. In addition, loss of the interactions between the pyrrolidine ring of the Pro-4 residue and the Pro-binding pocket, as a result of the lack of the N-terminal Pro residue in LHSpTA (SEQ ID NO: 3), appeared to be largely compensated by the van der Waals contacts generated by the C-terminal Ala+1 residue, thus explaining how LHSpTA (SEQ ID NO: 3) could achieve a relatively high affinity binding to the Plk1 PBD.

Apart from the phosphopeptide backbone region of the Leu-3 as mentioned above, the weak sum electron density (|Fo|−|Fc|) observed in the $PBD^{PL}$ structure suggested that the Leu side chain region is disordered and may not be involved in specific interactions with PBD. However, mutation of the Leu-3 of PLHSpT (SEQ ID NO: 1) to Ala significantly diminished (~3-fold) the level of Plk1 binding, while the mutation to Gln did not alter the Plk1 affinity (rather, it appeared to increase the level of Plk2 binding). Since the Leu-3 side chain does not appear to interact with other PBD residues, it is possible that the bulky side chain in the Leu or Gln residue contributes indirectly to the PBD binding by limiting the conformational flexibility of the phosphopeptide backbone in a way that the N-terminal Pro can better dock into the Pro-binding pocket.

The importance of the His at the −2 position for Plk1 specificity was next examined. In the crystal structure, the side chain of the His-2 residue did not directly mediate contacts with PBD residues. Strikingly, mutation of the His-2 to Gln substantially increased (24-fold) the level of Plk2 binding. In calorimetry experiments, titration of the PLQSpT mutant into Plk2 PBD produced initial heats of interaction on the order of −1.1 kcal/mol as compared to virtually baseline heats for the parent PLHSpT (SEQ ID NO: 1), suggesting that the mutant peptide mediates binding contacts with Plk2 PBD, whereas the parent peptide is selective only for Plk1 PBD. Since the NΔ1 of His at the −2 position was involved in a hydrogen bond with the carbonyl oxygen of Ser at the −1 position, it has been speculated that the hydrogen bond between these two residues is critical for conferring Plk1 specificity. Alternatively, the presence of a Gln residue at the −2 position could be important for strong Plk2-mediated interactions.

Taken together, the results provided herein demonstrate that the N-terminal Pro-Leu motif at the −4 and −3 positions is crucial for high affinity and specificity interactions with Plk1 PBD, while the His residue at the −2 position is important to assure an additional layer of Plk1 specificity. These findings explain in part why MQSpTPL (SEQ ID NO: 5), bearing the N-terminal Met for the Pro-binding pocket and lacking the critical His-2 residue, exhibits a low Plk1 specificity with a significant level of Plk2 affinity. In addition, the T78 residue in PBIP1 is followed by Ala in place of the commonly found Pro residue. Since Plk1, but not the Pro-directed Cdc2, is responsible for generating the p-T78 epitope, the Ala+1 residue may play a critical role in directing a non-Pro-directed kinase to phosphorylate the T78 residue.

Example 10: Inhibition of the Function of the Plk1 PBD by a p-T78 Mimetic Peptide A growing body of evidence suggests that the PBD-dependent interactions with various S-p-S/T-containing targets are critical for Plk1 localization to the centrosomes, kinetochores, and mid-body. In line with this notion, acute inhibition of the activity of Cdc2, one of the major kinases that prime the PBD-binding sites, drastically diminished the level of Plk1 localization to the centrosomes and kinetochores in prometaphase cells. This observation, together with the high affinity and specificity of the minimal p-T78 peptides to the Plk1 PBD, prompted us to test whether the minimal p-T78 peptides can interfere with the function of Plk1 by disrupting its localization in vivo. Consistent with the PBD pull-down assays, PLHSpT (SEQ ID NO: 1), but not the respective non-phosphopeptide, efficiently inhibited the p-T78-dependent PBD interaction in vitro, while LHSpTA (SEQ ID NO: 3) inhibited the PBD at a moderately reduced level. Since the phosphate group of the T78 residue is strictly required for the PBD binding but is susceptible to dephosphorylation by intracellular phosphatase activity, phosphatase-resistant p-Thr mimetic, (2S,3R)-2-amino-3-methyl-4-phosphonobutyric acid (Pmab) was synthesized, in protected form and incorporated it into peptides in place of the p-Thr residue. The bead-immobilized PLHS-Pmab (SEQ ID NO: 19) precipitated Plk1, but not Plk2 or Plk3, from mitotic HeLa cells as efficiently as the respective PLHSpT (SEQ ID NO: 1) peptide (the experiment was carried out in the presence of phosphatase inhibitors).

As expected if the binding were PBD-dependent, a mutation of the invariably required Ser-1 residue to Ala {PLHA-Pmab (SEQ ID NO: 20); in short, Pmab(S77A)} abolished the Plk1 binding. Furthermore, the PLHS-Pmab (SEQ ID NO: 19) peptide, but not the respective Pmab(S77A) mutant, efficiently interfered with a p-T78-dependent Plk1 PBD interaction, suggesting that the PLHS-Pmab (SEQ ID NO: 19) peptide is suitable for testing the PBD inhibition in vivo.

Microinjection studies using HeLa cells released from an S phase block were performed to examine the effect of the Pmab-containing mimetic peptide in vivo and to overcome poor membrane permeability of a negatively charged peptide. Cells microinjected with the non-phospho T78 peptide proceeded through the cell cycle normally. However, as expected if the function of Plk1 were inhibited, the Pmab peptide, but not the respective Pmab(S77A) mutant, induced a drastic mitotic arrest in ~60% of the microinjected population. Reminiscent of the phenotype associated with the loss of the PBD function ~25% of the arrested population (n>180 cells) exhibited a chromosome congression defect. Due to the increasing level of apoptotic cell death following a prolonged mitotic block, the total numbers of arrested cells began to shrink at later time points (the 12 h and 13 h time points). Consistent with these observations, the Pmab peptide, but not the respective Pmab(S77A) or non-phospho T78 peptide, interfered with Plk1 localization at both mitotic centrosomes and kinetochores and diminished Plk1 fluorescence signals to a level similar to that observed after the treatment of the Cdk1 inhibitor, BMI-1026. In a second experiment, another type of p-T78 mimetic peptide, a 6-mer $F_2$Pmab-containing PLHS-$F_2$Pmab-A (SEQ ID NO: 7) was synthesized (synthesis of a 5-mer PLHS-$F_2$Pmab (SEQ ID NO: 8) mimetic peptide did not yield sufficient amounts because of an inefficient coupling of $F_2$Pmab to the resin), and examined for its effect in HeLa cells.

Although not as efficient as the PLHS-Pmab (SEQ ID NO: 19) peptide likely as a result of a strong electronegativity of the difluoride, PLHS-$F_2$Pmab-A (SEQ ID NO: 7), but not the respective $F_2$Pmab(S77A) mutant, significantly precipitated Plk1, and, as such, induced defects in proper Plk1 localization and chromosome congression that ultimately led to mitotic arrest and apoptotic cell death. Taken together, these data strongly suggest that inhibition of the PBD by the p-T78 mimetic peptide is sufficient to interfere with subcellular localization and mitotic functions of Plk1.

Example 11: Application of Oxime-Based Post Solid-Phase Diversification to Optimization of Polo Box Domain-Binding Peptides Plk1 possesses a phosphopeptide-binding PBD that is essential for intracellular localization and substrate recognition. Because PBDs are unique to Plks, they are ideal targets for selectively inhibiting Plk1 functions. By examining various PBD-binding phosphpeptides, a 5-mer phosphopeptide "PLHSpT" (SEQ ID NO: 1) that specifically interacts with the Plk1 PBD with a high affinity (Kd=0.45 µM), but not with the two closely-related Plk2 and Plk3, has been identified.

Application of Peptoid-Peptide Hybrid Libraries to Optimization of Polo Box Domain-Binding Peptides Structural studies are provided herein of the 5-mer PLHSpT (SEQ ID NO: 1) peptide bound to PBD protein. In the PLHSpT (SEQ ID NO: 1)*PBD complex, the Ser and pThr residues provide important protein contacts. However, the N-terminal Pro residue provides further interactions with the protein by docking into a hydrophobic pocket formed by the two aromatic residues Trp414 and Phe535. Importantly, this Pro is crucial for the peptide's binding specificity for Plk1 as compared to Plk2 and Plk3. In the current EIR solid-phase synthesis of NSG-containing libraries was achieved by the "submonomer approach," in which the N-terminal Leu residue of peptide 8 was first bromoacetylated to yield 9, and then reacted with various amines to yield the corresponding NSG containing peptoid-peptide hybrids. Acetylation provided the final peptides [11].

Hybrids 11D and 11E had dramatically diminished binding affinity, which indicated that both positive and negative charges are not tolerated at this position. As compared to the original 5-mer, hybrids 11A, 11C and 11J (substituents as indicated) showed slightly higher binding affinity, while 11F and 11I showed similar affinity and the remaining analogues were weaker binders. Work is in progress to examine additional NSG residues at the Pro site and to apply the methodology to examine NSG residue replacements of other critical residues.

Example 12: Monocharged Phosphates and Cyclic Peptides

Monocharged phosphate peptoids and cyclic peptides were generated and tested for specific binding to Plk1.

To quantitatively determine the efficiency of PBD-binding inhibition by the indicated peptides, an ELISA-based inhibition assay was carried out. The level of HA-EGFP-Plk1 bound to an immobilized biotinylated p-T78 peptide was quantified in the presence of various amounts of the competitor peptides. The minor isomer of monocharged phosphate FA508 had equivalent binding potency as WT 5-mer. The cyclic peptide FA507 bound better than FA509.

Example 13: The Ability of Pmab- and F$_2$Pmab-Containing Peptides to Inhibit PBD-Dependent Interactions

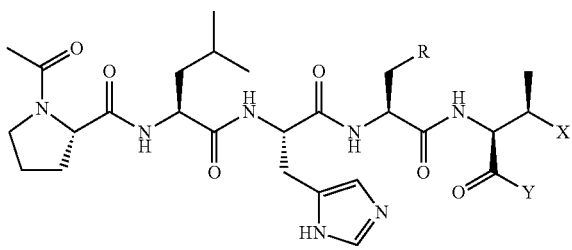

21 R = OH; Y = NH$_2$; X = OH
22 R = OH; Y = NH$_2$; X = O—PO(OH)$_2$
23 R = OH; Y = NH$_2$; X = CH$_2$—PO(OH)$_2$
24 R = H; Y = NH$_2$; X = CH$_2$—PO(OH)$_2$

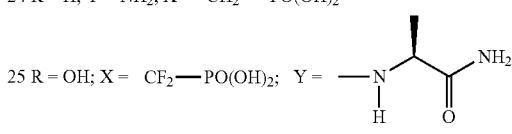

25 R = OH; X = CF$_2$—PO(OH)$_2$; Y =

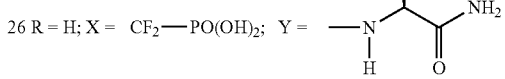

26 R = H; X = CF$_2$—PO(OH)$_2$; Y =

Plk1 PBD-binding inhibition assays were conducted in the presence of various concentrations of synthetic peptides. It was found that "PLHS-Pmab" (SEQ ID NO: 19) (23) inhibits the interaction of the Plk1 PBD with a biotinylated 9-mer p-T78 peptide [Biotin-Cys-(CH$_2$)$_5$—CO-DPPLHSpTAI-NH$_2$ (SEQ ID NO: 21)] as effectively as the wild-type peptide, "PLHSpT" (SEQ ID NO: 1) (22). In contrast, the peptide, "PLHS-F$_2$Pmab-A" (SEQ ID NO: 7) (25), inhibits the interaction at a somewhat reduced level. Replacement of the critical (pThr-1) Ser residue with an alanine (equivalent to S77A mutation) is known to significantly attenuate PBD binding affinity. The non-phosphorylated control peptide "PLHST" (SEQ ID NO: 11) (21) and the S77A mutants of the Pmab- and the F$_2$Pmab-containing peptides (24 and 26, respectively), did not inhibit PBD binding even at 1000-fold higher molar concentrations). The ELISA-based PBD-binding inhibition assay was carried out using an immobilized biotinylated 9-mer p-T78 peptide [Biotin-Cys-(CH$_2$)$_5$—CO-DPPLHSpTAI-NH$_2$ (SEQ ID NO: 21)] and cellular lysates expressing HA-EGFP-Plk1.

Evidence suggests that the PBD plays critical roles in the proper sub-cellular localization and mitotic functions of Plk1. Disruption of PBD-dependent Plk1 functions by expressing a dominant-negative form of PBD results in a mitotic arrest that ultimately leads to apoptotic cell death. To investigate the effects of inhibiting Plk1 PBD interactions peptides 21, 23 and 24 were introduced into HeLa cells. In order to overcome poor membrane permeability of the negatively charged Pmab-containing peptides, microinjection was employed. HeLa cells were arrested at the G1/S boundary by double thymidine treatment and released into fresh medium. Six hours after release, the cells were microinjected with a mixture of 3 mM of peptides 21, 23 or 24 and 30 ng/µL of pEGFP-C1 vector and the cells were then photographed 15 h after G1/S release. Co-injected EGFP plasmid provided a convenient marker to identify the microinjected cells. The Pmab-containing peptide (23), but not the non-phosphorylated peptide 21 or the respective S77A mutant (24), induced mitotically arrested, rounded-up, morphology in approximately 50% of the microinjected, green fluorescent protein (GFP)-positive population (FIG. 16B). These results demonstrate that inhibition of PBD function by the Pmab-containing p-T78 mimetic peptide is sufficient to interfere with the mitotic functions of Plk1.

Example 14: Proline-Oxime and Proline-Ether Containing PDB-Binding Peptides

Proline Oxime Derivatives were prepared. Of the series 4a-4p (4a-4j) peptides 4b, 4i and 4j gave the highest PBD-binding affinity. Peptide 4b (i.e., a carbon chain length of four units) represented the optimum linker length. To further optimize 4b, a "methyl scan" was performed (4k-4m), where methyl groups were substituted on the phenyl ring. Methyl groups at the ortho-, para-positions (4k and 4m, respectively) had little effect on binding affinity. However, a meta-methyl substitutent (4l) slightly increased the binding affinity. Three more meta-substituted analogues (4n-4p) were prepared, all gave similar binding potency as 4b; the 3-methoxy (4n) slightly increased the binding potency, and the 3-phenyl (4p) slightly decreased the binding potency.

Example 16: Proline Amidooxy and Ether Derivatives

To simplify further modification of 4b, the oxime bond was replaced with amidooxy or ether functionality. To prepare the amidooxy analogue 6, MTT was used as the aminooxy protective group instead of previous Boc. The MTT group can be cleaved by 1% TFA in DCM. Following amino deprotection amidation was achieved with hydrocinnamic acid. Unfortunately, the amide analogue 6 showed significantly decreased the binding affinity. The ether analogue 7 was also prepared using a pre-derivatized proline analogue. Surprisingly, the binding potency of 7 was enhanced compared to 4b. Therefore, 5b was converted to its ether format 8, which also gave higher binding affinity. The non-phosphate form of 7 (peptide 10), and S/A mutants of 7 and 8 (peptides 9 and 11) were also prepared, and these showed greater than 100 fold-loss of binding affinity or no affinity.

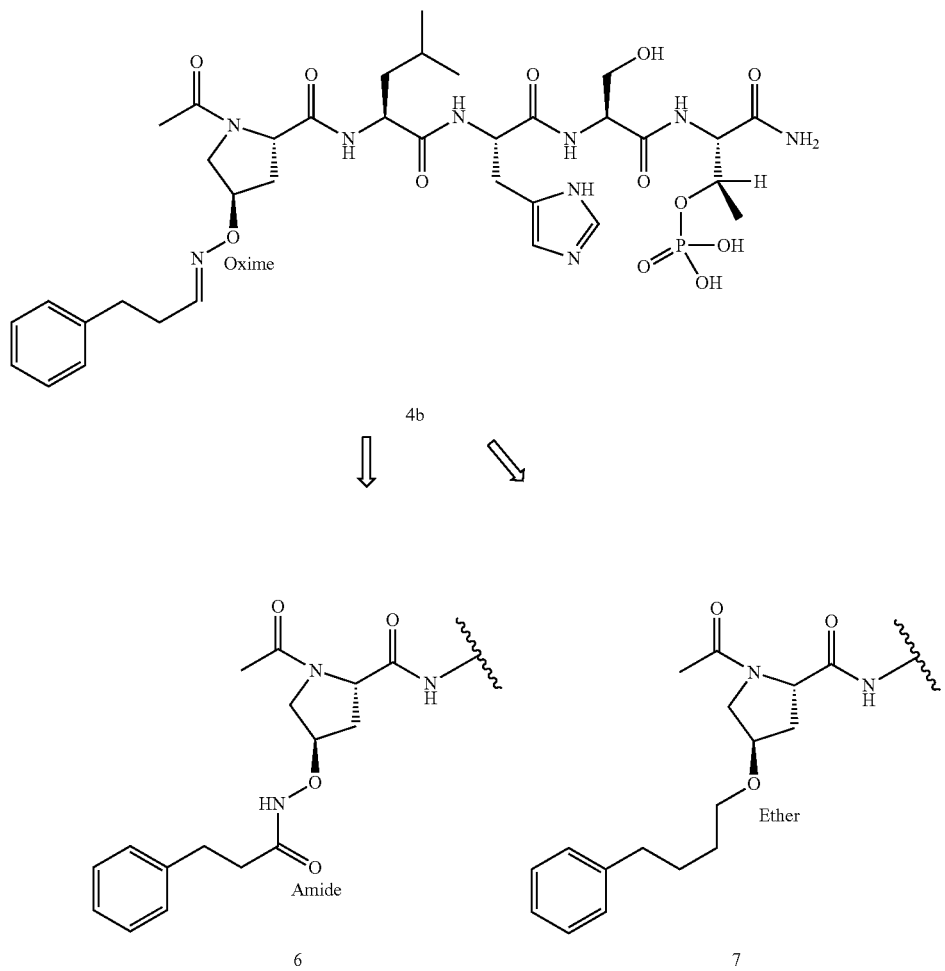
4b
6 Amide
7 Ether
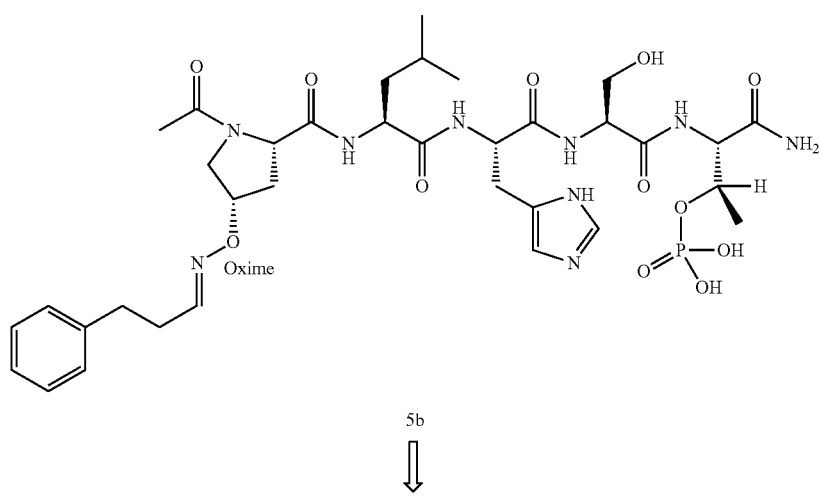
5b

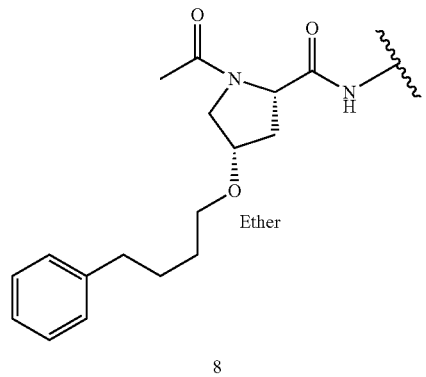
Ether
8
Oxime bond replacements.
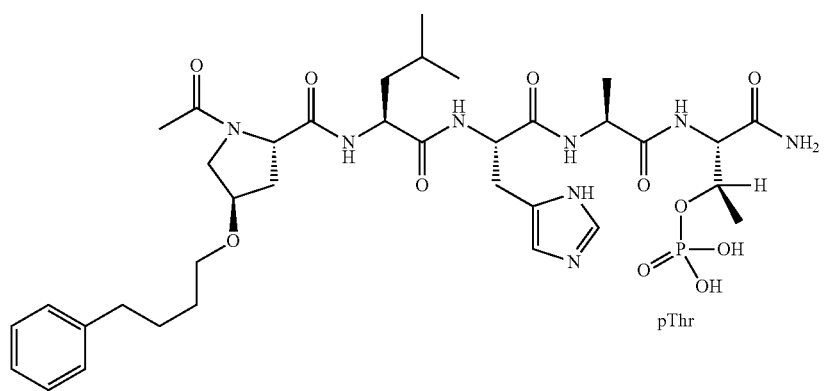
pThr
9
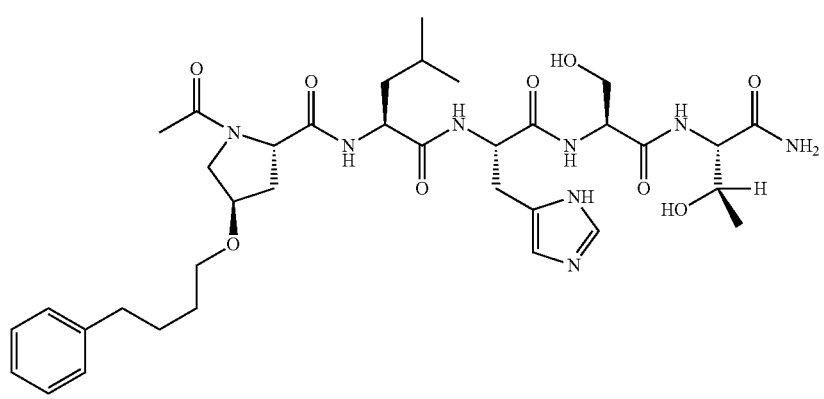
10

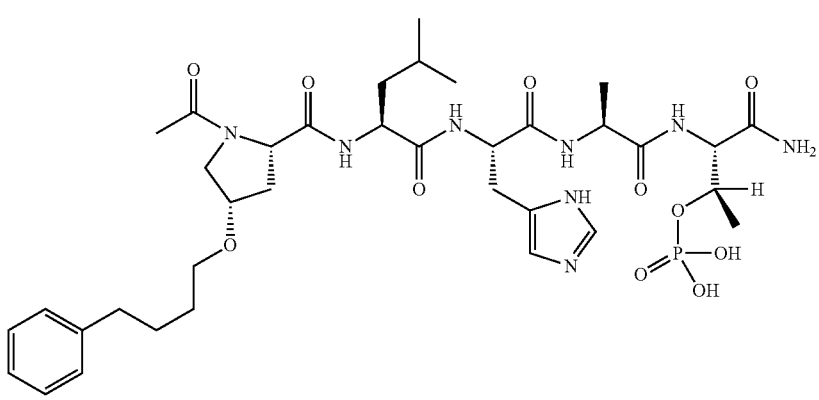

11

Non-phophate peptide and S/A mutants.

Example 17. Biological Evaluation of Further Peptoid-Peptide Hybrids

Synthesis of NSG-containing libraries was achieved by the "submonomer approach" (discussed above).

ELISA based Plk1 PBD-binding inhibition assays were conducted in the presence of 5 different concentrations of these peptoid-peptide hybrids. Hybrids 4d and 4e had dramatically diminished binding affinity, which indicated that both positive and negative charges are not tolerated at this position. As compared to the WT 5-mer (Ac-PLHSpT-NH$_2$ (SEQ ID NO: 1)), hybrids 4a, 4c and 4j (substituents as indicated in the Figure below) showed slightly higher binding affinity, while 11f and 11i showed similar affinity and the remaining analogues were weaker binders.

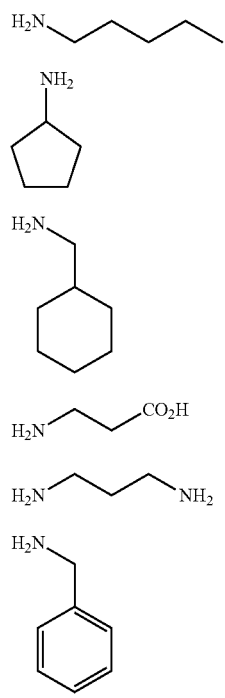

a
b
c
d
e
f

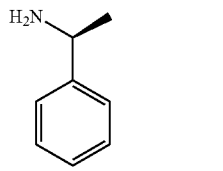

g

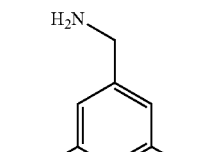

h

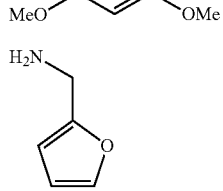

i

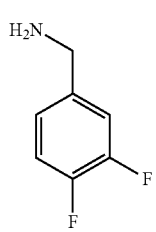

j

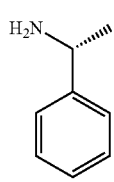

k

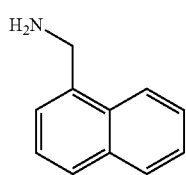

l

Structures of amines used to prepare peptide-peptoid hybrid 4.

Based on the above results that non-charged hydrophobic group is preferred, while too bulky group compromised the binding affinity, we further explored the phenyl group linked by a serious of linkers with gradually increased length. Surprisingly, the binding potency of this serious of peptoid-peptide hybrids (4f and 4m-4r) increased along with the linker length, 4q and 4r gave the highest potency according to the ELISA assay results. Peptide 5, Ser to Ala mutant of 4q, is not active.

| | |
|---|---|
| $NH_2—(CH_2)_2$-Ph, | m |
| $NH_2—(CH_2)_3$-Ph, | n |
| $NH_2—(CH_2)_4$-Ph, | o |
| $NH_2—(CH_2)_5$-Ph, | p |
| $NH_2—(CH_2)_6$-Ph, | q |
| $NH_2—(CH_2)_7$-Ph, | r |

Structures of amines used to further explore peptide-peptoid hybrid 4.

Ser to Ala mutant of 4q.

A tetra-peptide 6 with the same linker length as 4q was prepared and gave same binding potency as 4q. Click chemistry was attempted to partially restrict the flexibility of the long linker in 6. Alkyne containing peptide 7 was prepared on the resin, the following Cu(I) catalyzed 1,4-Huisgen cyclization with azides followed by resin cleavage gave 8 and 9. Conventional heat (100° C. in DMF, 2 days) condition gave a mixture of 1,4 and 1,5-triazole product, therefore provided analogue 10 and 11. But all of these peptides (8-11) gave diminished binding potency.

Example 18: Plk1 Specificity Test

Further conversion of peptoid-peptide hybrids into peptoid inhibitors was undertaken to generate. a whole peptoid ligand. A systematical peptide library by using natural amino acids has been constructed and evaluated in the literature, which gave the information that preferred side chains at the other 4 residues. Keeping the best NSG (4q) at the Pro position, the inventors firstly tried to further explore the Leu position. Although all of them gave decreased binding potency compared to 4q, interestingly, the hybrid with a NSG of Leu mimetic (16s) is the best compound.

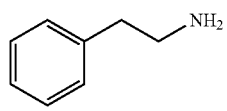
m

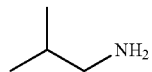
s

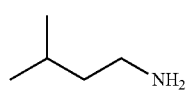
t

Peptoid-peptide hybrid library with variations at Leu position.

The inventors further developed peptoid-peptide hybrid ligand based on 16s, three hybrids were prepared, but all of them (17f-fu) showed further decreased binding.

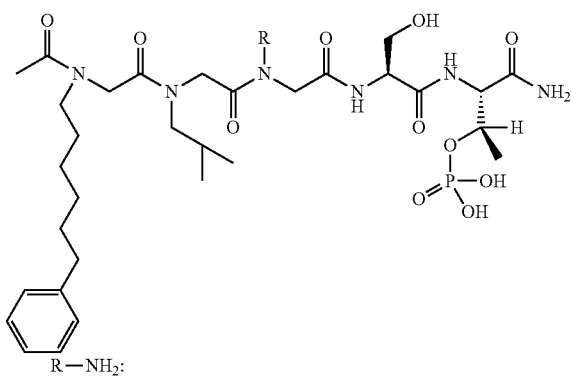

17

f

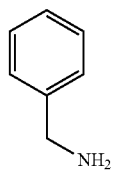
m

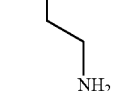

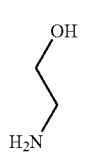
u

Peptoid-Peptide hybrids library at His position.

Example 19-Peptides Containing Phosphate Monoesters and Arylalkyl-Histine-Containing PBD-Binding Peptides The inventors used a structure-based rational design method based on the Mitsunobu reaction to make di-ester. The approach provides numerous advantages including, but not limited to, highly efficient library construction, resistance to phosphatase, and increased cell permeability.

Post-modification of the peptide on the resin gave two products 3 and 4 with the same molecular weight as about 1 to 4 ratio, the minor product 3 consistently gave higher potency than the major product 4.

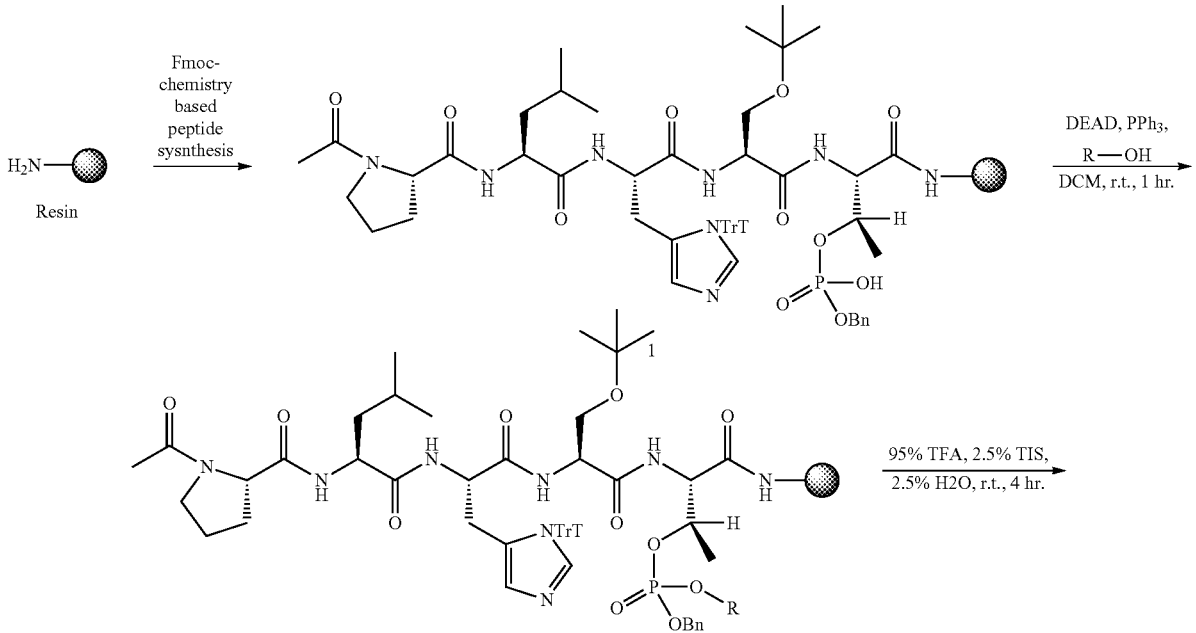

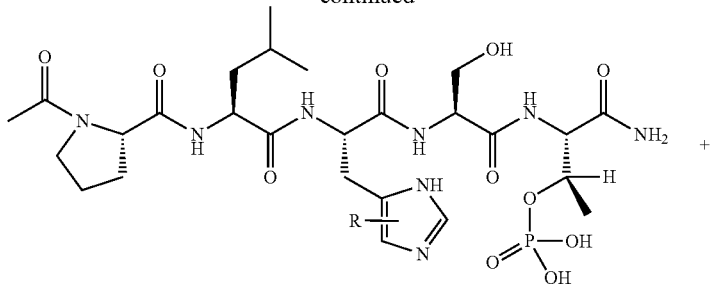

minor pdt, 3

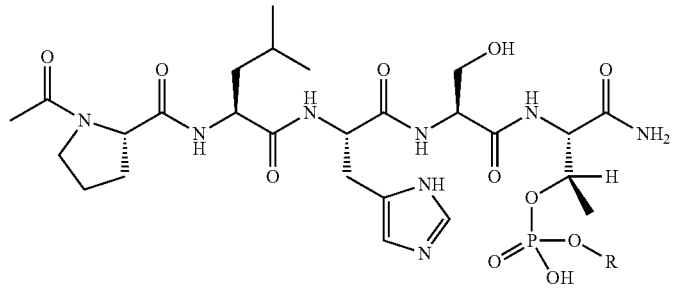

major pdt, 4

Post-modification on the solid phase by using Mitsunobu reaction.

In the first round alcohol library, a variety of functional groups including di-ol, carbon chains, carboxylic acid, amine, and hetero ring were examined. It was determined that the hydrophobic group Ph-(CH$_2$)$_4$— gave the highest binding affinity for minor product 3. 4h was much less active than 3h, also less active than the WT.

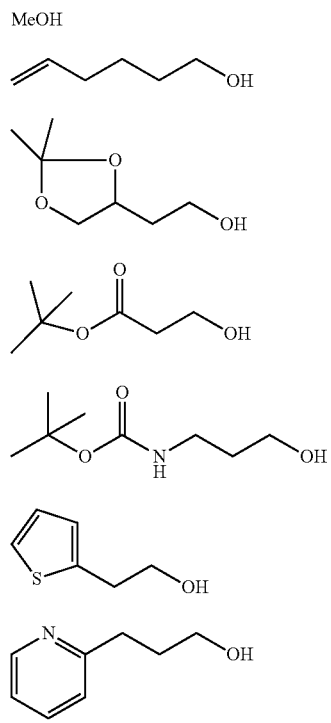

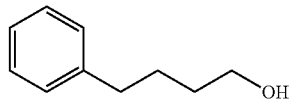

Initial alcohol library used prepare peptide 3 and 4.

In the second round focused alcohol library, the linker length was systematically examined, and alcohol 1 found to be the best hit according to the ELISA assay results.

| | |
|---|---|
| Ph-(CH$_2$)$_5$—OH, | i |
| Ph-(CH$_2$)$_6$—OH, | j |
| Ph-(CH$_2$)$_7$—OH, | k |
| Ph-(CH$_2$)$_8$—OH, | l |
| Ph-(CH$_2$)$_9$—OH, | m |
| Ph-(CH$_2$)$_{10}$—OH, | n |

Focused alcohol library to prepare peptide 3 and 4.

The S/A mutants of peptide 3l and 4l were also prepared and determined by ELISA. 5 gave 100-fold decreased binding compared to 3l, and 6 didn't show any activity.

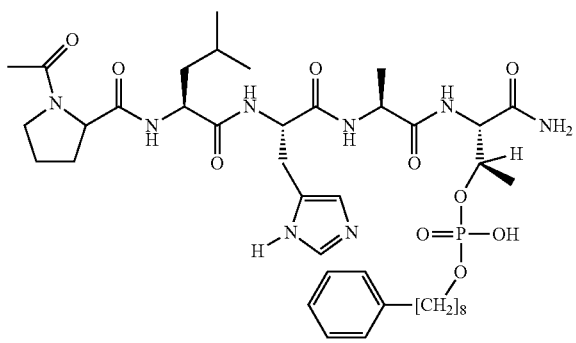

S/A mutants of peptide 31 and 41, respectively. (The X-ray crystal structure of 31 bound PBD protein has been solved. This structural information provide valuable information for ligand design).

Example 20—Evaluation of HIV-Tat Tagged PEGylated Peptides on HIV Budding Inhibition As it was reported the p6 region of HIV Gag and the UEV domain of TSG101 are both necessary and sufficient for the Gag-TSG101 interaction, DNA fragments encoding the p6 region of Gag and the UEV domain of TSG101 are introduced into the RTHS plasmid and these constructs in E. coli are cloned (see, Tavassoli et al., ACS Chem. Bio., 3, 12, 2008, 757-764). Expression of the gene fragments is under the control of an isopropyl 13-D-thiogalactoside (IPTG) inducible promoter (see also Tavassoli et al). The cassette coding for the p6-P22.434 and UEV-434 repressor fusion proteins are integrated into the chromosome of an E. coli reporter strain (see also Tavassoli et al.; and Tavassoli et al., Angew. Chem. Int. Ed. Engl. 44, 2005, 2760-2763). Upon chromosomal integration of the p6-UEV reverse two-hybrid system, o-nitrophenyl13-galactoside (ONPG) assays are carried out to measure the IPTG-dependent repression of the LacZ gene product (13-galactosidase). Increased IPTG-dependent expression of the fusion proteins resulted in decreased 13-galactosidase activity, indicating that UEV and p6 interact in the reverse two-hybrid system (see Tavassoli et al., ACS Chem. Bio., 3, 12, 2008, 757-764).

Gag-VLP (viral-like particles) assays are conducted to monitor the effects of the PEGylated Peptides of the invention on HIV viral budding. A short peptide sequence derived from HIV Tat was attached to the PEGylated Peptides (see above for synthetic scheme).

Gag VLP Assay:

A GFP-tagged wild-type Gag expression construct (see L. Hermida-Matsumoto et al. J. Virol, 74, 2000, 8670-8679) or a GFP-tagged PTAP (SEQ ID NO: 22) minus mutant Gag (PTAP (SEQ ID NO: 22) changed to LIRL (SEQ ID NO: 23)) construct (see J. E. Garrus et al. Cell, 107, 2001, 55-65) is transfected into 293T cells. Forty-eight hours after the initiation of transfection, the culture supernatants are collected and filtered through a 0.45-pm-pore-size filter. Virus-like particles in the culture supernatants are isolated by ultracentrifugation through a cushion of 20% sucrose at 45,000 rpm for 90 min at 4° C. using a Beckman SW50.1Ti rotor. The viral particles in the pellets are resuspended in SDS sample loading buffer and subjected to SDS-PAGE and Western blotting.

Example 21. ELISA-Based PBD-Binding Inhibition Assays

Peptide pull-down assays were carried out essentially as described (Nat. Struct. Mol. Biol. 16(8):876-882; Nat Chern Biol 7:595-601). A biotinylated p-T78 peptide was first diluted with IX coating solution (KPL Inc., Gaithersburg, Md.) to a final concentration of 0.3 µM, and then 100 µL of the resulting solution was immobilized onto a 96-well streptavidin-coated plate (Nalgene Nunc, Rochester, N.Y.). The wells were washed once with PBS plus 0.05% Tween20 (PBST), and incubated with 200 µL of PBS plus 1% BSA (blocking buffer) for 1 h to prevent non-specific binding. Mitotic 293A lysates expressing HA-EGFP-Plk1 were prepared in TBSN buffer (~60 µg total lysates in 100 µg buffer), mixed with the indicated amount of peptide ligands and applied immediately onto the biotinylated p-T78 peptide-coated ELISA wells, and then incubated with constant rocking for 1 h at 25° C. Following incubation, the ELISA plates were washed 4 times with PBST. To detect bound HA-EGFPPlk1, the plates were probed for 2 h with 100 µL/well of anti-HA antibody at a concentration of 0.5 µg/mL in blocking buffer and then washed 5 times. The plates were further probed for 1 h with 100 µL/well of HRPconjugated secondary antibody (GE Healthcare, Piscataway, N.J.) at a 1:1,000 dilution in blocking buffer. The plates were washed 5 times with PBST and incubated with 100 µL/well of 3,3',5,5'-tetramethylbenzidine (TMB) substrate solution (Sigma, St. Louis, Mo.) until a desired absorbance was achieved. The reactions were stopped by the addition of 100 µL/well of stop solution (Cell Signaling Technology, Danvers, Mass.) and the optical densities (O.D.) were measured at 450 nm using an ELISA plate reader (Molecular Devices, Sunnyvale, Calif.). See FIG. 1 and FIG. 2.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

We claim:

1. A compound of Formula (a):

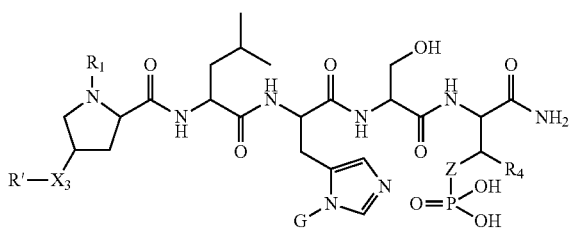

Formula (a)

wherein

Z is O, $CH_2$, or $CF_2$;

$R_1$ is

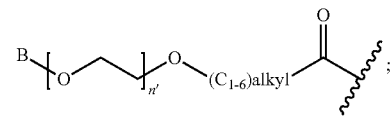

B is H, $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;

n' is an integer selected from 5-20;

R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl;

R' is H, $H_2$NO—, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$cycloalkyl, imidazolyl, quinolinyl, pyridinyl, pyrimidinyl, dioxo-pyrimidinyl, phenanthrenyl, or bicyclo[2.2.1]hept-2-enyl, wherein R' is further optionally substituted by one or more substituents selected from the group of halogen, $(C_{6-10})$aryl, heteroaryl, $(C_{1-6})$alkyl, $(C_{1-6})$alkoxy, hydroxyl, hydrosulfide, $(C_{1-6})$alkoxy-carbonyl, cyano, $(C_{6-10})$aryl-$(C_{1-6})$alkoxy, hydroxyl$(C_{1-6})$alkyl, trifluoromethyl, amino, and nitro; and G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino $(C_{1-20})$alkyl, aryl-$(C_{1-20})$alkyl, $(C_{1-20})$alkyl, or heretoaryl-$(C_{1-20})$alkyl, wherein each of alkyl, aryl and heretoaryl moieties is optionally substituted by one or more halogen, hydroxyl or alkoxy groups;

or a pharmaceutically acceptable salt, solvate, hydrate, or stereoisomer thereof.

2. The compound of claim 1, wherein

Z is O or $CH_2$;

n' is an integer between 5 and 20;

B is $(C_{1-6})$alkyl,

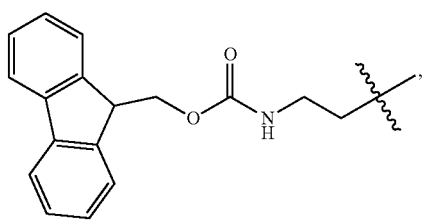 [SMILES: *CCNC(=O)OCC1c2ccccc2-c2ccccc21]

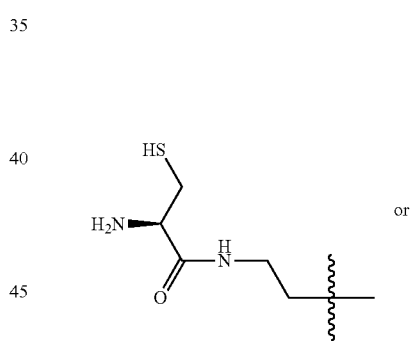

or

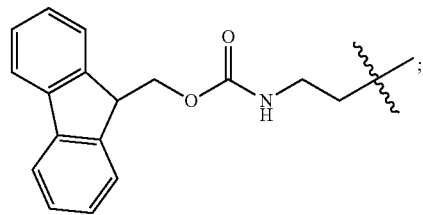

R'—$X_3$ is R', R'—CH=N—O—, R'—C(O)—NH—O—, or R'—$(CH_2)_2$—O—;

R' is H, $H_2$NO—, or phenyl-$(C_{1-6})$alkyl; and

G is H.

3. The compound of claim 2, wherein said compound is selected from the group of

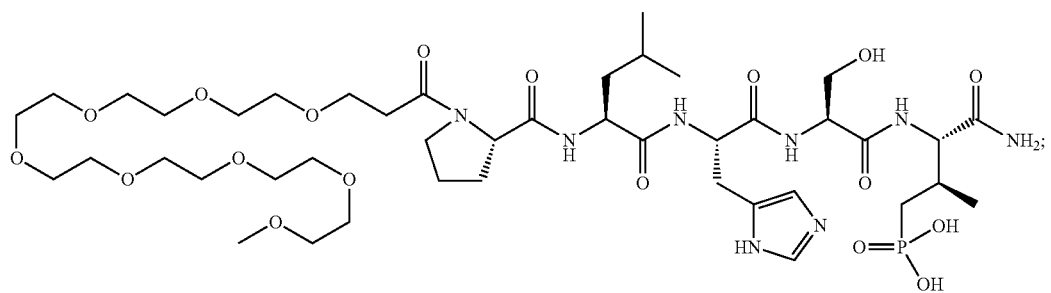
PEG-1*
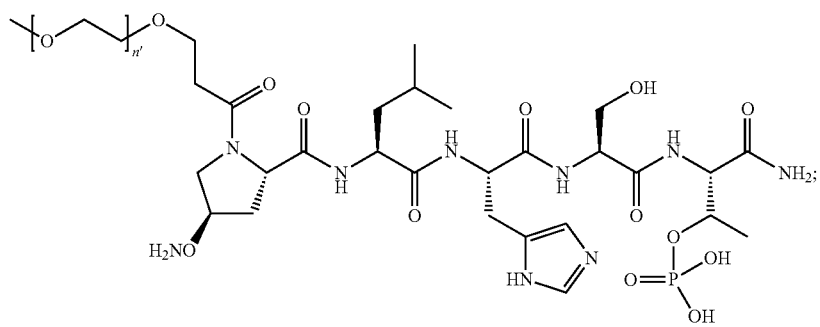
a-1
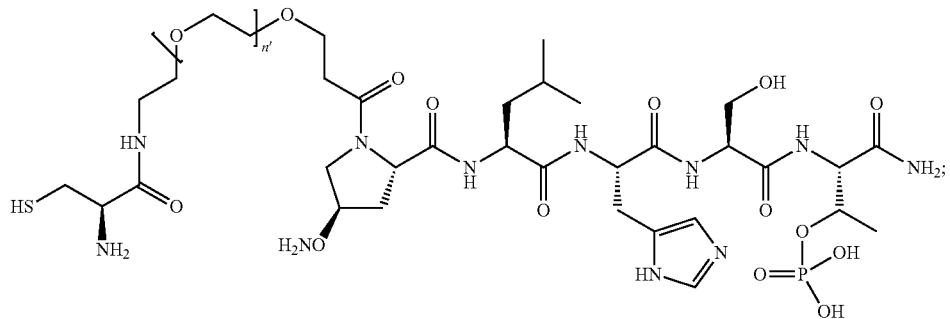
a-1A
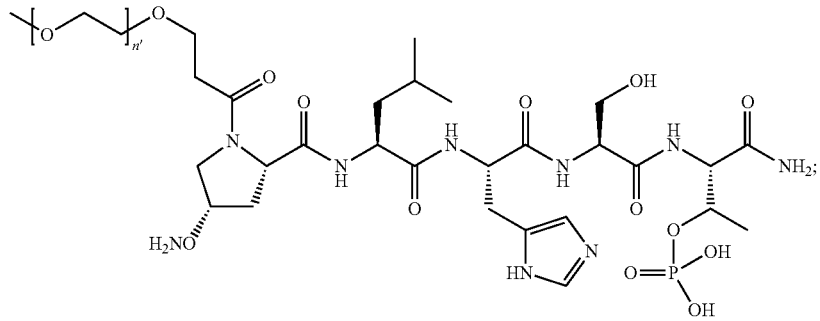
a-2
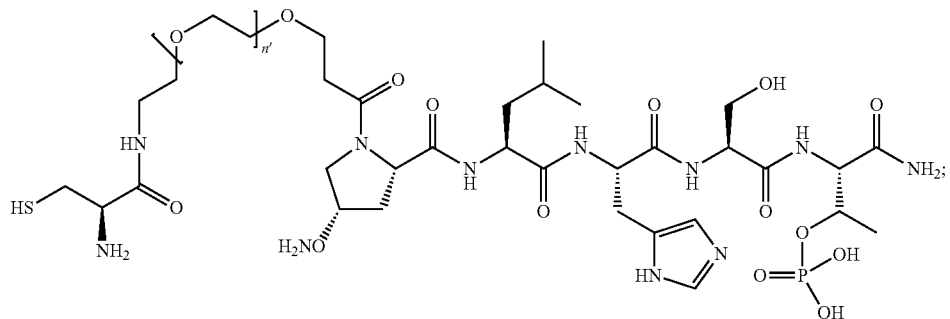
a-2A -continued
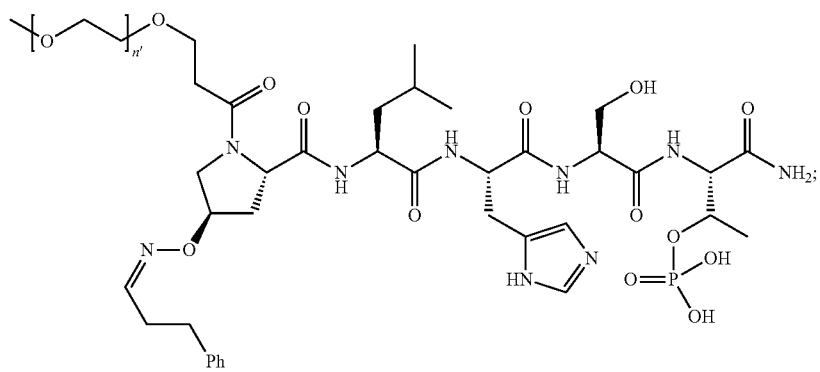
a-3
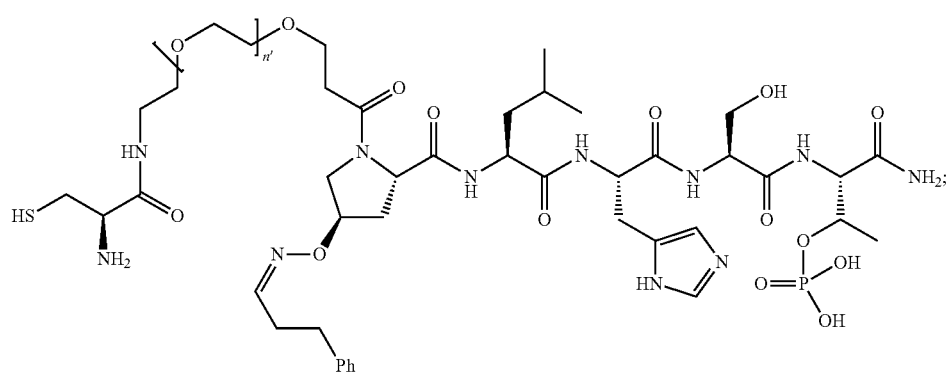
a-3A
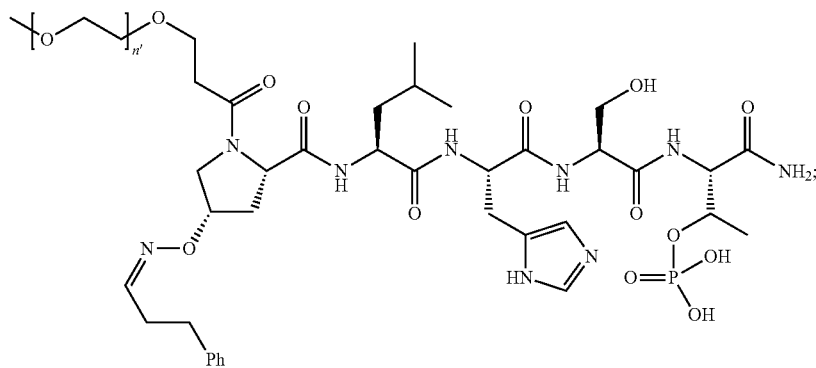
a-4
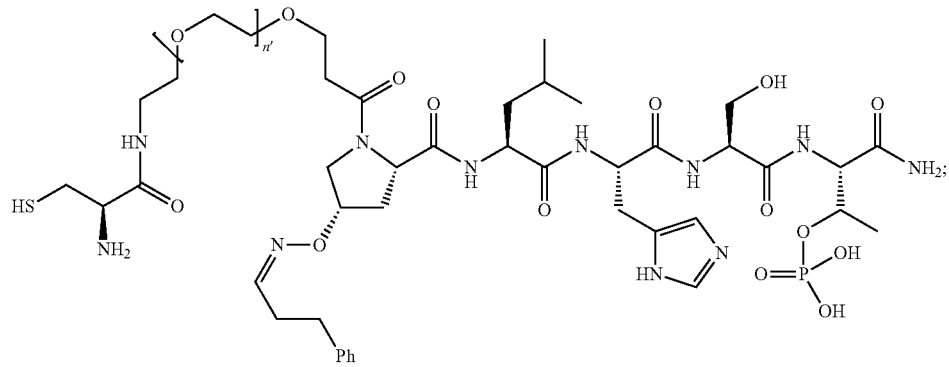
a-4A a-5
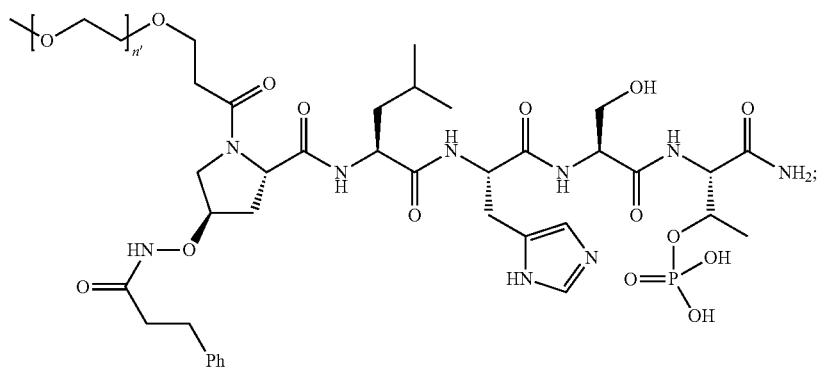
a-5A
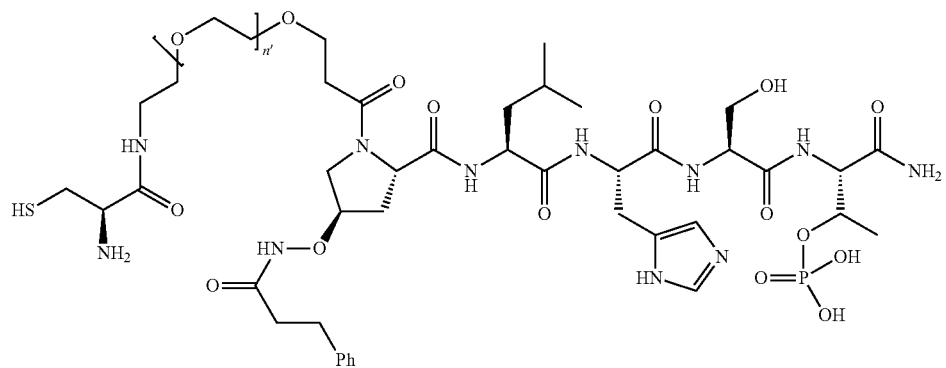
a-6
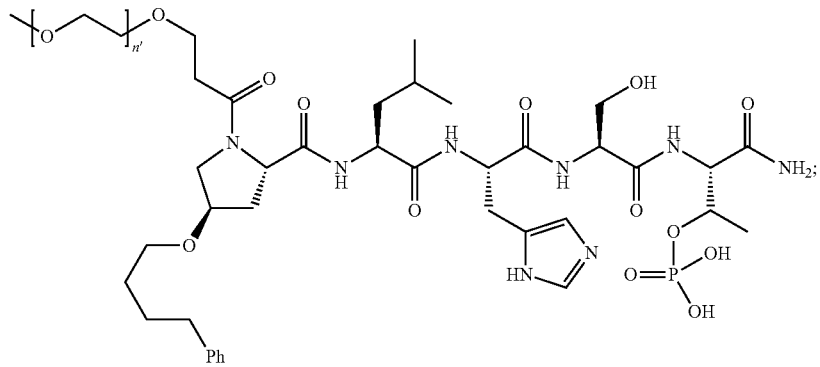
a-6A
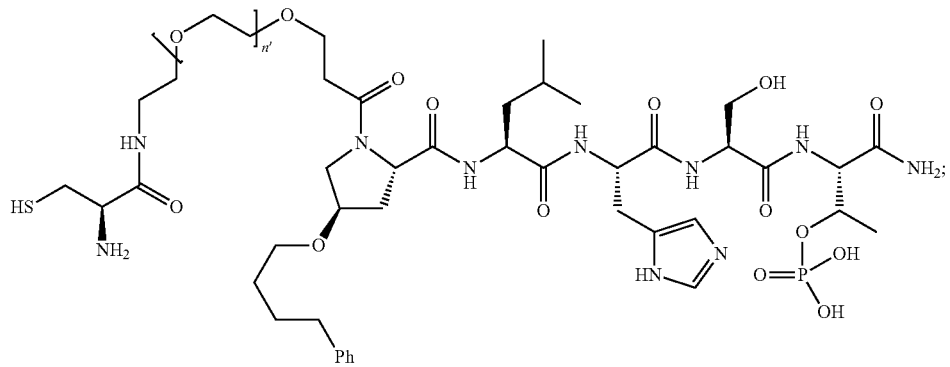

-continued
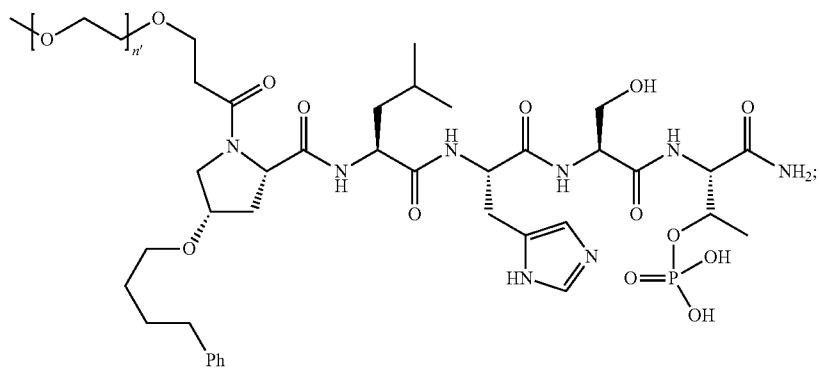
a-7
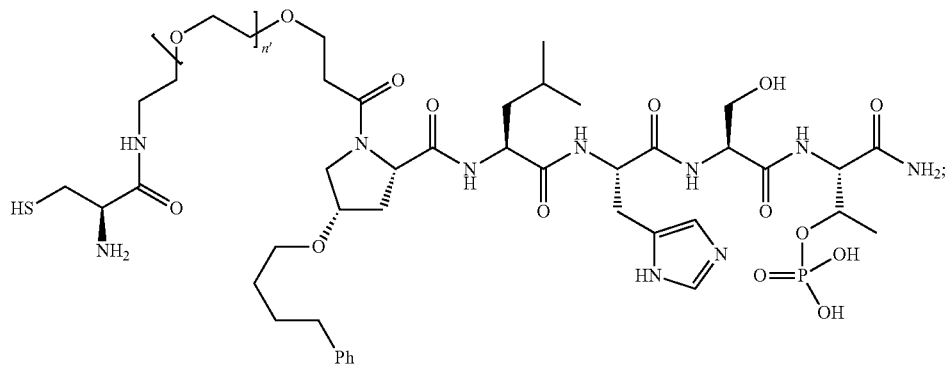
a-7A
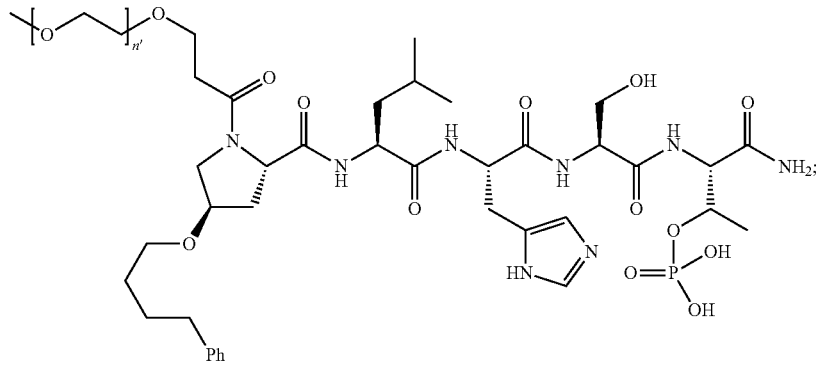
a-8
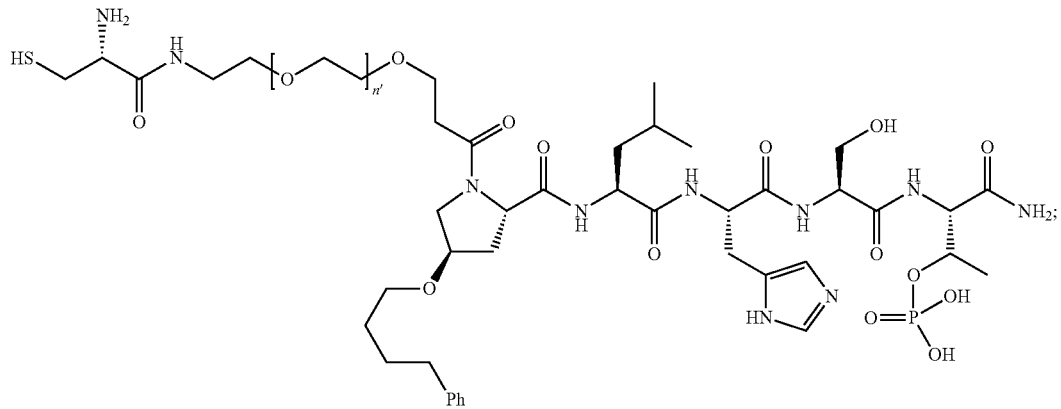
a-8A

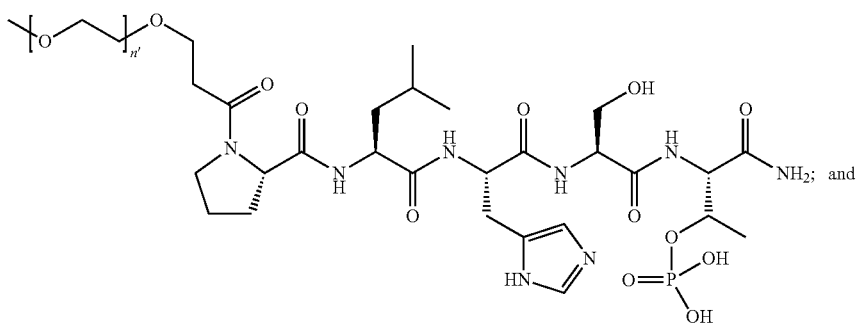

a-9

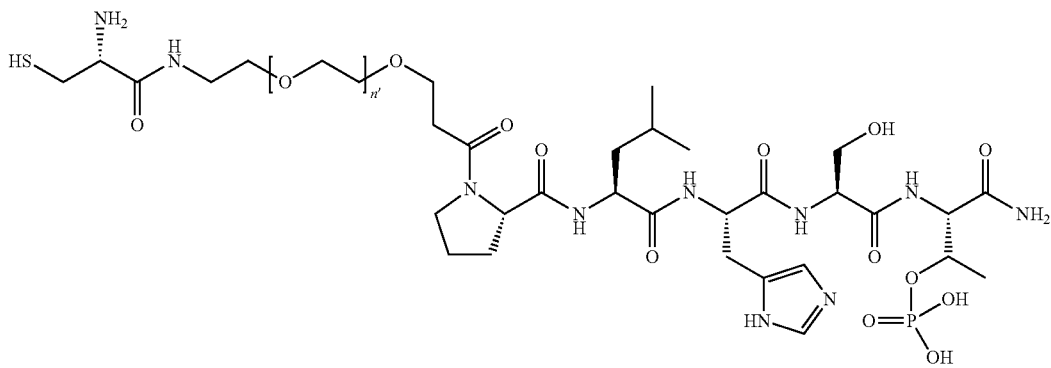

a-9A wherein n', each independently, is an integer selected from 5-8; or a pharmaceutically acceptable salt, solvate, hydrate, or stereoisomer thereof.

4. The compound of claim 2, wherein said compound is

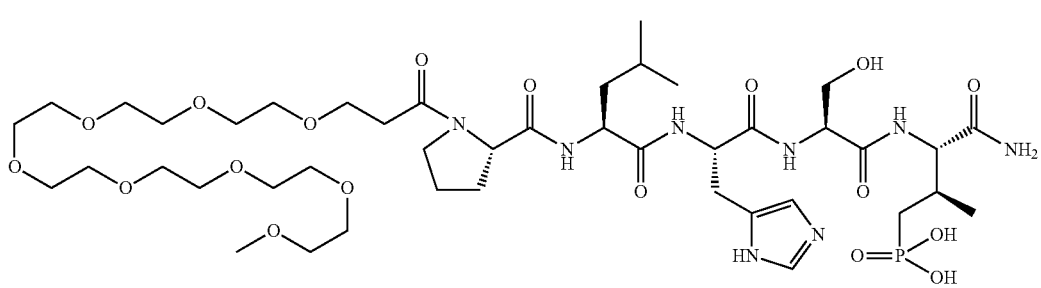

PEG-1* or a pharmaceutically acceptable salt, solvate, hydrate, or stereoisomer thereof.

5. The compound of claim 1, wherein

Z is O or CH$_2$;

n' is an integer between 5 and 20,

B is (C$_{1-6}$)alkyl, or hydrosulfide-(C$_{1-6}$)alkyl-C(O)—NH—(C$_{1-6}$)alkyl, wherein each (C$_{1-6}$)alkyl moiety, independently, is further optionally substituted by an amino or N-Fmoc-amino group;

R'—X$_3$ is R', R'—CH=N—O—, R'—C(O)—NH—O—, or R'—(CH$_2$)$_2$—O—;

R' is H, H$_2$NO—, or phenyl-(C$_{1-6}$)alkyl; and

G is alkenyl-(C$_{1-10}$)alkyl, hydroxyl-carbonyl-(C$_{1-6}$)alkyl, amino(C$_{1-6}$)alkyl, aryl-(C$_{1-10}$)alkyl, (C$_{1-10}$)alkyl, or heretoaryl-(C$_{1-10}$)alkyl; wherein each alkyl moiety is further optionally substituted by one or more hydroxyl or amino groups.

6. The compound of claim 5, wherein Z is O; R'—X$_3$ is H; and B is methyl,

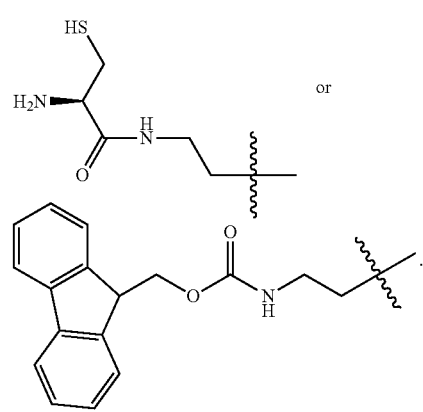

7. The compound of claim 6, wherein said compound has one of the following structures:
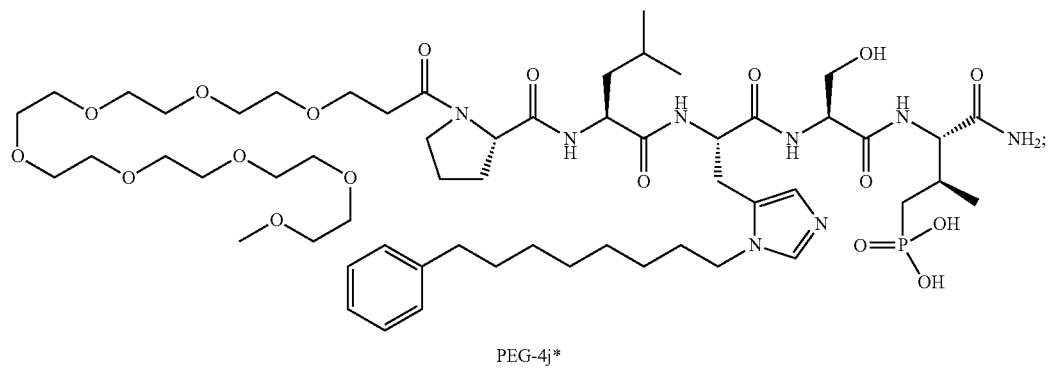
PEG-4j*
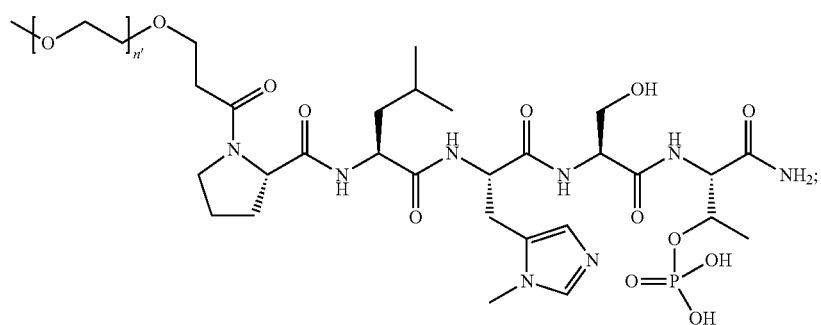
a-10
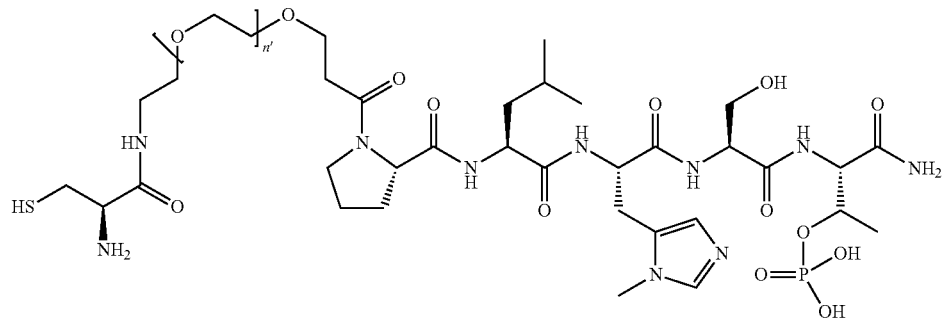
a-10A
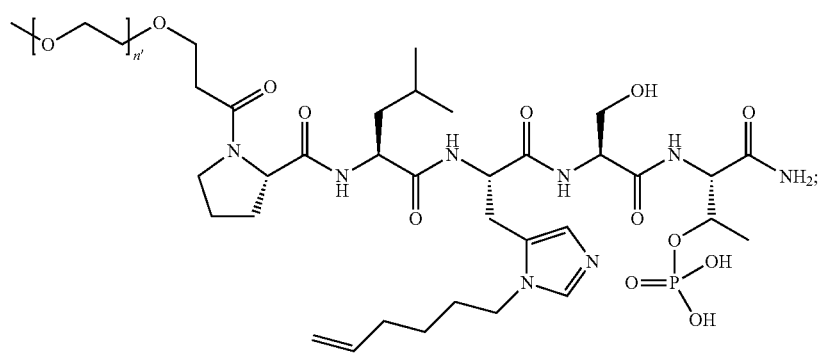
a-11

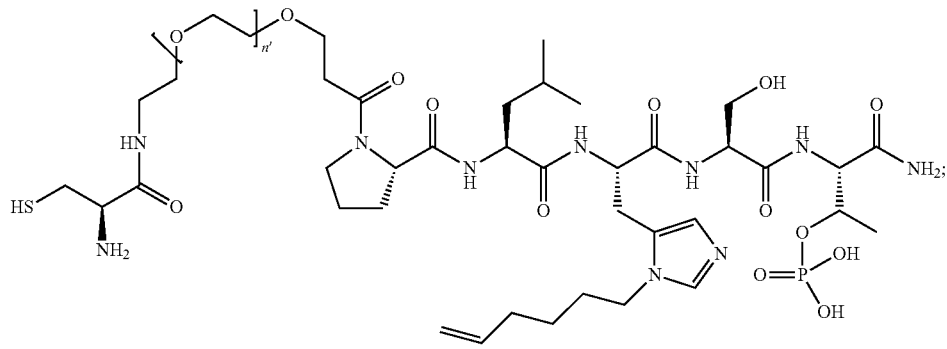
a-11A
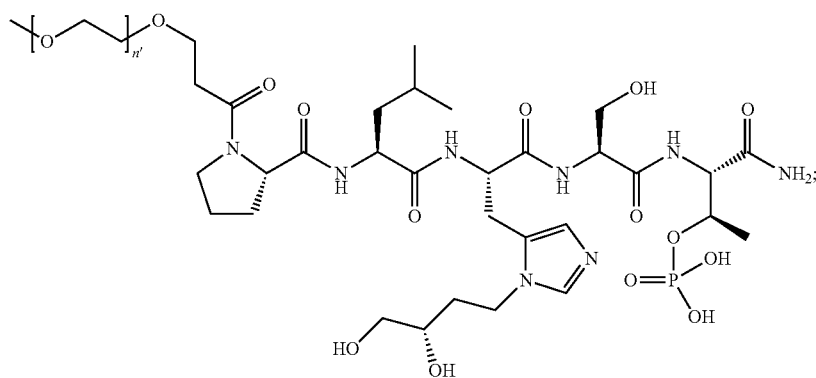
a-12
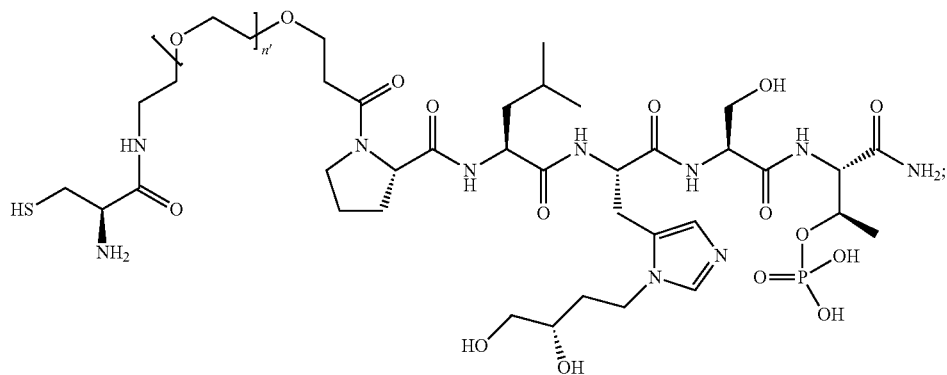
a-12A
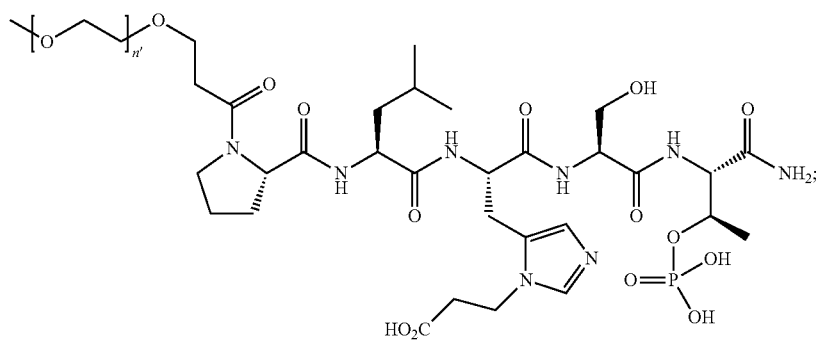
a-13

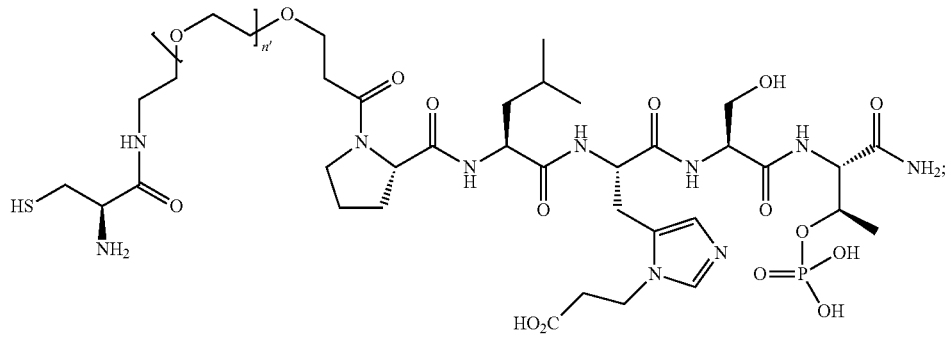
a-13A
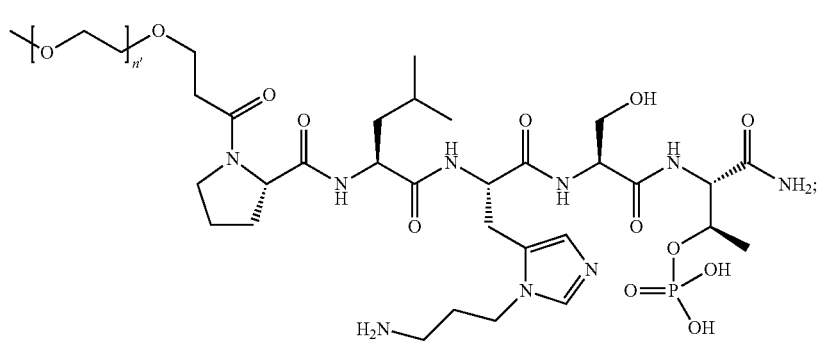
a-14
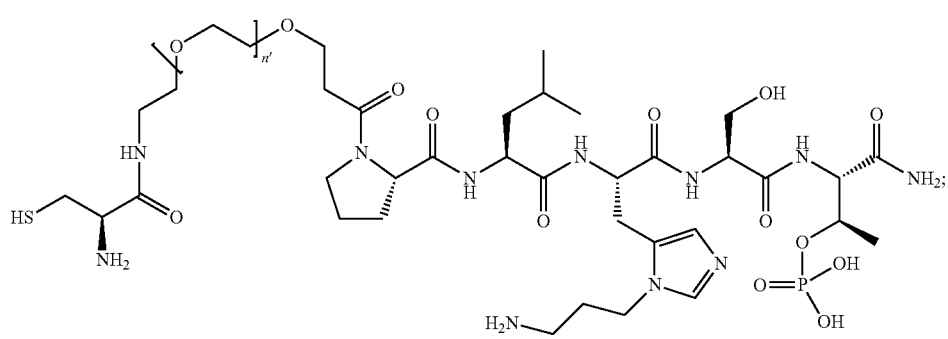
a-14A
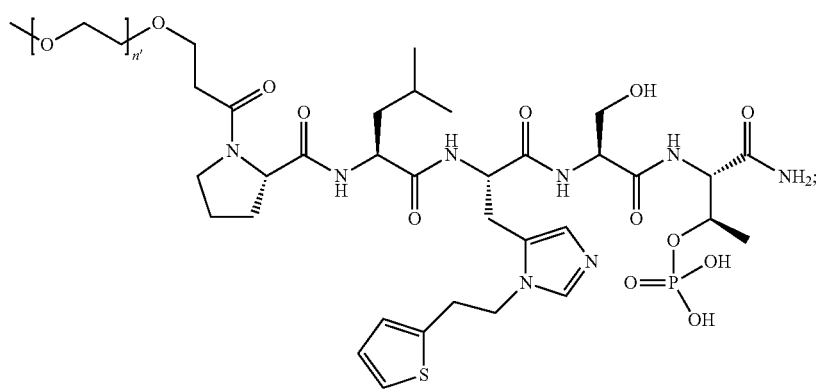
a-15 a-15A
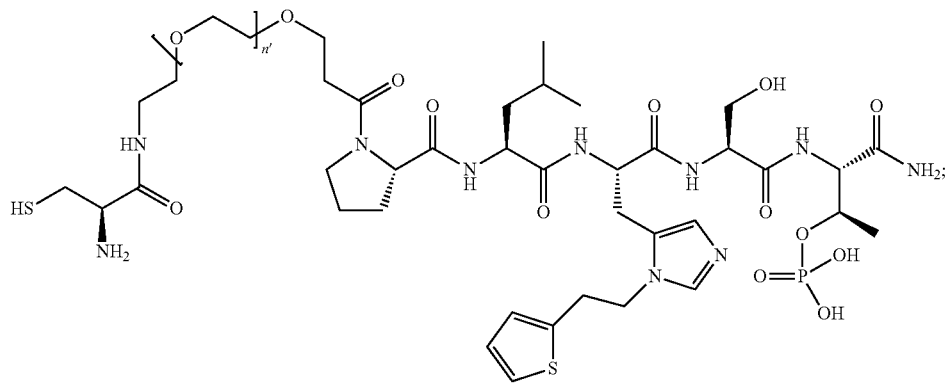
a-16
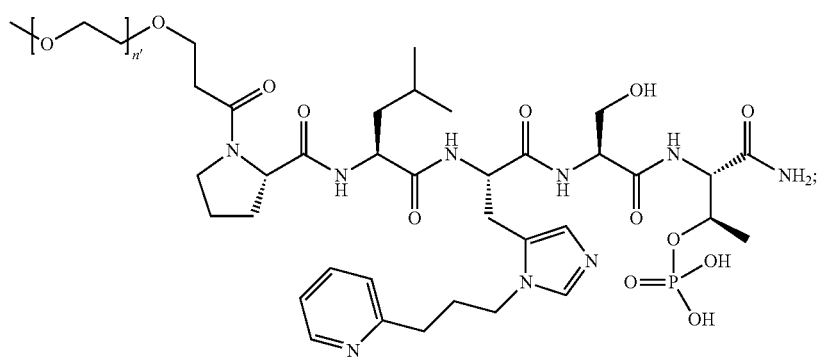
a-16A
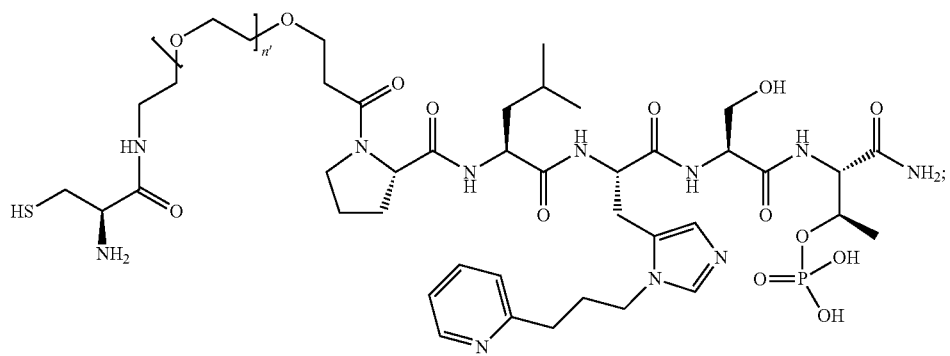
a-17
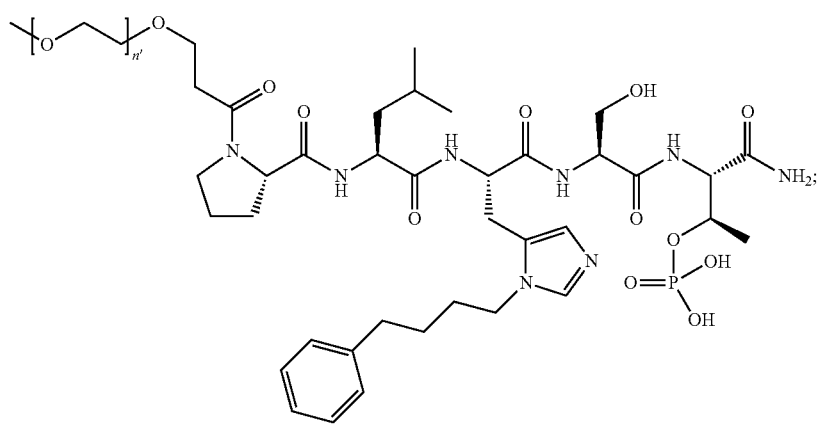

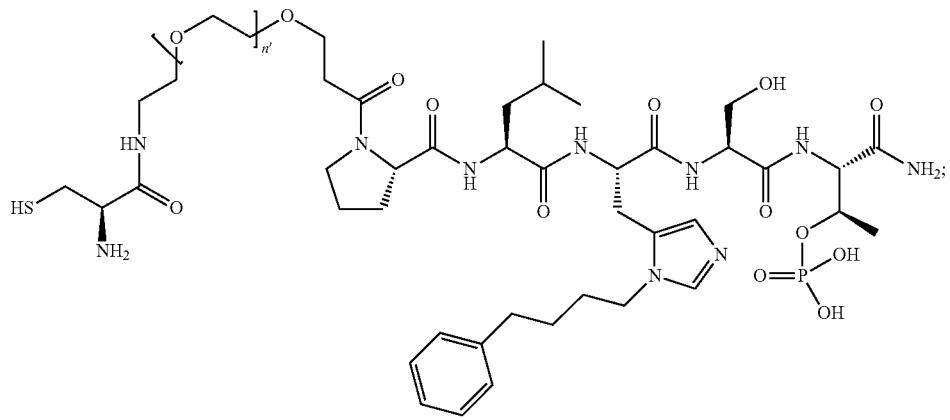
a-17A
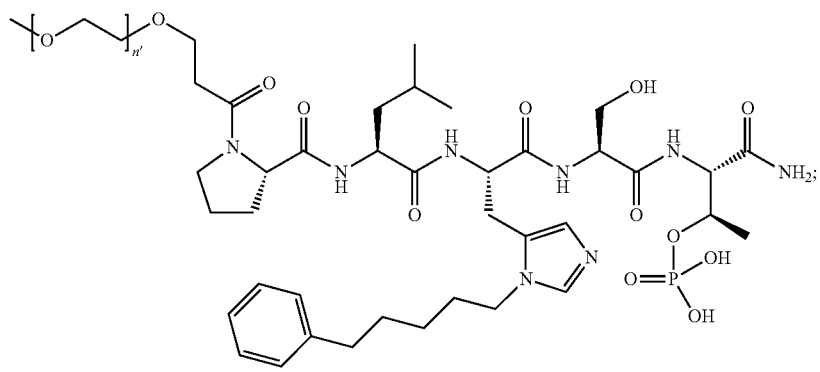
a-18
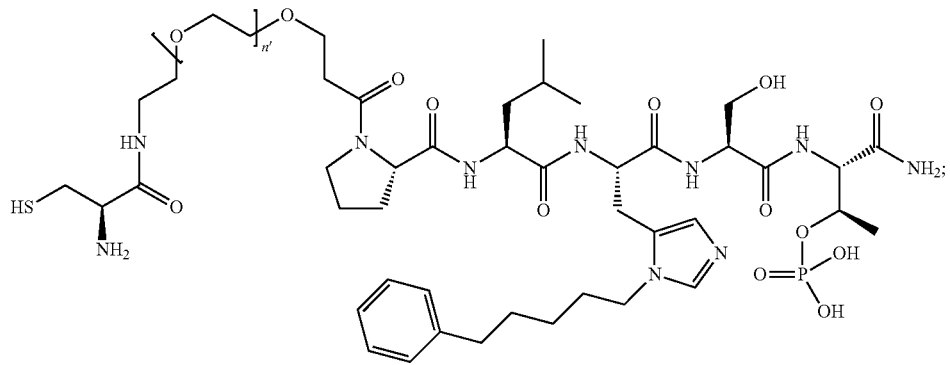
a-18A
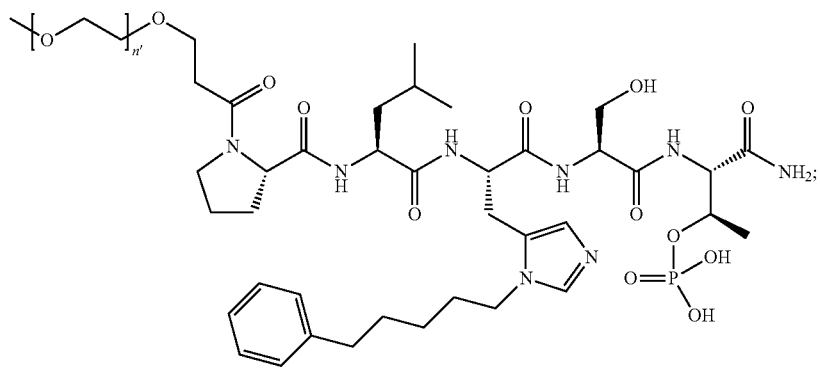
a-19

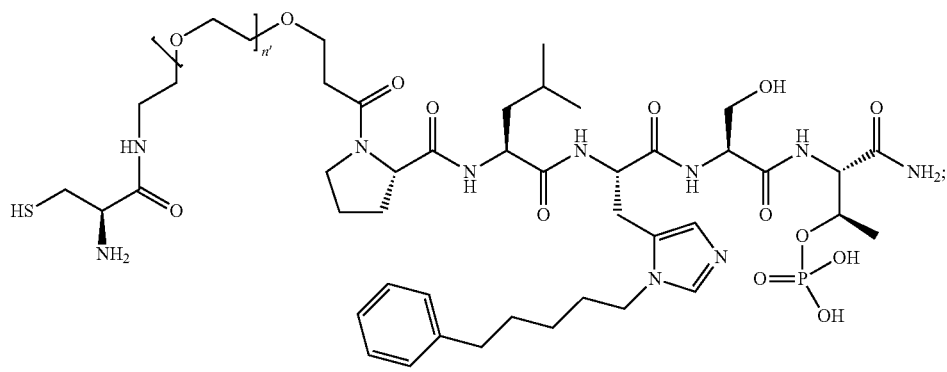
a-19A
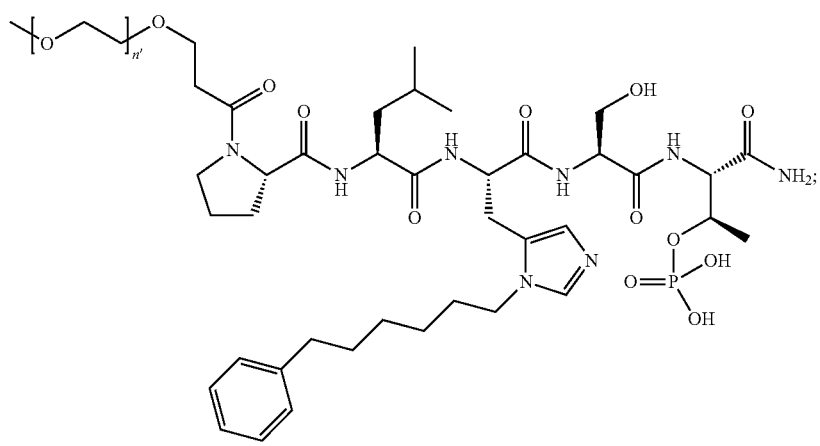
a-20
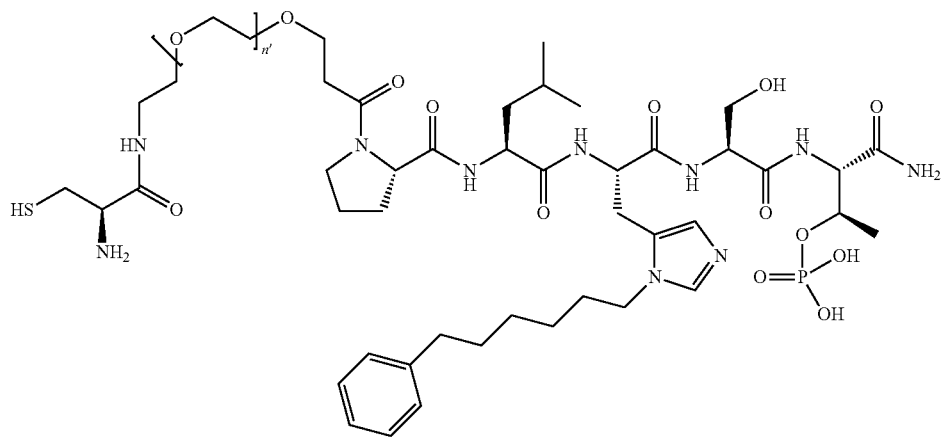
a-20A
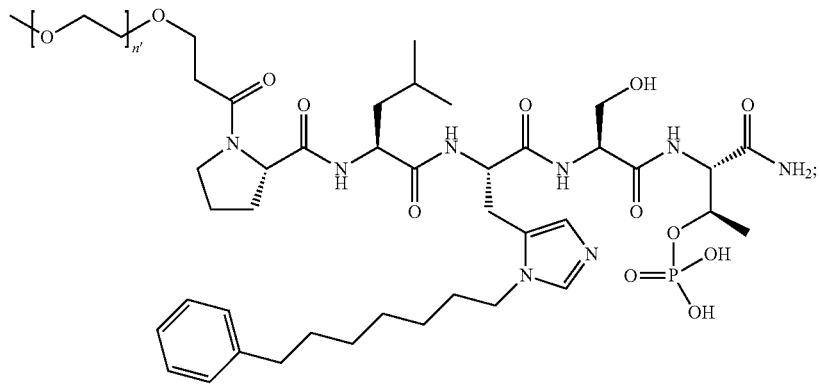
a-21

-continued
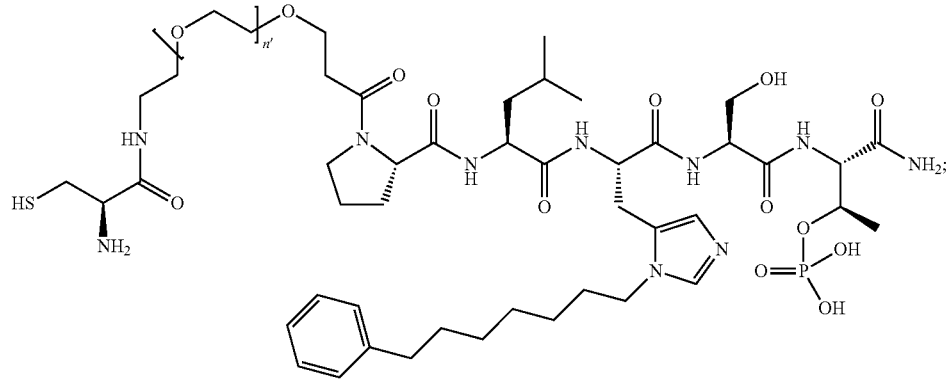
a-21A
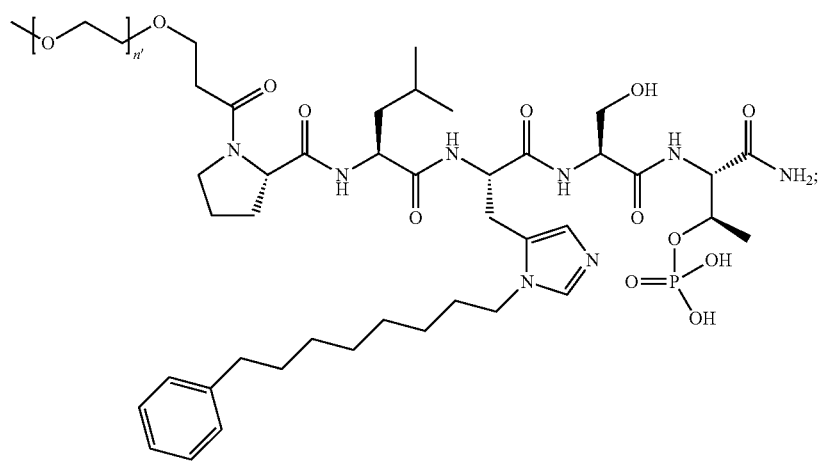
a-22
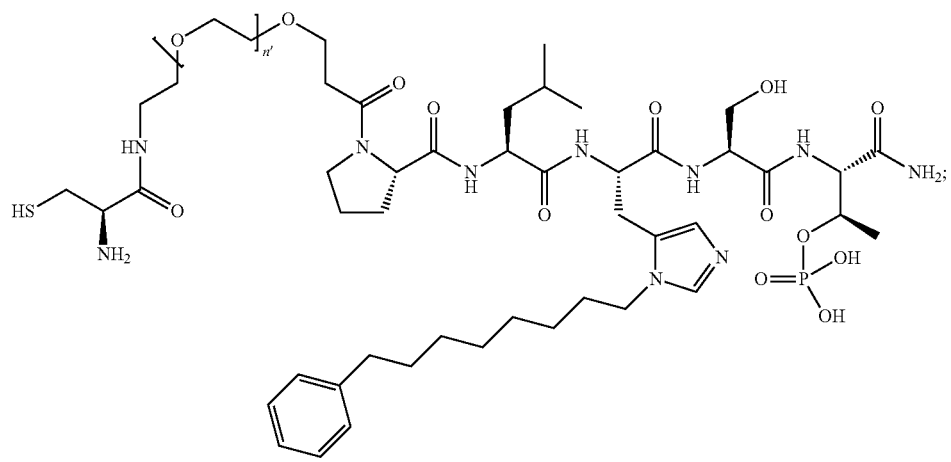
a-22A

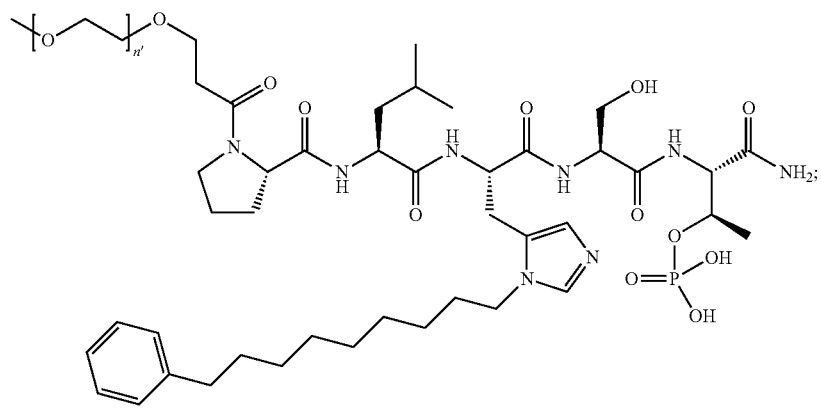
a-23
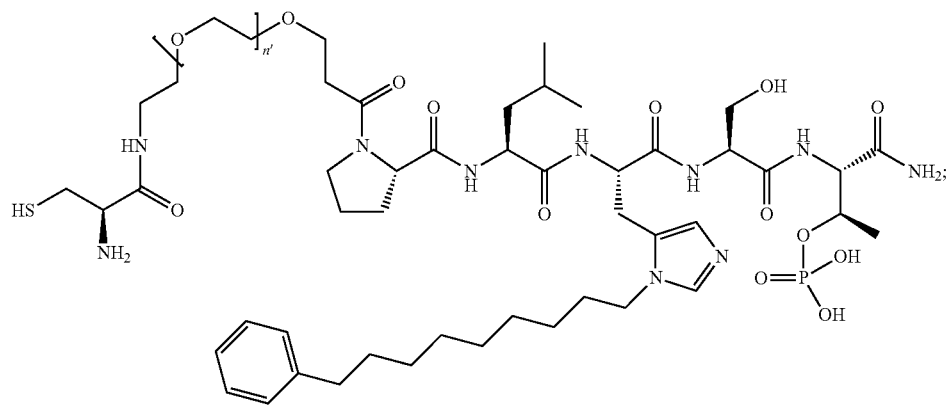
a-23A
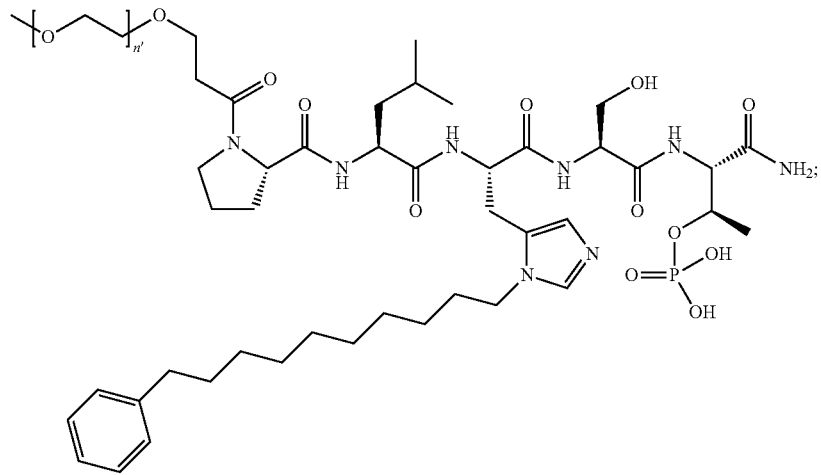
a-24

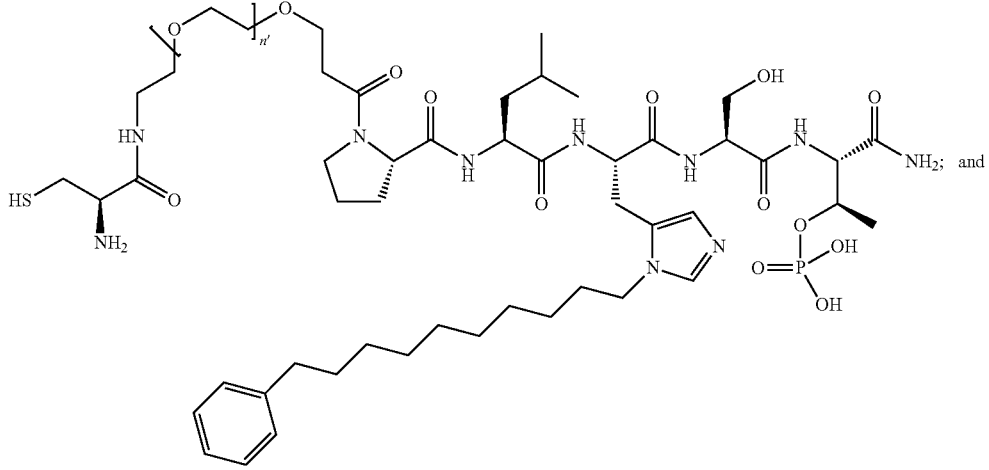

a-24A

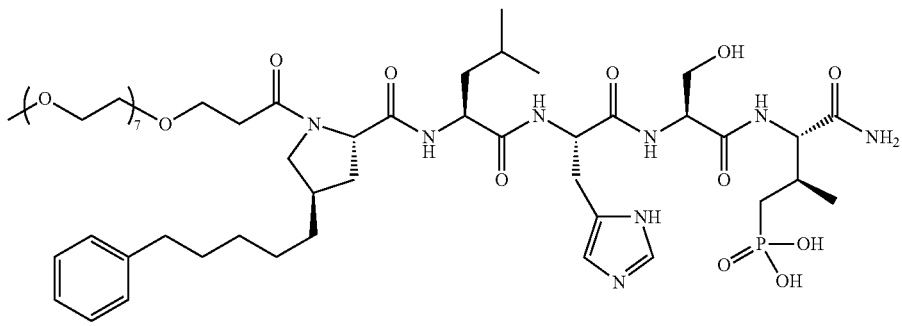

a-25 wherein n', each independently, is an integer selected from 5-8; or a pharmaceutically acceptable salt, solvate, hydrate, or stereoisomer thereof.

8. The compound of claim 6, wherein said compound is or a pharmaceutically acceptable salt, solvate, hydrate, or stereoisomer thereof.

9. The compound of claim 5, wherein Z is O; R'—X$_3$ is H; and B is hydrosulfide-(C$_{1-6}$)alkyl-C(O)—NH—(C$_{1-6}$)alkyl, wherein the (C$_{1-6}$)alkyl moiety is substituted by amino.

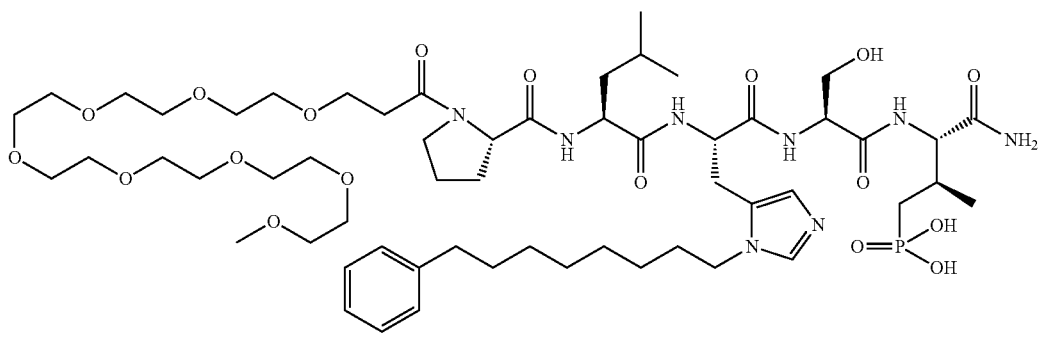

PEG-4j*

10. The compound of claim 9, wherein said compound is

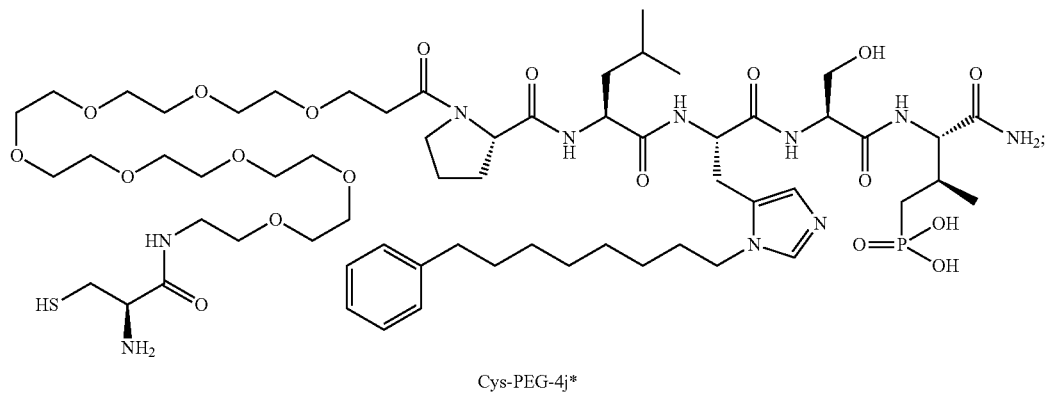 [SMILES: CC(C)C[C@H](NC(=O)[C@@H]1CCCN1C(=O)CCOCCOCCOCCOCCOCCOCCOCCOCCNC(=O)[C@@H](N)CS)C(=O)N[C@@H](Cc1cncn1CCCCCCCCc1ccccc1)C(=O)N[C@@H](CO)C(=O)N[C@H](C(N)=O)[C@@H](C)CP(=O)(O)O]

Cys-PEG-4j* or a pharmaceutically acceptable salt, solvate, hydrate, or stereoisomer thereof.

11. A composition comprising the compound of claim 1 in a pharmaceutically acceptable carrier.

12. A kit comprising at least one compound of claim 1 and instructions for use.

13. A chemical library comprising two or more compounds of claim 1.

14. The compound of claim 1, wherein R' is H, $H_2NO-$, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$ cycloalkyl, imidazolyl, quinolinyl, pyridinyl, pyrimidinyl, dioxo-pyrimidinyl, phenanthrenyl, or bicyclo[2.2.1]hept-2-enyl.

* * * * *